US011226340B2

(12) United States Patent
Gunn et al.

(10) Patent No.: US 11,226,340 B2
(45) Date of Patent: Jan. 18, 2022

(54) THERAPEUTICALLY TRIGGERING AN INNATE IMMUNE RESPONSE IN A TARGET TISSUE

(71) Applicant: Qu Biologics Inc., Burnaby (CA)

(72) Inventors: Harold David Gunn, Vancouver (CA); David W. Mullins, Norwich, VT (US); Shirin Kalyan, Burnaby (CA); Momir Bosiljcic, Burnaby (CA); Monan Angela Zhang, Burnaby (CA); Mark Bazett, Burnaby (CA); Marcel Thalen, Burnaby (CA); Dermot McGovern, Los Angeles, CA (US); Boyko Traychev Kabakchiev, Guelph (CA); Ho Pan Sham, Burnaby (CA)

(73) Assignee: Qu Biologics Inc., Burnaby (CA)

( * ) Notice: Subject to any disclaimer, the term of this patent is extended or adjusted under 35 U.S.C. 154(b) by 0 days.

(21) Appl. No.: 16/096,120

(22) PCT Filed: Apr. 26, 2017

(86) PCT No.: PCT/CA2017/050513
§ 371 (c)(1),
(2) Date: Oct. 24, 2018

(87) PCT Pub. No.: WO2017/185180
PCT Pub. Date: Nov. 2, 2017

(65) Prior Publication Data
US 2019/0134172 A1 May 9, 2019

Related U.S. Application Data

(60) Provisional application No. 62/327,953, filed on Apr. 26, 2016, provisional application No. 62/385,798, filed on Sep. 9, 2016, provisional application No. 62/395,783, filed on Sep. 16, 2016, provisional application No. 62/421,511, filed on Nov. 14, 2016, provisional application No. 62/442,759, filed on Jan. 5, 2017, provisional application No. 62/457,618, filed on Feb. 10, 2017, provisional application No. 62/472,394, filed on Mar. 16, 2017.

(51) Int. Cl.
G01N 33/68 (2006.01)
C12Q 1/6883 (2018.01)
A61K 39/108 (2006.01)
C12Q 1/6886 (2018.01)

(52) U.S. Cl.
CPC ....... *G01N 33/6863* (2013.01); *C12Q 1/6883* (2013.01); *G01N 33/6866* (2013.01); *G01N 33/6869* (2013.01); *A61K 39/0258* (2013.01); *C12Q 1/6886* (2013.01); *C12Q 2600/106* (2013.01); *C12Q 2600/112* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| 8,034,359 | B2 | 10/2011 | Gunn |
| 8,501,198 | B2 | 8/2013 | Gunn |
| 8,980,279 | B2 * | 3/2015 | Gunn ................... A61K 39/085 424/206.1 |
| 9,107,864 | B2 | 8/2015 | Gunn |
| 9,320,787 | B2 | 4/2016 | Gunn |
| 9,320,788 | B2 | 4/2016 | Gunn |
| 9,775,896 | B2 | 10/2017 | Gunn |
| 10,086,066 | B2 | 10/2018 | Gunn |
| 10,130,692 | B2 | 11/2018 | Gunn et al. |
| 10,251,946 | B2 | 4/2019 | Gunn et al. |
| 10,946,083 | B2 | 3/2021 | Gunn et al. |
| 2002/0009748 | A1 | 1/2002 | Cook |
| 2006/0205012 | A1 | 9/2006 | Debad et al. |

FOREIGN PATENT DOCUMENTS

| WO | WO0209748 A1 | 2/2002 |
| WO | WO03051305 A2 | 6/2003 |
| WO | WO2005120560 A1 | 12/2005 |
| WO | WO2007035368 A2 | 3/2007 |
| WO | WO2008049231 A1 | 5/2008 |
| WO | WO2009003905 A2 | 1/2009 |
| WO | WO2010062960 A2 | 6/2010 |
| WO | WO2012012874 A1 | 2/2012 |
| WO | WO2012154987 A1 | 11/2012 |

(Continued)

OTHER PUBLICATIONS

Smith et al J. Exp. Med. 2009. 206(9): 1883-1897 (Year: 2009).*
Langdahl et al Journal of Bone and Mineral Research (2000) 15: 402-414 (Year: 2000).*
Wall et al. Nature Reviews Genetics (2003) 4:587-597 (Year: 2003).*
Zill et al. Molecular Psychiatry. 2004. 9: 1030-1036 (Year: 2004).*
Li et al BMC Genetics. 2010. 11:47 (Year: 2010).*
Manuc et al Clinical Experimental Gastroenterology. Mar. 2016. 6(9):59-70 (Year: 2016).*
Altschul et al., Basic Local Alignment Search Tool, J. Mol. Biol., May 1990, 215:403-10.
Andersen-Nissen et al., Evasion of Toll-like receptor 5 by flagellated bacteria, PNAS, Jun. 28, 2005, 102(26):9247-9252.

(Continued)

*Primary Examiner* — Carla J Myers
(74) *Attorney, Agent, or Firm* — Shweta Chandra; Bret E. Field; Bozicevic, Field & Francis LLP

(57) ABSTRACT

The invention provides therapeutic compositions that present an artificial repertoire of mammalian pattern recognition receptor (PRR) agonists, so that the pattern of PRR agonists recapitulates a distinct portion of a PRR agonist signature of a mammalian pathogen. The artificial repertoire of PRR agonists may be formulated together in a therapeutic vehicle for combined presentation to an innate immune cell resident in a target tissue in a mammalian host, and the vehicle adapted to deliver the PRR agonists to the target tissue, so as to modulate an immune response.

14 Claims, 66 Drawing Sheets

(56) References Cited

FOREIGN PATENT DOCUMENTS

| WO | WO2013030670 A3 | 8/2013 |
|---|---|---|
| WO | WO2015164979 A1 | 11/2015 |
| WO | WO2018085937 A1 | 5/2018 |
| WO | WO2019134036 A1 | 7/2019 |

OTHER PUBLICATIONS

Best et al., Development of a Crohn's Disease Activity Index, Gastroenterology, 1976, 70(3) :439-444.
Bordon, Innate memory training, 2014, Nature Reviews Immunology, AOP, published online Oct. 10, 2014, 14, 713.
Bressler et al., Site-Specific Immunomodulator: A Novel Treatment for Crohn's Disease, Gastroenterology Research and Practice, May 12, 2015, vol. 2015, doi:10.1155/2015/231243, ISSN 1687-6121, pp. 1-8.
Broz et al., Newly described pattern recognition receptors team up against intracellular pathogens, Nature Reviews Immunology, published online Jul. 12, 2013; Nature Reviews Immunology 13, 551-565.
Cameron et al., Inhibition of lipopolysaccharide-induced macrophage IL-12 production by Leishmania mexicana amastigotes: the role of cysteine peptidases and the NF-kappaB signaling pathway, J Immunol, Sep. 1, 2004;173(5):3297-304.
Carattoli et al., In silico detection and typing of plasmids using PlasmidFinder and plasmid multilocus sequence typing, Antimicrob Agents Chemother, Jul. 2014; 58(7):3895-903.
Chen et al., Identification of genes subject to positive selection in uropathogenic strains of *Escherichia coli*: a comparative genomics approach, Proc Natl Acad Sci USA, Apr. 11, 2006;103(15):5977-82.
Cirl et al., Subversion of Toll-like receptor signaling by a unique family of bacterial Toll/interleukin-1 receptor domain-containing proteins, Nat Med. Apr. 2008;14(4):399-406.
Cleynen et al., Inherited determinants of Crohn's disease and ulcerative colitis phenotypes: a genetic association study, Lancet. Jan. 9, 2016;387(10014):156-67.
Cosentino et al., PathogenFinder—Distinguishing Friend from Foe Using Bacterial Whole Genome Sequence Data, Oct. 28, 2013, PLoS ONE 8(10):e77302.
Franke et al., Genome-wide meta-analysis increases to 71 the number of confirmed Crohn's disease susceptibility loci, Nature Genetics, Dec. 2010, 42(12) :1118-1125.
Henikoff et al., Amino Acid Substitution Matrics from Protein Blocks, PNAS, Nov. 1992, 89(22): 10915-10919.
Hornef et al., Bacterial strategies for overcoming host innate and adaptive immune responses, Nat Immunol. Nov. 2002;3(11):1033-40.
Italiani et al., From monocytes to M1/M2 macrophages: phenotypical vs. functional differentiation, Frontiers in Immunology, Oct. 2014, vol. 5, article 514.
Iwasaki et al., Control of adaptive immunity by the innate immune system, Nat Immunol, Apr. 2015; 16(4): 343-353.
Jernigan et al., Parasitic infections of the small intestine, Gut 1994; 35:289-93.
Jostins et al., Host-microbe interactions have shaped the genetic architecture of inflammatory bowel disease, Nature. Nov. 1, 2012; 491(7422): 119-124.
Jostins et al., Using Genetic Prediction from Known Complex Disease Loci to Guide the Design of Next-Generation Sequencing Experiments, PLoS One. Oct. 18, 2013; 8(10):e76328.
Kaczanowska et al., TLR agonists: our best frenemy in cancer immunotherapy, Journal of Leukocyte Biology, Jun. 30, 2013, 93(6):847-863.
Larsen et al., Multilocus Sequence Typing of Total-Genome-Sequenced Bacteria, 2012, O.J. Clin. Micobiol, 50(4): 1355-1361.
Lery et al., Comparative analysis of Klebsiella pneumoniae genomes identifies a phospholipase D family protein as a novel virulence factor, BMC Biology, 2014, vol. 12, Article No. 41.
Levast et al., Vaccine Potentation by Combination Adjuvants, Vaccines 2014, 2, 297-322.
Liu et al., Association analyses identify 38 susceptibility loci for inflammatory bowel disease and highlight shared genetic risk across populations, Nature Genetics. 47.9 (Sep. 2015): p. 979-986.
Maisonneuve et al., Unleashing the potential of NOD- and Toll-like agonists as vaccine adjuvants, PNAS, Aug. 26, 2014, 111(34): 12294-12299.
Mills et al., A Breakthrough: Macrophage-Directed Cancer Immunotherapy, Jan. 15, 2016, Cancer Res; 76(3) :1-4.
Mogensen, Pathogen Recognition and Inflammatory Signaling in Innate Immune Defenses, Apr. 2009, Clinical Microbiology Reviews, 22(2):240-273.
Needleman et al., A general method applicable to the search for similarities in the amino acid sequence of two proteins J Mol Biol, Mar. 1970;48(3):443-53.
Netea et al., Innate immune memory: a paradigm shift in understanding host defense, Nature Immunology, Jul. 2015, 16(7):675-679.
Pearson et al., Improved tools for biological sequence comparison, PNAS USA, Apr. 1988, 85:2444-2448.
Rodriguez-Bores et al., Novel genetic markers in inflammatory bowel disease, World J Gastroenterol. Nov. 14, 2007; 13(42): 5560-5570.
Schafer et al., Parasites of the small intestine, Curr Gastroenterol Rep, Aug. 2006, 8(4):312-20.
Sewell, An investigation of molecular defects underlying impaired acute inflammation in Crohn's disease, Doctoral thesis, UCL (University College London), 2011, 320 pages.
Smith et al., Comparison of Biosequences, Adv. Appl. Math, 1981, 2:482-489.
So et al., The application of Toll like receptors for cancer therapy, International Journal of Biological Sciences, 2010, 6(7):675-681.
Sutcliffe et al., Novel Microbial-Based Immunotherapy Approach for Crohn's Disease, Front Med (Lausanne). Jul. 19, 2019;6:170.
Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y.
Turner et al., Cytokines and chemokines: At the crossroads of cell signalling and inflammatory disease, Biochim Biophys Acta, Nov. 2014;1843(11):2563-2582.
Vanderlugt et al., Epitope spreading in immune-mediated diseases: implications for immunotherapy, Nat Rev Immunol. Feb. 2002; 2(2):85-95.
International Search Report & Written Opinion for PCT Application No. PCT/CA2017/050513 dated Aug. 9, 2017, 12 pages.
Extended European Search Report for European Application No. 17788461.6 dated Dec. 6, 2019, 12 pages.

* cited by examiner

Treatment timeline for murine pre-infection model to assess SSI-mediated anti-tumor efficacy Day -31: intra-tracheal instillation of *Klebsiella pneumoniae* or *Streptococcus pneumoniae*
Day -10 to +16: Subcutaneous injection of QBKPN or Placebo
Day 0: Intravenous injection of LLC
Day +18: Sacrifice, enumerate tumor nodules (A)
IFN-gamma (B)
IL-17A (C)
IL-17A combined all data (D)

(A)

(B)

(C)

(A)

(B)

(A)

(B)

Ex-Vivo Imaging of Cy5.5 labelled QBKPN measured in organs after 24 hrs after 3rd SSI injection (A)

| 95% Confidence Intervals | |
|---|---|
| Slope | 0.2875 to 0.8917 |
| Y-intercept when X=0.0 | -6.470 to 1.786 |
| X-intercept when Y=0.0 | -5.953 to 7.569 |
| Goodness of Fit | |
| R square | 0.5169 |

(B)

PD1 expression on NKG2D expressing cells in lungs (Day 5)

QB112 (Day 5)

| Dunnett's multiple comparisons test | Mean Diff. | 95% CI of diff. | Significant? | Summary |
|---|---|---|---|---|
| Placebo vs. QBKPN | 2.879 | -10.65 to 16.41 | No | ns |
| Placebo vs. QBSAU (10X) | 15.99 | 2.464 to 29.52 | Yes | * |

47A i) Outer Membrane 47A ii) DNA
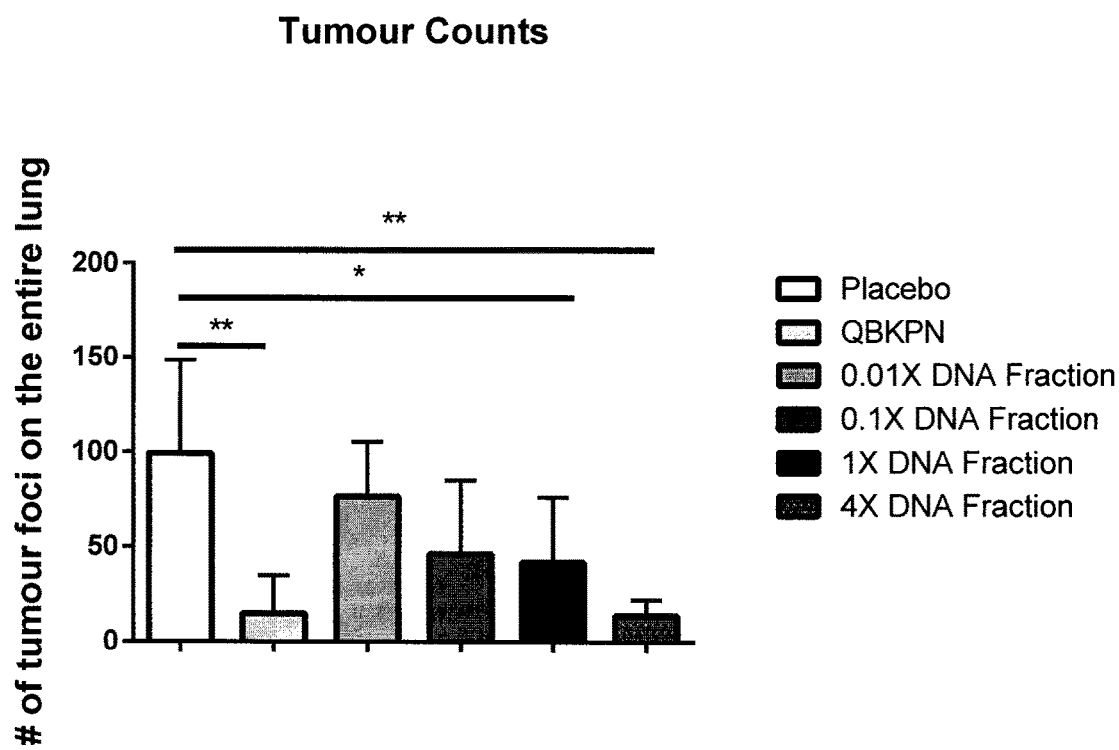

47A iii) Inner Membrane
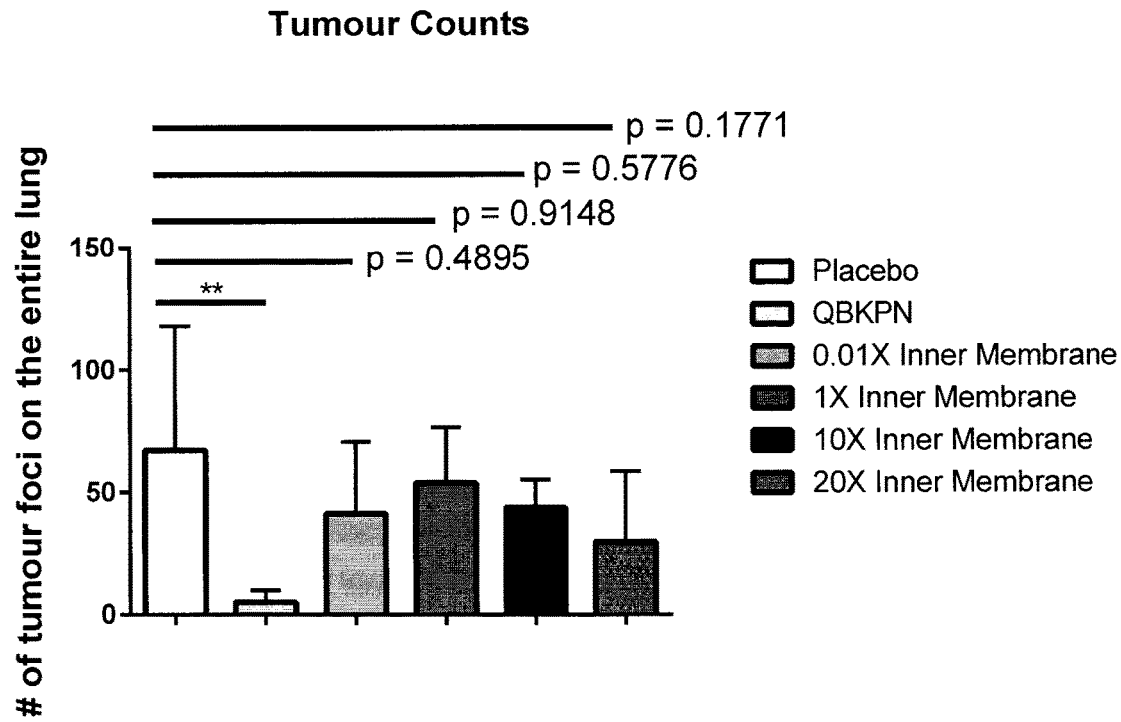
Figure 47B
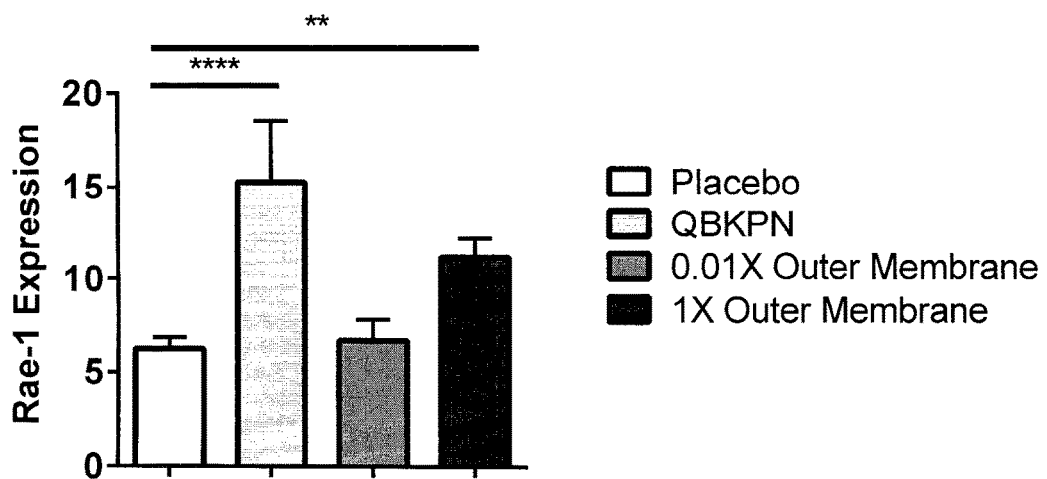

C57BL/6 wildtype mice

NKG2D KO mice

Neutrophils (CD45+ CD11b+ Ly6G+ Ly6C+ cells) in lung samples

* $p < 0.05$
** $p < 0.01$
**** $p < 0.0001$

Neutrophils (CD45+ CD11b+ Ly6G+ Ly6C+ cells) in spleen samples

** $p < 0.01$
**** $p < 0.0001$

Figrure 59B

Trial Week---->

THERAPEUTICALLY TRIGGERING AN INNATE IMMUNE RESPONSE IN A TARGET TISSUE

FIELD

Innovations are disclosed in the field of medical and veterinary science, relating to preparations that contain immunogens, such as microbial components. The preparations are formulated for medical purposes, and methods of using the preparations in therapy are provided.

BACKGROUND

There is growing recognition that immunological dysregulation, an imbalance between immune response and immune tolerance, is not only a primary factor in allergic and autoimmune disease, it also has an underlying mechanistic role in a wide variety of pathologies, including cancer (see Mills et al., 2016, Cancer Res; 76(3); 1-4), metabolic disease (obesity, diabetes), degenerative disease (Alzheimer's, Parkinson's, Amyotrophic Lateral Sclerosis, osteoporosis), respiratory and cardiovascular disease (see Immune Rebalancing, 1st Edition: The Future of Immunosuppression, 2016, Boraschi and Penton-Rol Eds, Academic Press).

In vertebrates, an important aspect of immunological regulation involves the concerted activity of the innate immune system and the adaptive immune system. This concerted activity involves metabolic, enzymatic and molecular genetic changes within immune cells, orchestrating an elaborate system of cellular, cytokine and chemokine communication pathways mediating the coordinated activity of the disparate components of these complementary systems (see Iwasaki & Madzhitov, 2015, Nature Immunology 16:343-353; WO0209748; WO03051305; Turner et al., 2014, BBA-Molecular Cell Research 1843:11 2563-2582). An aspect of this coordinated activity underlies the recognition that ligands of the pattern recognition receptors (PRRs) of the innate immune system may be used as vaccine adjuvants to improve an adaptive immune response (see Maisonneuve et al., 2014, PNAS 111(34), 12294-9; WO2007035368).

Immunological memory, involving the recognition of specific antigens by B and T cell receptors, is a long recognized and central feature of the adaptive immune system, and the basis for vaccine efficacy (see Nature Immunology, Focus on immunological memory: June 2011, Volume 12 No 6 pp 461-575). Innate immune memory is a more recently recognized and less well understood characteristic of the immune system (see Netea et al., 2015, Nature Immunology 16, 675-679; and Bordon, 2014, Nature Reviews Immunology 14, 713).

A wide variety of innate and adaptive immune cells are understood to be resident in non-lymphoid tissues, with diverse roles in tissue homeostasis (see Nature Immunology, Focus on tissue-resident leukocytes, October 2013, Volume 14 No 10 pp 977-1100). The complexities of this homeostasis are evident in the observation that even the ontogeny of tissue resident immune cells may in some cases be distinct from the ontogeny of similar immune cells that are not tissue resident (Italiani and Boraschi, Frontiers in Immunology, October 2014, Vol 5, article 514).

SUMMARY

Immunomodulatory or immunogenic compositions are provided that constitute an artificial repertoire of mammalian pattern recognition receptor (PRR) agonists. The PRR agonist repertoire is selected so that it in effect recapitulates a distinct portion of a PRR agonist signature of a microbial pathogen, and more specifically a pathogen that is pathogenic in a selected target tissue. The PRR agonist signature is distinct in the sense that it is different from PRR agonist signatures of microbes that are not pathogenic in the target tissue, and it is also distinct in the sense that it is different from the native PRR agonist signature of the wild-type pathogen. This distinct artificial repertoire of PRR agonists may then be formulated so that the PRR agonists are presented together in a therapeutic vehicle, for example so that the PRR agonist repertoire may be presented in combination. The therapeutic vehicle may for example be a recombinant microbe, a cellular fraction of a microbial cell, a microparticle or a liposome. The composition may for example comprise microbial agonists for at least a minimum number of distinct mammalian PRRs, for example at least 5, as described in more detail herein. The vehicle may then be delivered, for example systemically, so that the PRR agonist repertoire is presented to an innate immune cell resident in the target tissue in a host, such as a mammalian host. The therapeutic vehicle may for example aggregate the artificial repertoire of PRR agonists, so that the proximity of the plurality of PRR agonists is maintained during systemic distribution in a host. Compositions of this kind may be used to treat a wide variety of diseases characterized by immune dysregulation, including neoplastic diseases and autoimmune diseases.

Aspects of the innovation involve the use of an immunogenic composition in methods of treating an immune dysregulation in a target tissue in a mammalian host, wherein the composition comprises the foregoing artificial repertoire of mammalian PRR. The artificial repertoire of PRR agonists may be formulated together in a therapeutic vehicle for combined presentation following administration to a mammalian host. Composition may for example include components of the microbial mammalian pathogen that are agonists for a select number of distinct mammalian PRRs, as discussed in more detail below, for example at least 5. Compositions may for example be adapted for use so as to modulate an innate immune response in the target tissue. The therapeutic vehicle may for example include a recombinant microbe, a cellular fraction of the recombinant microbe, a cellular fraction of a microbial cell, a microparticle or a liposome, each comprising components of the microbial mammalian pathogen that provide the PRR agonists that together make up the artificial repertoire of PRR agonists. A recombinant microbe may for example include a recombinant gene encoding a component of at least one of the PRR agonists. In select aspects, the therapeutic vehicle may for example include a whole killed or attenuated cell of the recombinant microbe. Alternatively, the cellular fraction of the microbial mammalian pathogen may be used, for example, a bacterial outer membrane fraction; a bacterial inner membrane fraction; a pellet from a gradient centrifugation of microbial cell components; or chromosomal DNA. The therapeutic vehicle may for example be formulated for use for delivering the PRR agonists to the target tissue.

In select embodiments, the PRRs and the corresponding PRR agonists may for example be selected from the group consisting of:

| PRR | PRR Agonist |
|---|---|
| TLR2 | Microbial cell wall components/preparations, Pam2C- |

-continued

| PRR | PRR Agonist |
| --- | --- |
| | Aca-Benzyl-Murabutide (Pam2C-conjugated murabutide) |
| TLR3 | Polyadenylic-polyuridylic acid, Polyinosine-polycytidylic acid |
| TLR4 | Lipopolysaccharide, Monophosphoryl Lipid A |
| TLR5 | Flagellin |
| TLR7/8 | Single-stranded RNAs, Nucleoside analogs, Imidazoquinolines/Thiazoquinolines |
| TLR9 | unmethylated CpG DNA motifs |
| NOD1 | iE-DAP, Acylated iE-DAP, D-gamma-Glu-mDAP, L-Ala-gamma-D-Glu-mDAP |
| NOD2 | MDP (MurNAc-L-Ala-D-isoGln, muramyl dipeptide), N-glycolylated muramyldipeptide, N-Acetyl-muramyl-L-Alanyl-D-Glutamin-n-butyl-ester, MurNAc-Ala-D-isoGln-Lys, N-Acetylmuramyl-L-Alanyl-D-Isoglutamine (L-D isoform), 6-O-stearoyl-N-Acetyl-muramyl-L-alanyl-D-isoglutamine, Pam2C-Aca-Benzyl-Murabutide, |
| TLR2/NOD2 | Pam2C-conjugated murabutide |
| NOD1/NOD2 | PGN, Pam2C-conjugated murabutide |
| RIG1/MDA5 | 5' triphosphate double stranded RNA (18-20mer), polyriboinosinic:polyribocytidylic acid |
| DAI, LRRFIP1, AIM2, RIG1 | dsDNA, poly(dA-dT)•poly(dT-dA) |
| Dectin-1 | Beta-glucan peptide, fungal cell wall preparations |
| Mincle | damaged microbial cells, fungus, yeast and mycobacteria, Trehalose-6,6-dibehenate, trehalose-6,6-dimycolate |
| STING | Cyclic dinucleotides (c-di-nucleotides), xanthenone derivatives, 3'3'-cGAMP, 2'3'-cGAMP, 2'2'-cGAMP, 2'2'-cGAMP, c-di-AMP (cyclic di-adenylate monophosphate), c-di-GMP, c-di-IMP, c-di-UMP, c-di-AMP |
| RIG-I | PPP-ssRNA (PPP-ssRNA, ssRNA with a 5'-triphosphate group), RNA with base pairing and polyI:C |
| MDA5 | Long dsRNA |
| LGP2 | dsRNA |
| DDX41 | B-form DNA and CDNs (cyclic dinucleotides) |
| DHX9 | DNA, RNA, CpG-A oligodeoxynucleotids and CpG-B ODNs |
| DDX3 | Viral RNA |
| DHX36 | DNA, RNA, CpG-A oligodeoxynucleotids and CpG-B oligodeoxynucleotids |
| DDX1-DDX21-DDX36 | RNA and polyI:C |
| DDX60 | ssRNA, dsRNA and dsDNA |
| KU70 | DNA |
| cGAS | DNA |
| STING | CDNs (c-di-GMP and c-di-AMP) |
| NOD2 | ssRNA |
| NLRP3 | ssRNA, dsRNA, bacterial mRNA and oxidized mitochondrial DNA |
| AIM2 | DNA |
| IFI16 | dsDNA |
| LRRFIP1 | B-form DNA, Z-form DNA and dsRNA |
| DAI | DNA |
| IFIT1, 2, 3 and 5 | PPP-ssRNA |

The therapeutic vehicle may for example include additional therapeutic moieties, such as one or more of: GMCSF, vitamin D, NOHA, alph1 antitrypsin, glutathione, an isoprenoid, or α-galactosylceramide. In alternative embodiments, the therapeutic vehicle further comprises an antigen, such as a cancer antigen. Alternatively, the therapeutic vehicle may further include a heterologous PRR agonist, such as a PRR agonist that is not a component of the microbial mammalian pathogen.

The subject of treatment, such as a mammalian host or human patient, may for example be suffering from a disease or condition characterized by the immune dysregulation in the target tissue, such as a cancer or an inflammatory disorder.

The composition may be adapted for use in an amount effective to modulate a biomarker, for example one or more of PD1, PDL1, IP-10, MIG, RANTES, neutrophils, Ly6C monocytes, and NKG2D. In select embodiments, the composition may for example be adapted for use in an amount effective to down-regulate PD1 and/or PDL1 expression in cells present in the target tissue. The composition may accordingly be adapted for use so as to modulate an adaptive immune response in the host, for example as a concomitant of modulating an innate immune response.

the therapeutic vehicle is for administration at an administration site that is not the target tissue, and the site may for example be the skin, subcutaneous tissue, the respiratory tract. Administration may be enteric, or non-enteric. The therapeutic vehicle may be formulated for systemic distribution of the PRR agonists following administration at a localized administration site. The the therapeutic vehicle may be administered in a plurality of doses over a dosage duration, and the dosage duration may for example be at least two weeks, or any of other wide range of dosage regimens disclosed herein or known in the art.

In select embodiments, human patient treated in accordance with the invention may for example be immunosuppressed or immunocompromised, or may be geriatric or pediatric patients.

The therapeutic uses recited herein are reflected in corresponding methods of treatment, and vice versa.

BRIEF DESCRIPTION OF THE DRAWINGS

FIG. 27B illustrates BAL cell counts and differentials following placebo and KPN SSI treatment in filtered air or cigarette smoke-exposed groups: (a) BAL total cells, (b) lymphocytes, (c), macrophages (d), and neutrophils. * $p<0.05$ comparing to the groups relative control; #$p<0.05$ comparing KB group to relative placebo control. Data are means±SD of 9-10 mice per group.

FIG. 28A illustrates data showing that a KPN SSI intervention attenuated cigarette smoke exposure induced increases Th1-skewed lung inflammatory responses, as follows. BAL supernatant fluid analysis following placebo and KB treatment in filtered air or cigarette smoke-exposed groups. (a) IFNγ, (b) CXCL9, (c) CXCL10, (d) CCL5, (e) IL-6, (f) G-CSF, (g) CXCL1, (h) IL-17. * $p<0.05$ comparing to the groups relative control; #$p<0.05$ comparing KPN SSI group to relative placebo control. Data are means±SD of 10 mice per group. FIG. 28B provides data illustrating that KPN SSI intervention differentially modulates cigarette smoke exposure induced changes in serum immune mediators, as follows. Serum analysis following placebo and KPN treatment in filtered air or cigarette smoke-exposed groups: (a) VEGF, (b) (c) CCL2, (d) CXCL9, (e) CXCL10 and (f) CCL5. * $p<0.05$ comparing to the groups relative control; #$p<0.05$ comparing KB group to relative placebo control. Data are means±SD of 9-10 mice per group. FIG. 28C provides data illustrating that KPN SSI intervention increased blood and lung Ly6CHI monocytes and neutrophils, as follows. Flow cytometric analysis of blood (a-b) and lung (c-d) $Ly6C^{HI}$ monocytes and neutrophils following placebo and KB treatment in filtered air or cigarette smoke-exposed groups. * $p<0.05$ comparing to the groups relative control. #$p<0.05$ comparing KB group to relative placebo control. Data are means±SD of 10 mice per group. FIG. 28D is series of bar graphs (A-C) illustrating aspects of an anti-inflammatory SSI treatment for COPD from an animal model, particularly select lung gene expression profiles.

FIG. 33 includes three bar graphs.

FIG. 47 is a series of graphs illustrating efficacy of alternative cellular fractions in a B16 melanoma model in the lung, including dose-dependant and site-specific efficacy. FIG. 47B is a bar graph illustrating results following 10 injections of outer membrane SSI, showing that Rae-1 expression was elevated by the outer membrane fraction in a dose dependant manner.

DETAILED DESCRIPTION

Figures 1, 2:
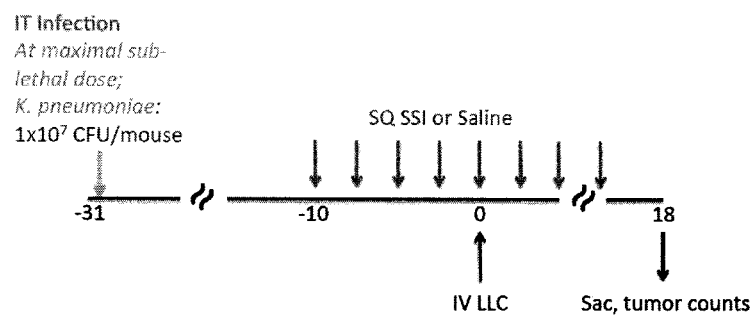
FIG. 1 is a schematic timeline of a site specific immunotherapy (SSI) in accordance with one aspect of the invention, illustrating intra-tracheal (IT) instillation of a K. pneumoniae (KPN) whole killed cell SSI at day −31, and subcutaneous (SQ) injections of SSI or saline (placebo) every other day starting on day −10, with intravenous (IV) Lewis lung carcinoma (LLC) administration on day 0, followed by sacrifice (sac) on day 18.
FIG. 2 is a graph illustrating therapeutic efficacy of alternative SSI formulations in a murine cancer model.

In the following detailed description, various examples are set out of particular embodiments, together with experimental procedures that may be used to implement a wide variety of modifications and variations in the practice of the present invention. For clarity, a variety of technical terms are used herein in accordance with what is understood to be the commonly understood meaning, as reflected in definitions set out below.

General Definitions

An "immunogen" refers to a molecule, or a composition comprising the molecule, that is capable of eliciting an immune response by an organism's immune system. An "antigen" refers to a molecule that is capable of binding to the product of an immune response.

"Pathogenic" agents are agents, such as microbes, such as bacteria or viruses, which are known to cause infection in a host in nature, and in this sense, "pathogenic" is used in the context of the present invention to mean "naturally pathogenic". Although a wide variety of microbes may be capable of causing infection under artificial conditions, such as artificial inoculations of a microbe into a tissue, the range of microbes that naturally cause infection is necessarily limited, and well established by medical practice.

An "infection" is the state or condition in which the body or a part of it is invaded by a pathogenic agent (e.g., a microbe, such as a bacterium) which, under favorable conditions, multiplies and produces effects that are injurious (Taber's Cyclopedic Medical Dictionary, 14th Ed., C. L. Thomas, Ed., F. A. Davis Company, PA, USA). An infection may not always be apparent clinically and may result in only localized cellular injury. Infections may remain subclinical, and temporary if the body's defensive mechanisms are effective. Infections may spread locally to become clinically apparent as an acute, a subacute, or a chronic clinical infection or disease state. A local infection may also become systemic when the pathogenic agent gains access to the lymphatic or vascular. Infection is usually accompanied by inflammation, but inflammation may occur without infection.

"Inflammation" is the characteristic tissue reaction to injury (marked by swelling, redness, heat, and pain), and includes the successive changes that occur in living tissue when it is injured. Infection and inflammation are different conditions, although one may arise from the other (Taber's Cyclopedic Medical Dictionary, supra). Accordingly, inflammation may occur without infection and infection may occur without inflammation (although inflammation typically results from infection by pathogenic bacteria or viruses). Inflammation is characterized by the following symptoms: redness (rubor), heat (calor), swelling (tumour), pain (dolor). Localized visible inflammation on the skin may be apparent from a combination of these symptoms, particularly redness at a site of administration.

Various subjects may be treated or assayed or sampled in accordance with alternative aspects of the invention. As used herein, a "subject" is an animal, for e.g., a vertebrate or a mammal. Accordingly, a subject may be a patient, e.g., a human, suffering from an immune dysregulation. A subject may also be an experimental animal, e.g., an animal model of an immune dysregulation. In some embodiments, the terms "subject" and "patient" may be used interchangeably, and may include a human, a non-human mammal, a non-human primate, a rat, mouse, or dog. A healthy subject may be a human who is not suffering from a disease, such as a cancer or immune dysfunction, or suspected of having the disease, or who is not suffering from a chronic disorder or condition. A "healthy subject" may also be a subject who is not immunocompromised. By immunocompromised is meant any condition in which the immune system functions in an abnormal or incomplete manner. Immunocompromisation may be due to disease, certain medications, or conditions present at birth. Immunocompromised subjects may be found more frequently among infants, the elderly, and individuals undergoing extensive drug or radiation therapy.

A "sample" from a subject may include any relevant biological material, including for example a cell, tissue or bodily fluid sample taken from a patient. For example, a sample may conveniently include samples of skin, cheek, blood, stool, hair or urine. Sample nucleic acids for use in diagnostic and prognostic methods can for example be obtained from a selected cell type or tissue of a subject. For example, a subject's bodily fluid (e.g. blood) can be obtained by known techniques. Alternatively, nucleic acid tests can be performed on dry samples (e.g., hair or skin).

The term "polymorphism" refers to a location within a biological sequence, such as a genomic sequence, which varies within a population. Polymorphisms are comprised of different "alleles". The term "genotype" refers to the specific alleles in a genome, for example in a cell, tissue sample or an individual. The location of a polymorphism may be identified by its position, for example within the genome or within a sequence such as a protein that is reflective of a genomic locus. This may for example be provided in the form of a characterization of the different amino acids or bases that are found at a designated location. For diploid genomes, the genotype is typically comprised of at least two alleles, which may be the same (homozygous) or different (heterozygous). Individual polymorphisms are typically assigned unique identifiers in the art (such as "Reference SNP", "refSNP" or "rs #"), for example in the Single Nucleotide Polymorphism Database (dbSNP) of Nucleotide Sequence Variation available on the NCBI website.

Characterization of polymorphisms, alleles or a genotype may be performed by any of very wide variety of methods. These methods may for example variously involve hybridization, labeling, cloning, sequencing and/or amplification of nucleic acids, such as genomic DNA, for example using using PCR, LCR, xMAP, invader assays, mass spectrometry, pyrosequencing, selective oligonucleotide hybridization, selective amplification, selective primer extension or probes. In this context, the term "probes" includes naturally occurring or recombinant single- or double-stranded nucleic acids or chemically synthesized nucleic acids. A probe can for example be a polynucleotide of a length suitable for selective hybridization to a nucleic acid containing a polymorphic region. Labeled probes also can be used in conjunction with amplification of a polymorphism. DNA microarray technologies, sometimes referred to as DNA chips or gene chips, may for example be used for genomic characterization, for example to characterize point mutations, single nucleotide polymorphisms (SNPs), and/or short tandem repeats (STRs). For example, several probes capable of hybridizing specifically to an allelic variant may be attached to a solid phase support by a variety of processes, including lithography. Additional methods include laser capture microdissection (LCM), comparative genomic hybridization (CGH) and chromatin immunoprecipitation (ChiP). Allele specific hybridization may for example make use of probes overlapping the polymorphic site and having about 5, or alternatively 10, or alternatively 20, or alternatively 25, or alternatively 30 nucleotides around the polymorphic region. Alternatively, the presence of the specific allele in DNA from a subject can in some case be characterized by restriction enzyme analysis. Similarly, protection from cleavage agents (such as a nuclease, hydroxylamine or osmium tetroxide) can be used to detect mismatched bases in RNA/RNA DNA/DNA, or RNA/DNA heteroduplexes, using technique that may be described as "mismatch cleavage" assays. Alterations in electrophoretic mobility may be used to characterize allelic variants, for example to detect single strand conformation polymorphisms.

Many of the methods described herein may be performed using kits, for example comprising at least one probe or primer nucleic acid, or one of more of the compositions described herein and instructions for use of the kit. Kits can for example comprise at least one probe or primer which is capable of specifically hybridizing to a polymorphic region or adjacent to the polymorphic region, so that the oligonucleotides are "specific for" the polymorphic region. Kits may also comprise at least one reagent necessary to perform a particular assay. Kits can also include positive controls, negative controls, sequencing markers, or antibodies, for example for determining a subject's genotype or biological marker profile.

An "immune response" includes, but is not limited to, one or more of the following responses in a mammal: induction or activation of antibodies, neutrophils, monocytes, macrophages (including both M1-like macrophages and M2-like macrophages as described herein), B cells, or T cells (including helper T cells, natural killer cells, cytotoxic T cells, gamma-delta (γδ) T cells), such as induction or activation by one or more immunogens in an immunogenic composition, following administration of the composition. An immune response to a composition thus generally includes the development in the host animal of a cellular and/or antibody-mediated response to the composition. In some embodiments, the immune response is such that it will also result in slowing or stopping the progression of an immune dysregulation, or a disease characterized by immune dysregulation. An immune response may accordingly include one or both of a cellular immune response and/or a humoral immune response, and may be an adaptive response or an innate immune response.

"Immune dysregulation" is an inappropriately regulated immune response, such as an inappropriately restrained or inappropriately robust immune response. The immune dysregulation may for example be in the context of an autoimmune, inflammatory, or degenerative disease (such as rheumatoid arthritis, Crohn's disease, inflammatory bowel disease, multiple sclerosis, neurodegenerative disease, or allergies) or a neoplastic disease, such as a cancer, or a host defense against pathogens. Inflammatory bowel disease (IBD) is a name frequently given to a group of inflammatory conditions of the colon and small intestine, generally characterized by similar symptoms of immune dysregulation and indeterminate etiology. Major sub-types of IBD are recognized clinically as Crohn's disease and ulcerative colitis. In addition to Crohn's disease and ulcerative colitis, IBD may also include conditions recognized as any one of the following: collagenous colitis, lymphocytic colitis, ischaemic colitis, diversion colitis, Behçet's syndrome or indeterminate colitis. The difference between these conditions relate primarily to the location and nature of the inflammatory changes in the gastrointestinal tract (GIT). Crohn's disease, for example, is generally recognized as potentially affecting any part of the gastrointestinal tract, from mouth to anus, with a majority of the cases marked by relapsing and remitting granulomatous inflammation of the alimentary tract in the terminal ileum and colon. Ulcerative colitis, in contrast, is generally considered to be restricted to the colon and the rectum. The various regions of the gastrointestinal tract in which these inflammatory conditions may exhibit symptoms include: the bowel or intestine, including: the small intestine (which has three parts: the duodenum, the jejunum, and the ileum); the large intestine (which has three parts: the cecum, the colon, which includes the ascending colon, transverse colon, descending colon and sigmoid flexure; and the rectum); and, the anus.

A "site specific immunotherapy" (SSI) is an immunomodulatory treatment that is effective to therapeutically or prophylactically alter an aspect of the immune state, or immune system physiology, at an anatomical site or sites, such as an organ or tissue. In some instances, for example, an SSI may be adapted to ameliorate an immune dysregulation, or to treat a condition characterized by an immune dysregulation.

A "cancer" or "neoplasm" is any unwanted growth of cells serving no physiological function. In general, a cancer cell has been released from its normal cell division control, i.e., a cell whose growth is not regulated by the ordinary biochemical and physical influences in the cellular environment. Thus, "cancer" is a general term for diseases characterized by abnormal uncontrolled cell growth. In most cases, a cancer cell proliferates to form clonal cells that are malignant. The lump or cell mass, "neoplasm" or "tumour," is generally capable of invading and destroying surrounding normal tissues. By "malignancy", as used herein, is meant as an abnormal growth of any cell type or tissue that has a deleterious effect in the organism having the abnormal growth. The term "malignancy" or "cancer" includes cell growths that are technically benign but which carry the risk of becoming malignant. Cancer cells may spread from their original site to other parts of the body through the lymphatic system or blood stream in a process known as "metastasis." Many cancers are refractory to treatment and prove fatal. Examples of cancers or neoplasms include, without limitation, transformed and immortalized cells, tumours, carcinomas, in various organs and tissues as described herein or known to those of skill in the art.

Most cancers fall within three broad histological classifications: carcinomas, which are the predominant cancers and are cancers of epithelial cells or cells covering the external or internal surfaces of organs, glands, or other body structures (for e.g., skin, uterus, lung, breast, prostate, stomach, bowel), and which tend to metastasize; carcinomas, which are derived from connective or supportive tissue (for e.g., bone, cartilage, tendons, ligaments, fat, muscle); and hematologic tumours, which are derived from bone marrow and lymphatic tissue. Carcinomas may be adenocarcinomas (which generally develop in organs or glands capable of secretion, such as breast, lung, colon, prostate or bladder) or may be squamous cell carcinomas (which originate in the squamous epithelium and generally develop in most areas of the body). Sarcomas may be osteosarcomas or osteogenic sarcomas (bone), chondrosarcomas (cartilage), leiomyosarcomas (smooth muscle), rhabdomyosarcomas (skeletal muscle), mesothelial sarcomas or mesotheliomas (membranous lining of body cavities), fibrosarcomas (fibrous tissue), angiosarcomas or hemangioendotheliomas (blood vessels), liposarcomas (adipose tissue), gliomas or astrocytomas (neurogenic connective tissue found in the brain), myxosarcomas (primitive embryonic connective tissue), or mesenchymous or mixed mesodermal tumours (mixed connective tissue types). Hematologic tumours may be myelomas, which originate in the plasma cells of bone marrow; leukemias which may be "liquid cancers" and are cancers of the bone marrow and may be myelogenous or granulocytic leukemia (myeloid and granulocytic white blood cells), lymphatic, lymphocytic, or lymphoblastic leukemias (lymphoid and lymphocytic blood cells) or polycythemia vera or erythremia (various blood cell products, but with red cells predominating); or lymphomas, which may be solid tumours and which develop in the glands or nodes of the lymphatic system, and which may be Hodgkin or Non-Hodgkin lymphomas. In addition, mixed type cancers, such as adenosquamous carcinomas, mixed mesodermal tumours, carcinosarcomas, or teratocarcinomas also exist.

Cancers named based on primary site may be correlated with histological classifications. For example, lung cancers are generally small cell lung cancers or non-small cell lung cancers, which may be squamous cell carcinoma, adenocarcinoma, or large cell carcinoma; skin cancers are generally basal cell cancers, squamous cell cancers, or melanomas. Lymphomas may arise in the lymph nodes associated with the head, neck and chest, as well as in the abdominal lymph nodes or in the axillary or inguinal lymph nodes. Identification and classification of types and stages of cancers may be performed by using for example information provided by the Surveillance, Epidemiology, and End Results (SEER) Program of the National Cancer Institute, which is an authoritative source of information on cancer incidence and survival in the United States and is recognized around the world. The SEER Program currently collects and publishes cancer incidence and survival data from 14 population-based cancer registries and three supplemental registries covering approximately 26 percent of the US population. The program routinely collects data on patient demographics, primary tumour site, morphology, stage at diagnosis, first course of treatment, and follow-up for vital status, and is the only comprehensive source of population-based information in the United States that includes stage of cancer at the time of diagnosis and survival rates within each stage. Information on more than 3 million in situ and invasive cancer cases is included in the SEER database, and approximately 170,000 new cases are added each year within the SEER coverage areas. The incidence and survival data of the SEER Program may be used to access standard survival for a particular cancer site and stage. For example, to ensure an optimal comparison group, specific criteria may be selected from the database, including date of diagnosis and exact stage (for example, in the case of the lung cancer example herein, the years were selected to match the time-frame of the retrospective review, and stage 3B and 4 lung cancer were selected; and in the case of the colon cancer example herein, the years were also selected to match the time-frame of the retrospective review, and the stage 4 colon cancer was selected).

Cancers may also be named based on the organ in which they originate i.e., the "primary site," for example, cancer of the breast, brain, lung, liver, skin, prostate, testicle, bladder, colon and rectum, cervix, uterus, etc. This naming persists even if the cancer metastasizes to another part of the body that is different from the primary site. With the present invention, treatment is directed to the site of the cancer, not type of cancer, so that a cancer of any type that is symptomatic or etiologically located in the lung, for example, would be treated on the basis of this localization in the lung.

PRR Ligands

Aspects of the invention relate to the use of PRR ligands. PRR ligands may for example be available commercially, for example in widely available preparations of attenuated or killed recombinant bacteria, which may for example be ligands for TLR2, TLR4 and TLR5. Compositions of pathogen-associated molecular patterns (PAMPs) may include PAMPS that are recognized by PRRs, including: Toll-like receptors (TLRs), NOD-like receptors (NLRs), RIG-I-like receptors (RLRs), C-type lectin receptors (CLRs) including Dectin-1, cytosolic dsDNA sensors (CDSs) and NLRs involved in the formation of inflammasomes.

Toll-like receptor 2 (TLR2) is involved in the recognition of a wide array of microbial molecules representing broad groups of species including Gram-positive and Gram-negative bacteria, as well as *mycoplasma* and yeast. TLR2 recognizes cell-wall components such as peptidoglycan, lipoteichoic acid and lipoprotein from Gram-positive bacteria, lipoarabinomannan from mycobacteria, and zymosan from the yeast cell wall. Toll-like receptor 3 (TLR3) recognizes double-stranded RNA (dsRNA). Bacterial lipopolysaccharide (LPS) is recognized by Toll-like receptor 4 (TLR4) which interacts with at least three different extracellular proteins: LPS-binding protein (LBP), CD14 and, myeloid differentiation protein 2 (MD-2), to induce a signaling cascade leading to the activation of NF-κB and the production of proinflammatory cytokines. LPS generally consists of a polysaccharide region that is anchored in the outer bacterial membrane by a carbohydrate lipid moiety: lipid A, which is largely responsible for the immunostimulatory activity of LPS. Particularly active forms of lipid A contain six fatty acyl groups, as for example may be found in pathogenic bacteria that are strains of *Escherichia coli* or *Salmonella* spp. Toll-like receptor 5 (TLR5) recognizes flagellin from both Gram-positive and Gram-negative bacteria. Toll-like receptor 7 (TLR7) and TLR8 recognize single stranded RNAs and small synthetic molecules such as imidazoquinolines and nucleoside analogs. Toll-like receptor 9 (TLR9) recognizes specific unmethylated CpG motifs prevalent in microbial but not vertebrate genomic DNA.

NLRs are a family of at least 22 cytoplasmic innate immune sensors, including NOD1 (CARD4) and NOD2 (CARD15) which are intracellular pattern-recognition receptors involved in the recognition of peptidoglycan (PGN). These receptors detect specific motifs within PGN. NOD1 senses the diaminopimelatic acid (DAP)-containing muropeptide (specifically d-Glu-meso-DAP dipeptide "iE-DAP" dipeptide) which is found primarily in PGN of Gram-negative bacteria, as well as certain Gram-positive bacteria. NOD2 recognizes the muramyl dipeptide (MDP) structure found in almost all bacterial PGN.

The RIG-I-Like receptors (RLRs), particularly RIG-I and MDA-5, detect viral RNA species.

CLR ligands include Dectin-1 and Mincle (macrophage-inducible C-type lectin) agonists. Dectin-1 is a specific receptor for β-glucans, which are glucose polymers found in the cell walls of fungi. Mincle is a multi-tasking danger signal receptor that recognizes a wide variety of ligands such as damaged cells, fungal components, yeast components and components of mycobacteria.

Cytosolic DNA Sensors (CDS) bind intracellular DNA from pathogens, and there are multiple CDSs which may display contextual preferences for the recognition of particular DNAs.

Cyclic dinucleotides (CDNs) and xanthenone derivatives, such as DMXAA, bind to and activate STING (STimulator of INterferon Genes).

The inflammasome is a multi-protein complex involved in the production of mature IL-1β, specifically through cleavage of pro-IL-1β and pro-IL-18 into active and secretable forms. Inflammasomes may be segregated into NLRP1, NLRP3, NLRC4 and AIM2 subtypes, which are activated by a wide variety of microbial molecules, danger signals and crystalline substances.

TABLE 1

PRR Receptors and their Ligands

| PRR | Ligand |
|---|---|
| TLR2 | Microbial cell wall components/preparations, Pam2C-Aca-Benzyl-Murabutide (Pam2C-conjugated murabutide) |
| TLR3 | Polyadenylic-polyuridylic acid, Polyinosine-polycytidylic acid |
| TLR4 | Lipopolysaccharide, Monophosphoryl Lipid A |
| TLR5 | Flagellin |
| TLR7/8 | Single-stranded RNAs, Nucleoside analogs, Imidazoquinolines/Thiazoquinolines |
| TLR9 | unmethylated CpG DNA motifs |
| NOD1 | iE-DAP, Acylated iE-DAP, D-gamma-Glu-mDAP, L-Ala-gamma-D-Glu-mDAP |
| NOD2 | MDP (MurNAc-L-Ala-D-isoGln, muramyl dipeptide), N-glycolylated muramyldipeptide, N-Acetyl-muramyl-L- Alanyl-D-Glutamin-n-butyl-ester, MurNAc-Ala-D-isoGln-Lys, N- |

TABLE 1-continued

PRR Receptors and their Ligands

| PRR | Ligand |
| --- | --- |
| | Acetylmuramyl-L-Alanyl-D-Isoglutamine (L-D isoform), 6-O-stearoyl-N-Acetyl-muramyl-L-alanyl-D-isoglutamine, Pam2C-Aca-Benzyl-Murabutide, |
| TLR2/NOD2 | Pam2C-conjugated murabutide |
| NOD1/NOD2 | PGN, Pam2C-conjugated murabutide |
| RIG1/MDA5 | 5' triphosphate double stranded RNA (18-20mer), polyriboinosinic:polyribocytidylic acid |
| DAI, LRRFIP1, AIM2, RIG1 | dsDNA, poly(dA-dT)•poly(dT-dA) |
| Dectin-1 | Beta-glucan peptide, fungal cell wall preparations |
| Mincle | damaged microbial cells, fungus, yeast and mycobacteria, Trehalose-6,6-dibehenate, trehalose-6,6-dimycolate |
| STING | Cyclic dinucleotides (c-di-nucleotides), xanthenone derivatives, 3'3'-cGAMP, 2'3'-cGAMP, 2'2'-cGAMP, 2'2'-cGAMP, c-di-AMP (cyclic di-adenylate monophosphate), c-di-GMP, c-di-IMP, c-di-UMP, c-di-AMP |

TABLE 2

Cytosolic nucleic acid-sensing PRRs and their Ligands (Broz & Monack, 2013, Nature Reviews Immunology 13, 551-565).

| PRR | Ligands |
| --- | --- |
| RIG-I | PPP-ssRNA (PPP-ssRNA, ssRNA with a 5'-triphosphate group), RNA with base pairing and polyI:C |
| MDA5 | Long dsRNA |
| LGP2 | dsRNA |
| DDX41 | B-form DNA and CDNs (cyclic dinucleotides) |
| DHX9 | DNA, RNA, CpG-A oligodeoxynucleotids and CpG-B ODNs |
| DDX3 | Viral RNA |
| DHX36 | DNA, RNA, CpG-A oligodeoxynucleotides and CpG-B oligodeoxynucleotids |
| DDX1-DDX21-DDX36 | RNA and polyI:C |
| DDX60 | ssRNA, dsRNA and dsDNA |
| KU70 | DNA |
| cGAS | DNA |
| STING | CDNs (c-di-GMP and c-di-AMP) |
| NOD2 | ssRNA |
| NLRP3 | ssRNA, dsRNA, bacterial mRNA and oxidized mitochondrial DNA |
| AIM2 | DNA |
| IFI16 | dsDNA |
| LRRFIP1 | B-form DNA, Z-form DNA and dsRNA |
| DAI | DNA |
| IFIT1, 2, 3 and 5 | PPP-ssRNA |

Aspects of the invention accordingly involve using PRR agonists derived from a selected microbial pathogen. For example, peptidoglycan (PGN) may be obtained from a bacteria or bacterial strain that is pathogenic in a selected target tissue or organ, for use as a NOD1/NOD2 agonist. Similarly, cell wall components may be obtained from a bacteria or bacterial strain that is pathogenic in a selected target tissue or organ, for use as a TLR2 agonist. Similarly, DNA, including double stranded DNA, particularly repetitive double stranded DNA, may be obtained from a microbial pathogen, such as a bacteria or bacterial strain that is pathogenic in a selected target tissue or organ, for use as a DAI, LRRFIP1, RIG1, TLR9, AIM2 or cytosolic DNA sensor (CDS) agonist. Beta-glucan peptides may be obtained from fungi or yeast that are pathogenic in a selected target tissue or organ, for use as a Dectin-1 agonists. Cyclic dinucleotides may be obtained from a microbial pathogen that is pathogenic in a selected target tissue or organ, for use as a STING agonist.

Aspects of the invention involve compositions that have a distinct PRR agonist signature, which connotes a repertoire of PRR agonists that are together collected in a therapeutic vehicle, so that the selected collection of PRR agonists is distinct. A "therapeutic vehicle" in this context is a formulation that aggregates and retains the PRR agonists, for example in a pharmaceutically acceptable particle or vesicle, such as a recombinant microbe. For example, the PRR agonist signature may be different from a reference PRR agonist signature, for example different from the collection of PRR agonists that would be present on a microbe that is not pathogenic in the target tissue. The PRR signature may also be distinct in the sense that it is different than a native PRR agonist signature of the microbial mammalian pathogen, for example altered by way of the recombinant expression of genes that alter what would otherwise be the wildtype PRR agonist signature of the pathogen. For purposes of determining the distinctiveness of a PRR agonist signature, the levels or kinds of PRR agonist may be directly measured, or may be measured for example by determining the activation or inhibition of a signalling pathway in a cell consequent to PRR agonist/receptor binding.

Recombinant Embodiments

Various genes and nucleic acid sequences of the invention may be recombinant sequences. The term "recombinant" means that something has been recombined, so that when made in reference to a nucleic acid construct the term refers to a molecule that is comprised of nucleic acid sequences that are joined together or produced by means of molecular biological techniques. Nucleic acid "constructs" are accordingly recombinant nucleic acids, which have been generally been made by aggregating interoperable component sequencers. The term "recombinant" when made in reference to a protein or a polypeptide refers to a protein or polypeptide molecule which is expressed using a recombinant nucleic acid construct created by means of molecular biological techniques. The term "recombinant" when made in reference to the genetic composition or an organism or cell refers to new combinations of alleles that did not occur in the parental genomes. Recombinant nucleic acid constructs may include a nucleotide sequence which is ligated to, or is manipulated to become ligated to, a nucleic acid sequence to which it is not ligated in nature, or to which it is ligated at a different location in nature. Referring to a nucleic acid construct as "recombinant" therefore indicates that the nucleic acid molecule has been manipulated using genetic engineering, i.e. by human intervention (so that it is anthropogenic). Recombinant nucleic acid constructs may for example be introduced into a host cell by transformation. Such recombinant nucleic acid constructs may include sequences derived from the same host cell species or from different host cell species, which have been isolated and reintroduced into cells of the host species. Recombinant nucleic acid construct sequences may become integrated into a host cell genome, either as a result of the original transformation of the host cells, or as the result of subsequent recombination and/or repair events.

Recombinant constructs of the invention may include a variety of functional molecular or genomic components, as required for example to mediate gene expression or suppression in a transformed plant. In this context, "DNA regulatory sequences," "control elements," and "regulatory elements," refer to transcriptional and translational control sequences, such as promoters, enhancers, polyadenylation signals, terminators, and protein degradation signals that regulate gene expression, as well as epigenetic regulatory signals for example involving methylation or acetylation of histones (e.g. histone methyltransferase or acetyltransferase), leading to conformational changes in the transcriptional landscape and gene expression differences. In the context of the present disclosure, "promoter" means a sequence sufficient to direct transcription of a gene when the promoter is operably linked to the gene. The promoter is accordingly the portion of a gene containing DNA sequences that provide for the binding of RNA polymerase and initiation of transcription. Promoter sequences are commonly, but not universally, located in the 5' non-coding regions of a gene. A promoter and a gene are "operably linked" when such sequences are functionally connected so as to permit gene expression mediated by the promoter. The term "operably linked" accordingly indicates that DNA segments are arranged so that they function in concert for their intended purposes, such as initiating transcription in the promoter to proceed through the coding segment of a gene to a terminator portion of the gene. Gene expression may occur in some instances when appropriate molecules (such as transcriptional activator proteins) are bound to the promoter. Expression is the process of conversion of the information of a coding sequence of a gene into mRNA by transcription and subsequently into polypeptide (protein) by translation, as a result of which the protein is said to be expressed. As the term is used herein, a gene or nucleic acid is "expressible" if it is capable of expression under appropriate conditions in a particular host cell.

An "isolated" nucleic acid or polynucleotide as used herein refers to a component that is removed from its original environment (for example, its natural environment if it is naturally occurring). An isolated nucleic acid or polypeptide may contain less than about 50%, less than about 75%, less than about 90%, less than about 99.9% or less than any integer value between 50 and 99.9% of the cellular or biological components with which it was originally associated. A polynucleotide amplified using PCR so that it is sufficiently distinguishable (on a gel from example) from the rest of the cellular components is, for example, thereby "isolated". The polynucleotides of the invention may be "substantially pure," i.e., having the high degree of isolation as achieved using a purification technique.

In the context of biological molecules "endogenous" refers to a molecule such as a nucleic acid that is naturally found in and/or produced by a given organism or cell. An "endogenous" molecule may also be referred to as a "native" molecule. Conversely, in the context of biological molecules "exogenous" refers to a molecule, such as a nucleic acid, that is not normally or naturally found in and/or produced by a given organism or cell in nature.

As used herein to describe nucleic acid or amino acid sequences, the term "heterologous" refers to molecules or portions of molecules, such as DNA sequences, that are artificially introduced into a particular host cell, for example by transformation. Heterologous DNA sequences may for example be introduced into a host cell by transformation. Such heterologous molecules may include sequences derived from the host cell. Heterologous DNA sequences may become integrated into the host cell genome, either as a result of the original transformation of the host cells, or as the result of subsequent recombination events.

Various aspects of the present disclosure encompass nucleic acid or amino acid sequences that are homologous to other sequences. As the term is used herein, an amino acid or nucleic acid sequence is "homologous" to another sequence if the two sequences are substantially identical and the functional activity of the sequences is conserved (as used herein, sequence conservation or identity does not infer evolutionary relatedness). Nucleic acid sequences may also be homologous if they encode substantially identical amino acid sequences, even if the nucleic acid sequences are not themselves substantially identical, for example as a result of the degeneracy of the genetic code.

With reference to biological sequences "substantial homology" or "substantial identity" is meant, in the alternative, a homology of greater than 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% up to 100% sequence identity. Homology may refer to nucleic acid or amino acid sequences as the context dictates. In alternative embodiments, sequence identity may for example be at least 75%, at least 90% or at least 95%. Optimal alignment of sequences for comparisons of identity may be conducted using a variety of algorithms, such as the local homology algorithm of Smith and Waterman (1981) *Adv. Appl. Math* 2: 482, the homology alignment algorithm of Needleman and Wunsch (1970) *J. Mol. Biol.* 48:443, the search for similarity method of Pearson and Lipman (1988) *Proc. Natl. Acad. Sci. USA* 85: 2444, and the computerized implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al. (1990), *J. Mol. Biol.* 215:403-10 (using the published default settings). Software for performing BLAST analysis may be available through the National Center for Biotechnology Information (NCBI) at their Internet site. The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold. Initial neighborhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff (1992) *Proc. Natl. Acad. Sci. USA* 89: 10915-10919) alignments (B) of 50, expectation (E) of 10, M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments, nucleotide or amino acid sequences are considered substantially identical if the smallest sum probability in a comparison of the test sequences is less than about 1, less than about 0.1, less than about 0.01, or less than about 0.001.

An alternative indication that two amino acid sequences are substantially identical is that one peptide is specifically immunologically reactive with antibodies that are also specifically immunoreactive against the other peptide. Antibodies are specifically immunoreactive to a peptide if the antibodies bind preferentially to the peptide and do not bind in a significant amount to other proteins present in the sample, so that the preferential binding of the antibody to the peptide is detectable in an immunoassay and distinguishable from non-specific binding to other peptides. Specific immunoreactivity of antibodies to peptides may be assessed using a variety of immunoassay formats, such as solid-phase ELISA immunoassays for selecting monoclonal antibodies specifically immunoreactive with a protein (see Harlow and Lane (1988) *Antibodies, A Laboratory Manual*, Cold Spring Harbor Publications, New York).

An alternative indication that two nucleic acid sequences are substantially identical is that the two sequences hybridize to each other under moderately stringent, or stringent, conditions. Hybridization to filter-bound sequences under moderately stringent conditions may, for example, be performed in 0.5 M NaHPO$_4$, 7% sodium dodecyl sulfate (SDS), 1 mM EDTA at 65° C., and washing in 0.2×SSC/ 0.1% SDS at 42° C. (see Ausubel, et al. (eds), 1989, *Current Protocols in Molecular Biology*, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M NaHPO$_4$, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y.). Generally, stringent conditions are selected to be about 5° C. lower than the thermal melting point for the specific sequence at a defined ionic strength and pH. The term "a polynucleotide that hybridizes under stringent (low, intermediate) conditions" is intended to encompass both single and double-stranded polynucleotides although only one strand will hybridize to the complementary strand of another polynucleotide. Washing in the specified solutions may be conducted for a range of times from several minutes to several days and those skilled in the art will readily select appropriate wash times to discriminate between different levels of homology in bound sequences.

It is well known in the art that some modifications and changes can be made in the structure of a polypeptide without substantially altering the biological function of that peptide, to obtain a biologically equivalent polypeptide. As used herein, the term "conserved amino acid substitutions" refers to the substitution of one amino acid for another at a given location in the peptide, where the substitution can be made without any appreciable loss or gain of function, to obtain a biologically equivalent polypeptide. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing. Conversely, as used herein, the term "non-conserved amino acid substitutions" refers to the substitution of one amino acid for another at a given location in the peptide, where the substitution causes an appreciable loss or gain of function of the peptide, to obtain a polypeptide that is not biologically equivalent.

In some embodiments, conserved amino acid substitutions may be made where an amino acid residue is substituted for another having a similar hydrophilicity value (e.g., within a value of plus or minus 2.0), where the following hydrophilicity values are assigned to amino acid residues (as detailed in U.S. Pat. No. 4,554,101): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4). Non-conserved amino acid substitutions may be made were the hydrophilicity value of the residues is significantly different, e.g. differing by more than 2.0.

In alternative embodiments, conserved amino acid substitutions may be made where an amino acid residue is substituted for another having a similar hydropathic index (e.g., within a value of plus or minus 2.0). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5). Non-conserved amino acid substitutions may be made were the hydropathic index of the residues is significantly different, e.g. differing by more than 2.0.

In alternative embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr. Non-conserved amino acid substitutions may be made were the residues do not fall into the same class, for example substitution of a basic amino acid for a neutral or non-polar amino acid.

Microorganisms

Most animals are colonized to some degree by microorganisms, such as bacteria, which exist in symbiotic or commensal relationships with the host animal. Thus, many species of normally harmless bacteria are found in healthy animals, and are usually localized to the surface of specific organs and tissues. Often, these microbial communities aid in the normal functioning of the body, as members of what is termed the microbiome. Microbes that are generally harmless, such as *Escherichia coli*, can cause infection in healthy subjects, with results ranging from mild infection to death. Whether or not a microorganism is pathogenic (i.e., causes infection) depends on factors such as: the route of entry and access to specific host cells, tissues, or organs; the intrinsic virulence of the microorganism; the amount of the microorganism present at the site of potential infection; or the health of the host animal. Thus, microorganisms that are normally harmless can become pathogenic given favorable conditions for infection, and even the most virulent microorganism generally requires specific circumstances to cause infection. Accordingly, microbial species that are members of the normal flora can be pathogens when they move beyond their normal ecological role in the endogenous flora. For example, endogenous species can cause infection outside of their ecological niche in regions of anatomical proximity, for example by contiguous spread. When this occurs, these normally harmless endogenous bacteria are pathogenic.

Specific microbial species are known to cause infections in specific cells, tissues, or organs in otherwise healthy subjects. Examples of bacteria and viruses that commonly cause infections in specific organs and tissues of the body are listed below; and these examples are not limiting in the sense that a skilled person would be able to recognize and identify infectious or pathogenic bacteria that cause infections, or commonly cause infections, in various organs and tissues in otherwise healthy organisms (and recognize the relative frequency of infection with each bacterial species) based on the knowledge in the field as represented, for example, by the following publications: Manual of Clinical Microbiology 8th Edition, Patrick Murray, Ed., 2003, ASM Press American Society for Microbiology, Washington D. C., USA; Mandell, Douglas, and Bennett's Principles and Practice of Infectious Diseases 5th Edition, G. L. Mandell, J. E. Bennett, R. Dolin, Eds., 2000, Churchill Livingstone, Philadelphia, Pa., USA, all of which are incorporated by reference herein.

Infections of the skin are commonly caused by the following bacterial species: *Staphylococcus aureus*, Beta hemolytic streptococci group A, B, C or G, *Corynebacterium diptheriae*, *Corynebacterium ulcerans*, or *Pseudomonas aeruginosa*; or viral pathogens: rubeola, rubella, varicella-zoster, echoviruses, coxsackieviruses, adenovirus, vaccinia, herpes simplex, or parvo B19.

Infections of the soft tissue (e.g., fat and muscle) are commonly caused by the following bacterial species: *Streptococcus pyogenes*, *Staphylococcus aureus*, *Clostridium perfringens*, or other *Clostridium* spp.; or viral pathogens: influenza, or coxsackieviruses.

Infections of the breast are commonly caused by the following bacterial species: *Staphylococcus aureus*, or *Streptococcus pyogenes*.

Infections of the lymph nodes of the head and neck are commonly caused by the following bacterial species: *Staphylococcus aureus*, or *Streptococcus pyogenes*; or viral pathogens: Epstein-Barr, cytomegalovirus, adenovirus, measles, rubella, herpes simplex, coxsackieviruses, or varicella-zoster.

Infections of the lymph nodes of the arm/axillae are commonly caused by the following bacterial species: *Staphylococcus aureus*, or *Streptococcus pyogenes*; or viral pathogens: measles, rubella, Epstein-Barr, cytomegalovirus, adenovirus, or varicella-zoster.

Infections of the lymph nodes of the mediastinum are commonly caused by the following bacterial species: *viridans streptococci*, *Peptococcus* spp., *Peptostreptococcus* spp., *Bacteroides* spp., *Fusobacterium* spp., or *Mycobacterium tuberculosis*; or viral pathogens: measles, rubella, Epstein-Barr, cytomegalovirus, varicella-zoster, or adenovirus.

Infections of the pulmonary hilar lymph nodes are commonly caused by the following bacterial species: *Streptococcus pneumoniae*, *Moraxella catarrhalis*, *Mycoplasma pneumoniae*, *Klebsiella pneumoniae*, *Haemophilus influenza*, *Chlamydophila pneumoniae*, *Bordetella pertussis* or *Mycobacterium tuberculosis*; or viral pathogens: influenza, adenovirus, rhinovirus, coronavirus, parainfluenza, respiratory syncytial virus, human metapneumovirus, or coxsackievirus.

Infections of the intra-abdominal lymph nodes are commonly caused by the following bacterial species: *Yersinia enterocolitica*, *Yersinia pseudotuberculosis*, *Salmonella* spp., *Streptococcus pyogenes*, *Escherichia coli*, *Staphylococcus aureus*, or *Mycobacterium tuberculosis*; or viral pathogens: measles, rubella, Epstein-Barr, cytomegalovirus, varicella-zoster, adenovirus, influenza, or coxsackieviruses.

Infections of the lymph nodes of the leg/inguinal region are commonly caused by the following bacterial species: *Staphylococcus aureus*, or *Streptococcus pyogenes*; or viral pathogens: measles, rubella, Epstein-Barr, cytomegalovirus, or herpes simplex.

Infections of the blood (i.e., septicemia) are commonly caused by the following bacterial species: *Staphylococcus aureus*, *Streptococcus pyogenes*, coagulase-negative staphylococci, *Enterococcus* spp., *Escherichia coli*, *Klebsiella* spp., *Enterobacter* spp., *Proteus* spp., *Pseudomonas aeruginosa*, *Bacteroides fragilis*, *Streptococcus pneumoniae*, or group B streptococci; or viral pathogens: rubeola, rubella, varicella-zoster, echoviruses, coxsackieviruses, adenovirus, Epstein-Barr, herpes simplex, or cytomegalovirus.

Infections of the bone are commonly caused by the following bacterial species: *Staphylococcus aureus*, coagulase-negative staphylococci, *Streptococcus pyogenes*, *Streptococcus pneumoniae*, *Streptococcus agalactiae*, other *streptococci* spp., *Escherichia coli*, *Pseudomonas* spp., *Enterobacter* spp., *Proteus* spp., or *Serratia* spp.; or viral pathogens: parvovirus B19, rubella, or hepatitis B.

Infections of the joint are commonly caused by the following bacterial species: *Staphylococcus aureus*, coagulase-negative staphylococci, *Streptococcus pyogenes*, *Streptococcus pneumoniae*, *Streptococcus agalactiae*, other *streptococci* spp., *Escherichia coli*, *Pseudomonas* spp., *Enterobacter* spp., *Proteus* spp., *Serratia* spp., *Neisseria* gonorrhea, *salmonella* species, Mycobacterim tuberculosis, Hemophilus influenza; or viral pathogens: parvovirus B19, rubella, hepatitis B; or fungal pathogen: Scedosporium prolificans Infections of the meninges are commonly caused by the following bacterial species: *Haemophilus influenzae*, *Neisseria meningitidis*, *Streptococcus pneumoniae*, *Streptococcus agalactiae*, or *Listeria monocytogenes*; or viral pathogens: echoviruses, coxsackieviruses, other enteroviruses, or mumps.

Infections of the brain are commonly caused by the following bacterial species: *Streptococcus* spp. (including *S. anginosus*, *S. constellatus*, *S. intermedius*), *Staphylococcus aureus*, *Bacteroides* spp., *Prevotella* spp., *Proteus* spp., *Escherichia coli*, *Klebsiella* spp., *Pseudomonas* spp., *Enterobacter* spp., or *Borrelia burgdorferi*; or viral pathogens: coxsackieviruses, echoviruses, poliovirus, other enteroviruses, mumps, herpes simplex, varicella-zoster, flaviviruses, or bunyaviruses.

Infections of the spinal cord are commonly caused by the following bacterial species: *Haemophilus influenzae*, *Neisseria meningitidis*, *Streptococcus pneumoniae*, *Streptococcus agalactiae*, *Listeria monocytogenes*, or *Borrelia burgdorferi*; or viral pathogens: coxsackieviruses, echoviruses, poliovirus, other enteroviruses, mumps, herpes simplex, varicella-zoster, flaviviruses, or bunyaviruses.

Infections of the eye/orbit are commonly caused by the following bacterial species: *Staphylococcus aureus*, *Streptococcus pyogenes*, *Streptococcus pneumoniae*, *Streptococcus milleri*, *Escherichia coli*, *Bacillus cereus*, *Chlamydia trachomatis*, *Haemophilus influenza*, *Pseudomonas* spp., *Klebsiella* spp., or *Treponema pallidum*, or viral pathogens: adenoviruses, herpes simplex, varicella-zoster, or cytomegalovirus.

Infections of the salivary glands are commonly caused by the following bacterial species: *Staphylococcus aureus*, *viri-* dans streptococci (e.g., *Streptococcus salivarius*, *Streptococcus sanguis*, *Streptococcus mutans*), *Peptostreptococcus* spp., or *Bacteroides* spp., or other oral anaerobes; or viral pathogens: mumps, influenza, enteroviruses, or rabies.

Infections of the mouth are commonly caused by the following bacterial species: *Prevotella melaninogenicus*, anaerobic streptococci, viridans streptococci, *Actinomyces* spp., *Peptostreptococcus* spp., or *Bacteroides* spp., or other oral anaerobes; or viral pathogens: herpes simplex, coxsackieviruses, or Epstein-Barr.

Infections of the tonsils are commonly caused by the following bacterial species: *Streptococcus pyogenes*, or Group C or G B-hemolytic streptococci; or viral pathogens: rhinoviruses, influenza, coronavirus, adenovirus, parainfluenza, respiratory syncytial virus, or herpes simplex.

Infections of the sinuses are commonly caused by the following bacterial species: *Streptococcus pneumoniae*, *Haemophilus influenza*, *Moraxella catarrhalis*, α-streptococci, anaerobic bacteria (e.g., *Prevotella* spp.), or *Staphylococcus aureus*; or viral pathogens: rhinoviruses, influenza, adenovirus, or parainfluenza.

Infections of the nasopharynx are commonly caused by the following bacterial species: *Streptococcus pyogenes*, or Group C or G B-hemolytic streptococci; or viral pathogens: rhinoviruses, influenza, coronavirus, adenovirus, parainfluenza, respiratory syncytial virus, or herpes simplex.

Infections of the thyroid are commonly caused by the following bacterial species: *Staphylococcus aureus*, *Streptococcus pyogenes*, or *Streptococcus pneumoniae*; or viral pathogens: mumps, or influenza.

Infections of the larynx are commonly caused by the following bacterial species: *Mycoplasma pneumoniae*, *Chlamydophila pneumoniae*, or *Streptococcus pyogenes*; or viral pathogens: rhinovirus, influenza, parainfluenza, adenovirus, corona virus, or human metapneumovirus.

Infections of the trachea are commonly caused by the following bacterial species: *Mycoplasma pneumoniae*; or viral pathogens: parainfluenza, influenza, respiratory syncytial virus, or adenovirus.

Infections of the bronchi are commonly caused by the following bacterial species: *Mycoplasma pneumoniae*, *Chlamydophila pneumoniae*, *Bordetella pertussis*, *Streptococcus pneumoniae*, or *Haemophilus influenzae*; or viral pathogens: influenza, adenovirus, rhinovirus, coronavirus, parainfluenza, respiratory syncytial virus, human metapneumovirus, or coxsackievirus.

Infections of the lung are commonly caused by the following bacterial species: *Streptococcus pneumoniae*, *Moraxella catarrhalis*, *Mycoplasma pneumoniae*, *Klebsiella pneumoniae*, or *Haemophilus influenza*; or viral pathogens: influenza, adenovirus, respiratory syncytial virus, or parainfluenza.

Infections of the pleura are commonly caused by the following bacterial species: *Staphylococcus aureus*, *Streptococcus pyogenes*, *Streptococcus pneumoniae*, *Haemophilus influenzae*, *Bacteroides fragilis*, *Prevotella* spp., *Fusobacterium nucleatum*, *peptostreptococcus* spp., or *Mycobacterium tuberculosis*; or viral pathogens: influenza, adenovirus, respiratory syncytial virus, or parainfluenza.

Infections of the mediastinum are commonly caused by the following bacterial species: *viridans* streptococci, *Peptococcus* spp., *Peptostreptococcus* spp., *Bacteroides* spp., *Fusobacterium* spp., or *Mycobacterium tuberculosis*; or viral pathogens: measles, rubella, Epstein-Barr, or cytomegalovirus.

Infections of the heart are commonly caused by the following bacterial species: *Streptococcus* spp. (including *S.*

*mitior, S. bovis, S. sanguis, S. mutans, S. anginosus*), *Enterococcus* spp., *Staphylococcus* spp., *Corynebacterium* diptheriae, *Clostridium perfringens*, *Neisseria meningitidis*, or *Salmonella* spp.; or viral pathogens: enteroviruses, coxsackieviruses, echoviruses, poliovirus, adenovirus, mumps, rubeola, or influenza.

Infections of the esophagus are commonly caused by the following bacterial species: *Actinomyces* spp., *Mycobacterium avium*, *Mycobacterium tuberculosis*, or *Streptococcus* spp.; or viral pathogens: cytomegalovirus, herpes simplex, or varicella-zoster.

Infections of the stomach are commonly caused by the following bacterial species: *Streptococcus pyogenes* or *Helicobacter pylori*; or viral pathogens: cytomegalovirus, herpes simplex, Epstein-Barr, rotaviruses, noroviruses, or adenoviruses.

Infections of the small bowel are commonly caused by the following bacterial species: *Escherichia coli*, *Clostridium difficile*, *Bacteroides fragilis*, *Bacteroides vulgatus*, *Bacteroides thetaiotaomicron*, *Clostridium perfringens*, *Salmonella enteriditis*, *Yersinia enterocolitica*, or *Shigella flexneri*; or viral pathogens: adenoviruses, astroviruses, caliciviruses, noroviruses, rotaviruses, or cytomegalovirus.

Infections of the colon/rectum are commonly caused by the following bacterial species: *Escherichia coli*, *Clostridium difficile*, *Bacteroides fragilis*, *Bacteroides vulgatus*, *Bacteroides thetaiotaomicron*, *Clostridium perfringens*, *Salmonella enteriditis*, *Yersinia enterocolitica*, or *Shigella flexneri*; or viral pathogens: adenoviruses, astroviruses, caliciviruses, noroviruses, rotaviruses, or cytomegalovirus.

Infections of the anus are commonly caused by the following bacterial species: *Streptococcus pyogenes*, *Bacteroides* spp., *Fusobacterium* spp., anaerobic streptococci, *Clostridium* spp., *Escherichia coli*, *Enterobacter* spp., *Pseudomonas aeruginosa*, or *Treponema pallidum*, or viral pathogens: herpes simplex.

Infections of the perineum are commonly caused by the following bacterial species: *Escherichia coli*, *Klebsiella* spp., *Enterococcus* spp., *Bacteroides* spp., *Fusobacterium* spp., *Clostridium* spp., *Pseudomonas aeruginosa*, anaerobic streptococci, *Clostridium* spp., or *Enterobacter* spp.; or viral pathogens: herpes simplex.

Infections of the liver are commonly caused by the following bacterial species: *Escherichia coli*, *Klebsiella* spp., *Streptococcus* (*anginosus* group), *Enterococcus*, spp. other *viridans* streptococci, or *Bacteroides* spp.; or viral pathogens: hepatitis A, Epstein-Barr, herpes simplex, mumps, rubella, rubeola, varicella-zoster, coxsackieviruses, or adenovirus.

Infections of the gallbladder are commonly caused by the following bacterial species: *Escherichia coli*, *Klebsiella* spp., *Enterobacter* spp., enterococci, *Bacteroides* spp., *Fusobacterium* spp., *Clostridium* spp., *Salmonella enteriditis*, *Yersinia enterocolitica*, or *Shigella flexneri*.

Infections of the biliary tract are commonly caused by the following bacterial species: *Escherichia coli*, *Klebsiella* spp., *Enterobacter* spp., enterococci, *Bacteroides* spp., *Fusobacterium* spp., *Clostridium* spp., *Salmonella enteriditis*, *Yersinia enterocolitica*, or *Shigella flexneri*; or viral pathogens: hepatitis A, Epstein-Barr, herpes simplex, mumps, rubella, rubeola, varicella-zoster, cocsackieviruses, or adenovirus.

Infections of the pancreas are commonly caused by the following bacterial species: *Escherichia coli*, *Klebsiella* spp., *Enterococcus* spp., *Pseudomonas* spp., Staphylococcal spp., *Mycoplasma* spp., *Salmonella typhi*, Leptospirosis spp., or *Legionella* spp.; or viral pathogens: mumps, coxsackievirus, hepatitis B, cytomegalovirus, herpes simplex 2, or varicella-zoster.

Infections of the spleen are commonly caused by the following bacterial species: *Streptococcus* spp., *Staphylococcus* spp., *Salmonella* spp., *Pseudomonas* spp., *Escherichia coli*, or *Enterococcus* spp.; or viral pathogens: Epstein-Barr, cytomegalovirus, adenovirus, measles, rubella, coxsackieviruses, or varicella-zoster.

Infections of the adrenal gland are commonly caused by the following bacterial species: *Streptococcus* spp., *Staphylococcus* spp., *Salmonella* spp., *Pseudomonas* spp., *Escherichia coli*, or *Enterococcus* spp.; or viral pathogens: varicella-zoster.

Infections of the kidney are commonly caused by the following bacterial species: *Escherichia coli, Proteus mirabilis, Proteus vulgatus, Providentia* spp., *Morganella* spp., *Enterococcus faecalis*, or *Pseudomonas aeruginosa*; or viral pathogens: BK virus, or mumps.

Infections of the ureter are commonly caused by the following bacterial species: *Escherichia coli, Proteus mirabilis, Proteus* vulgatus, Providentia spp., *Morganella* spp., or *Enterococcus* spp.

Infections of the bladder are commonly caused by the following bacterial species: *Escherichia coli, Proteus mirabilis, Proteus* vulgatus, Providentia spp., *Morganella* spp., *Enterococcus faecalis*, or *Corynebacterium jekeum*, or viral pathogens: adenovirus, or cytomegalovirus.

Infections of the peritoneum are commonly caused by the following bacterial species: *Staphylococcus aureus, Streptococcus pyogenes, Streptococcus pneumoniae, Escherichia coli, Klebsiella* spp., *Proteus* spp., *enterococci, Bacteroides fragilis, Prevotella melaninogenica, Peptococcus* spp., *Peptostreptococcus* spp., *Fusobacterium* spp., or *Clostridium* spp.

Infections of the retroperitoneal area are commonly caused by the following bacterial species: *Escherichia coli*, or *Staphylococcus aureus*.

Infections of the prostate are commonly caused by the following bacterial species: *Escherichia coli, Klebsiella* spp., *Enterobacter* spp., *Proteus mirabilis, enterococci* spp., *Pseudomonas* spp., *Corynebacterium* spp., or *Neisseria gonorrhoeae*; or viral pathogens: herpes simplex.

Infections of the testicle are commonly caused by the following bacterial species: *Escherichia coli, Klebsiella pneumoniae, Pseudomonas aeruginosa, Staphylococcus* spp., *Streptococcus* spp., or *Salmonella enteriditis*; or viral pathogens: mumps, coxsackievirus, or lymphocytic choriomeningitis virus.

Infections of the penis are commonly caused by the following bacterial species: *Staphylococcus aureus, Streptococcus pyogenes, Neisseria gonorrhoeae*, or *Treponema pallidum*, or viral pathogens: herpes simplex.

Infections of the ovary/adnexae are commonly caused by the following bacterial species: *Neisseria gonorrhoeae, Chlamydia trachomatis, Gardenerella vaginalis, Prevotella* spp., *Bacteroides* spp., *Peptococcus* spp. *Streptococcus* spp., or *Escherichia coli.*

Infections of the uterus are commonly caused by the following bacterial species: *Neisseria gonorrhoeae, Chlamydia trachomatis, Gardenerella vaginalis, Prevotella* spp., *Bacteroides* spp., *Peptococcus* spp., *Streptococcus* spp., or *Escherichia coli.*

Infections of the cervix are commonly caused by the following bacterial species: *Neisseria gonorrhoeae, Chlamydia trachomatis*, or *Treponema pallidum*, or viral pathogens: herpes simplex.

Infections of the vagina are commonly caused by the following bacterial species: Gardenerella *vaginalis, Prevotella* spp., *Bacteroides* spp., *peptococci* spp., *Escherichia coli, Neisseria gonorrhoeae, Chlamydia Trachomatis*, or *Treponema pallidum*, or viral pathogens: herpes simplex.

Infections of the vulva are commonly caused by the following bacterial species: *Staphylococcus aureus, Streptococcus pyogenes*, or *Treponema pallidum*, or viral pathogens: herpes simplex.

Bacterial species are classified operationally as collections of similar strains (which generally refers to groups of presumed common ancestry with identifiable physiological but usually not morphological distinctions, and which may be identified using serological techniques against bacterial surface antigens). Thus, each bacterial species (e.g., *Streptococcus pneumoniae*) has numerous strains (or serotypes), which may differ in their ability to cause infection or differ in their ability to cause infection in a particular organ/site. For example, although there are at least 90 serotypes of *Streptococcus pneumoniae*, serotypes 1, 3, 4, 7, 8, and 12 are most frequently responsible for pneumococcal disease in humans.

Certain strains of *Escherichia coli*, referred to as extraintestinal pathogenic *E. coli* (ExPEC), are more likely to cause urinary tract infection or other extraintestinal infections such as neonatal meningitis, whereas other strains, including enterotoxigenic *E. coli* (ETEC), enteropathogenic *E. coli* (EPEC), enterohemorrhagic *E. coli* (EHEC), Shiga toxin-producing *E. coli* (STEC), enteroaggregative *E. coli* (EAEC), enteroinvasive *E. coli* (EIEC) and diffuse adhering *E. coli* (DAEC) are more likely to cause gastrointestinal infection/diarrhea. Even among the sub-category of ExPEC strains, specific virulence factors (e.g., production of type-1 fimbriae) enable certain strains to be more capable of causing infection of the bladder, while other virulence factors (e.g., production of P fimbriae) enable other strains to be more capable of causing infection in the kidneys. In accordance with the present invention, an ExPEC strain(s) that is more likely to cause infection in the bladder may be chosen for a formulation to target immune dysregulation in the bladder cancer, whereas an ExPEC strain(s) that is more likely to cause infection in the kidney may be chosen for a formulation to target immune dysregulation in the kidney cancer. Likewise, one or more of an ETEC, EPEC, EHEC, STEC, EAEC, EIEC or DAEC strains of *E. coli* (i.e., strains that cause colon infection), may be chosen for a formulation to treat immune dysregulation in the colon.

Similarly, there may be numerous subtypes of specific viruses. For example, there are three types of influenza viruses, influenza A, influenza B and influenza C, which differ in epidemiology, host range and clinical characteristics. For example, influenza A is more likely to be associated with viral lung infection, whereas influenza B is more likely to be associated with myositis (i.e., muscle infection). Furthermore, each of these three types of influenza virus have numerous subtypes, which also may differ in epidemiology, host range and clinical characteristics. In accordance with the present invention, one may choose an influenza A subtype most commonly associated with lung infection to target immune dysregulation in the lung, whereas one may choose an influenza B strain most commonly associated with myositis to treat immune dysregulation in the muscle/soft tissues.

There are specific microbiota associated with some pathological tissue states, for example microbiota of specific tumours. For example, *Fusobacterium* and *Providencia* have been associated with colorectal cancer.

The compositions of the invention include immunogens of pathogenic microbial species (bacterial, viral or fungal) that are pathogenic in a specific tissue or organ, in which the immunogens are provided in the form of an artificial repertoire of mammalian PRR agonists that recapitulate a distinct portion of the PRR agonist signature of the microbial mammalian pathogen that is pathogenic in the target tissue. In select embodiments, the portion of the PRR agonist signature is distinct in the sense that it is both: different from a reference PRR agonist signature of a microbe that is not pathogenic in the target tissue; and, different than the native PRR agonist signature of the microbial mammalian pathogen. This distinct artificial repertoire of mammalian PRR agonists are formulated together in a therapeutic vehicle for combined presentation to an innate immune cell resident in the target tissue in the mammalian host.

Formulations and Therapeutic Vehicles

Compositions of the invention may be provided alone or in combination with other compounds (for example, nucleic acid molecules, small molecules, peptides, or peptide analogues), in the presence of a liposome, an adjuvant, or any pharmaceutically acceptable carrier, in a form suitable for administration to mammals, for example, humans (a "therapeutic vehicle"). As used herein "pharmaceutically acceptable carrier" or "excipient" includes any and all solvents, dispersion media, coatings, antibacterial and antifungal agents, isotonic and absorption delaying agents, and the like that are physiologically compatible. The carrier can be suitable for any appropriate form of administration, including subcutaneous, intradermal, intravenous, parenteral, intraperitoneal, intramuscular, sublingual, inhalational, intratumoural or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound (i.e., the specific bacteria, bacterial antigens, or compositions thereof of the invention), use thereof in the pharmaceutical compositions of the invention is contemplated. Supplementary active compounds can also be incorporated into the compositions.

Aspects of the invention involve the use of nanoparticle (NP) formulations. For example, virus-like particles (VLPs) are in essence empty viral particles with an intact protein hull and, in some embodiments, membrane envelopes. In general, VLPs lack genetic material. Production of VLPs may for example be by expression of viral proteins in mammalian, avian, insect, plant, yeast, or bacterial cells. Alternatively, fully synthetic VLPs may be produced. Alternative nanoparticle formulations emulsions, liposomes alginates, chitosan, and polylactide-coglycolide (PLGA) NPs. Examples of NP/TLR ligand preparations that may be adapted for use to induce immune responses are ligands for TLR2 (Pam(3)Cys), TLR9 (Poly I: C), TLR4 (3-O-desacyl-4 0-monophosphoryl lipid A (MPL)), TLR7 (9-benzyl-8-hydroxyadenine), TLR7/8 (resiquimod, R848), and TLR9 (CpG DNA).

In addition to selected co-formulations, a wide variety of adjuvants may be used to potentiate a desired immune response (see Levast et al., 2014, *Vaccines*, 2, 297-322).

Treatment with PRR ligands according to the invention may be combined with more traditional and existing therapies. For cancer, for example, these may include chemotherapy, radiation therapy, surgery, etc., or with a therapy that stimulates the immune system, reduces inflammation or otherwise benefits the subject, such as nutrients, vitamins and supplements. For example, vitamin A, vitamin D, vitamin E, vitamin C, vitamin B complex, selenium, zinc, co-enzyme Q10, beta carotene, fish oil, curcumin, green tea, bromelain, resveratrol, ground flaxseed, garlic, lycopene, milk thistle, melatonin, other antioxidants, cimetidine, indomethacin, or COX-2 Inhibitors (e.g., Celebrex™ [celecoxib] or Vioxx™ [rofecoxib]) may be also be administered to the subject.

Conventional pharmaceutical practice may be employed to provide suitable formulations or compositions to administer the compounds to subjects. Alternative routes of administration may be employed, for example, parenteral, intravenous, intradermal, subcutaneous, intramuscular, intracranial, intraorbital, ophthalmic, intraventricular, intracapsular, intraspinal, intrathecal, intracisternal, intraperitoneal, intranasal, inhalational, aerosol, topical, intratumoural, sublingual or oral administration. Therapeutic formulations may be in the form of liquid solutions or suspensions; for oral administration, formulations may be in the form of tablets or capsules; for intranasal formulations, in the form of powders, nasal drops, or aerosols; and for sublingual formulations, in the form of drops, aerosols or tablets.

Methods well known in the art for making formulations are found in, for example, "Remington's Pharmaceutical Sciences" (20th edition), ed. A. Gennaro, 2000, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel. For therapeutic or prophylactic compositions, the pathogenic bacterial species are administered to an individual in an amount effective to stop or slow progression or metastasis of the cancer, or to increase survival of the subject (relative to, for example, prognoses derived from the SEER database) depending on the disorder.

Pharmaceutical compositions or formulations may be packaged in a variety of ways depending upon the method used for administering the drug. For example, an article of manufacture or package may include a container having deposited therein the pharmaceutical formulation in an appropriate form. Suitable containers may for example include materials such as bottles (plastic and glass), sachets, ampoules, plastic bags, metal cylinders, and vials. The container may have a sterile access port, for example the container may be an intravenous solution bag or a vial having a stopper pierceable by a hypodermic injection needle. The package or container may also include a tamper-proof or multi-use mechanism adapted to control access to the contents of the package or the container, for example a multi dose vial adapter matched to a vial contained in the package. The container or package may include a label, for example a lable that describes the contents of the container, for example a drug label identifying the pharmaceutical composition therein and/or specifying modes or routes of administration. The label may also include appropriate warnings, for example specifying storage conditions for the container or package, or setting out contraindications or adverse effects of a mode of treatment. Articles of manufacture may accordingly take the form of a "kit" comprising pharmaceutical compositions or accessories adapted to facilitate use of pharmaceutical compositions. Kits may include a label or package insert, where the term "package insert" is used to refer to instructions customarily included in commercial packages of therapeutic products, that contain information about the indications, usage, dosage, administration, contraindications and/or warnings concerning the use of such therapeutic products. Kits may further include accessories associated with use of the pharmaceutical composition, including buffers, diluents, filters, needles, and syringes. Kits may also be adapted for the delivery of selected dosage forms of a pharmaceutical composition, for example including a number of unit dosages. Such kits can include a memory aid or mechanism, in the form of a physical or written indication of the intended timing of a treatment schedule in which the dosages are to be used.

A "companion diagnostic" may be associated with a pharmaceutical treatment or composition. Companion diagnostics are assays that facilitate the associated treatment, by providing diagnostic or prognostic information, typically in the form of a diagnostic test to determine the applicability of a treatment to a specific patient. Point-of-care companion diagnostics may for example involve providing diagnostic compositions and/or articles of manufacture in conjunction with providing a pharmaceutical formulation, for example as part of a kit. Alternatively, companion diagnostics may be separately provided, as assays to monitor the therapy of subjects or to predict the therapeutic efficacy of an intended treatment. A companion diagnostic may for example take the form of a medical device, such as an imaging tool, or a process carried out by such a device, for example for conducting assays in vitro, which provides information that is relevant for the safe and effective use of a corresponding drug or biological product. Companion diagnostics may be used with therapies disclosed herein so as to provide diagnostic or prognostic information about therapeutic efficacy or evidence of undesirable side effects or risks. The use of a companion diagnostic with a particular therapeutic may be stipulated in instructions, for example on the labeling of a diagnostic device and/or the labeling of the corresponding therapeutic product. Types of companion diagnostic tests may for example include: screening and detection, in form of tests that screen for genetic patterns, such as genetic SSI response markers; prognosis and theranostics, such as assays for biochemical SSI response markers that help to predict the future course of a disease, or indicate a patient's response to a therapy; monitoring, for example to evaluate the effectiveness and appropriate dosing of a prescribed therapy; or, recurrence, involving tests that analyze the patient's risk for a recurrence of the disease.

An "effective amount" of a composition according to the invention includes a therapeutically effective amount or a prophylactically effective amount. A "therapeutically effective amount" refers to an amount effective, at dosages and for periods of time necessary, to achieve the desired therapeutic result, such as reduction or elimination of the immune dysregulation. A therapeutically effective amount of a composition may vary according to factors such as the disease state, age, sex, and weight of the individual, and the ability of the compound to elicit a desired response in the individual. Dosage regimens may be adjusted to provide the optimum therapeutic response. A therapeutically effective amount may also be one in which any toxic or detrimental effects of the composition are outweighed by the therapeutically beneficial effects. A "prophylactically effective amount" refers to an amount effective, at dosages and for periods of time necessary, to achieve the desired prophylactic result, such as amelioration of immune dysregulation. Typically, a prophylactic dose is used in subjects prior to or at an earlier stage of cancer, so that a prophylactically effective amount may be less than a therapeutically effective amount.

For any particular subject, the timing and dose of treatments may be adjusted over time (e.g., timing may be daily, every other day, weekly, monthly) according to the individual need and the professional judgment of the person administering or supervising the administration of the compositions. For example, in the context of subcutaneous or intradermal administration, the compositions may be administered every second day. An initial dose of approximately 0.05 ml may be administered subcutaneously, followed by increases from 0.01-0.02 ml every second day until an adequate skin reaction is achieved at the injection site (for example, a 1 inch to 2 inch diameter delayed reaction of visible redness at the injection site). Once this adequate immune reaction is achieved, this dosing is continued as a maintenance dose. The maintenance dose may be adjusted from time to time to achieve the desired visible skin reaction (inflammation) at the injection site. Dosing may be for a dosage duration, for example of at least 1 week, 2 weeks, 2 months, 6 months, 1, 2, 3, 4, or 5 years or longer.

Oral dosages may for example range from 4 times per day, daily or weekly. Dosing may be for a dosage duration, for example of at least 1 week, 2 weeks, 2 months, 6 months, 1, 2, 3, 4, or 5 years or longer. In some embodiments, the invention may include compositions administered sublingually or by inhalation, or administered to one or more epithelial tissues (i.e., skin by intradermal or subcutaneous injection; lung epithelium by inhalation; gastrointestinal mucosa by oral ingestion; mouth mucosa by sublingual administration) simultaneously or sequentially. Accordingly, in some embodiments the compositions of the invention are administered so as to provoke an immune response in an epithelial tissue. In some embodiments, one or more epithelial routes of administration may be combined with one or more additional routes of administration, such as intratumoural, intramuscular or intravenous administration.

In the case of immunogenic formulations, an immunogenically effective amount of a composition of the invention can be provided, alone or in combination with other compounds, for example with an immunological adjuvant. The composition may for example include compounds linked with a carrier molecule, such as bovine serum albumin or keyhole limpet hemocyanin to enhance immunogenicity. An immunogenic composition is a composition that includes materials that elicit a desired immune response. An immunogenic composition may select, activate or expand, without limitation: memory B, T cells, neutrophils, monocytes or macrophages of the immune system.

An antigenic composition comprising killed recombinant bacteria for administration by injection may be made as follows. The bacteria may be grown in suitable media, and washed with physiological salt solution. The bacteria may then be centrifuged, resuspended in saline solution, and killed with heat. The suspensions may be standardized by direct microscopic count, mixed in required amounts, and stored in appropriate containers, which may be tested for safety, shelf life, and sterility in an approved manner. In addition to the pathogenic bacterial species and/or antigens thereof, a killed bacterial vaccine suitable for administration to humans may include 0.4% phenol preservative and/or 0.9% sodium chloride. The bacterial vaccine may also include trace amounts of brain heart infusion (beef), peptones, yeast extract, agar, sheep blood, dextrose, sodium phosphate and/or other media components.

In select embodiments, medicaments may be administered at an administration site in successive doses given at a dosage interval of between one hour and one month, over a dosage duration of at least one week. Optionally, the medicament may be administered intradermally or subcutaneously. Optionally, the medicament may be administered in a dose so that each dose is effective to cause a visible localized inflammatory immune response at the administration site. Optionally, the medicament may be administered so that visible localized inflammation at the administration site occurs within 1 to 48 hours. However, a visible localized inflammatory immune response may not always be present in all circumstances despite an immune response being initiated. There are other methods by which the mounting of an immune response can be monitored. For example, the profile (and relative change in characterization) of immune cells from a subject undergoing an immune reaction can be compared with those from a subject that is not undergoing an immune reaction.

In another aspect, a method of monitoring efficacy of a treatment regime in an individual being treated for an immune dysfunction in a specific organ or tissue is provided. The method involves measuring a characteristic of an immune response in a post-treatment immune sample obtained from the specific organ or tissue after the individual has been subject to the treatment regime for a period of time.

In some embodiments, PRR agonists derived from bacteria that are members of the endogenous flora of a particular region of the GIT may be used to formulate immunogenic compositions of the invention. The rows of Table 3 list a number of bacterial species, together with the biological regions in which each species may form a part of the endogenous flora. For example, *Abiotrophia* spp. are typically members of the endogenous flora of the mouth.

TABLE 3

Human Bacterial Normal Flora (Endogenous Bacterial Human Pathogens)

| Bacterial species CFU/mL | Mouth $10^5$ | Stomach $10^2$ | Duodenum/ Jejunum $10^5$ | Ileum $10^8$ | Colon $10^{11}$ |
|---|---|---|---|---|---|
| *Abiotrophia* spp | + | | | | |
| *Acholeplasma laidlawii* | + | | | | |
| *Acidaminococcus fermentans* | + | | + | + | + |
| *Acinetobacter* spp. | + | | + | + | + |
| *Actinobacillus* spp. | + | | | | |
| *Actinobaculum* spp. | + | | + | + | + |
| *Actinomyces* spp. | + | | + | + | + |
| *Aeromonas* spp. | | | + | + | + |
| *Anaerorhabdus furcosus* | | | | + | + |
| *Anaerococcus hydrogenalis* | | | | + | + |
| *Anaerococcus lactolyticus* | | | | + | + |
| *Anaerococcus prevotii* | | | | + | + |
| *Atopobium* spp. | + | | + | + | + |
| *Bacillus* spp. | | | | + | + |
| *Bacteroides caccae* | | | | + | + |
| *Bacteroides distasonis* | | | | + | + |
| *Bacteroides eggerthii* | | | | + | + |
| *Bacteroides fragilis* | | | | + | + |
| *Bacteroides merdae* | | | | + | + |
| *Bacteroides ovatus* | | | | + | + |
| *Bacteroides splanchnicus* | | | | + | + |
| *Bacteroides thetaiotaomicron* | | | | + | + |
| *Bacteroides vulgatus* | | | | + | + |
| *Bifidobacterium adolescentis* | | | + | + | + |
| *Bifidobacterium bifidum* | | | + | + | + |
| *Bifidobacterium breve* | | | + | + | + |
| *Bifidobacterium catenulatum* | | | + | + | + |
| *Bifidobacterium dentium* | + | | + | + | + |
| *Bifidobacterium longum* | | | + | + | + |
| *Bilophila wadsworthia* | + | | + | + | + |
| *Burkholderia cepacia* | | | + | + | + |
| *Butyrivibrio fibrisolvens* | | | + | + | + |
| *Campylobacter concisus* | | | + | + | + |
| *Campylobacter curvus* | | | + | + | + |
| *Campylobacter gracilis* | | | + | + | + |
| *Campylobacter jejuni* | | | + | + | + |
| *Campylobacter rectus* | | | + | + | + |
| *Campylobacter showae* | + | | + | + | + |
| *Campylobacter sputorum* | + | | | | |
| *Capnocytophaga granulosum* | + | | | | |
| *Capnocytophaga gingivalis* | + | | | | |
| *Campylobacter haemolytica* | + | | | | |
| *Capnocytophaga ochracea* | + | | + | + | + |
| *Capnocytophaga sputigena* | + | | | | |
| *Cardiobacterium hominis* | + | | | | |
| *Cedecea* spp | | | | | + |
| *Centipeda periodontii* | + | | | | |
| *Citrobacter freundii* | | | + | + | + |
| *Citrobacter koseri* | | | + | + | + |
| *Clostridium* spp. | | | + | + | + |
| *Corynebacterium accolens* | + | | | | |

TABLE 3-continued

Human Bacterial Normal Flora (Endogenous Bacterial Human Pathogens)

| Bacterial species CFU/mL | Mouth $10^5$ | Stomach $10^2$ | Duodenum/Jejunum $10^5$ | Ileum $10^8$ | Colon $10^{11}$ |
|---|---|---|---|---|---|
| Corynebacterium afermentans | + | | | | |
| Desulfomonas pigra | | | + | + | + |
| Dysgonomonas spp. | | | + | + | + |
| Eikenella corrodens | + | | + | + | + |
| Enterobacter aerogenes | | | + | + | + |
| Enterobacter cloacae | | | + | + | + |
| Enterobacter gergoviae | | | + | + | + |
| Enterobacter sakazakii | | | + | + | + |
| Enterobacter taylorae | | | + | + | + |
| Enterococcus spp. | | | + | + | + |
| Escherichia coli | | | + | + | + |
| Escherichia fergusonii | | | + | + | + |
| Escherichia hermannii | | | + | + | + |
| Escherichia vulneris | | | + | + | + |
| Eubacterium spp. | + | | + | + | + |
| Ewingella americana | + | | | | |
| Finegoldia magnus | | | + | + | + |
| Fusobacterium alocis | + | | | | |
| Fusobacterium gonidiaformans | | | + | + | + |
| Fusobacterium mortiferum | | | + | + | + |
| Fusobacterium naviforme | | | + | + | + |
| Fusobacterium necrophorum | + | | + | + | + |
| Fusobacterium nucleatum | + | | | | + |
| Fusobacterium sulci | + | | | | |
| Fusobacterium russii | | | + | + | + |
| Fusobacterium varium | | | + | + | + |
| Gardnerella vaginalis | | | + | + | + |
| Gemella haemolysans | + | | | | |
| Gemella morbillorum | + | | + | + | + |
| Globicatella spp. | + | | | | + |
| Granulicatella spp. | + | | | | |
| Haemophilus spp. | + | | | | |
| Hafnia alvei | | | + | + | + |
| Helcococcus kunzii | | | | | |
| Helicobacter spp. | | | + | + | + |
| Kingella spp. | + | | | | |
| Klebsiella spp. | + | | + | + | + |
| Lactobacillus acidophilus | + | + | + | + | + |
| Lactobacillus breve | + | | | | |
| Lactobacillus casei | + | | | | |
| Lactobacillus fermentum | + | + | + | + | + |
| Lactobacillus reuteri | | + | + | + | + |
| Lactobacillus salivarius | + | + | + | + | + |
| Leclercia adecarboxylata | | | + | + | + |
| Leminorella spp. | | | + | + | + |
| Leptotrichia buccalis | + | | | | |
| Megasphaera elsdenii | | | + | + | + |
| Micrococcus luteus | + | | | | |
| Micrococcus lylae | + | | | | |
| Micromonas micros | + | | | | |
| Mitsuokella multiacidus | | | + | + | + |
| Mobiluncus curisii | | | + | + | + |
| Mobiluncus mulieris | | | + | + | + |
| Moellerella wisconsensis | | | + | + | + |
| Moraxella catarrhalis | + | | | | |
| other Moraxella spp. | + | | | | |
| Morganella morganii | | | + | + | + |
| Mycoplasma buccale | + | | | | |
| Mycoplasma fermentans | + | | | | |
| Mycoplasma hominis | + | | | | |
| Mycoplasma lipophilum | + | | | | |
| Mycoplasma orale | + | | | | |
| Mycoplasma pneumoniae | + | | | | |
| Mycoplasma salivarium | + | | | | |
| Pantoea agglomerans | | | + | + | + |
| Pasteurella multocida | + | | | | |
| Pediococcus spp. | + | | | | + |
| Peptoniphilus asaccharolyticus | | | + | + | + |
| Peptostreptococcus anaerobus | + | | + | + | + |
| Peptostreptococcus productus | | | + | + | + |
| Porphyromonas asaccharolytica | + | | | + | + |
| Porphyromonas catoniae | + | | | | + |
| Porphyromonas endodontalis | + | | | | + |
| Porphyromonas gingivalis | + | | | | + |
| Prevotella buccae | + | | | | + |
| Prevotella buccalis | + | | | | + |
| Prevotella corporis | + | | | | + |

TABLE 3-continued

Human Bacterial Normal Flora (Endogenous Bacterial Human Pathogens)

| Bacterial species CFU/mL | Mouth $10^5$ | Stomach $10^2$ | Duodenum/ Jejunum $10^5$ | Ileum $10^8$ | Colon $10^{11}$ |
|---|---|---|---|---|---|
| Prevotella dentalis | + | | + | | |
| Prevotella denticola | + | | + | | |
| Prevotella enoeca | + | | + | | |
| Prevotella heparinolytica | + | | + | | |
| Prevotella intermedia | + | | + | | |
| Prevotella loescheii | + | | + | | |
| Prevotella melaninogenica | + | | + | | |
| Prevotella nigrescens | + | | + | | |
| Prevotella oralis | + | | + | | |
| Prevotella oris | + | | + | | |
| Prevotella oulorum | + | | + | | |
| Prevotella tannerae | + | | + | | |
| Prevotella veroralis | + | | + | | |
| Prevotella zoogleoformans | + | | + | | |
| Propionibacterium propionicum | + | | | | |
| Proteus mirabilis | | | | + | + |
| Proteus penneri | | | | + | + |
| Proteus vulgaris | | | | + | + |
| Providencia rettgeri | | | | + | + |
| Providencia stuartii | | | + | + | + |
| Pseudomonas aeruginosa | | | + | + | + |
| Retortamonas intestinalis | | | + | + | + |
| Rothia dentocariosa | + | | | | |
| Rothia mucilaginosa | + | | | | |
| Ruminococcus productus | | | + | + | + |
| Selenomonas spp. | + | | | | |
| Serratia liquefaciens | | | | + | + |
| Serratia marcescens | | | | + | + |
| Serratia odorifera | | | | + | + |
| Staphylococcus aureus | + | | | | |
| Staphylococcus epidermidis | + | | | | |
| Streptococcus agalactiae | | | + | + | + |
| Streptococcus anginosus | + | | + | + | + |
| Streptococcus bovis | | | + | + | + |
| Streptococcus constellatus | + | | + | + | + |
| Streptococcus criceti | + | | | | |
| Streptococcus crista | + | | | | |
| Streptococcus equisimilis | + | | | | |
| Streptococcus gordonii | + | | | | |
| Streptococcus intermedius | + | | | + | + |
| Streptococcus mitis | + | + | | | |
| Streptococcus mutans | + | | | | |
| Streptococcus oralis | + | | | | |
| Streptococcus parasanguis | + | | | | |
| Streptococcus pyogenes | + | + | | | |
| Streptococcus salivarius | + | + | | | |
| Streptococcus sanguis | + | + | | | |
| Streptococcus sobrinus | + | | | | |
| Streptococcus vestibularis | + | | | | |
| Group C + G Streptococci | + | | | | + |
| Succinivibrio dextrinosolvens | | | + | + | + |
| Sutterella spp. | + | | | + | + |
| Suttonella indologenes | + | | | | |
| Tissierella praeacuta | | | + | + | + |
| Treponema denticola | + | | | | |
| Treponema maltophilum | + | | | | |
| Treponema socranskii | + | | | | |
| Treponema vincentii | + | | | | |
| Ureaplasma urealyticum | + | | | | |
| Veillonella spp. | + | | + | + | + |

Endogenous microbial flora, such as bacteria, have access to tissues for pathogenesis either through contiguous spread or bacteremic spread. Under favorable conditions, endogenous organisms can become pathogenic and invade locally and spread by contiguous spread to adjacent tissues and organs. Endogenous bacterial flora of the skin, mouth and colon are species that are understood to also be amenable to bacteremic spread. Bacteria that are members of a particular endogenous flora domain may therefore cause infection in tissues or organs to which these bacteria may spread. Accordingly, one aspect of the invention involves the use of PRR agonists derived from endogenous microbial pathogens to treat an immune dysregulation having symptoms localized to a region of the GIT in which the endogenous bacteria may spread to cause infection. The columns of Table 2 list domains for endogenous flora. The rows of Table 4 list regions of the GIT within which immune dysregulation may be symptomatic or etiologically located. Accordingly, one aspect of the invention involves the use of PRR agonists derived from endogenous microbial pathogens to formulate immunogenic compositions for treating an immune dysregulation symptomatic or etiologically located in the region of the GIT to which the pathogen may spread to cause an infection. Accordingly, in alternative embodiments, an immune dysregulation that is symptomatic in the region listed in the first column of Table 2 may be treated with immunogenic compositions comprising an artificial repertoire of mammalian PRR agonists that recapitulates a distinct portion of a PRR agonist signature of a microbial mammalian pathogen that is a member of the endogenous flora of one or more of the endogenous flora domains listed in the first row of Table 2 and indicated with an X or a check mark in the appropriate row.

TABLE 4

Tissue/Organ Pathogenicity of Endogenous Flora

| Tissue | organ site | | | | |
|---|---|---|---|---|---|
| | Mouth | Stomach | Duo-denum/Jejunum | Ileum | Colon |
| Oral | x | | | | |
| Tonsil | x | | | | |
| Nasopharynx/Sinus | x | | | | |
| Esophagus | | x | | | |
| Stomach | | x | | | |
| Small bowel | | | x | x | |
| Colon/Rectum | | | | | x |
| Anus | | | | | x |

In accordance with the combined information in Tables 1 and 2, an immune dysregulation manifest in a particular region of the GIT set out in column 1 of Table 2 may be treated with antigenic compositions comprising an artificial repertoire of mammalian PRR agonists that recapitulates a distinct portion of a PRR agonist signature of a microbial mammalian pathogen that is one of the corresponding bacterial species of Table 1, so that the column headings in Table 2 are in effect replaced with the bacterial species of Table 1.

In some embodiments, PRR agonists may be derived from exogenous bacterial pathogens. For example, PRR agonists derived from the organisms listed in Table 5 may be used in an artificial repertoire of PRR agonists to treat an immune dysregulation that is symptomatic in the region of the GIT listed with the relevant organism in Table 5. In some embodiments, PRR agonists derived from both endogenous and exogenous microbial species may be used in combination.

TABLE 5

Exogenous Bacterial Human Pathogens, and their Sites of Infection in the GIT.

| Bacterial Species | Region of the GIT |
|---|---|
| *Aerobacter* spp. | small bowel, colon, |
| *Bacillus anthracis* | oral, small bowel, colon, hematological |
| *Bacillus cereus* | colon, |
| other *Bacillus* spp. | colon, stomach, small bowel |
| *Brucella* spp. | small bowel, colon |
| *Campylobacter coli* | small bowel, colon |
| *Campylobacter jejuni* | colon |
| *Campylobacter sputorum* | small bowel, colon |
| *Clostridium bifermentans* | small bowel, colon, stomach |
| *Clostridium botulinum* | colon, small bowel |
| *Clostridium difficile* | colon |
| *Clostridium indolis* | small bowel, colon, stomach, |
| *Clostridium mangenolii* | small bowel, colon, stomach |
| *Clostridium perfringens* | small bowel, colon, stomach |
| *Clostridium sordellii* | small bowel, colon, stomach |

TABLE 5-continued

Exogenous Bacterial Human Pathogens, and their Sites of Infection in the GIT.

| Bacterial Species | Region of the GIT |
|---|---|
| *Clostridium sporogenes* | small bowel, colon, stomach |
| *Clostridium subterminale* | small bowel, colon, stomach |
| *Edwarsiella tarda* | small bowel, colon |
| *Francisella tularensis* | small bowel |
| *Helicobacter pylori* | stomach |
| *Leptospirosis* spp. | oral |
| *Listeria monocytogenes* | small bowel, colon |
| *Mycobacterium bovis* | colon, small bowel |
| *Mycobacterium tuberculosis* | small bowel, colon |
| *Pediococcus* spp. | colon |
| *Plesiomonas shigelloides* | small bowel, colon |
| *Rickettsia rickettsiae* | small bowel |
| *Salmonella* spp. | stomach, small bowel, colon |
| *Shigella boydii* | colon |
| *Shigella dysenteriae* | colon |
| *Shigella flexneri* | colon |
| *Shigella sonnei* | colon |
| other *Spirillum* spp. | colon |
| *Streptococcus zooepidemicus* | small bowel |
| *Treponema pallidum* | oral, anus |
| *Tropheryma whipplei* | small bowel, colon |
| *Vibrio cholerae* | colon, small bowel |
| *Vibrio fluvialis* | small bowel, colon |
| *Vibrio furnissii* | small bowel, colon |
| *Vibrio hollisae* | small bowel, colon |
| *Vibrio parahaemolyticus* | colon, small bowel |
| *Yersinia enterocolitica* | small bowel, colon |
| *Yersinia pseudotuberculosis* | small bowel, colon |

In some embodiments, PRR agonists for use in the invention may be derived from viral pathogens. Table 6 provides an exemplary list of viral pathogens together with the tissue and organ sites for which each viral species is reportedly a pathogen. Accordingly, one aspect of the invention involves utilizing immunogenic compositions of PRR agonists derived from the named viruses to treat an immune dysregulation that is symptomatic in the region of the GIT that is identified adjacent to the name of the virus in Table 6.

TABLE 6

Viral Human Pathogens and Their Sites of Infection

| Virus | Region of the GIT |
|---|---|
| Herpes Simplex virus (1 and 2) | rectum, anus |
| Cytomegalovirus | small bowel, colon/rectum |
| Epstein-Barr virus | oral |
| Adenovirus | oral, small bowel, colon |
| Human papillomavirus | anus, oral |
| Orthoreoviruses | small bowel, colon, oral |
| Coltiviruses | oral |
| Rotaviruses | small bowel, colon |

TABLE 6-continued

Viral Human Pathogens and Their Sites of Infection

| Virus | Region of the GIT |
|---|---|
| Alphaviruses | small bowel, colon, |
| Coronaviruses | oral, small bowel, colon |
| Toroviruses | small bowel, colon |
| Parainfluenza viruses | oral |
| Respiratory syncytial virus | oral |
| Human metapneumovirus | oral, small bowel, colon |
| Vesicular stomatitis virus | oral, small bowel, colon |
| Rabies virus | oral |
| Influenza virus | oral |
| Hantaviruses | oral |
| Machupo virus | small bowel, colon |
| Junin virus | small bowel, colon |
| Poliovirus | small bowel, colon |
| Coxsackieviruses | small bowel, colon |
| Echoviruses | oral, small bowel, colon |
| Hepatitis A virus | small bowel, colon |
| Rhinoviruses | oral |
| Noroviruses and other Caliciviruses | small bowel, colon |
| Astroviruses | small bowel, colon |
| Picobirnaviruses | small bowel, colon |
| Hepatitis E virus | small bowel, colon |

In some embodiments, the pathogen from which PRR agonists are derived for use in immunogenic compositions of the invention may be one that is a common cause of acute infection in the region of the GIT in which the immune dysregulation to be treated is symptomatic. Table 7 identifies bacterial and viral pathogens of this kind, together with the region of the GIT in which they commonly cause infection. Accordingly, in selected embodiments, an immune dysregulation that is symptomatic in a region of the GIT identified in the first column of Table 7 may be treated with an immunogenic composition that comprises an artificial repertoire of mammalian PRR agonists that recapitulates a distinct portion of the PRR agonist signature of a pathogenic organism listed in the second column of Table 7.

TABLE 7

Common causes of acute infection (bacteria and viruses) for selected regions of the GIT

| Selected regions of the GIT | Common Bacterial or Viral Pathogens |
|---|---|
| Oral | *Prevotella melaninogenicus*, anaerobic *streptococci*, *viridans streptococci*, *Actinomyces* spp., *Peptostreptococcus* spp., *Bacteroides* spp., and other oral anaerobes |
| | herpes simplex, coxsackieviruses, Epstein-Barr |
| Stomach | *Streptococcus pyogenes*, *Helicobacter pylori* |
| | cytomegalovirus, herpes simplex, Epstein-Barr, rotaviruses, noroviruses, adenoviruses |
| Small bowel | *Escherichia coli*, *Clostridium difficile*, *Bacteroides fragilis*, *Bacteroides vulgatus*, *Bacteroides thetaiotaomicron*, *Clostridium perfringens*, *Salmonella enteriditis*, *Yersinia enterocolitica*, *Shigella flexneri* |
| | adenoviruses, astroviruses, caliciviruses, noroviruses, rotaviruses, cytomegalovirus |
| Colon/Rectum | *Escherichia coli*, *Clostridium difficile*, *Bacteroides fragilis*, *Bacteroides vulgatus*, *Bacteroides thetaiotaomicron*, *Clostridium perfringens*, *Salmonella enteriditis*, *Yersinia enterocolitica*, *Shigella flexneri* |
| | adenoviruses, astroviruses, caliciviruses, noroviruses, rotaviruses, cytomegalovirus |

TABLE 7-continued

Common causes of acute infection (bacteria and viruses) for selected regions of the GIT

| Selected regions of the GIT | Common Bacterial or Viral Pathogens |
|---|---|
| Anus | *Streptococcus pyogenes*, Bacteroides spp., *Fusobacterium* spp., anaerobic *streptococci*, *Clostridium* spp., *E. coli*, *Enterobacter* spp., *Pseudomonas aeruginosa*, *Treponema pallidum* |
| | herpes simplex |

Humans are hosts to a wide range of gastrointestinal parasites, including various protozoa and helminths, which for purposes of the present invention constitute pathogens of the GIT (Schafer, T. W., Skopic, A. Parasites of the small intestine. Curr Gastroenterol Reports 2006; 8:312-20; Jernigan, J., Guerrant, R. L., Pearson, R. D. Parasitic infections of the small intestine. Gut 1994; 35:289-93; Sleisenger & Fordtran's Gastrointestinal and liver disease. 8th ed. 2006; Garcia, L. S. Diagnostic medical parasitology. 5th ed. 2007). Compositions of the invention may accordingly include PRR agonists of various protozoa, including for example: *Giardia lamblia*, *Cryptosporidium parvum*, *Cryptosporidium hominus*, *Isospora belli*, *Sarcocystis* species, Coccidian like bodies (*Cyclospora* species), *Enterocytozoon bieneusi*, *Entamoeba histolytica*, *Entamoeba dispar*, *Entamoeba coli*, *Entamoeba hartmanni*, *Endolimax nana*, *Iodamoeba bütschlii*, *Dientameoba fragilis*, *Blastocystis hominus*, *Cyclospora cayetanensis*, *Microsporidia*, *Trypanosoma cruzi*, *Chilomastix mesnili*, *Pentatrichomonas hominis*, *Balantidium coli*. Similarly, compositions of the invention may include antigenic components of various helminths, including for example: Cestodes (tapeworms), *Taenia saginata*, *Taenia solium*, *Diphyllobothrium species*, *Hymenolepis nana*, *Hymenolepis diminuta*, *Dipylidium caninum*, Nematodes (round worms), *Ascaris lumbricoides*, *Strongyloides stercoralis*, *Necator americanus*, *Ancylostoma duodenale*, *Ancylostoma caninum*, *Tichuris trichiura*, *Capillaria philippinensis*, *Trichostrongylus species*, *Trichinella* species, *Necator americanus*, *Anisakis* and related species, *Angiostrongylus costaricensis*, *Enterobius vermicularis*, Trematodes (flukes), *Fasciolopsis buski*, *Heterophyes* speicies, *Echinostoma* species, *Clonorchis sinensis*, *Opisthorchis* species, *Fasciola* species, *Metagonimus yokogawi*, *Schistosoma mansoni*, *Schistosoma japonicum*, *Schistosoma mekongi*, *Schistosoma intercalatum*, *Echinostoma* species and *Paragonimus* species.

In accordance with the foregoing, in various aspects, the invention may involve the treatment of an immune dysregulation with formulations of an artificial repertoire of mammalian PRR agonists that recapitulates a distinct portion of a PRR agonist signature of a microbial pathogen that is an: Acidaminococcus *fermentans*; Acinetobacter spp.; Actinobaculum spp.; Actinomyces spp.; Aeromonas spp.; Anaerorhabdus *furcosus*; Anaerococcus *hydrogenalis*; Anaerococcus *lactolyticus*; Anaerococcus *prevotii*; Atopobium spp.; Bacillus spp.; Bacteroides *caccae*; Bacteroides *distasonis*; Bacteroides *eggerthii*; Bacteroides *fragilis*; Bacteroides *merdae*; Bacteroides *ovatus*; Bacteroides *splanchnicus*; Bacteroides *thetaiotaomicron*; Bacteroides *vulgatus*; Bifidobacterium *adolescentis*; Bifidobacterium *bifidum*, Bifidobacterium *breve*; Bifidobacterium *catenulatum*, Bifidobacterium *dentium*; Bifidobacterium *longum*, Bilophila *wadsworthia*; Burkholderia *cepacia*; Butyrivibrio *fibrisolvens*; Campylobacter *concisus*; Campylobacter *curvus*;

*Campylobacter gracilis; Campylobacter jejuni, Campylobacter rectus; Campylobacter showae; Capnocytophaga ochracea; Cedecea* spp; *Citrobacter freundii, Citrobacter koseri; Clostridium* spp.; *Desulfomonas pigra; Dysgonomonas* spp.; *Eikenella corrodens; Enterobacter aerogenes; Enterobacter cloacae; Enterobacter gergoviae; Enterobacter sakazakii; Enterobacter taylorae; Enterococcus* spp.; *Escherichia coli; Escherichia fergusonii; Escherichia hermannii; Escherichia vulneris; Eubacterium* spp.; *Finegoldia magnus; Fusobacterium gonidiaformans; Fusobacterium mortiferum; Fusobacterium naviforme; Fusobacterium necrophorum; Fusobacterium nucleatum, Fusobacterium russii; Fusobacterium varium; Gardnerella vaginalis; Gemella morbillorum; Globicatella* spp.; *Hafnia alvei; Helicobacter* spp.; *Klebsiella* spp.; *Lactobacillus acidophilus; Lactobacillus fermentum, Lactobacillus reuteri; Lactobacillus salivarius; Leclercia adecarboxylata; Leminorella* spp.; *Megasphaera elsdenii; Mitsuokella multiacidus; Mobiluncus curisii; Mobiluncus mulieris; Moellerella wisconsensis; Morganella morganii; Pantoea agglomerans; Pediococcus* spp.; *Peptoniphilus asaccharolyticus; Peptostreptococcus anaerobus; Peptostreptococcus productus; Porphyromonas asaccharolytica; Proteus mirabilis; Proteus penneri; Proteus vulgaris; Providencia rettgeri; Providencia stuartii; Pseudomonas aeruginosa; Retortamonas intestinalis; Ruminococcus productus; Serratia liquefaciens; Serratia marcescens, Serratia odorifera; Streptococcus agalactiae; Streptococcus anginosus; Streptococcus bovis; Streptococcus constellatus; Streptococcus intermedius*; Group C+G Streptococci; Succinivibrio dextrinosolvens; *Sutterella* spp.; *Tissierella praeacuta; Veillonella* spp.; *Aerobacter* spp.; *Bacillus anthracis; Bacillus cereus*; other *Bacillus* spp.; *Borrelia recurrentis; Brucella* spp.; *Campylobacter coli; Campylobacter fetus; Campylobacter jejuni, Campylobacter sputorum; Clostridium bifermentans; Clostridium botulinum; Clostridium difficile; Clostridium indolis; Clostridium mangenolii; Clostridium perfringens; Clostridium sordellii; Clostridium sporogenes; Clostridium subterminale; Edwarsiella tarda; Francisella tularensis; Listeria monocytogenes; Mycobacterium bovis; Mycobacterium tuberculosis; Pediococcus* spp.; *Plesiomonas shigelloides; Rickettsia rickettsiae; Salmonella* spp.; *Shigella boydii; Shigella dysenteriae; Shigella flexneri; Shigella sonnei*; other *Spirillum* spp.; *Streptococcus zooepidemicus; Tropheryma whipplei; Vibrio cholerae; Vibrio fluvialis; Vibrio furnissii; Vibrio hollisae; Vibrio parahaemolyticus; Yersinia enterocolitica; Yersinia pseudotuberculosis*; Herpes Simplex virus (1 and 2); Cytomegalovirus; Adenovirus; Orthoreoviruses; Rotaviruses; Alphaviruses; Coronaviruses; Toroviruses; Human metapneumovirus; Vesicular stomatitis virus; Machupo virus; Junin virus; Poliovirus; Coxsackieviruses; Echoviruses; Hepatitis A virus; Noroviruses and other Caliciviruses; Astroviruses; Picobirnaviruses; or Hepatitis E virus.

In alternative aspects, the invention may involve the treatment of an immune dysregulation with formulations of an artificial repertoire of mammalian PRR agonists that recapitulates a distinct portion of a PRR agonist signature of a microbial mammalian pathogen that is a common small and larger bowel pathogens, for example: *Escherichia coli, Clostridium difficile, Bacteroides fragilis, Bacteroides vulgatus, Bacteroides thetaiotaomicron, Clostridium perfringens, Salmonella enteriditis, Yersinia enterocolitica, Shigella flexneri*; adenoviruses, astroviruses, caliciviruses, noroviruses, rotaviruses, and cytomegalovirus.

In selected embodiments, the invention involves diagnostic steps to assess a patient's previous exposure to an organism. For example, the diagnostic steps may include taking a medical history of exposure to selected pathogens, and/or evaluating a patient's immune response to a selected pathogen. For example, a serology test may be conducted to detect antibodies to selected pathogens in a patient's sera. In connection with this aspect of the invention, antigenic determinants of a selected pathogen may be chosen for use in an immunogenic composition on a selected patient based on a diagnostic indication that the patient has had one or more prior exposure(s) to the pathogen, for example by virtue of the presence of antibodies to antigenic determinants of that pathogen in the patient's sera.

In further selected embodiments, the invention involves diagnostic steps to assess a patient's immunological response to treatment with a selected immunogenic composition. For example, the diagnostic steps may include evaluating a patient's immune response to the immunological determinants of that immunogenic composition, for example using a serological test to detect antibodies to those immunogenic determinants. In connection with this aspect of the invention, a treatment with a selected immunogenic composition may be continued if the evaluation indicates that there is an active immunological response to the immunogenic determinants of that composition, and the treatment may be discontinued, and an alternative treatment with a different immunogenic composition may be initiated, if the evaluation indicates that there is not a sufficiently active immunological response to the immunogenic determinants of the immunogenic composition.

The immunomodulatory properties of formulations of the invention can be employed for use in the treatment of a variety of diseases characterized by pathological immune dysregulation, for example using PRR agonists derived from endogenous pathogens or exogenous pathogens that are pathogenic in the tissue or organ within which the immune dysregulation is symptomatic or manifest, including bacterial, viral and fungal pathogens. Table 8 lists diseases characterized by immune dysregulation, which may be treated in accordance with alternative aspects of the invention.

TABLE 8

List of Diseases of Immune Dysregulation.

Acne vulgaris
Acute disseminated encephalomyelitis
Acute hemorrhagicleukoencephalitis
Addison's Disease
Agammaglobulinemia
Allergies
Alopecia areata
Alzheimer's
Amyotrophic Lateral Sclerosis
Anaemia, autoimmune hemolytic
Anaemia, pernicious
Ankylosing spondylitis
Anti-GBM/TBM Nephritis
Antiphospholipid syndrome
Antisynthetase syndrome
Arteritis, temporal (also known as "giant cell arteritis")
Arthritis, juvenile
Arthritis, psoriatic
Arthritis, reactive (Reiter's syndrome, rea)
Arthritis, rheumatoid
Asthma
Atherosclerosis
Atopic allergy
Atopic dermatitis
Autoimmune enteropathy
Autoimmune aplastic anemia
Balo disease/Balo concentric sclerosis
Bartter syndrome TABLE 8-continued List of Diseases of Immune Dysregulation.

Bechets Syndrome
Berger's disease
Bickerstaff's encephalitis
Blau syndrome
Bronchitis, chronic
Bullous pemphigoid
Bursitis
Cardiomyopathy, autoimmune
Castleman's disease
Celiac disease
Chronic fatigue syndrome
Chronic inflammatory demyelinating polyneuropathy
Chronic recurrent multifocal osteomyelitis
Churg-Strauss syndrome
Cicatricialpemphigoid
Cirrhosis, primary biliary
Cogan syndrome
Cold agglutinin disease
Colitis
Complement component 2 deficiency
Connective tissue disease, mixed
Connective tissue disease, undifferentiated
COPD (chronic obstructive lung disease)
Cranial arteritis
CREST syndrome
Cryoglobulinemia
Cushing's Syndrome
Cutaneous leukocytoclasticangiitis
Cystitis, interstitial
Dacryadenitis
Dego's disease
Dercum's disease
Dermatitis
Dermatitis herpetiformis
Dermatitis, autoimmune progesterone
Dermatomyositis
Diabetes
Diabetes insipidus, nephrogenic
Diabetes mellitus type 1
Diffuse cutaneous systemic sclerosis
Discoid lupus erythematosus
Diverticulitis
Dressier's syndrome
Dysmenorrhea (menstrual cramps/pain)
Eczema
Eczema
Endometriosis
Enthesitis-related arthritis
Eosinophilic fasciitis
Eosinophilic gastroenteritis
Epidermolysisbullosaacquisita
Erythema nodosum
Essential mixed cryoglobulinemia
Evan's syndrome
Fibrodysplasiaossificansprogressiva
Fibromyalgia
Fibrosingaveolitis
Fungal infections (tinea pedis, onchomycosis, etc.)
Gastritis, atrophic
Gastritis, atrophic
Gastrointestinal pemphigoid
Giant cell arteritis
Glomerulonephritis
Glomerulonephritis
Goodpasture's syndrome
Gout, acute
Gout, arthritic
Graves' disease
Guillain-Barré syndrome (GBS)
Haemolytic anaemia
Hashimoto's encephalitis
Hashimoto's thyroiditis
Hemolyticanemia, autoimmune
Henoch-Schonleinpurpura
Hepatitis, autoimmune
Hepatitis, viral
Herpes gestationis
Hypogammaglobulinemia
Idiopathic Inflammatory Demyelinating Diseases
Idiopathic pulmonary fibrosis
Iga nephropathy
Ileus (bowel obstruction)
Inclusion body myositis
Inflammatory bowel disease, Crohn's disease
Inflammatory bowel disease, ulcerative colitis
Inflammatory demyelinating polyneuopathy
Inner ear disease, autoimmune
Interstitial cystitis
Irritable bowel syndrome (IBS)
Juvenile idiopathic arthritis
Juvenile rheumatoid arthritis
Kawasaki's Disease
Kidney stones
Lambert-Eaton myasthenic syndrome
Leukocytoclasticvasculitis
Lichen planus
Lichen sclerosus
Linear iga disease (LAD)
Lou Gehrig's disease (Also Amyotrophic lateral sclerosis)
Lupoid hepatitis
Lupus
Lupus erythematous
Lymphoproliferative syndrome, autoimmune
Majeed syndrome
Ménière's disease
Meningitis
Metabolic Syndrome
Microscopic polyangiitis
Miller-Fisher syndrome
Morphea
Mucha-Habermann disease
Multiple sclerosis
Myasthenia gravis
Myositis
Myositis, inclusion body
Nephritis
Nephrotic syndrome
Neuromyelitisoptica (Also Devic's Disease)
Neuromyotonia
Occular cicatricial pemphigoid
Ocular inflammation (acute and chronic non-bacterial
inflammation of the anterior part of the eyes)
Opsoclonus myoclonus syndrome
Ord thyroiditis
Osteoarthritis
Osteoporosis
Paget's disease of bone
Palindromic rheumatism
Pancreatitis, autoimmune
PANDAS (pediatric autoimmune neuropsychiatric
disorders associated with streptococcus)
Paraneoplastic cerebellar degeneration
Parkinsonism
Paroxysmal nocturnal hemoglobinuria (PNH)
Parry Romberg syndrome
Pars planitis
Parsonnage-Turner syndrome
Pelvic inflammatory disease
Pemphigus
Pemphigus vulgaris
Pericarditis, non-rheumatic
Peripheral neuropathy, autoimmune
Perivenous encephalomyelitis
POEMS syndrome
Polyarteritisnodosa
Polychondritis, relapsing
Polycystic ovary syndrome (PCOS)
Polyendocrine syndrome, autoimmune
Polymyalgia rheumatica
Polymyalgia rheumatica
Polymyositis
Primary sclerosing cholangitis
Progressive inflammatory neuropathy
Prostatitis, chronic
Pseudogout
Psoriasis TABLE 8-continued List of Diseases of Immune Dysregulation.

Psoriasis
Pure red cell aplasia
Pyodermagangrenosum
Rasmussen's encephalitis
Raynaud phenomenon
Reiter's syndrome
Restless leg syndrome
Retinopathy of prematurity
Retroperitoneal fibrosis
Rheumatoid fever
Rhinitis, allergic
Sarcoidosis
Schmidt syndrome
Schnitzler syndrome
Scleritis
Scleroderma
Sclerosis, systemic
Sjögren's syndrome
Spondyloarthropathy
Still's disease
Subacute bacterial endocarditis (SBE)
Susac's syndrome
Sweet's syndrome
Sydenham chorea
Sympathetic ophthalmia
Takayasu's arteritis
Temporomandibular joint disorder (TMJD or TMD), or TMJ syndrome
Thrombocytopenic purpura, autoimmune
Thrombocytopenic purpura, idiopathic
Tolosa-Hunt syndrome
Toxic Shock Syndrome
Transplant rejection
Transverse myelitis
Undifferentiated spondyloarthropathy
Urticaria
Uveitis, autoimmune
Valvular disease, non -rheumatic
Vasculitis
Vitiligo
Wegener's granulomatosis As provided in the Table above, arthritis is a chronic inflammatory disease. In particular, arthritis is understood to be a description of inflammation of one or more joints. There are many types of arthritis, or conditions that have arthritic symptoms, which include (but are not limited to) the following: Ankylosing spondylitis, Behcet's disease, Ehlers-Danlos Syndrome, Familial Mediterranean fever, Fibromyalgia, Fifth disease, Giant cell arteritis, Gout, Haemochromatosis, Henoch-Schönleinpurpura, Hyperimmunoglobulinemia D with recurrent fever, Inflammatory bowel disease arthritis (including Crohn's Disease and Ulcerative Colitis), Juvenile rheumatoid arthritis, Juvenile spondyloarthropathy, Lyme disease, Marfan syndrome, Osteoarthritis, Pseudo-gout, Psoriatic arthritis, Reactive Arthritis (Reiter's syndrome), Rheumatoid arthritis, Sarcoidosis, Scleroderma, SEA syndrome (seronegativity, enthesopathy, arthropathy), Sjogren's syndrome, Still's disease, Systemic lupus erythematosus (SLE), TNF receptor associated periodic syndrome, and Wegener's granulomatosis (and other vasculitis syndromes).

Screening

Patients may advantageously be screened for disorders of innate immunity, such as genetic disorders, for example by primary sequence analysis or by analysis of epigenetic changes. A variety of genetic disorders have for example been identified that are associated with gene products involved in innate immunity (see Mogensen T., 2009, Clinical Microbiology Reviews, Vol. 22, No. 2, p. 240-273), such as TLR genes (TLR2, TLR3, TLR4, TLR5, TLR7, and TLR9), signalling protein genes (MyD88, Mal, IRAK1, IRAK4, NEMO, IκBα, IRF5), NLR genes (NOD2, NALP1, NALP3) and others (CD14, UNC93B). Patients identified as having a Medelian primary immunodeficiency associated with impaired TLR signaling or NF-κB activation may for example not benefit from some embodiments, or may require an approach adapted to their condition. Patients having polymorphisms in genes encoding components of innate signalling pathways may also be identified prior to treatment with an SSI, for example having mutations in the gene encoding TIR-domain-containing adaptor-inducing beta interferon (TRIF).

There are a variety of microbial strategies for evading the innate immune system (Mogensen T., 2009, Clinical Microbiology Reviews, Vol. 22, No. 2, p. 240-273), and embodiments of the invention may accordingly be adapted to avoid the inhibitory effect of such strategies on the triggered innate response. Select embodiments provide recombinant microorganisms that lack virulence factors that impede TLR signalling, such as recombinant E. coli that lack TIR domain-containing proteins (Cirl, C. et al., 2008, Nat. Med. 14:399-406). Gram negative bacterial formulation may advantageously comprise an LPS that is recognized by a TLR, such as TLR4, rather than a form of LPS that is not recognized by a TLR (Hornef, M. W. et al., 2002, Nat. Immunol. 3:1033-1040). Similarly, bacterial formulations may advantageously include a class of flagellin that activates a TLR, such as TLR5, rather than one that does not (Andersen-Nissen, E. et al., 2005, Proc. Natl. Acad. Sci. USA 102:9247-9252). In some embodiments, it may be advantageous to exclude peptidases that proteolytically degrade important components of the triggered innate response, such as the amastigote-specific cysteine peptidases of Leishmania mexicana that proteolytically degrade IκB and NF-κB (Cameron, P. et al., 2004, J. Immunol. 173:3297-3304). In alternative embodiments, these undesirable components may be removed from a formulation by an appropriate step of manufacturing, for example to wash or fractionate a microbial preparation so as to remove a component.

Patients may be genotyped, for example by identifying polymorphisms in PRR genes (see WO 2009003905). Genes associated with inflammation and immune related diseases and disorders may for example be the subject of screening, such as: AIDS (KIR3DL1, NKAT3, NKB1, AMB11, KIR3DS1, IFNgamma, CXCL12, SDF1); Autoimmune lymphoproliferative syndrome (TNFRSF6, APT1, FAS, CD95, ALPS1A); Combined immunodeficiency, (IL2RG, SCIDX1, SCIDX, IMD4), HIV-1 (CCL5, SCYA5, D17S136E, TCP228), HIV susceptibility or infection (IL10, CSIF, CMKBR2, CCR2, CMKBR5, CCCKR5 (CCR5)); Immunodeficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACO; Inflammation (IL-10, IL-1 (IL-1a, IL-1b), IL-13, IL-17 (IL-17a (CTLA8), IL-17b, IL-17c, IL-17d, IL-17f), 11-23, Cx3cr1, ptpn22, TNFa, NOD2/CARD15 for IBD, IL-6, IL-12 (IL-12a, IL-12b), CTLA4, Cx3cl1), Severe combined immunodeficiencies (SCIDs)(JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4). Alternatively, genes involved in selected signalling pathways may for example be screened, identifying for example patients that are more or less susceptible to an SSI treatment, such as: GM-CSF Signaling (LYN; ELK1; MAPK1; PTPN11; AKT2; PIK3CA, CAMK2A; STAT5B, PIK3CB, PIK3C3, GNB2L1; BCL2L1, MAPK3; ETS1; KRAS; RUNX1;

PIM1, PIK3C2A, RAF1; MAP2K2; AKT1; JAK2; PIK3R1, STAT3; MAP2K1; COND1; AKT3; STAT1); IL-10 Signaling (TRAF6, CCR1; ELK1, IKBK13, SP1, FOS; NFKB2; MAP3K14, MAPK8; MAPK13, RELA; MAPK14, TNF; IKBKG; REL13, MAP3K7; JAK1, CHUK; STAT3; NFKB1; JUN; IL1R1; IL6); Toll-like Receptor Signaling (IRAK1, EIF2AK2, MYD88; TRAF6; PPARA; ELK1, IKBKB, FOS; NFKB2; MAP3K14, MAPK8; MAPK13, RELA; TLR4; MAPK14, IKBKG; REL13, MAP3K7; CHUK; NFKB1; TLR2; JUN).

In addition, patients may for example be genotyped for SNPs located in the non-coding regions of the genome that are linked to inflammatory disorders, such as SNP's identified through publicly available GWAS datasets, for example SNPs in genomic regions linked to sequences which serve a regulatory role in immune-function-related gene expression.

Alternative Embodiments

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range, and inclusive of all numbers and fractions subsumed within the respective ranges. The word "comprising" is used herein as an open-ended term, substantially equivalent to the phrase "including, but not limited to", and the word "comprises" has a corresponding meaning. Terms such as "consisting essentially of" and "consists essentially of" allow for elements not explicitly recited, but exclude elements that are found in the prior art or that affect a basic or novel characteristic of the invention. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) and all publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings. Nothing herein is intended as a promise of any specific utility for all embodiments.

The term "about" or "approximately" as used herein when referring to a measurable value such as a parameter, an amount, a temporal duration, and the like, is meant to encompass variations of +/−20% or less, preferably +/−10% or less, more preferably +/−5% or less, and still more preferably +/−1% or less of and from the specified value, insofar such variations are appropriate to perform in the disclosed invention. It is to be understood that the value to which the modifier "about" or "approximately" refers is itself also specifically, and preferably, disclosed.

All references cited in the present specification are hereby incorporated by reference in their entirety. In particular, the teachings of all references herein specifically referred to are incorporated by reference, along with all documents cited in documents that are cited herein.

Standard reference works setting forth the general principles of recombinant DNA technology include Molecular Cloning: A Laboratory Manual, 2nd ed., vol. 1-3, ed. Sambrook et al., Cold Spring Harbor Laboratory Press, Cold Spring Harbor, N.Y., 1989; Current Protocols in Molecular Biology, ed. Ausubel et al., Greene Publishing and Wiley-Interscience, New York, 1992 (with periodic updates) ("Ausubel et al. 1992"); the series Methods in Enzymology (Academic Press, Inc.), Innis et al., PCR Protocols: A Guide to Methods and Applications, Academic Press: San Diego, 1990; PCR 2: A Practical Approach (M. J. MacPherson, B. D. Hames and G. R. Taylor eds. (1995); Harlow and Lane, eds. (1988) Antibodies, a Laboratory Manual; and Animal Cell Culture (R. I. Freshney, ed. (1987). General principles of microbiology are set forth, for example, in Davis, B. D. et al., Microbiology, 3rd edition, Harper & Row, publishers, Philadelphia, Pa. (1980).

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In this description of the invention, reference is made to the accompanying drawings that form a part hereof, and in which are shown by way of illustration only of specific embodiments in which the invention may be practiced. It is to be understood that other embodiments may be utilized and structural or logical changes may be made without departing from the scope of the present invention. The description, therefore, is not to be taken in a limiting sense, and the scope of the present invention is defined by the appended claims.

Preferred statements (features) and embodiments may be combined with any other features or embodiments unless clearly indicated to the contrary. In particular, any feature indicated as being preferred or advantageous may be combined with any other feature or features or statements indicated as being preferred or advantageous.

In some embodiments, the invention excludes steps that involve medical or surgical treatment. Similarly, in some embodiments, the invention disclaims naturally occurring embodiments, so that aspects of the invention relate only to anthropogenic compositions. Further, in select aspects of the invention, previously known products, process of making products, or methods of using products are hereby disclaimed.

General Codes and Abbreviations

SSI Site Specific Immunomodulator
MC-38 Murine Colon Adenocarcinoma cell line
PD1 Programmed cell death 1
OD Optical density IP Intraperitoneal
SC Subcutaneous
SOP Standard operating protocol
RPM Revolutions per minute
EDTA Ethylenediaminetetraacetic acid
ANOVA Analysis of variance
Ly6G Lymphocyte antigen 6 complex, locus G
Ly6C Lymphocyte antigen 6 complex, locus C
CD45 Cluster of differentiation 45
SD Standard deviation
NA No value; not applicable; not present
Rae1 Ribonucleic acid export 1
CD3 Cluster of differentiation 3
CD11 b Cluster of differentiation molecule 11B
KO knockout
PBS Phosphate Buffered Saline
NKG2D Natural killer group 2, member D
g Gram
µM micrometre
µL Microliter
hr Hours
min Minute
QBECO *Escherishia coli* whole killed cell SSI
QBKPN *Klebsiella pneumoniae* phylogroup III (also known as *K. varicola*) whole killed cell SSI
QBSAU *Staphylococcus aureus* whole killed cell SSI

EXAMPLES

Example 1: Recombinant Microbes

A family of virulence factors in *Escherichia coli* and *Brucella melitensis*, named TIR domain-containing proteins, impede TLR signalling through direct binding to MyD88, thus suppressing innate immunity and increasing bacterial virulence. Aspects of the invention accordingly provide recombinant bacteria that lack expression of TIR domain-containing proteins, or other virulence factors that interfere with an innate host immune response to the pathogen.

*Staphylococcus aureus*

In select embodiments, compositions may be prepared from recombinant *S. aureus* strains. For example strains of sequence type ST-291, having the following alleles, or homologous sequences being at least 99% identical thereto: arcc-3, aroe-37, glpf-19, gmk-2, pta-20, tpi-26, and yqil-32 (Larsen et al., 2012, O. J. Clin. Micobiol 50(4): 1355-1361). Strains may totally lack resistance genes to the following classes of antibiotic: aminoglycoside, beta-lactam, fluoroquinolone, fosfomycin, fusidic acid, MLS—macrolide, lincosamide and streptogramin B, nitroimidazole, oxazolidinone, phenicol, rifampicin, sulphonamide, tetracycline, trimethoprim, and glycopeptide. Alternatively, strains may have one or more resistance genes, such as the blaZ beta-lactam resistance gene (accession AP004832). Similarly, strains may or may not include one or more virulence factor genes (Cosentino et al., 2013, PLoS ONE 8(10):e77302), having for example at least 90%, 95%, 99% or 100% identity to selected database sequences (identified by accession number in the following tables). [Recite strains lacking leukotoxins, particularly targeting the innate immune system]

TABLE 9

*S. aureus* - Adherence Virulence Factors

| Virulence factor | Protein function | Accession number |
|---|---|---|
| eap | extracellular adherence protein | CP002110.1 |
| fnbB | fibronectin-binding protein B | AM990992.1 |
| fnbB | fibronectin-binding protein B | AM990992.1 |
| icaA | intercellular adhesion protein A | CP003808.1 |
| atl | bifunctional autolysin Atl | AM990992.1 |
| eap | extracellular adherence protein | CP002114.2 |
| icaB | intercellular adhesion protein B | AM990992.1 |
| vwb | von Willebrand factor-binding protein | CP002643.1 |
| spa | spa immunoglobulin G binding protein A | BA000033.2 |
| spa | spa immunoglobulin G binding protein A | AM990992.1 |
| vwb | von Willebrand factor-binding protein | AM990992.1 |
| vwb | von Willebrand factor-binding protein | AM990992.1 |
| icaC | intercellular adhesion protein C | CP003808.1 |
| ebpS | cell surface elastin binding protein | CP001996.1 |
| clfA | fibrinogen-binding protein A, clumping factor | AM990992.1 |
| icaR | intercellular adhesion regulator | AJ938182.1 |
| sdrC | Ser-Asp rich fibrinogen-binding protein C | CP001996.1 |
| spa | spa immunoglobulin G binding protein A | CP002110.1 |
| efb | extracelular fibrinogen-binding protein | CP003045.1 |
| fib | fibrinogen-binding protein | CP003045.1 |
| sdrH | Ser-Asp rich fibrinogen-binding portein H | CP003194.1 |

TABLE 10

*S. aureus* - Toxin Virulence Factors

| Virulence factor | Protein function | Accession number |
|---|---|---|
| SEntA | putative enterotoxin type A | CP003194.1 |
| hlgA | gamma-hemolysin chain II precursor | CP002110.1 |
| hlgC | gamma-hemolysin component C | BX571856.1 |
| hlgB | gamma-hemolysin component B precursor | HE681097.1 |
| lukE | leukotoxin LukE | AJ938182.1 |
| hlgB | gamma-hemolysin component B precursor | FR821779.1 |
| eta | exfoliative toxin A | AM990992.1 |
| SExo | exotoxin | CP003045.1 |
| SExo | exotoxin | CP003045.1 |
| SExo | exotoxin | CP003045.1 |
| hla | alpha-hemolysin precursor | AM990992.1 |
| SExo | exotoxin | CP003045.1 |
| hlb | beta-hemolysin | CP003166.1 |
| lukF-PV | LukF-PV | BX571856.1 |
| set16 | exotoxin homolog | BA000033.2 |
| SExo | exotoxin | CP003045.1 |
| SExo | exotoxin | CP003045.1 |
| SExo | exotoxin | CP003045.1 |
| set1 | superantigen-like protein | BX571856.1 |
| set5 | superantigen-like protein 5 | CP003045.1 |
| set4 | superantigen-like protein | AM990992.1 |
| hld | delta-hemolysin | HE681097.1 |
| set26 | exotoxin homolog | BA000033.2 |

TABLE 11

S. aureus - Exoenzyme Virulence Factors

| Virulence factor | Protein function | Accession number |
|---|---|---|
| geh | glycerol ester hydrolase | HE681097.1 |
| hysA | hyaluronate lyase | BA000018.3 |
| nuc | thermonuclease | BA000018.3 |
| sspA | serine V8 protease | FR821779.1 |
| sspB | cysteine protease | BX571856.1 |
| sspC | cysteine protease | CP003808.1 |
| nuc | thermonuclease | CP003808.1 |
| splA | serine protease splA | CP003194.1 |
| splC | serine protease splC | BX571856.1 |
| splB | serine protease splB | CP002110.1 |
| sak | staphylokinase | CP000253.1 |
| scn | complement inhibitor SCIN | CP002120.1 |
| splE | serine protease splE | BX571856.1 |
| splF | serine protease splF | CP002110.1 |
| geh | glycerol ester hydrolase | AM990992.1 |
| sspB | cysteine protease | CP002110.1 |
| hysA | hyaluronate lyase | AM990992.1 |

TABLE 12

S. aureus - Host Immune Evasion Virulence Factors

| Virulence factor | Protein function | Accession number |
|---|---|---|
| capP | capsular polysaccharide synthesis enzyme capP | CP001996.1 |
| capO | capsular polysaccharide synthesis enzyme capO | CP003808.1 |
| capN | capsular polysaccharide synthesis enzyme capN | FR821779.1 |
| capM | capsular polysaccharide synthesis enzyme capM | CP003808.1 |
| cap5L | capsular polysaccharide biosynthesis protein cap5L | CP002120.1 |
| cap5K | capsular polysaccharide biosynthesis protein cap5K | CP003045.1 |
| cap5I | capsular polysaccharide biosynthesis protein cap5I | AM990992.1 |
| cap5H | capsular polysaccharide biosynthesis protein cap5H | AM990992.1 |
| capG | capsular polysaccharide synthesis enzyme capG | CP003808.1 |
| capF | capsular polysaccharide synthesis enzyme capF | CP003808.1 |
| capE | capsular polysaccharide synthesis enzyme capE | CP003808.1 |
| capD | polysaccharide biosynthesis protein capD | CP003808.1 |
| cap5C | capsular polysaccharide biosynthesis protein cap5C | CP001844.2 |
| capB | capsular polysaccharide biosynthesis protein capB | HE681097.1 |
| cap8A | truncated capsular polysaccharide synthesis enzyme cap5A | BA000033.2 |
| isb | IgG-binding protein SBI | BX571856.1 |
| capD | polysaccharide biosynthesis protein capD | AP009351.1 |
| capC | capsular polysaccharide synthesis protein capC | AM990992.1 |
| cap1B | capsular polysaccharide biosynthesis protein cap1B | CP002120.1 |
| cap1A | capsular polysaccharide biosynthesis protein cap1A | CP002110.1 |
| cap5M | capsular polysaccharide biosynthesis protein cap5M | AJ938182.1 |

TABLE 13

S. aureus - Secretion system Virulence Factors

| Virulence factor | Protein function | Accession number |
|---|---|---|
| esxB | virulence factor EsxB family protein | FR821777.2 |
| esaC | EsaC protein within ESAT-6 gene cluster | CP000730.1 |
| essC | type VII secretion protein EssC | BA000018.3 |
| esaC | EsaC protein within ESAT-6 gene cluster | CP003166.1 |
| essB | putative secretion system component EssB | CP003808.1 |
| esaB | Putative secretion accessory protein EsaB/YukD | CP001844.2 |
| essA | protein secretion system EssA | CP001844.2 |
| esaA | type VII secretion protein EsaA | CP001844.2 |
| esxA | ESAT-6/WXG100 family secreted protein EsxA/YukE | CP002120.1 |

Recombinant strains may include one or more plasmids (Carattoli et al., 2014, Antimocrobial Agents and Chemotherapy 58(7): 3895-3903), for example having 90%, 95%, 99% or 100% identity to plasmid rep5 (accession NC005011) or plasmid rep16 (accession CP002115.1).

*Klebsiella* spp.

In select embodiments, compositions may be prepared from recombinant *Klebsiella* strains, such as *K. pneumoniae* or *K. varicola* (formerly identified as *K. pneumoniae*). For example, strains of a sequence type having the following alleles, or homologous sequences being at least 99% identical thereto: gapa16, infb24, mdh30, pgi40, phoe92, rpob17, tonb67. Strains may totally lack resistance genes to the following classes of antibiotic: aminoglycoside, beta-lactam, fluoroquinolone, fosfomycin, fusidic acid, MLS—macrolide, lincosamide and streptogramin B, nitroimidazole, oxazolidinone, phenicol, rifampicin, sulphonamide, tetracycline, trimethoprim, and glycopeptide. Alternatively, strains may have one or more resistance genes, such as the biaLEN24 beta-lactam resistance gene (accession AM850914). Similarly, strains may or may not include one or more virulence factors identified in the following table (see Leticia et al., 2014, BMC Biology 12:41).

TABLE 14

KPN Virulence Factors

| Virulence-factor | Function |
|---|---|
| rmpA | Regulator of capsule expression |
| Aerobactin | Siderophore |
| Enterobactin | Siderophore |
| Yersiniabactin | Siderophore |
| Colibactin | Genotoxin |
| T4SS (virB) | Conjugative machinery/protein secretion |
| T2SS | Protein secretion |
| T6SS | Protein secretion |
| Pld-family | Lipid metabolism |
| Sel1 lipoproteins | Unknown |
| cOMP | Putative cytotoxin |
| Igg-like | Binding to extra cellular matrix compounds |
| SEFIR-domain | Potentially hijack IL17R signaling pathways |
| Bcl | Binding to hydrophobic ligands/putative regulation of homeostasis and immunity |

*Escherichia coli.* (Prostate)

In select embodiments, compositions may be prepared from recombinant *E. coli* strains specifically adapted for therapy of prostate immune dysfunction. For example, strains of a sequence type having the following alleles, or homologous sequences being at least 99% identical thereto: adk-37, fumc-38, gyrb-19, icd-37, mdh-151, pura-11, reca-26 (sequence type 1231). Strains may totally lack resistance genes to the following classes of antibiotic: aminoglycoside, beta-lactam, fluoroquinolone, fosfomycin, fusidic acid, MLS—macrolide, lincosamide and streptogramin B, nitroimidazole, oxazolidinone, phenicol, rifampicin, sulphonamide, tetracycline, trimethoprim, and glycopeptide. Similarly, strains may or may not include one or more virulence factor genes, having for example at least 90%, 95%, 99% or 100% identity to selected database sequences (identified by accession number in the following tables). The strain may also lack stx holotoxin virulence factors.

TABLE 15

E. coli - Virulence factors

| Virulence factor | Protein function | Accession number |
|---|---|---|
| iroN | Enterobactin siderophore receptor protein | CP000243 |
| sfaS | S-fimbriae minor subunit | CP000243 |
| senB | Plasmid-encoded enterotoxin | CP000038 |
| iss | Increased serum survival | CU928160 |
| gad | Glutamate decarboxylase | CP002167 |
| cnf1 | Cytotoxic necrotizing factor | CP002167 |
| ccl | Cloacin | DQ298019 |

The serotype of the E. coli strain may for example be O18ac:H7, for example representing the presence of H type serotype gene fliC (accession AF228492, and O type serotype genes wzx (accession GU299793), and wzy (accession GU299793).

Recombinant strains may include one or more plasmids, for example having 90%, 95%, 99% or 100% identity to plasmid IncFIB (accession AP001918) and/or plasmid IncFII (29) (accession CP003035), and/or plasmid ColRNAI (accession DQ298019) and/or plasmid Col156 (accession NC009781).

The recombinant E. coli may for example be, or be derived from an E. coli strain having at least 80%, 90% or 95% sequence identity to E. coli UT189 (see Chen et al., 2006, Proc Natl Acad Sci USA 103:5977-82).

*Escherichia coli.* (Colon)

In select embodiments, compositions may be prepared from recombinant E. coli strains specifically adapted for therapy of colon immune dysfunction. For example, strains of a sequence type having the following alleles, or homologous sequences being at least 99% identical thereto: adk-76, fumc-43, gyrb-9, icd-36, mdh-404, pura-14, reca-10 (sequence type ST-5292). Strains may totally lack resistance genes to the following classes of antibiotic: aminoglycoside, beta-lactam, fluoroquinolone, fosfomycin, fusidic acid, MLS—macrolide, lincosamide and streptogramin B, nitroimidazole, oxazolidinone, phenicol, rifampicin, sulphonamide, tetracycline, trimethoprim, and glycopeptide. Alternatively, strains may have one or more resistance genes, such as the strB or strA aminoglycoside resistance genes (accession numbers M96392 or AF321551), and/or sul1 sulphonamide resistance gene (accession AY224185), and/or sul2 sulphonamide resistance gene (accession GQ421466), and/or dfrA5 trimethoprim resistance (accession X12868). Similarly, strains may or may not include one or more virulence factor genes, having for example at least 90%, 95%, 99% or 100% identity to selected database sequences (identified by accession number in the following tables). The strain may also have a gene that is at least 95% or 99% or 100% identical to the stx holotoxin virulence factor gene stx1 (accession M19437).

TABLE 16

E. coli - Virulence factors

| Virulence factor | Protein function | Accession number |
|---|---|---|
| Gad | Glutamate decarboxylase | CP001671 |
| lha | Adherence protein | AE005174 |
| Gad | Glutamate decarboxylase | CP001671 |
| senB | Plasmid-encoded enterotoxin | CP000038 |
| sigA | *Shigella* IgA-like protease homologue | CP000038 |
| stx1B | Shiga toxin 1, subunit B, variant a | AM230663 |
| stx1A | Shiga toxin 1, subunit A, variant a | EF079675 |
| astA | EAST-1 heat-stable toxin | AB042002 |

The serotype of the E. coli strain may for example be O117:H7, for example representing the presence of H type serotype gene fliC (accession AF228492, and O type serotype genes wzx (accession EU694096).

Recombinant strains may include one or more plasmids, as set out in the following table.

TABLE 17

E. coli plasmids

| Plasmid | Note | Accession number |
|---|---|---|
| IncFII(pRSB107) | pRSB107 | AJ851089 |
| IncB/O/K/Z | | CU928147 |
| Col(BS512) | | NC_010656 |
| IncFIB(AP001918) | | AP001918 |
| IncB/O/K/Z | GU256641 | |
| Col156 | | NC_009781 |
| IncFII | | AY458016 |

The recombinant E. coli (colon) may for example be, or be derived from an E. coli strain having at least 80%, 90% or 95% sequence identity to E. coli SE15 or any O117:H7 serotype E. coli.

Example 2: Minimal SSI Formulations

This Example illustrates modest efficacy in a minimal SSI formulation comprising TLR agonists and a microbial antigen. In this Example, the TLR agonists are a TLR2/6 agonist, diacylated lipoprotein (InVivogen Pam2CSK4) and a TLR4 agonist (LPS, Sigma L1519). The microbial antigen was a recombinant outer membrane protein A (ompA) from *Klebsiella pneumoniae* (CUSABIO CSB-EP340587KBG). These components were formulated together in a liposomal vehicle, and administered in a murine model of SSI therapy in accordance with the treatment timeline illustrated in FIG. 1. As illustrated in FIG. 2, TLR-only liposomes did not have the same degree of activity as the TLR+Ag lipsome constructs, illustrating that the engagement of alternative immunogenic pathways can augment an SSI effect. It is important to note in the context of this data that the antigenic component of these minimal formulations was recombinantly expressed in E. coli, with a purity given by the manufacturer of >90% (SDS-PAGE) with the attendant characteristic that the antigen preparations included additional bacterial components, including additional PRR agonists, that act as additional innate immunogens.

Example 3: SSI Mediates Anti-Tumour Activity in MyD88−/− Mice

Pathogen recognition and inflammatory signalling in innate immune defenses involves a number of pathways, including MyD88 dependent and MyD88 independent pathways (Mogensen, 2009, Clinical Microbiology Reviews, 22(2): 240). In this Example, using a B16 melanoma model in a commercial strain of MyD88−/− mice, it was observed that B16 tumour burden is enhanced in MyD88 mice, relative to B6 mice (genetically matched except for the MyD88 knockout). This is consistent with literature reports to the effect that MyD88 knockouts are inherently less able to control disease. In the model of SSI therapy, with a *Klebsiella* SSI ("KPN SSI"), a significantly reduced tumour burden was observed following treatment with KPN SSI in both WT B6 and MyD88-knockout mice. This is evidence that SSIs can work in a MyD88-independent manner, at least in part, indicating that alternative PRR signalling pathways, beyond what are generally considered classic TLR signalling, are involved in the SSI mediated innate immune responses. This is consistent with another exemplary observation, that the NOD-like receptor NLRP3 is up-regulated in cultured cells treated with KPN SSI and ECO SSI. Alternatively, in some embodiments, SSIs may mediate classical TLR signalling via an adaptor other than MyD88 downstream of TLR, such as TRIF. Furthermore, in additional studies it has been shown that SSI therapies can engage the MyD88 signalling pathway. In combination, these results are evidence of the robust and diverse PRR signalling pathways that may be engaged by SSI therapies.

Example 4: Pre-Exposure to Related Strains Potentiates SSI Efficacy

This Example illustrates that in some embodiments, pre-exposure of an organism to a microbial pathogen potentiates subsequent SSI efficacy.

Figure 3:
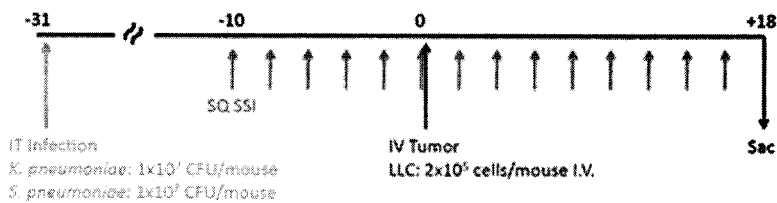
FIG. 3 is a schematic timeline illustrating a murine pre-infection model of SSI-mediated anti-tumour efficacy.
Figure 4:
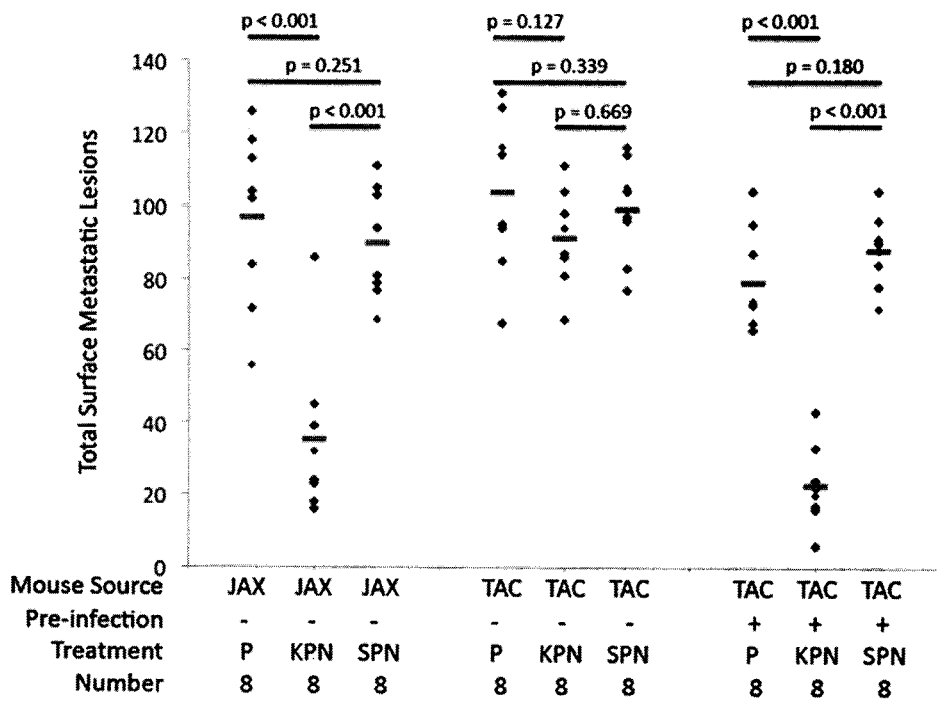
FIG. 4 is a graph illustrating anti-cancer efficacy of an SSI after pre-infection in a murine Lewis lung carcinoma (LLC) cancer model.

In an animal model of SSI therapy, treated in accordance with the treatment timeline illustrated in FIG. 3, pre-infection with *Klebsiella pneumoniae* potentiated KPN SSI efficacy using a distinct strain of *Klebsiella* sp., whereas pre-infection with *S. pneumoniae* failed to induce KPN SSI efficacy (in models of cancer in the lungs). The result, as illustrated in FIG. 4, indicates that an SSI response may require or benefit from pre-exposure of an organism to at least closely-related pathogens. This is consistent with another observation, of KPN SSI activity in mice from colonies that test negative for *K. pneumoniae*, but may carry *K. oxytoca*, a strain that's commonly found in research animal colonies, indicating that in some cases pre-exposure to *K. oxytoca* is adequate to induce responsiveness to KPN SSI. Differences in pre-exposure in mice from Jackson Labs (JAX) compared to mice from Taconic (TAC) are evident in FIG. 4, which illustrates that even without pre-infeaction, *S. pneumoniae* (SPN) did not elicit the same therapeutic efficacy that QBKPN did in mice sourced from JAX. In mice sourced from TAC, pre-infection was needed for QBKPN to show efficacy.

Example 5: Killed *Klebsiella pneumoniae* Treatment Reduces Tumour Burden in Murine Melanoma Model This Example illustrates *Klebsiella*-mediated anti-cancer efficacy in metastatic-like B16 melanoma using heat-killed *Klebsiella pneumoniae* SSI. Subcutaneous injection of KPN SSI significantly reduced tumour burden. Furthermore, subcutaneous treatment with heat-killed *E. coli* (ECO SSI) or *Staph. aureus* (SAU SSI) did not have a therapeutic effect in the lung tumour model. This illustrates that subcutaneous immune induction using a lung-specific pathogen activates a lung-specific antitumour response. To illustrate the effects of pre-exposure to *K. pneumoniae*, mice were exposed to live *K. pneumoniae* via intratracheal infection prior to subcutaneous injections with KPN SSI. Pre-exposure to *K. pneumoniae* significantly enhanced KPN SSI-induced anti-tumour immunity and control of metastatic-like B16 melanoma in the lungs. The anti-tumour efficacy in exposed mice correlated with an influx of monocytes and neutrophils, but did not correlate with an influx of T cells into the lungs. Collectively, these data illustrate that pre-exposure to *K. pneumoniae* may, in some embodiments, induce tissue-specific immunologic memory, for example an innate immunological memory, that mediates tumour cytolysis.

Example 6: Site Specificity in a Skin Cancer Model

This Example illustrates site specificity of a *S. aureus* SSI in a murine skin cancer model. This Example involved the use of a concentrated *S. aureus* SSI (10×QBSAU which is designated "QBSAUR" herein), as well as a *Klebsiella* sp. SSI, an *E. coli* SSI and placebo, in a B16 skin tumour model in which ~100,000 B16 melanoma cells were injected into the right flank of C57BL/6 mice in a volume of 100 ul on Day 0. SSI treatment started on Day −10 and continued till Day +12. Tumour volumes were monitored starting on Day 7, and the endpoint reached at Day 14. The tumour volume results of FIGS. 5-10 illustrate dramatically the site specificity of the *S. aureus* SSI formulation.

Example 7: Use of SSI Potentiates a Cancer Antigen Response

This Example illustrates the effect of combining an SSI (such as *Klebsiella* spp. SSI, abbreviated as "KPN SSI") with a model cancer antigen (in this case OVA, or hen egg ovalbumin) expressed by transformed cancer cells, in this case in a B16 melanoma animal model. OVA does not naturally occur in mammals or bacteria, and is immunogenic in C57Bl/6 mice, with known CD4- and CD8-associated epitopes. In this Example, B16 cells have been transfected to express cytoplasmic OVA protein, leading to presentation of the OVA epitopes in the tumour's MHC, thereby allowing OVA-specific T cell recognition of the melanoma. In some studies, whole protein was used; evidencing host immune system processing of the protein into relevant antigens. In other studies, purified OVA antigen (SIINFELK, a class I-restricted, CD8-specific antigen) was used. Some studies also used OT1 cells (transgenic CD8 cells that specifically recognize SIINFEKL through the T cell receptor) as a readout system.

The data generated provide evidence of enhanced efficacy of the model cancer antigen admixed with an SSI. In one result, decreased tumour nodule counts were found in conjunction with treatment using a *Klebsiella* spp. SSI +OVA, compared to PBS+OVA (assessed photographically and by quantitative PCR for Tyrp1, a melanoma-specific gene). Consistent with this, KPN SSI+OVA increased the proportion of OVA-specific CD8 T cells in the lungs. Similarly, expression of genes associated with effective anti-tumour immunity (granzyme B and IFN-gamma) was increased by KPN SSI+OVA vs. PBS+OVA. The same study showed survival data in lung cancer models, in which *Klebsiella* sp.

SSI+OVA showed extended survival compared with control; and an *E. coli* SSI+OVA showed much improved survival.

Figure 11:
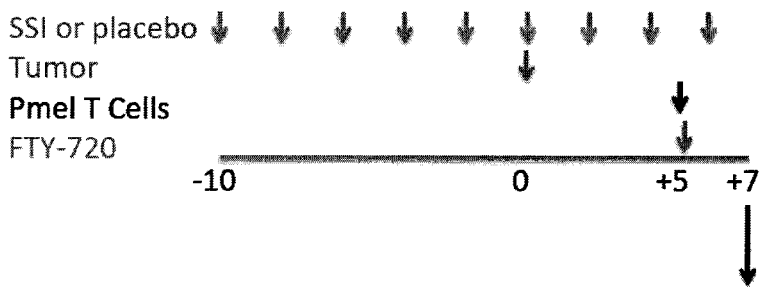
FIG. 11 is a schematic illustration, top panel, showing an SSI administration schedule, and a bar graph, bottom panel, illustrating therapeutic efficacy of an SSI in a murine cancer model.
Figure 11:
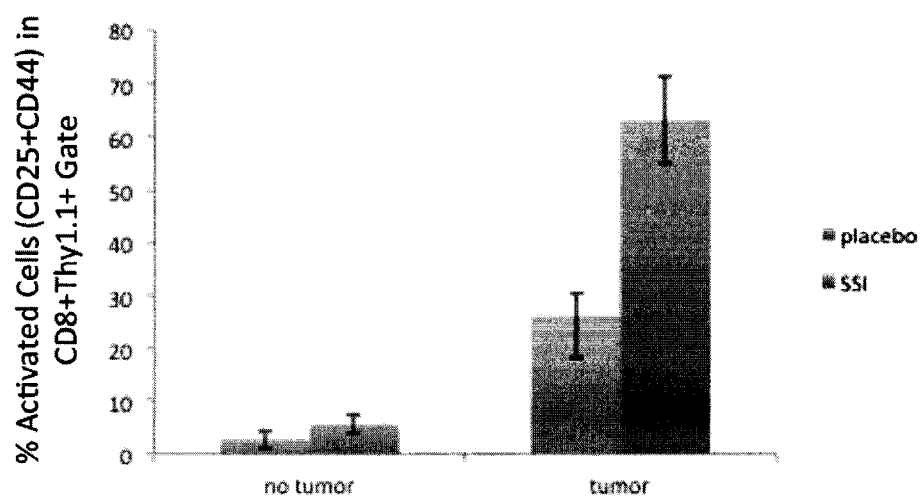

In an alternative study, it was observed that SSI induced or enhanced the process of epitope spreading (see FIG. 11; and for background see Vanderlugt & Miller, 2002, Nature Reviews Immunology 2, 85-95). In this study, mice were treated with *Klebsiella* sp. SSI, then challenged with B16 melanoma (IV). 5 days later, mice received an adoptive transfer of TCR transgenic cells (Pmel T cells) specific for a natural cancer antigen in melanoma. Mice were also treated with FTY-720 (fingolimod), to prevent T cell egress from lymph nodes and allow recovery of cells from the draining lymph node of a tumour. The activation status of the recovered pmel T cells was assessed, and it was found that SSI enhanced the proportion of T cells in the draining lymph node that were activated (i.e., antigen-exposed). This provides evidence that an SSI may be adapted to augment the processing and presentation of immunogenic cancer antigens, including self antigens and exogenously-administered cancer antigens.

Example 8: Component Formulations

This Example relates to the fractionation of microbial preparations for the purpose of formulating alternative SSIs. In alternative embodiments, fractions may for example be prepared from: bacterial outer membrane (for example from Gram negative spp.); bacterial inner membrane; the pellet of a gradient centrifugation (for example from a sucrose gradient); chromosomal DNA; a capsular glycoprotein fraction; or, a peptidoglycan fraction, such as peptidoglycan ghosts. In alternative embodiments, engineered or recombinant organisms may be used in SSIs, in which genes involved in pathways relevant to particular cellular fractions have been modified, in particular genes involved in determining the composition of the foregoing fractions.

For cell fraction preparations, bacteria may for example be grown and heat-inactivated. Cell fractions may for example be resuspended in sterile saline+0.4% phenol. Inner membranes may for example be collected using the 2-step sucrose density gradient, as for example described in Methods in Enzymology, Vol 125:309-328, 1986. The bacterial pellet obtained after cultivation of 250 mls of cells may be resuspended in 20% sucrose, 10 mM Tris-HCl pH 8.0 and 50 ug/ml DNase 1. Cells may be incubated at 23° C. for 10 min. Cells may then be placed on ice and lysed two times through a French pressure cell at 15,000 psi; unbroken cells may be removed by centrifugation at 5,000×g for 10 min at 4° C. Supernatants may be layered onto a 2-step sucrose gradient (60% and 70%) and centrifuged in a SW28 swinging bucket rotor at 23,000 rpm for 18 hours at a temperature of 4° C. The inner membranes may be collected at the junction between the 20% and 60% sucrose. Sucrose may be diluted to below 20% with sterile distilled water and the membranes may be pelleted in an ultracentrifuge at 41,000 rpm at 4° C. for 1 hour. The inner membranes may be washed once with sterile water, and then resuspended in sterile saline+0.4% phenol. Crude outer membrane preparations may also be collected from the junction between the 60% and 70% sucrose gradient steps.

Chromosomal DNA, for example for *Klebsiella pneumoniae*, may be prepared using a Qiagen Blood and Tissue midi kit. Cells from 15 or 40 mls of broth culture from each strain may be harvested. The manufacture's protocol for purification of total DNA may then be followed.

Figure 47A:
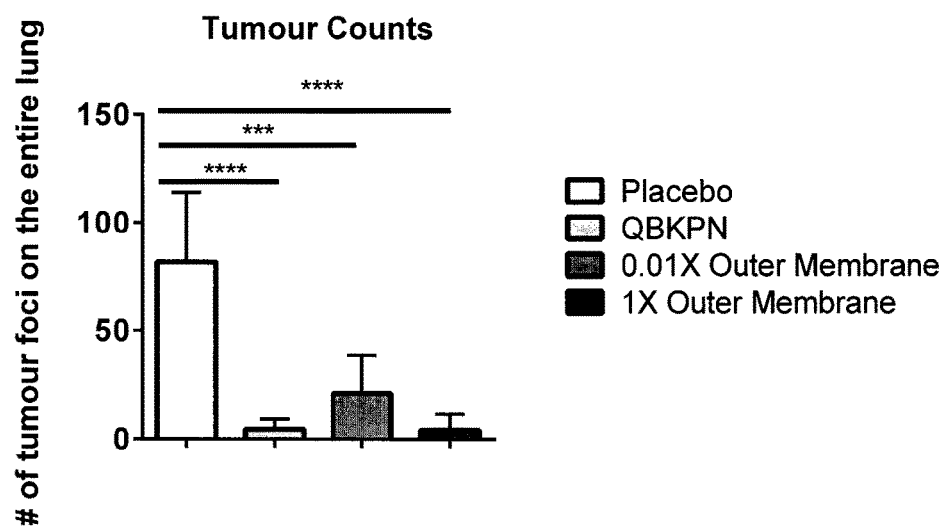
FIG. 47A includes three bar graphs illustrating that both 1× and 0.01×KPN outer membrane fractions (i) were efficacious, in a dose-dependant manner, with the 1× fraction having comparable efficacy to the whole killed cell formulation, as were the 1× and 4×DNA fractions (ii), while the inner membrane fraction showed a dose dependent trend that lacked strong statistical significance (iii).

The efficacy of a component formulation was demonstrated with a *Klebsiella pneumoniae* (KPN) outer membrane fraction in the B16 lung cancer model, in which SSIs were injected every other day beginning 10 days before tumour cell inoculation by intravenous injection. Three SSIs were compared, whole killed cell KPN (QBKPN), a 1× outer membrane (OM) fraction (having an outer membrane concentration that approximated the outer membrane concentration of the whole cell formulation) and a 0.01× dilution of the outer membrane fraction. As illustrated in FIG. 47A, both 1× and 0.01×KPN outer membrane fractions (i) were efficacious in the B16 melanoma model in the lung, in a dose-dependant manner, with the 1× fraction having comparable efficacy to the whole killed cell formulation, as were the 1× and 4×DNA fractions (ii), while the inner membrane fraction showed a dose dependent trend that lacked strong statistical significance (iii).

As illustrated in FIG. 47B, following 10 injections of outer membrane SSI, Rae-1 expression was elevated by the 1× outer membrane fraction in a dose dependant effect.

Figure 47C:
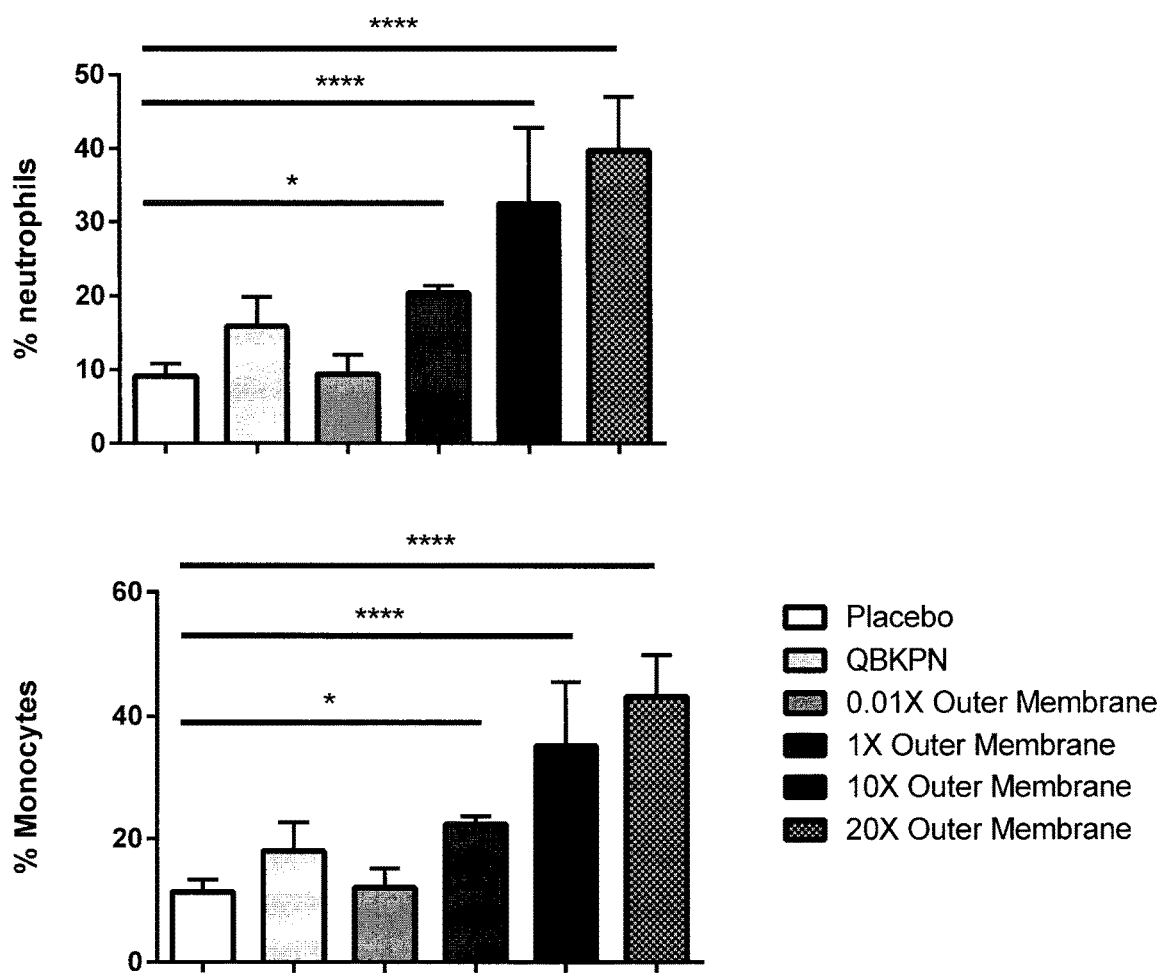
FIG. 47C includes two bar graphs illustrating OM dose-dependant elevated neutrophil and monocyte blood counts after 4 injections of QBKPN SSI, placebo, or various concentrations of OM fraction (0.01×, 1×, 10× or 20×) in blood collected 2 days prior to tumour implant.

Of note, higher concentrations of the membrane fraction caused pathology in animals prior to inoculation with tumour cells. In particular, 10× and 20× outer membrane fractions elicited strong toxicity in mice as evidenced by highly elevated innate cell (monocyte and neutrophil) recruitment to the blood with attendant deteriorating health conditions (e.g. dramatic weight loss, gait, hunched posture, eye conditions). Similarly, in some embodiments, concentrated whole cell preparations did not elicit toxicity. FIG. 47C illustrates elevated neutrophil and monocyte blood counts after 4 injections of SSI or placebo, in blood collected 2 days prior to tumour implant.

Figure 47D:
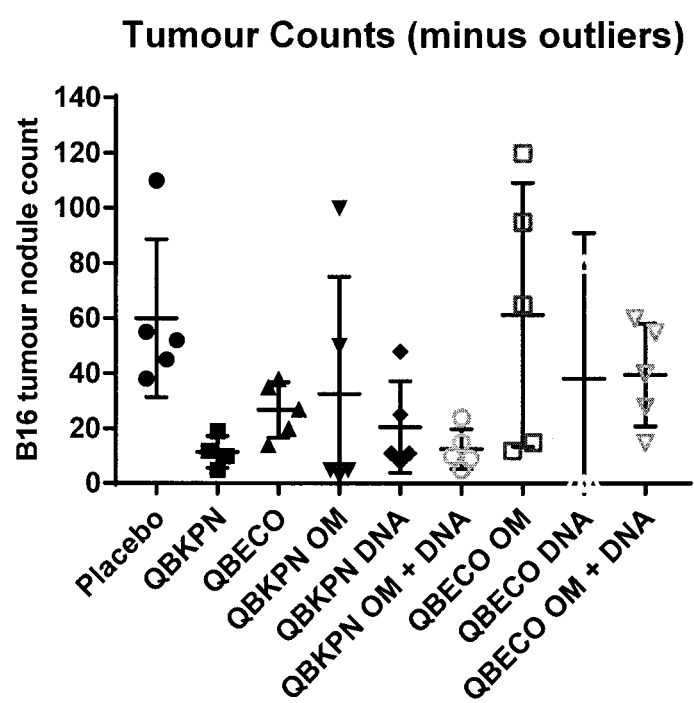
FIG. 47D is a column scatter graph plot illustrating the site-specific efficacy of KPN fractions compared to *E. coli* fractions in the B16 lung cancer model.

As illustrated in FIG. 47D, the KPN fractions illustrate site specific preferential lung activity compared to *E. coli* fractions in the B16 lung cancer model. In particular, compared to placebo control, whole QBKPN was efficacious in reducing lung tumour burden. A whole killed *E. coli* formulation (QBECO) was not as efficacious as QBKPN. QBKPN fractions (OM or DNA alone) were efficacious. When combined (OM+DNA), QBKPN fractions were approximately as efficacious as whole QBKPN. QBECO fractions (OM, DNA, or OM+DNA) did not show the same efficacy as QBKPN fractions. Together, this illustrates site specificity associated with QBKPN fractions, particularly combined DNA (4×) and OM (1×) fraction.

Example 9: Co-Formulations and Co-Administration

This Example illustrates embodiments in which an SSI is co-formulated with or co-administered with additional therapeutic components.

One class of additional therapeutic components comprises molecules or compositions for activating or recruiting innate immune cells, and these include:

GMCSF (particularly for cancer), for example in an amount that synergistically recruits and promotes the production of neutrophils and potentiates the SSI-induced innate immune response.

Vitamin D (for inflammatory disease, such as IBD, and cancer), for example in an amount that is effective to differentiate and activate monocytes and play a role in regulating innate immune function. In alternative embodiments, the vitamin D used in conjunction with SSIs may for example be one or more of vitamin $D_3$, $D_2$ or calcitriol (1,25-dihydroxycholecalciferol). In some embodiments, vitamin $D_3$ and/or $D_2$ may for example be given locally at a dosage that is effective to provide a locally effective amount of calcitriol at the site of SSI and vitamin D administration. For example, vitamin D precursors ($D_3$ and/or $D_2$) may be administered in an amount that is locally effective once it is converted into the calcitriol active form by local monocytes and/or macrophages (expressing CYP27B1) at the site of administration. In alternative embodiments, calcitriol may be administered in dose that is locally effective at the site of SSI administration, and this may for example be dose that is less than the dose required for other systemic effects.

An additional class of therapeutic components for co-formulation or co-administration comprise molecules or compositions that relieve immunosuppression:
NOHA (N(omega)-hydroxy-nor-L-arginine), an Arginase inhibitor—Arginase degrades arginine needed for immune activation. NOHA may for example be used in an amount effective to relieve immune suppression by making available free arginine.
Alpha1 antitrypsin—for example in an amount effective to relieve immune suppression mediated by neutrophils secreting proteases.

An additional class of therapeutic components for co-formulation or co-administration comprise molecules or compositions that prevent oxidative damage and improve immune function under stress:
Glutathione and other antioxidants, particularly for fibrotic diseases (such as IBD).

An additional class of therapeutic components for co-formulation or co-administration comprise co-stimulatory molecules for innate cytotoxic lymphocytes (for example for anticancer treatments):
Phospho-antigens (isoprenoid molecules, such as isopentenyl pyrophosphate)—recognized by human peripheral blood Vγ9Vδ2 T cells which play a central role in anticancer responses, for example in amounts effective for activating and differentiating monocytes working in concert with NK cells to target both solid and liquid cancers. In exemplary embodiments, it has been found that SSIs in co-formulation or co-administration with zoledronate increase markers of activation, for example CD25 and CD69, on human peripheral blood Vγ9Vδ2 T cells.
Glycolipid molecules recognized by Type I NKT cells (such as synthetic α-galactosylceramide)

Figure 12:
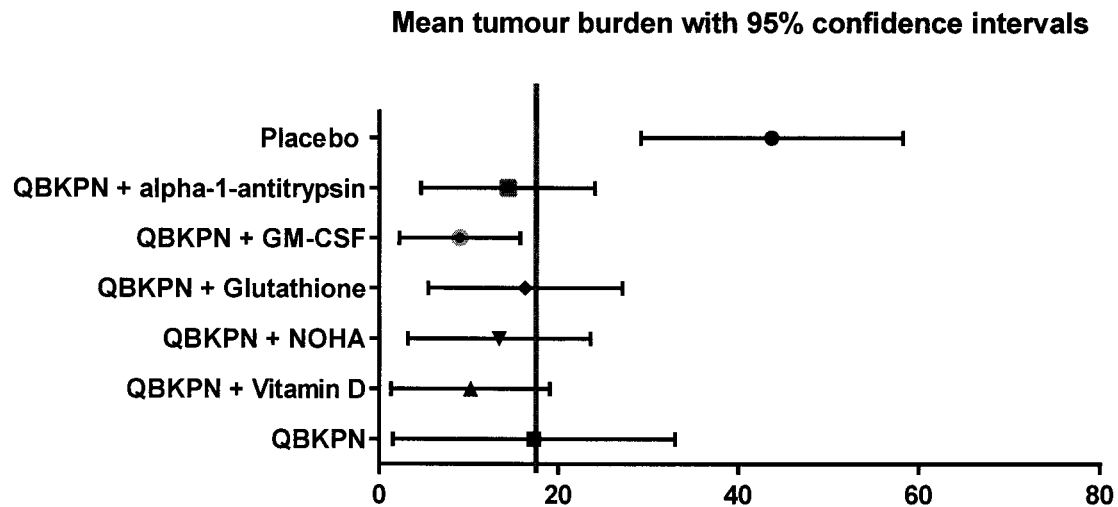
FIG. 12 is a chart illustrating the efficacy of various SSI co-formulations in a murine cancer model.
Figure 13:
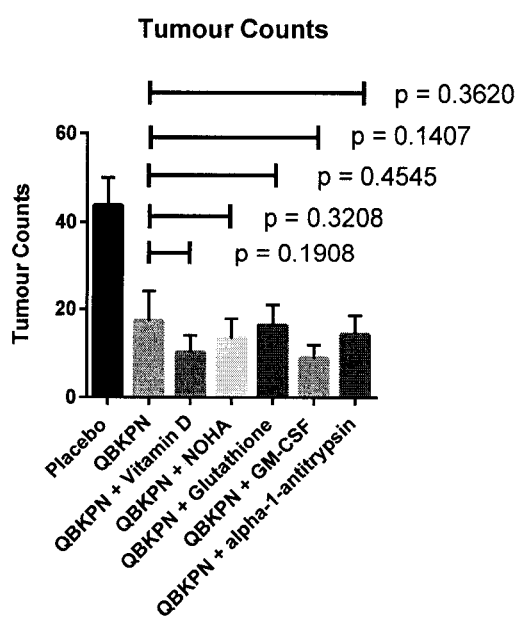
FIG. 13 is an alternative bar graph representation of the efficacy of various SSI co-formulations in a murine cancer model.

As set out in Table 18, and FIGS. 12 and 13, in an in vivo demonstration of SSI co-formulations that improve anticancer effects using the LLC model, co-formulations with GMCSF and Vitamin D ($D_3$) show the best performance, followed by NOHA (arginase inhibitor) and alpha1-antitrypsin.

TABLE 18

Co-Formulations - comparing the mean differences in tumour count vs placebo

| Dunnett's multiple comparisons test | Mean Diff. | 95% CI of diff. | |
|---|---|---|---|
| Placebo vs. QBKPN | 26.44 | 8.035 to 44.85 | ** |
| Placebo vs. QBKPN + Glutathione | 27.41 | 8.998 to 45.82 | ** |
| Placebo vs. QBKPN + alpha-1-antitrypsin | 29.33 | 10.92 to 47.74 | *** |
| Placebo vs. QBKPN + NOHA (arginase inhibitor) | 30.31 | 11.90 to 48.72 | *** |
| Placebo vs. QBKPN + Vitamin D | 33.50 | 15.09 to 51.91 | **** |
| Placebo vs. QBKPN + GM-CSF | 34.73 | 16.32 to 53.14 | **** |

Example 10: Colitis Animal Model, Anti-Inflammatory Efficacy

This Example illustrates results from a mouse spontaneous colitis model (Muc2 knockout "KO" mice) that mimics the underlying immune system defect and chronic bacterial infection associated with Crohn's disease and ulcerative colitis. IBD patients typically display structural and/or functional defects in their normally protective colonic mucosal barriers. The mucus barrier is largely dependent on the release of goblet cell-derived mucin (Muc2) which prevents microbes and luminal antigens from contacting the epithelial surface in the gastrointestinal tract. Muc2 KO mice are healthy just after weaning (1 month old), as they age, they develop progressive diarrhea and sporadic rectal prolapse. Histological analysis of colonic tissue shows crypt hyperplasia, crypt abscesses, inflammatory cell infiltration and submucosal edema. Accordingly, the Muc2 KO mice have a defective gastrointestinal mucosal barrier and after time spontaneously develop colitis, resembling ulcerative colitis in humans. In this model, young (2 month old) Muc2 KO mice have less severe colitis, and older (3 month old) Muc2 KO mice have more severe colitis.

Figure 14:
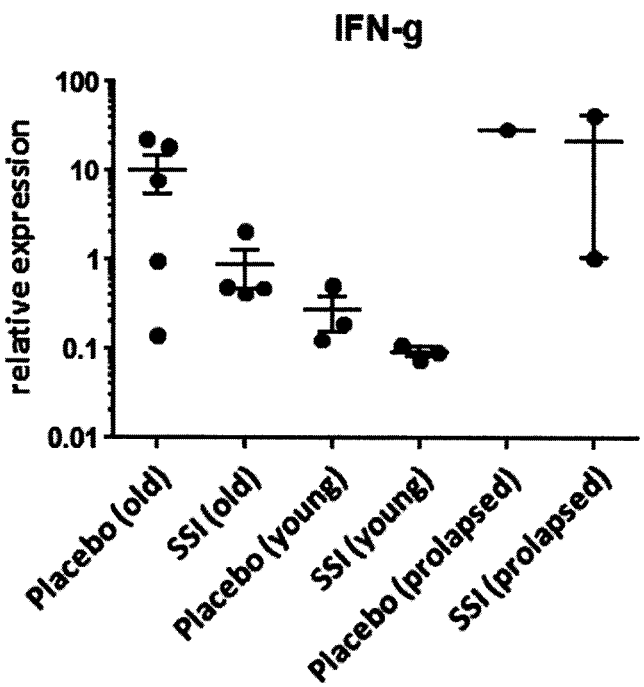
FIG. 14 is a series of graphs illustrating efficacy of SSI treatment in alternative model animals in the colitis model: a logarithmic Y axis scale illustrating relative levels of IFN-gamma (A) and IL-17A expression (B), and cumulative data for IL-17A expression (C), as well as site-specific evidence of QBECO efficacy in increasing IL-18 gene expression in colon tissue, compared to QBKPN (D).
Figure 14:
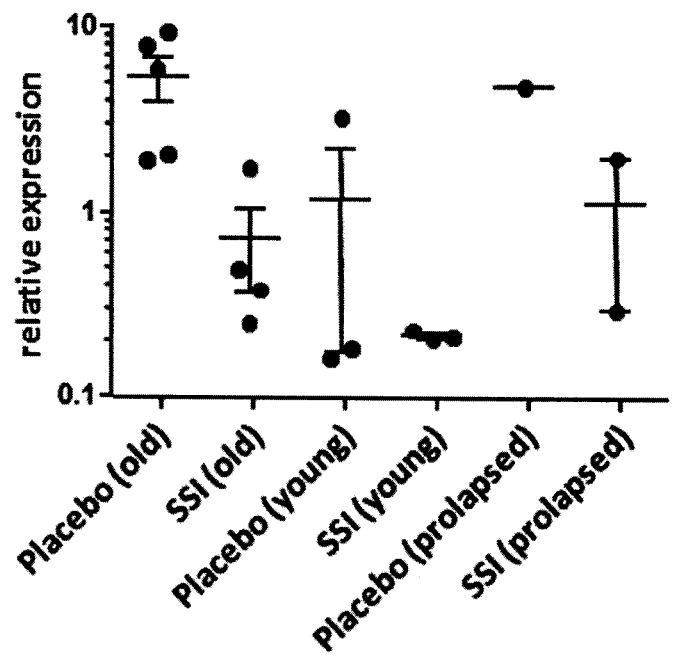
Figure 14:
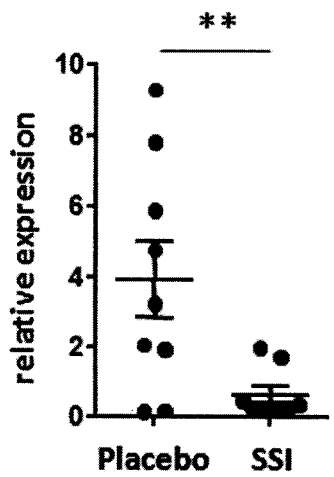
Figure 14:
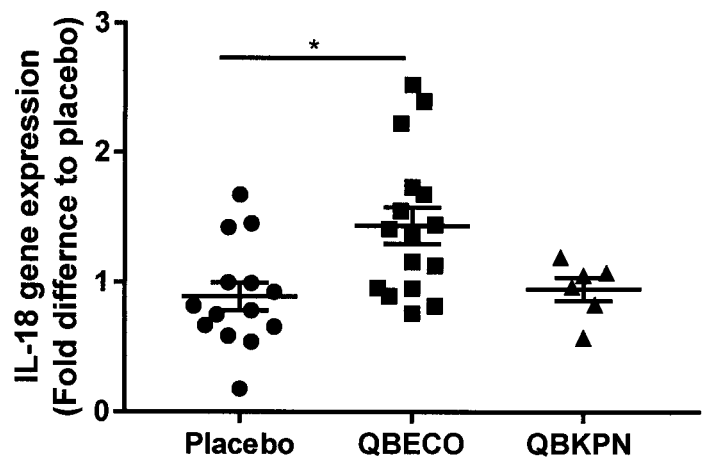

Results from this animal model, as shown in FIGS. 14A, 14B and 14C illustrate that an E. coli SSI (QBECO) decreases pro-inflammatory markers in the colon (using qPCR gene expression data). FIG. 14D illustrates the site specific activity of QBECO in increasing IL-18 gene expression in the colon, compared to QBKPN. The IFN-gamma expression data in particular illustrates how SSI efficacy can be affected by the stage of colitis (comparing expression data in old vs young mice). IL17A data, relating to a cytokine that is produced by activated T-cells (a marker of IBD inflammation), illustrates a significant decrease in this marker of inflammation after E. coli SSI treatment. Accordingly, QBECO treatment substantially improved all components of the histopathology score, including infiltration, integrity, hyperplasia, and edema. The infiltration of T lymphocytes in the colonic tissue, a hallmark of IBD in patients and mouse models, was markedly decreased with QBECO treatment. Accordingly, this Example illustrates that an SSI, such as QBECO, may be used to significantly decrease disease severity in IBD model, including so as to substantially dampen adaptive immune system over-response.

Figure 15:
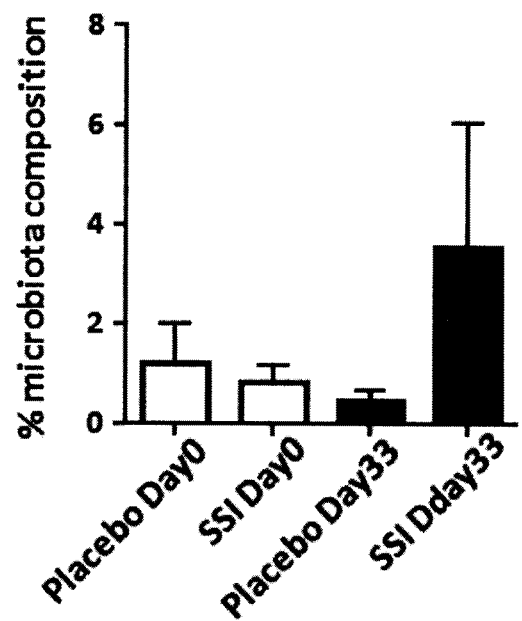
FIG. 15 is a series of graphs illustrating efficacy of SSI treatment in alternative model animals in the colitis model: mocrobiome (A and B) and histology (C).
Figure 15:
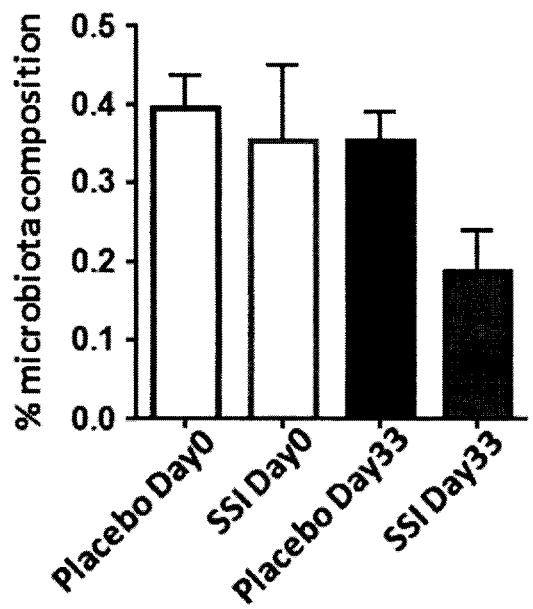
Figure 15:
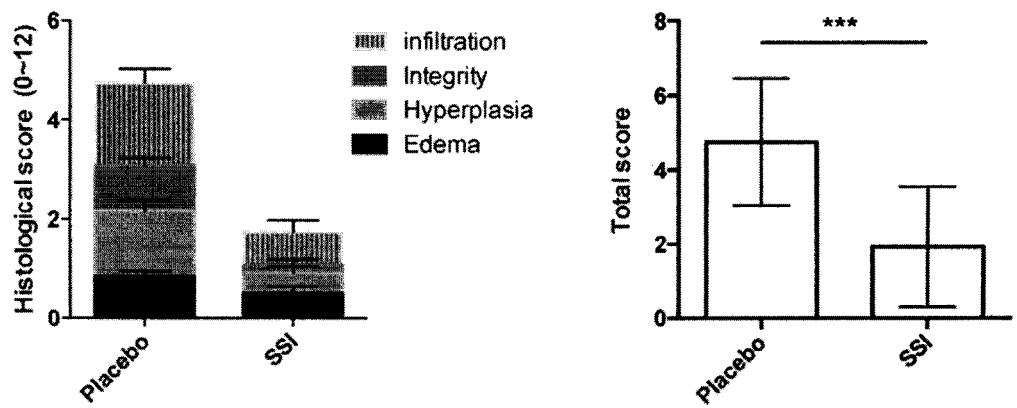

QBECO was also shown to have a positive impact on the gastrointestinal microbiome. Alterations in bacterial species in the intestinal microbiome can either be detrimental ('unhealthy' bacteria) or therapeutic ('healthy' bacteria) in IBD patients (and mouse models). Some bacteria promote a healthy immune environment and can improve symptoms (for example, *Lactobacillus* species), whereas others (for example, γ-proteobacteria) can have detrimental effects in IBD. We analyzed the intestinal microbiome before and after QBECO SSI treatment. As illustrated in FIGS. 15A and 15B, QBECO SSI improved dysbiosis in the colon of Muc2 mice, increasing the relative proportion of *Lactobacillus* (healthy bacterial species) and decreasing the relative proportion of gamma-proteobacteria (unhealthy bacterial species). As illustrated in FIG. 15C, QBECO SSI also reduced all aspects of the histological inflammation/damage score (infiltration, integrity, hyperplasia and edema) in the colon of MUC2 spontaneous colitis mice. These results illustrate that an SSI treatment using a formulation derived from a GI pathogen, such as QBECO, has a therapeutic effect on the gastrointestinal microbiome. Accordingly, aspects of the invention involve the use of an SSI, such as an E. coli derived SSI, for treating dysbiosis in IBD.

To summarize, QBECO treatment significantly improved the overall histological score and reduced T cell infiltration in the colonic tissues. Furthermore, a reduction in pro-inflammatory mediators in the colon (IL-17A) and serum (KC) was observed. QBECO treatment did not impact regulatory T cell marker (FoxP3) and anti-inflammatory growth factor (TGF-β) expressions in affected tissues. In addition, SSI treated mice demonstrated reduced levels of the antimicrobial lectins RegIII-β and RegIII-γ. The changes in antimicrobial lectins brought on by QBECO allowed for a modulation of the gut microbiome causing a reduction in gamma-proteobacteria and a significant increase in lactobacilli.

Example 11: SSI Efficacy in Asthma/Allergy

Figure 16:
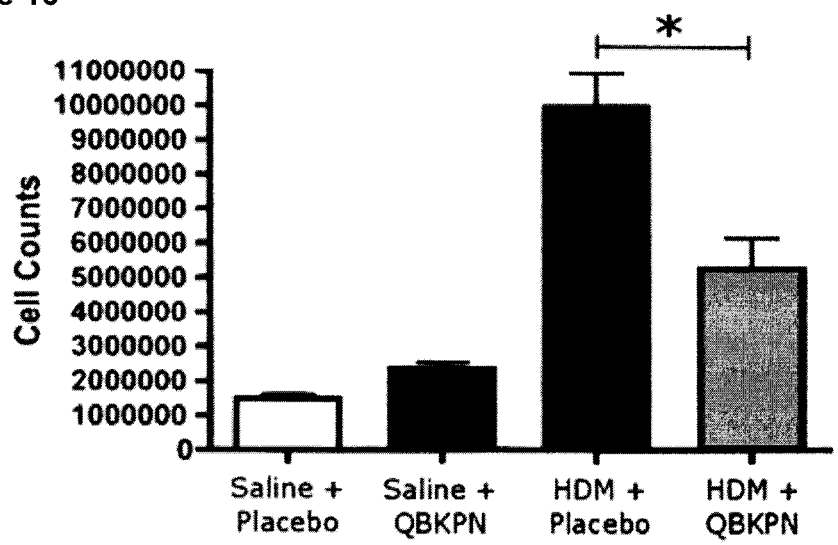
FIG. 16 is a bar graph illustrating efficacy of an SSI in a murine asthma/allergy model.
Figure 17:
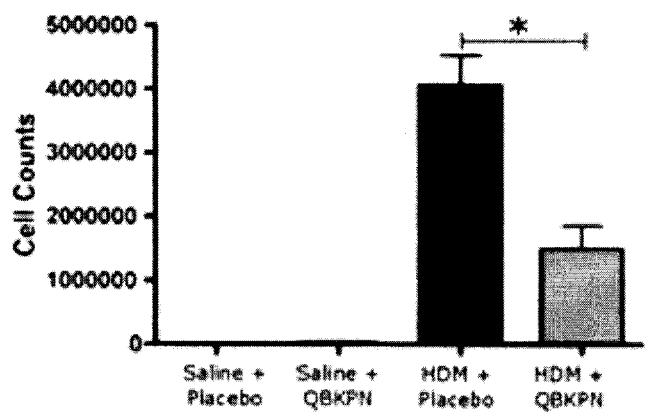
FIG. 17 includes two bar graphs illustrating efficacy of an SSI in a murine asthma/allergy model, showing counts of A) Eosinophils, B) Lymphocytes.
Figure 17:
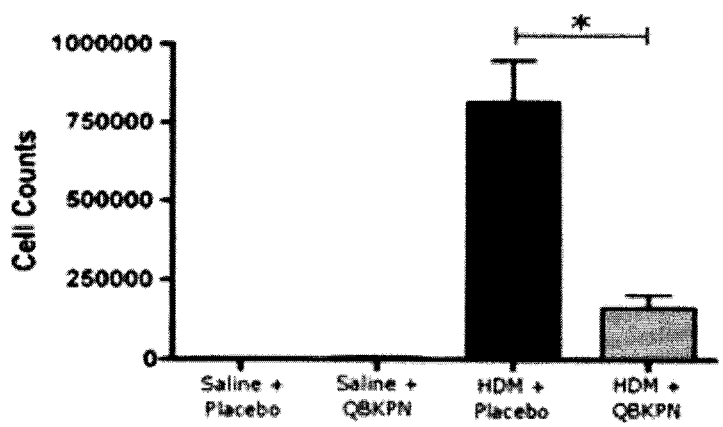
Figure 18:
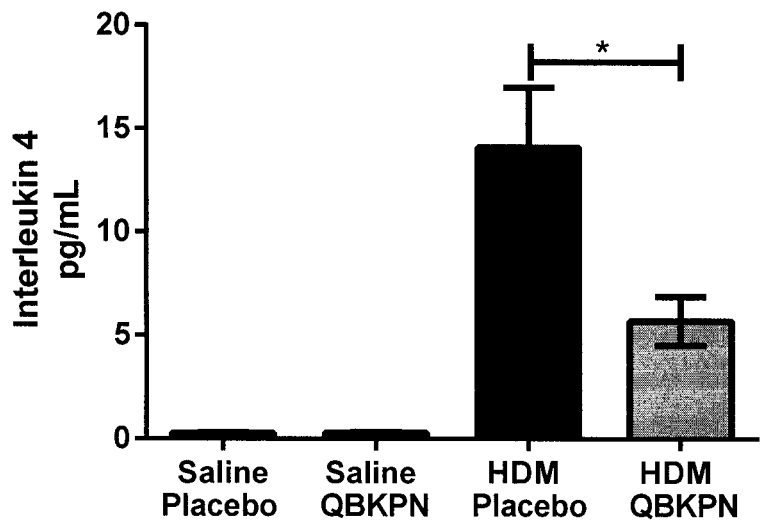
FIG. 18 includes two bar graphs illustrating efficacy of an SSI in a murine asthma/allergy model, showing A) IL-4 and B) IL-5 concentrations.
Figure 18:
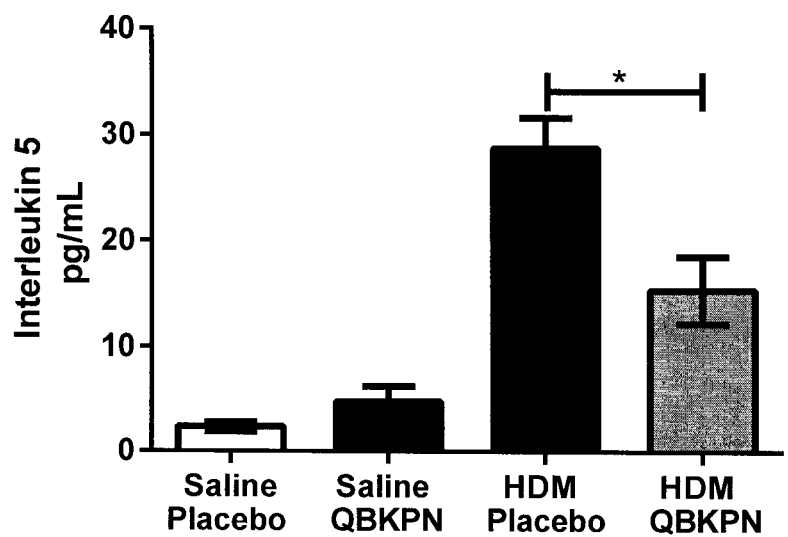

This Example provides animal model data illustrating the efficacy of an SSI therapy, KPN SSI, in treating asthma/allergy. As shown in FIG. 16, KPN SSI decreases total BAL cell count in asthmatic mice. As shown in FIG. 17, KPN SSI decreases eosinophil and lymphocyte counts in the BAL: A) Eosinophils, B) Lymphocytes. As shown in FIG. 18, KPN SSI decreases TH2 cytokines in the BAL supernatant: A) IL-4, B) IL-5.

Example 12: Systemic Distribution of SSI Administered SubQ

Figure 19:
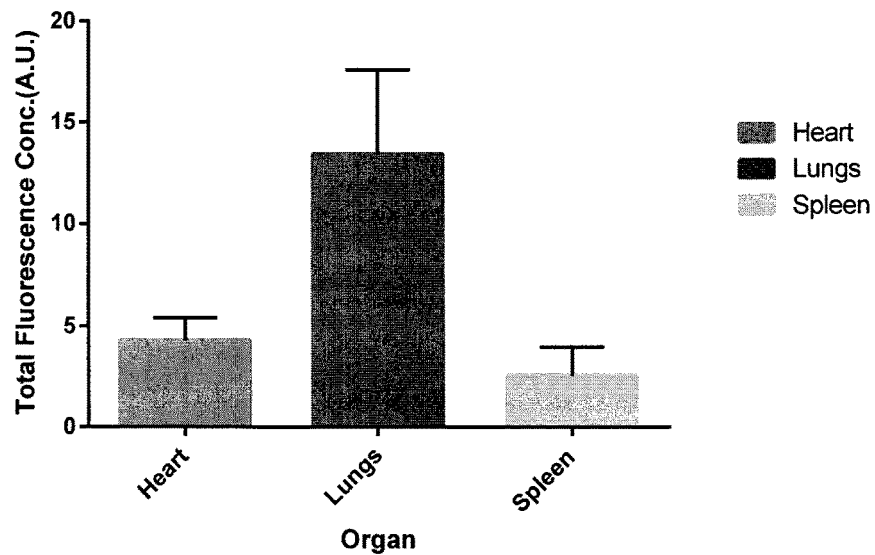
FIG. 19 is a bar graph illustrating results of ex-vivo imaging of Cy5.5 labelled KPN SSI (QBKPN) measured in organs (heart, lungs and spleen) 24 hours after a third SQ SSI injection.

This example illustrates systemic distribution of a KPN SSI administered subcutaneously in a murine model; using cyanine dye (Cy5.5) labeled whole killed KPN cells and optical in-vivo dorsal and ventral whole-body imaging. After a first injection, imaging (at 1 hr, 3 hr, 6 hr, 24 hr and 47 hr) revealed systemic distribution with the highest concentrations of the SSI at the injection site. Following the first injection, the SSI was cleared from circulation within approximately 24 hours. Subsequent injections took place at alternative injection sites, and imaging (at 1 hr, 3 hr, 6 hr and 24 hr) revealed systemic distribution with highest concentrations seen at the new sites of injection and, surprisingly, at previous sites of injection. This provides an illustration of preferential SSI delivery/retention at sites of inflammation following systemic dispersal of locally administered formulations. Microscopic evaluation of blood samples confirmed that the Cy5.5 fluorescence detected in the blood was not free dye. As illustrated in FIG. 19, the distribution of SSI in organs after 24 hours showed a preferential accumulation of KPN SSI in the lungs, compared to the heart and the spleen.

Example 13: Surgical Wound Treatment

In this Example, a topical formulation of an SSI is formulated for administration to wounds, for example surgical wounds, partial-thickness burns, lacerations, chronic wounds, or vascular ulcers. The topical SSI formulation may for example include PPR agonists derived from microbes that are skin pathogens, formulated in an ointment or gel.

Example 14: Durability of Treatment Response in IBD

This Example illustrates that efficacious treatment for Crohn's disease may be carried out over an extended period of periodic dosing of an SSI. In particular, in a phase 1/2, randomized, placebo-controlled, double-blinded clinical trial involving adults with moderate to severe Crohn's disease, the Crohn's Disease Activity Index (CDAI, Best et al., 1976, Gastroenterology 70 (3): 439-444) declined on average by significantly more on week 16 of treatment compared to week 8. More specifically, by week 8, the average reduction in CDAI score in SSI treated patients was approximately 80 points; by week 16, the average reduction in CDAI score was approx 120 points. This illustrates continued clinical improvement through 16 weeks of SSI treatment.

This example involved use of a whole killed *E. coli* SSI preparation, administered every second day by subcutaneous injection. The dose was individualized to the patient by adjusting the dose so that each dose was effective to cause a visible localized inflammatory immune response at the administration site (a 1 inch to 2 inch diameter delayed reaction of visible redness at the injection site).

Accordingly, aspects of the invention involve use of an SSI over an extended duration period, with dosage intervals and dosage duration adapted to provide an increased therapeutic benefit over the entire dosage duration, such as a progressive reduction of CDAI score in Crohn's patients over a duration period of at last 16 weeks.

Example 15: Lung Inflammation—Asthma

This example illustrates therapeutic efficiency of an SSI (KPN SSI) in a murine House Dust Mite (HDM)-induced asthma model, explifying the underlying mechanistic basis for the use of SSIs in treating asthmatic inflammation. In this Example, BALB/c mice were exposed intranasally to HDM for two weeks. Mice were treated subcutaneously with either KPN SSI or placebo for one week prior to HDM exposure and throughout the two week exposure period. 24 hours after the last exposure, lungs were analysed for inflammatory cell infiltrate, gene expression, cytokine levels, goblet cell metaplasia, and serum was analysed for allergen-specific serum IgE levels.

Methods

Animals

Female mice (BALB/c) age 6-8 weeks old were purchased from Jackson Laboratory (Bar Harbor, Me.). 10 mice per group were used. Mice were housed in environmentally controlled specific pathogen free conditions with a 12:12 hour light/dark cycle for the duration of the study.

Allergen Exposure Protocol

Mice were exposed to saline (35 μL) or house dust mite (HDM, *Dermatophagoides pteronyssimus*, Greer Laboratories, Lenoir, N.C.), intranasally, 25 μg in 35 μL of saline, under isoflurane anesthesia. HDM or saline nasal exposure was done for 5 consecutive days in week 1 and 4 consecutive days in week 2 (experimental days: 1-5; 8-11, FIG. 1). Mice were euthanized 24 hours after the last exposure.

*Klebsiella* Intervention Strategy

KPN SSI was derived from *Klebsiella* originally isolated from a patient infection, with whole heat killed cells suspended in physiological saline containing 0.4% phenol as a preservative for a final $OD_{600}$ of 5.0. Placebo was physiological saline containing 0.4% phenol. KB or placebo was prophylactically given on day −7, −5, −3 of the experiment, and treatment was continued on experimental days 1, 3, 5, 8, 10. 30 μL of placebo or KB was injected subcutaneously at alternative sites access skin in lower right and left quadrant of the abdomen and upper right and left quadrant of the chest.

Blood Collection, Bronchoalveolar Lavage (BAL), and Cytospin Analysis for BAL Cell Differentials.

BAL cell differential counts were performed by examining cytospins according to cell morphology and Wright- Giemsa staining. A total of 100 cells per mouse were differentiated by a blinded observer.

Quantification of HDM-Specific Immunoglobulins by ELISA

HDM was coated onto 96-well plates (2.5 ug/well) and incubated overnight at 4° C. After blocking with 5% FBS in PBS, undiluted serum was added and incubated overnight at 4° C. After washing, biotin anti-mouse IgE (BD Bioscience—San Jose, Calif., USA) was added and incubated at 37° C. for one hour. Streptavidin-HRP/TMB substrate was used to visualize levels and absorbance was recorded at 450 nm.

Gene Expression

Right lung tissue was lysed by homogenizing with a TissueLyser LT (Qiagen—Toronto, Ontario, Canada) and RNA isolation performed using a PureLink RNA Mini Kit (Life Technologies—Carlsbad, Calif., USA). iScript cDNA Synthesis Kit-170-8891 was used for cDNA synthesis (Biorad). Gene expression was done by quantitative RT-PCR on a StepOnePLus RT-PCR machine (Applied Biosystems—Foster City, Calif., USA) using TaqMan Fast Advanced Master Mix (Applied Biosystems) with Taqman probes for IL-4 (Mn00445259_m1), IL-13 (Mn00434204_m1) and IFN-γ (Mn01168134_m1).

Cytokine and Chemokine Analysis of BAL and Serum Samples 31 cytokine/chemokine/growth factor biomarkers were quantified simultaneously using a Milliplex Mouse Cytokine/Chemokine kit (Millipore, St. Charles, Mo., USA) according to the manufacture's protocol. The multiplex was performed by using the Bio-Plex™ 200 system (Bio-Rad Laboratories, Inc., Hercules, Calif., USA). The 31-plex consisted of eotaxin, G-CSF, GM-CSF, IFNγ, IL-1α, IL-1β, IL-2, IL-3, IL-4, IL-5, IL-6, IL-7, IL-9, IL-10, IL-12 (p40), IL-12 (p70), IL-13, IL-15, IL-17, IP-10, KC, LIF, MCP-1, M-CSF, MIG, MIP-1α, MIP-1β, MIP-2, RANTES, TNFα, and VEGF. The assay sensitivities of these markers range from 0.1-33.3 pg/mL. As IL-13 levels in the multiplex were mainly below detection, IL-13 protein levels were measured in the BAL fluid by an ELISA (eBioscience San Diego, Calif., USA).

Histology

Lungs were dissected and inflated with 5 mL of 10% formalin. Tissues were embedded with paraffin and sectioned at 3 μm. Sections were stained with Periodic acid-Schiff to quantify mucus-containing goblet cells. Stained sections were scanned at 60× magnification using an Aperio Slidescanner (Vista, Calif.), version 11.1.2.760. Positively stained pixels were identified by colour segmentation in a cross-sectional manner in the lung airway using Aperio Image Scope software to express the number of strong positive pixels (Periodic acid-Schiff) normalized to basement membrane length (μM).

Data Analysis

Data were analysed using GraphPad Prism and are expressed as mean±SD. Multi-group comparisons were made by one-way ANOVA followed by Sidak post-hoc test. Four experimental group combinations were compared; Saline-placebo vs. Saline-*Klebsiella*, Saline-placebo vs. HDM-placebo, Saline-*Klebsiella* vs. HDM-*Klebsiella*, HDM-placebo vs. HDM-*Klebsiella*. For the purpose of statistical analysis, any value that was below the lowest value of the standard was recorded as half the lowest value of the standard. Principal component analysis (PCA) was performed for the BAL multiplex data, with and without the IL-13 ELISA. PCA was completed in R (version 3.2.4) using the prcomp command. (R Core Team (2016) R: A language and environment for statistical computing. R Foundation for Statistical Computing, Vienna, Austria. URL https://www.R-project.org/).

Results

Figure 20:
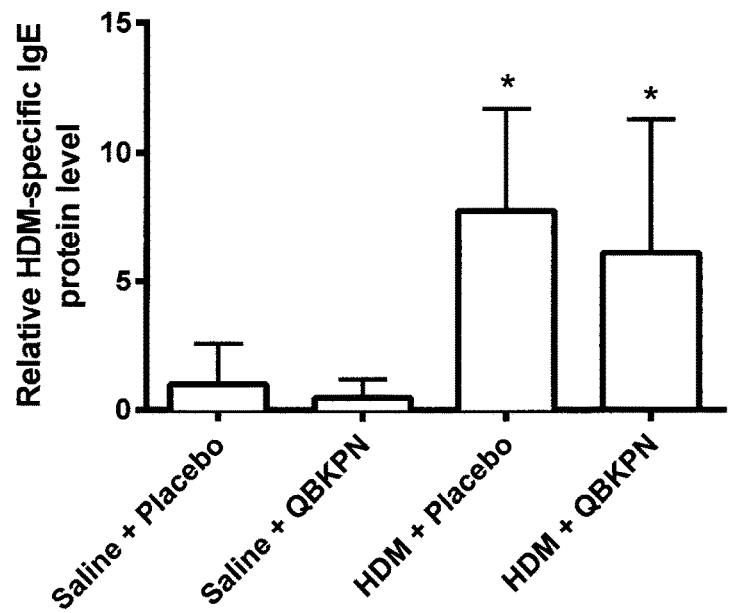
FIG. 20 is a bar graph illustrating house dust mite (HDM)-specific IgE responses following saline or HDM exposure, treated with either Placebo or QBKPN.

FIG. 20 is a graph illustrating HDM specific IgE responses following saline or HDM exposure, treated with either Placebo or QBKPN. * P<0.05 between HDM treated mice and their appropriate control (HDM Placebo vs Saline Placebo and HDM QBKPN vs Saline QBKPN).

Figure 21:
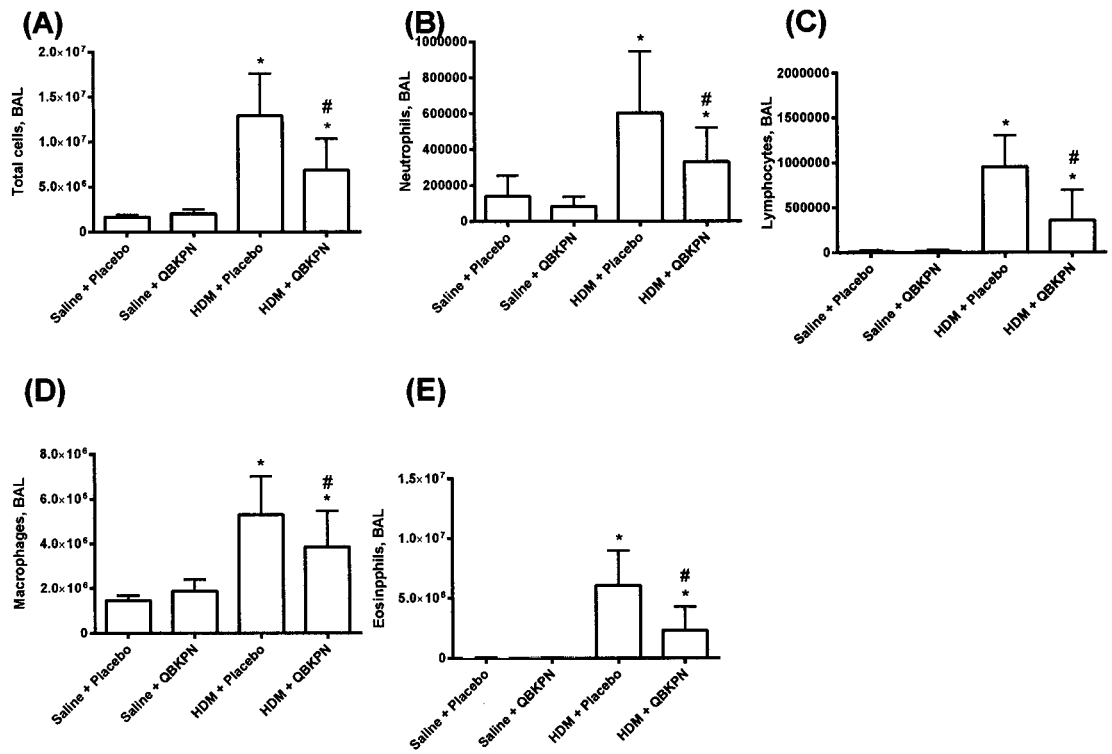
FIG. 21 is a series of bar graphs (A-E) illustrating aspects of an anti-inflammatory SSI treatment for asthma from an animal model, particularly BAL cell counts and differentials in Saline or HDM exposed mice treated with Placebo or QBKPN SSI.

FIG. 21 is a series of graphs illustrating BAL cell counts and differentials in Saline or HDM exposed mice treated with Placebo or QBKPN: A) BAL total cells; B) BAL neutrophils; C) BAL lymphocytes; D) BAL macrophages; Panel (E); BAL eosinophils. Data are means±SEM of 10 mice per group (*=p<0.05). Data are means±SD of 10 mice per group. * P<0.05 between HDM treated mice and their appropriate control. #P<0.05 between HDM QBKPN treated mice and HDM Placebo treated mice.

Figure 22:
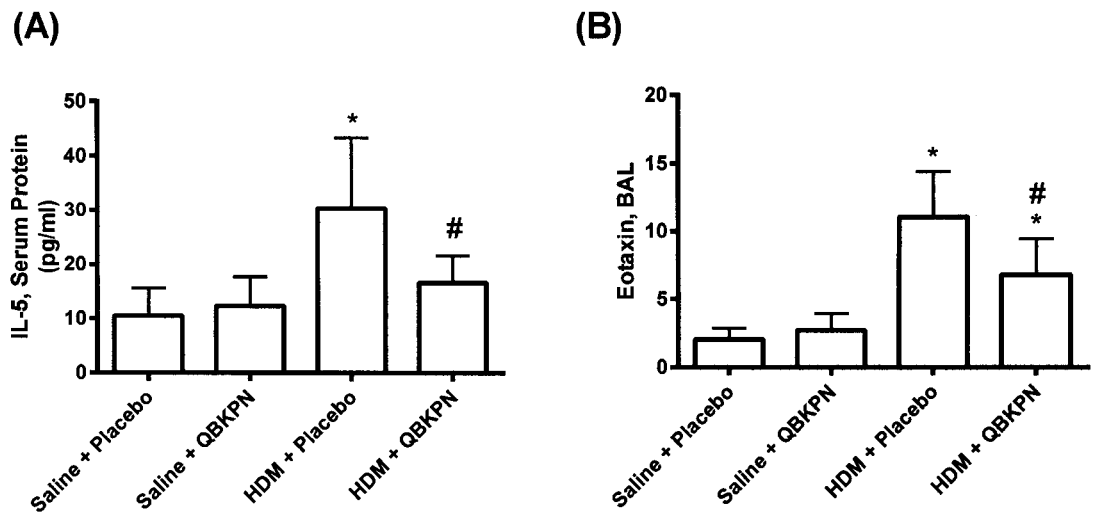
FIG. 22 includes two bar graphs illustrating aspects of an anti-inflammatory SSI treatment for asthma from an animal model, particularly serum (A) and BAL (B) mediators that are linked to eosinophilia.

FIG. 22 includes two graphs illustrating BAL and serum mediators that are linked to eosinophilia: Serum IL-5 (A) and BAL eotaxin (B). Data are means±SD of 10 mice per group (*=p<0.05) between HDM treated mice and their appropriate control. #P<0.05 between HDM QBKPN treated mice and HDM Placebo treated mice.

Figure 23:
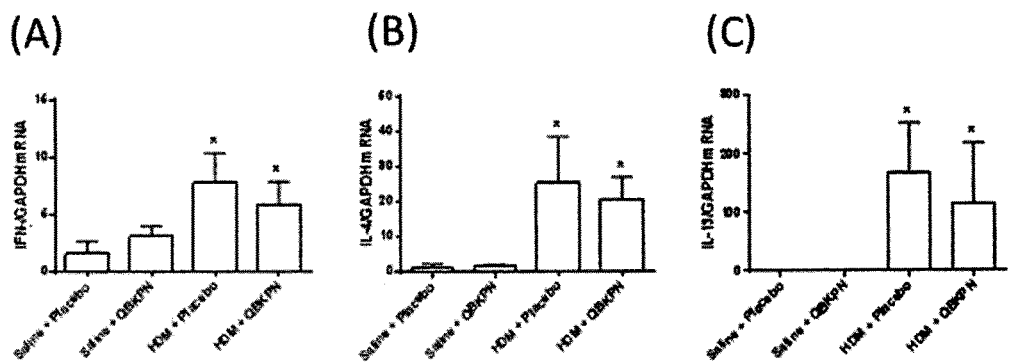
FIG. 23 is a series of bar graphs illustrating aspects of an anti-inflammatory SSI treatment for asthma from an animal model, particularly Th1 (A) and Th2 (B and C) lung gene expression following HDM exposure and QBPKN treatment.

FIG. 23 is a series of graphs illustrating Th1 and Th2 lung gene expression following HDM exposure and QBPKN treatment: A) Th-1-mediated response IFN-γ cytokine gene expression, B) Th-2-mediated response IL-4 cytokine gene expression, and C) IL-13 cytokine gene expression (data are means±SD of 10 mice per group; * P<0.05 between HDM treated mice and their appropriate control).

Figure 24:
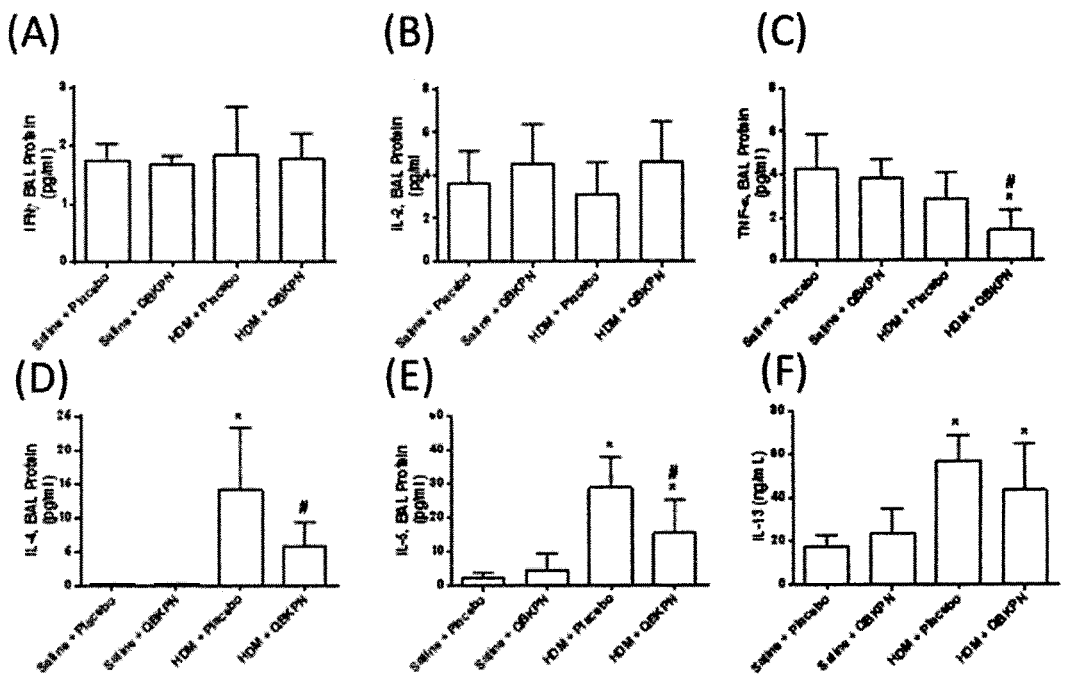
FIG. 24 is a series of bar graphs illustrating aspects of an anti-inflammatory SSI treatment for asthma from an animal model, particularly the effects of HDM exposure and QBPKN treatment on Th1- (A-C) and Th2- (D-F) mediated BAL fluid cytokine levels.

FIG. 24 is a series of bar graphs illustrating the effects of HDM exposure and QBKPN treatment on Th1- and Th2-mediated BAL fluid cytokine levels: A) IFN-γ cytokine level; B) IL-2 cytokine level; C) TNF-α cytokine level; D) IL-4 cytokine level; E) IL-5 cytokine level; F) IL-13 cytokine level (data are means±SD of 10 mice per group; * P<0.05 between HDM treated mice and their appropriate control).

Figure 25:
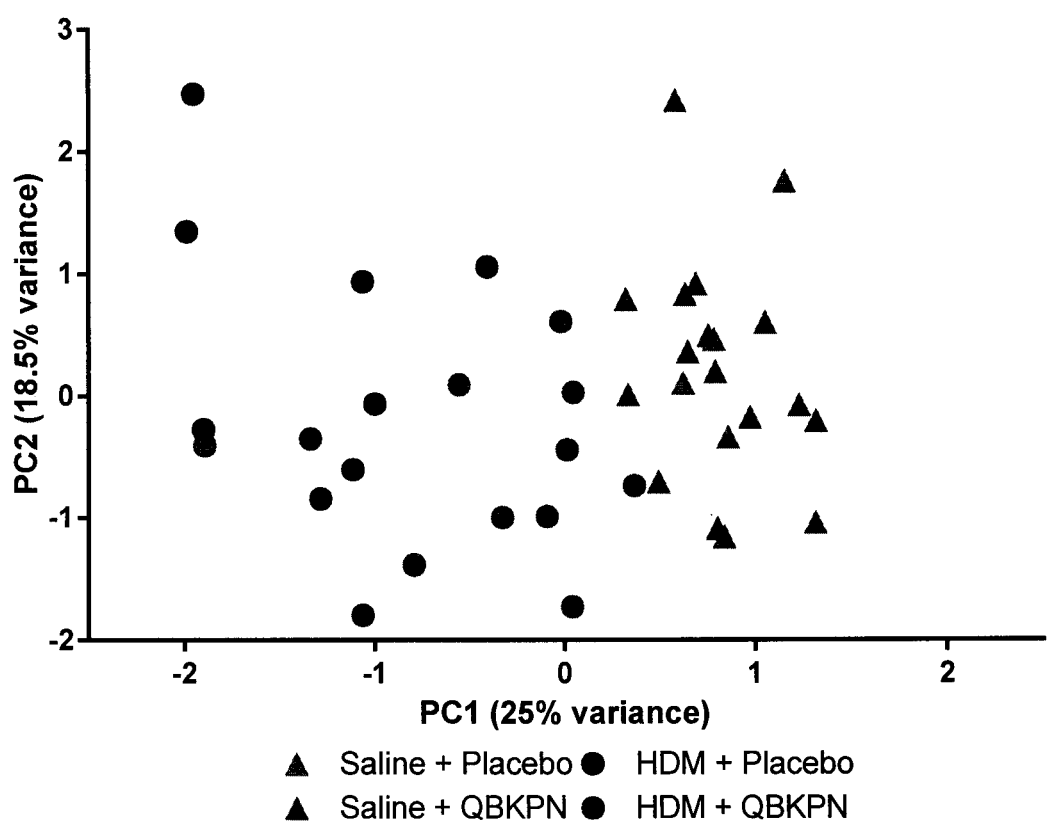
FIG. 25 is a graph illustrating aspects of an anti-inflammatory SSI treatment for asthma from an animal model, particularly a principal component analysis (PCA) of BAL cytokines showing partial normalization of overall cytokine profile.

FIG. 25 is a graph illustrating a principal component analysis (PCA) of BAL cytokines showing partial normalization of overall cytokine profile. This exemplifies overall BAL cytokine profile changes between groups, using a principle component analysis (PCA) based on all multiplex data. The different experimental groups clustered separately based on the 1st principle component (PC1). Within the placebo treated mice, saline-exposed mice clustered separately from HDM exposed mice. KB treatment minimized the separation of HDM exposed mice from saline controls. Within the saline control group, KB and placebo treated mice were similar—as shown by their clustering together. As PC1 appeared to best differentiate the mice into different groups, the cytokines that had the greatest contribution to PC1 were identified. The top 5 cytokines that determined PC1 were LIF (Lekemia Inhibitory Factor; 8.2%), IL-5 (8.2%), Eotaxin (8.1%), IL-4 (7.5%) and CXCL10 (7.3%). Completing the principle component analysis with an additional asthma markers (IL-13) measured by ELISA provided similar clustering with the top 5 cytokines that determined PC1 were IL-5 (7.3%), eotaxin (7.2%), LIF (Leukemia Inhibitory Factor; 7.2%), IL-4 (6.8%) and IL-13 (6.7%).

Figure 26:
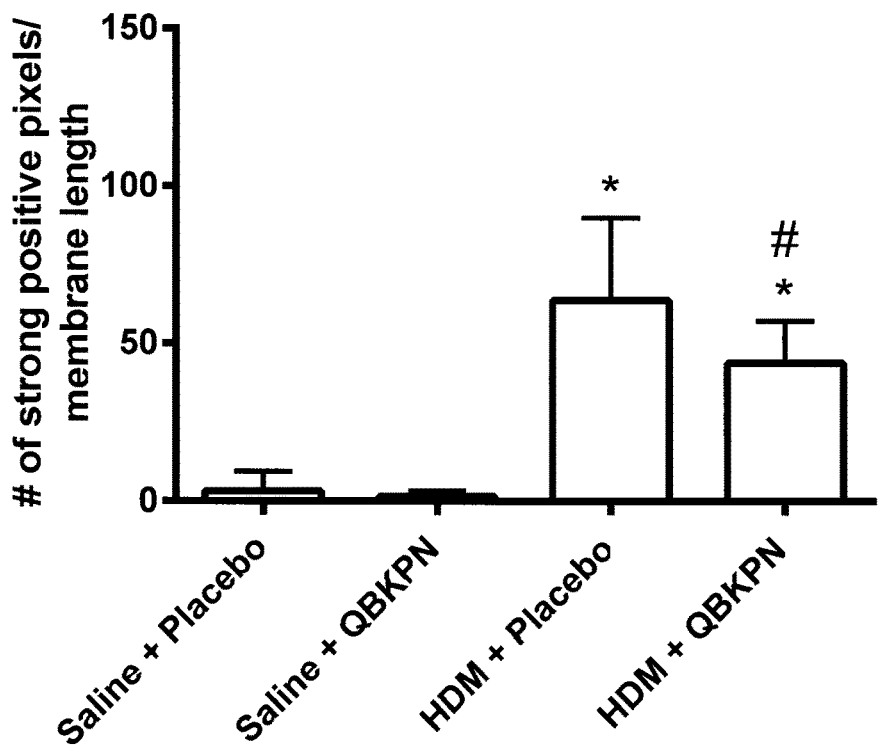
FIG. 26 is a bar graph illustrating aspects of an anti-inflammatory SSI treatment for asthma from an animal model, particularly illustrating airway goblet cell quantification following HDM exposure and QBPKN treatment.

FIG. 26 is a bar graph illustrating airway goblet cell quantification following HDM exposure and QBPKN treatment. Goblet cell quantification expressed as number of strong positive pixels/basement membrane length. Data are means±SD of 10 mice per group. * P<0.05 between HDM treated mice and their appropriate control. #P<0.05 between HDM QBKPN treated mice and HDM Placebo treated mice.

TABLE 19

BAL cytokine changes

| Analyte | Statistical significance Saline + Placebo vs. Saline + QBKPN | Statistical significance Saline + Placebo vs. HDM + Placebo | Statistical significance HDM + Placebo vs. HDM + QBKPN | Statistical significance Saline + QBKPN vs. HDM + QBKPN |
|---|---|---|---|---|
| G-CSF | ns | ns | ns | ns |
| GM-CSF | ns | ns | ns | ns |
| IFNg | ns | ns | ns | ns |
| IL-1a | ns | ** | ns | ns |
| IL-1b | ns | ns | ns | ns |
| IL-2 | ns | ns | ns | ns |
| IL-3 | ns | ns | ns | ns |
| IL-4 | ns | **** | ** | ns |
| IL-5 | ns | **** | *** | ** |
| IL-6 | ns | ns | ns | ns |
| IL-7 | ns | ns | ns | ns |
| IL-9 | ns | * | ns | ns |
| IL-10 | ns | ** | ns | ns |
| IL-12p40 | ns | ns | ns | ns |
| IL-12p70 | ns | ns | ns | ns |
| IL-13 | ns | ns | ns | ns |
| IL-15 | ns | ns | ns | ns |
| IL-17 | ns | ns | ns | ns |
| IP-10 | ns | **** | * | * |
| KC | ns | ns | ns | ns |
| LIX - CXCL5 | ns | ns | ns | ns |
| MCP-1 - CCL2 | ns | ns | ns | ns |
| M-CSF | ns | ns | ns | ns |
| MIG - CXCL9 | ns | **** | * | ns |
| MIP-1a-CCL3 | ns | ns | ns | ns |
| MIP-1b - CCL4 | ns | ns | ns | ns |
| RANTES - CCL5 | ns | ns | * | ns |
| TNFa | ns | ns | ns | ns |
| VEGF | ns | * | ns | ns |
| MIP-2 - CXCL2 | ns | ns | ns | ns |

TABLE 20

SERUM Cytokine Levels

| Analyte | Statistical significance Saline + Placebo vs. Saline + QBKPN | Statistical significance Saline + Placebo vs. HDM + Placebo | Statistical significance HDM + Placebo vs. HDM + QBKPN | Statistical significance Saline + QBKPN vs. HDM + QBKPN |
|---|---|---|---|---|
| G-CSF | ns | ** | *** | **** |
| GM-CSF | ns | ns | ns | ns |
| IFNg | ns | ns | ns | ns |
| IL-1a | ns | ns | ns | ns |
| IL-1b | ns | ns | ns | ns |
| IL-2 | ns | ns | ns | ns |
| IL-3 | ns | ns | ns | ns |
| IL-4 | ns | ns | ns | ns |
| IL-5 | ns | **** | ** | ns |
| IL-6 | **** | ns | * | ** |
| IL-7 | ns | ns | ns | ns |
| IL-9 | ** | ns | ns | ns |
| IL-10 | ns | ns | ns | ns |
| IL-12p40 | ns | ns | ns | ns |
| IL-12p70 | ns | ns | ns | ns |
| IL-13 | ns | ns | ns | ns |
| IL-15 | ns | ns | ns | ns |
| IL-17 | * | ns | ns | ns |
| IP-10 | * | ns | ** | ns |
| KC | ns | ns | ns | ns |
| LIX - CXCL5 | ns | ns | ns | ns |
| MCP-1 - CCL2 | ns | ns | ns | ns |
| M-CSF | ns | ns | ns | ns |
| MIG - CXCL9 | ns | ns | ns | ns |
| MIP-1a - CCL3 | ns | ns | ns | ns |

TABLE 20-continued

SERUM Cytokine Levels

| Analyte | Statistical significance Saline + Placebo vs. Saline + QBKPN | Statistical significance Saline + Placebo vs. HDM + Placebo | Statistical significance HDM + Placebo vs. HDM + QBKPN | Statistical significance Saline + QBKPN vs. HDM + QBKPN |
|---|---|---|---|---|
| MIP-1b - CCL4 | ns | ns | ns | ns |
| RANTES - CCL5 | ns | ns | ns | ns |
| TNFa | ns | ns | ns | ns |
| VEGF | ns | ns | ns | ns |
| MIP-2 - CXCL2 | ns | ns | ns | * |

As this example illustrates, in asthma QBKPN SSI: decreases the BAL total cells, neutrophils, lymphocytes, macrophages and eosinophils; decreases mediators of eosinophilia including serum IL-5 and BAL eotaxin; decreases Th2 cytokines in the BAL (IL-4 and IL-5); and, reduces goblet cell hyperplasia. In particular, in summary, this Example illustrated that HDM exposed mice developed classical symptoms of experimental allergic asthma including goblet cell hyperplasia, elevated allergen-specific serum IgE, airway eosinophilia, and a concomitant increase in TH2 cytokines including IL-4, IL-13 and IL-5. Treatment with KPN SSI attenuated HDM-mediated airway eosinophilia, total BAL cell numbers, bronchioalveolar lavage (BAL) $T_H2$ cytokine production, and goblet cell metaplasia. This Example demonstrates that treatment with KPN SSI attenuated HDM-induced $T_H2$-skewed airway inflammatory responses and the associated goblet cell metaplasia. An aspect of the invention accordingly provides a treatment, such as subcutaneous treatment, with microbial biologics, such as compositions derived from bacterial lung pathogens, as a treatment for allergic airway disease, for example so as to attenuate an allergen-induced $T_H2$-skewed airway inflammatory response, and/or an associated goblet cell metaplasia. These results accordingly indicate that an SSI treatment with a biologic is capable of simultaneously targeting two of the key molecular components that promote airway eosinophilia, in a process that is independent of the regulation of allergen specific IgE. In particular, a KPN SSI may be administered in a dosage and for a time that is efficacious at attenuating HDM-induced $T_H2$ skewed allergic airway inflammation, and/or airway eosinophilia, and/or mucus content in goblet cells, and this may for example be independent of modulating allergen-specific IgE levels.

Example 16: Lung Inflammation—COPD

This example illustrates anti-inflammatory efficacy in a murine model of COPD, a short term (3 week) smoking model. In this model, mice are pre-treated (with placebo or KPN SSI) every other day 3 times (Monday, Wednesday and Friday of week 1). Mice are then exposed to smoke over days 8-25 (air or cigarette smoke exposure was done for 5 consecutive week days for the first 2 weeks and for 4 consecutive week days in week 3 (with no treatment or exposure on weekends) with continued treatment (placebo or KPN SSI) every other week day (Monday, Wednesday and Friday). On day 26, mice were euthanized 24 hours after the last air/cigarette smoke exposure and samples are collected.

Briefly, cigarette smoke exposure (Kentucky Research Grade Cigarettes) was done by placing mice into plexiglass nose only exposure chambers, ensuring the nose extends from main chamber. Cigarettes were placed into smoking machine and lit with a lighter and vacuum in the fume hood. The 20 cc syringes in the smoking machine were filled with smoke, automatic valve was turned followed by smoke injection into the nose only exposure chambers. Each smoking puff cycle took 1.5 minutes. Each mouse smoked 3 cigarettes per day for a total of 45 minutes of exposure. Control air exposure mice were restrained for a similar duration without exposure to smoke. Animals were monitored throughout the smoke exposure procedure and for 30 minutes post smoke exposure.

The heat-killed *Klebsiella* strain (originating from a patient infection) was administered as follows. KPN SSI or placebo vehicle (physiological saline containing 0.4% phenol) was prophylactically administered 3× every other day, and the regimen continued therapeutically throughout the period of smoke administration. Subcutaneous injections of 30 μL placebo or KPN SSI were administered into the lower right abdomen, the lower left abdomen, the upper right chest, and the upper left chest, rotating clockwise for each injection.

Cytospins were performed and evaluated based on morphology and Wright-Giemsa staining. BAL cell differentials were then counted using the prepared cytospin slide with 100 cells per mouse counted in a blinded fashion.

Immune mediator profiling of BAL and serum samples was performed as follows. Soluble mediator analysis in BAL and serum was performed using a 31 cytokine/chemokine/growth factor multiplex kit according to the manufacture's protocol (Eve Technologies Corp, Calgary, AB, Canada) using the Bio-Plex™ 200 system (Bio-Rad Laboratories, Inc., Hercules, Calif., USA). The 31-plex assay included the following mediators: Eotaxin, G-CSF, GM-CSF, IFNγ, IL-1α, IL-1β, IL-2, IL-3, IL-4, IL-5, IL-6, IL-7, IL-9, IL-10, IL-12 (p40), IL-12 (p70), IL-13, IL-15, IL-17, IP-10 (CXCL10), KC (CXCL1), LIF, MCP-1 (CCL2), M-CSF, MIG (CXCL9), MIP-1a (CCL3), MIP-1β (CCL4), MIP-2 (CXCL2), RANTES (CCL5), TNFα, and VEGF. The assay sensitivities of these markers range from 0.1-33.3 pg/mL.

Flow cytometric analysis of blood Ly6CHI monocytes/macrophages and neutrophils was performed as follows. Blood was collected in EDTA coated tubes (BD Microtainer) to prevent clotting and stored on ice prior to staining. Blood was stained with CD11b-FITC, Ly6G-PE, CD11c-PerCPCy5.5 and Ly6C-APC before red blood cell lysis (BD lysis buffer). Flow cytometry was run on a FACSCalibur (BD Bioscience). Analysis was completed on a FlowJo V10.1. Neutrophils were defined as $Ly6G^+CD11b^+$ cells. Ly6CHI monocytes/macrophage were defined as $Ly6C^{HI}Ly6G^-CD11b^+$ cells.

Data Analysis was performed as follows. GraphPad Prism 6 Software (GraphPad Software, San Diego, Calif.) was used to perform statistical analysis of the results. Data are expressed as mean±SD. One-way ANOVA analysis followed by multiple comparisons using a Sidak post-hoc test was performed on the selected group comparisons. Four experimental group combinations were compared; air-placebo vs. air-KB, air-placebo vs. cigarette smoke-placebo, air-KB vs. cigarette smoke-KB, cigarette smoke-placebo vs. cigarette smoke-KB.

Body weight and clinical scores (e.g. hunched posture, interaction with other animals, activity levels) were used to monitor the overall health of mice exposed to filtered air or cigarette smoke in the presence or absence KPN. Body weight was normalized to the starting weight of each animal. No changes in body weight were recorded in air-exposed group treated with placebo or KPN (p>0.05). However, cigarette smoking exposed mice had a prominent loss in body weight (p<0.05) and KPN treatment did not reverse this detrimental effect (p>0.05). No observed changes for clinical scores were observed for any groups.

Figure 27A:
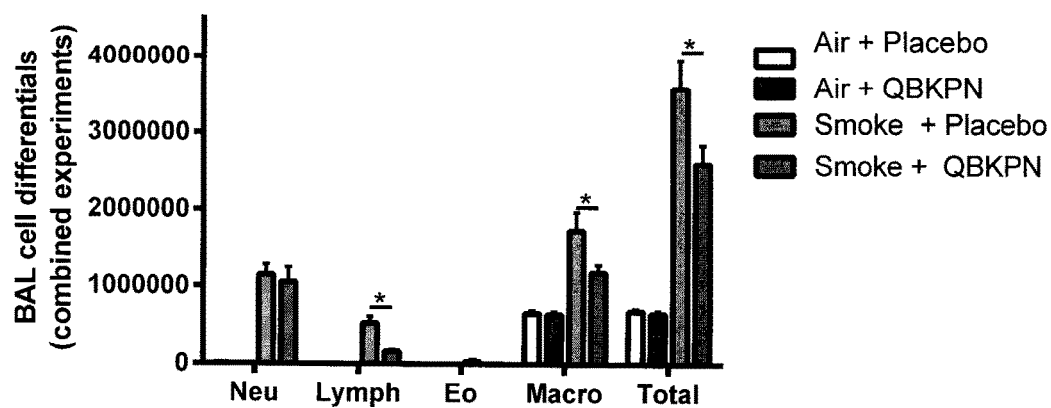
FIG. 27A is a bar graph illustrating aspects of an anti-inflammatory SSI treatment for COPD from an animal model, particularly BAL cell differential.
Figure 27B:
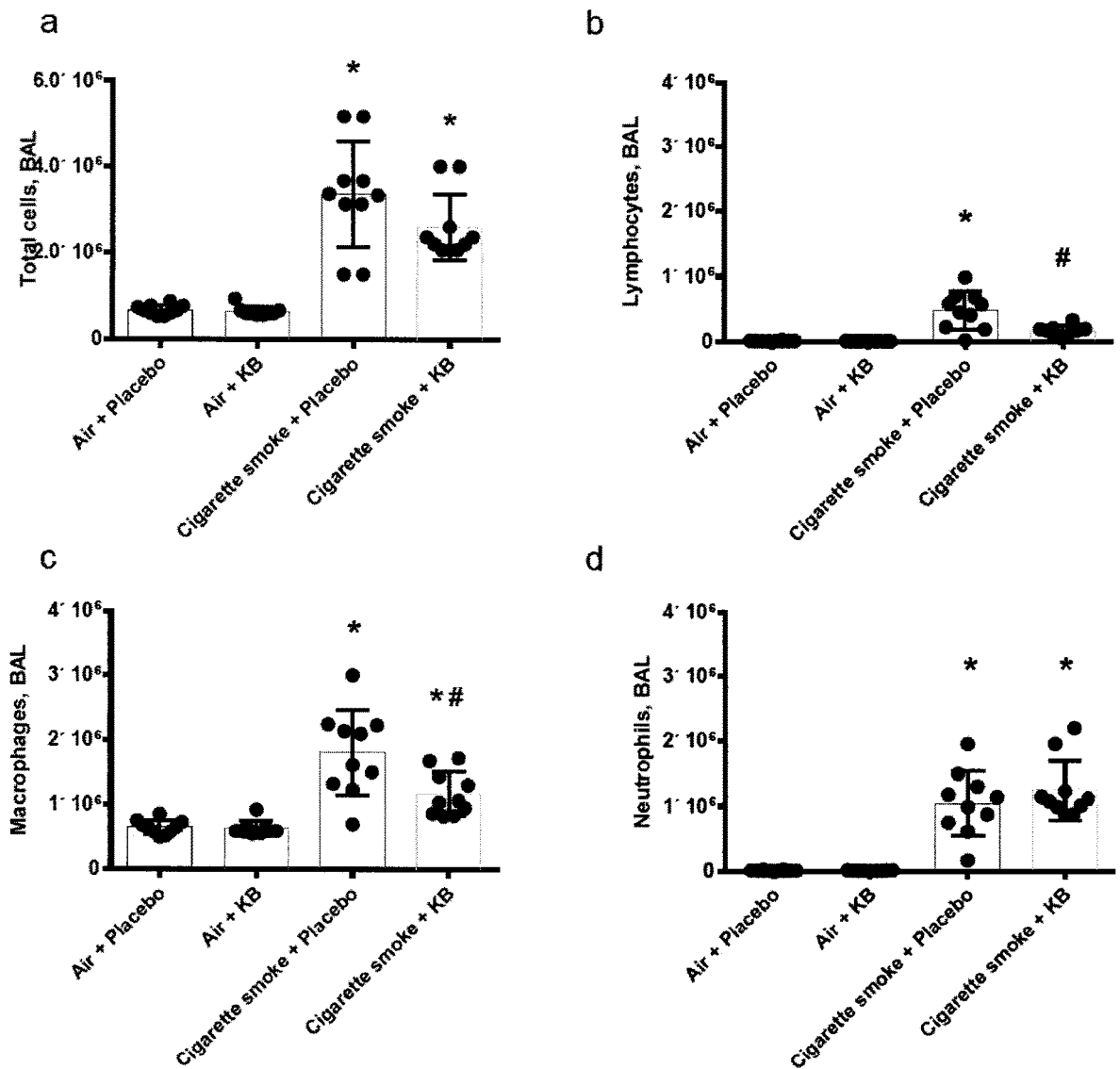
FIG. 27B reflects this data, illustrating that a KPN SSI intervention attenuated cigarette smoke exposure induced increases in lung macrophages and lymphocytes but not total cells or neutrophils.

Total BAL cell counts and cellular differentials were analysed to assess airway lung inflammation. FIG. 27A is a bar graph illustrating BAL cell differential, showing that QBKPN decreases the total BAL cell count after smoke exposure through reduction in lymphocyte and macrophage populations. In placebo treated animals, cigarette smoke exposure induced an elevation in total cell number in the BAL that was not attenuated with KPN intervention (FIG. 27B (a), p<0.05). The cigarette smoke exposure induced increase in BAL total cells was attributed to lymphocytes, macrophages, and neutrophils (FIG. 27B (b)-(d) p<0.05) but not eosinophils (p>0.05, data not shown). KPN intervention attenuated the increase in lymphocytes and macrophages in the cigarette smoke exposure group (p<0.05), although macrophages remained elevated relative to air+KPN (FIG. 27B (b)-(c). PN intervention had no impact on cigarette smoke induced increases in neutrophils (FIG. 27B (d)).

Figure 28A:
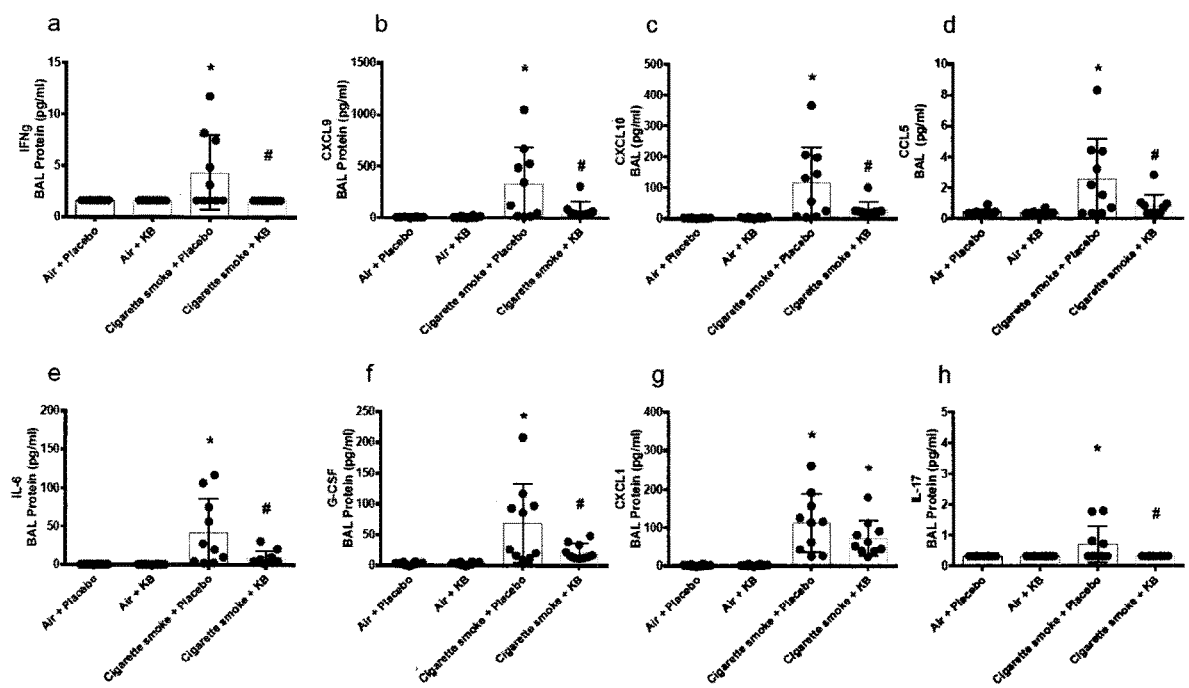
FIG. 28A-D.

Previous reports have indicated that mouse cigarette smoke exposure models result in a TH1 skewed inflammatory response. This Example illustrates that KPN SSI intervention attenuated cigarette smoke exposure-induced TH1-skewed lung inflammatory responses, as evidenced by multiplex analysis of 31 cytokines, chemokines, and growth factors that included TH1 and non-TH1 mediators. Cigarette smoke exposure induced 15 of 31 (46.7%) mediators measured in BAL fluid that included IFNγ, CXCL9, CXCL10, CCL5, IL-6, IL-17, G-CSF, CXCL1, LIF, CCL2, CCL3, CCL4, TNFα, eotaxin, and VEGF (p<0.05). IL-17 was elevated with cigarette smoke exposure in 4 of 10 samples at values close to the level of detection of this mediator (0.64 pg/ml). KPN intervention attenuated cigarette smoke-induced increases in IFNγ, CXCL9, CXCL10, CCL5, IL-6, G-CSF, and IL-17 (FIG. 28A), all mediators that are associated with a TH1 skewed inflammatory response. KPN SSI intervention had no impact on air-exposed animals for any mediator measured.

Figure 28B:
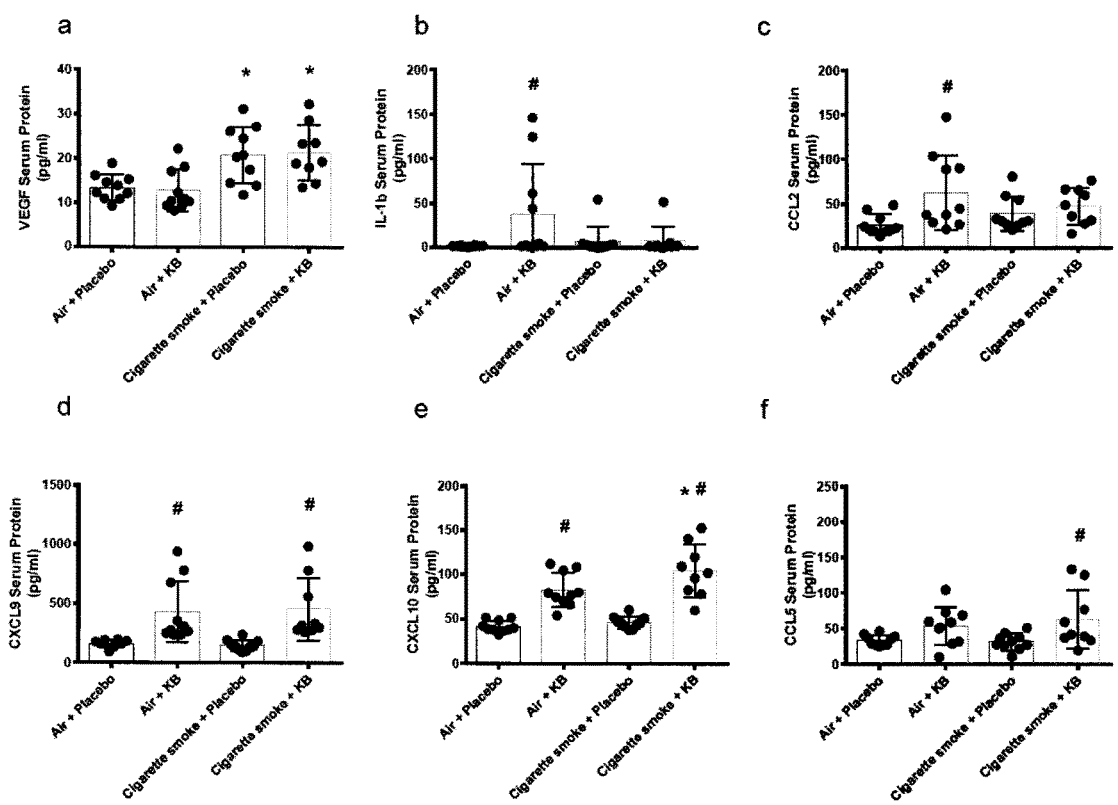

The serum immune mediator protein expression profile was minimally impacted by cigarette smoke exposure but is augmented by KPN intervention, as evidenced by the same multiplex assay of 31 mediators applied to the serum from the four experimental groups. Cigarette smoke exposure induced an increase in only VEGF, which had elevated levels relative to air exposed control (FIG. 28B(a), p<0.05). The KPN SSI intervention did not reverse the cigarette smoke exposure-induced elevation in serum VEGF. KPN intervention in air exposed animals decreased only 1 mediator, IL12p40, relative to air+placebo, while the levels of IL-1β, CCL2, CXCL9, and CXCL10 (FIG. 28B (b)-(d) p<0.05) were increased. In the smoke exposed mice, KPN intervention increased the levels of CXCL9, CXCL10, and CCL5 relative to the cigarette smoke+placebo group. Collectively these serum data illustrate that the SSI intervention induced a systemic impact independent of cigarette smoke exposure that may administered so as to be efficacious for the local suppression of cigarette smoke-induced lung inflammation.

Figure 28C:
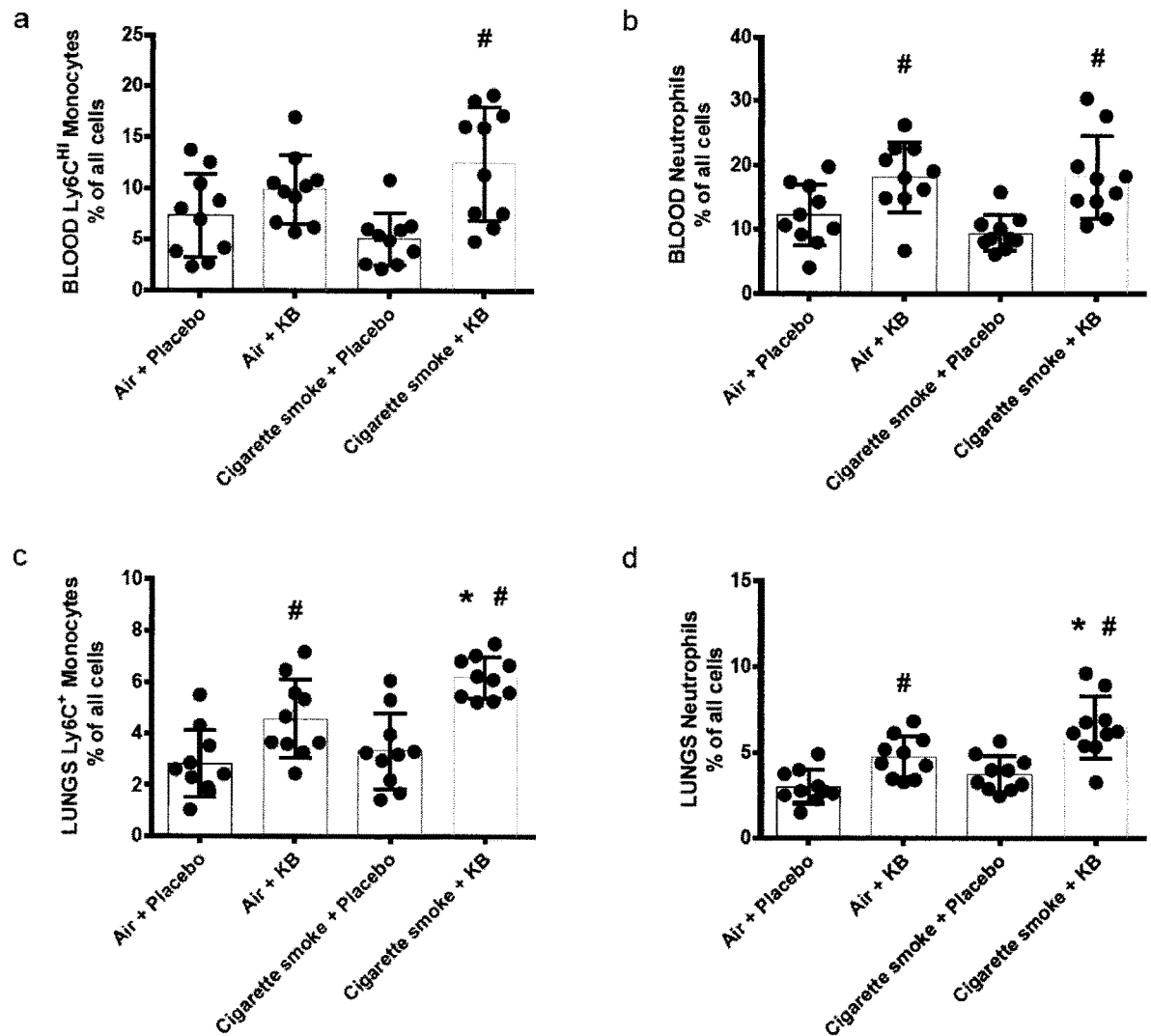

To illustrate a systemic cellular immune response in this COPD model, flow cytometry was used to assess the levels of Ly6C$^{HI}$ monocytes/macrophages, an inflammatory monocyte population, and neutrophils, in the blood after cigarette smoke exposure and KPN intervention. Cigarette smoke exposure induced no increase in blood Ly6C$^{HI}$ monocytes/macrophages or neutrophils (FIG. 28C (a)-(b)). Surprisingly, KPN SSI intervention increased the blood Ly6C$^{HI}$ monocytes/macrophages and neutrophils in the cigarette smoke exposure groups (p<0.05) and the neutrophils in the air-exposed animals. The increase in systemic Ly6C$^{HI}$ monocytes/macrophages and neutrophils was correlated with similar patterns for a local increase in the lung tissue (FIG. 28C (c)-(d)), where KB induced an increase in these cell types, which was further exacerbated by cigarette smoke exposure (p<0.05).

Figure 28D:
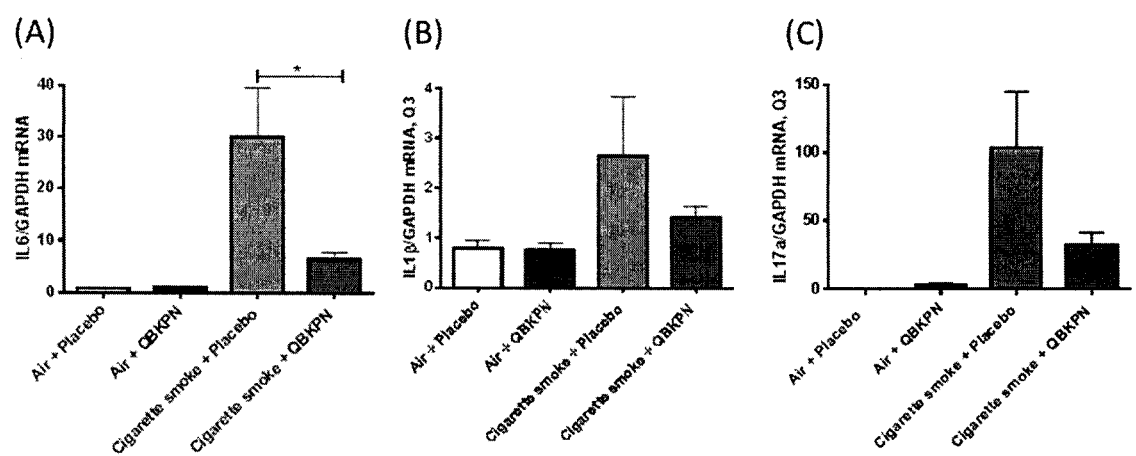

FIG. 28D includes three bar graphs for select lung gene expression profiles, illustrating that QBKPN decreases the expression of three important inflammatory cytokine genes (IL-6, IL-1beta, and IL-17A) in the lung tissue after smoke exposure.

Figure 29:
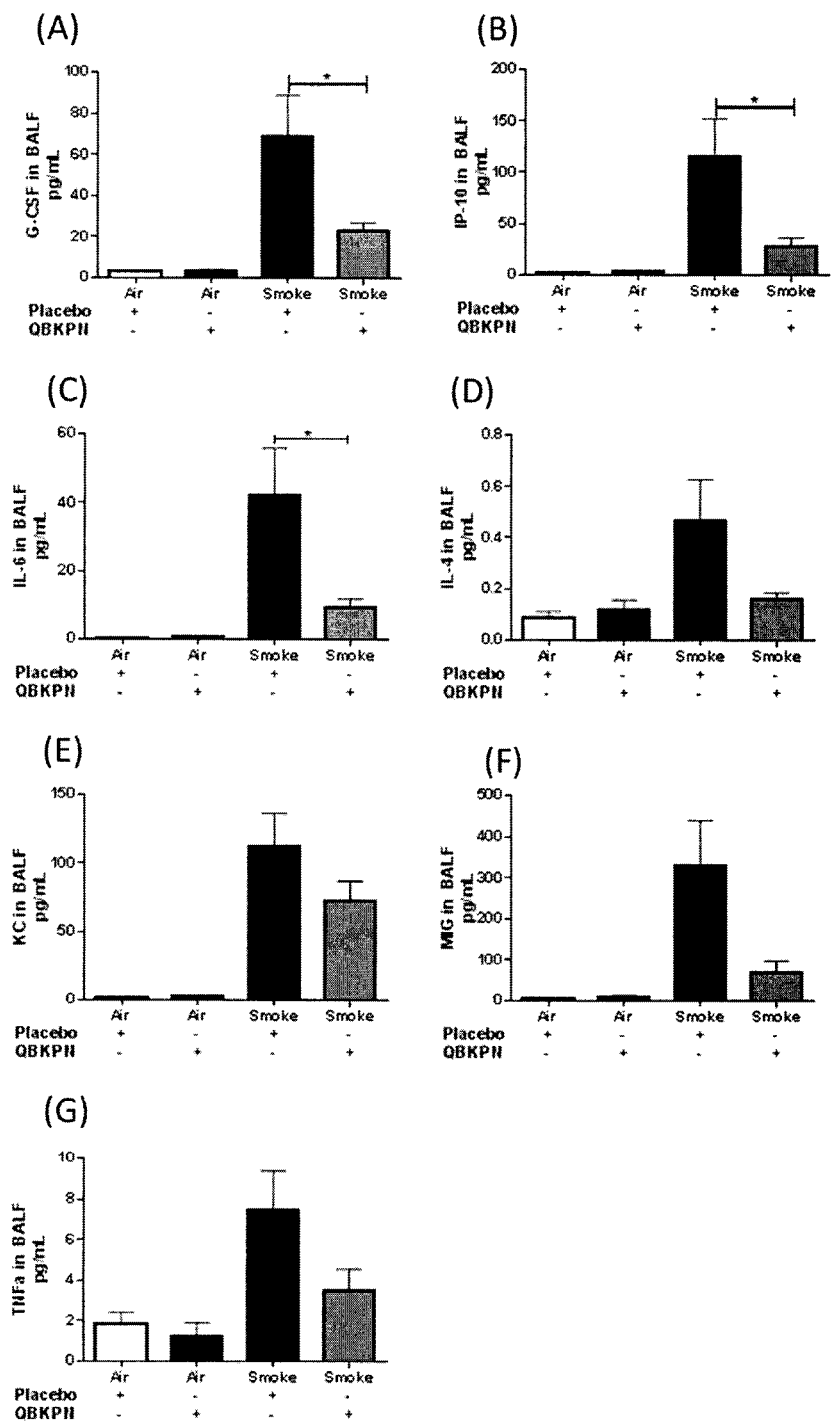
FIG. 29 is a series of bar graphs (A-G) illustrating aspects of an anti-inflammatory SSI treatment for COPD from an animal model, particularly select BAL cytokine expression profiles.

FIG. 29 illustrates select BAL cytokine expression profiles, with six bar graphs illustrating that QBKPN caused a significant decrease in G-CSF, IL-6 and IP-10 in the COPD model, and a downwards trend in IL-4, KC, MIG, TNFalpha.

Figure 30:
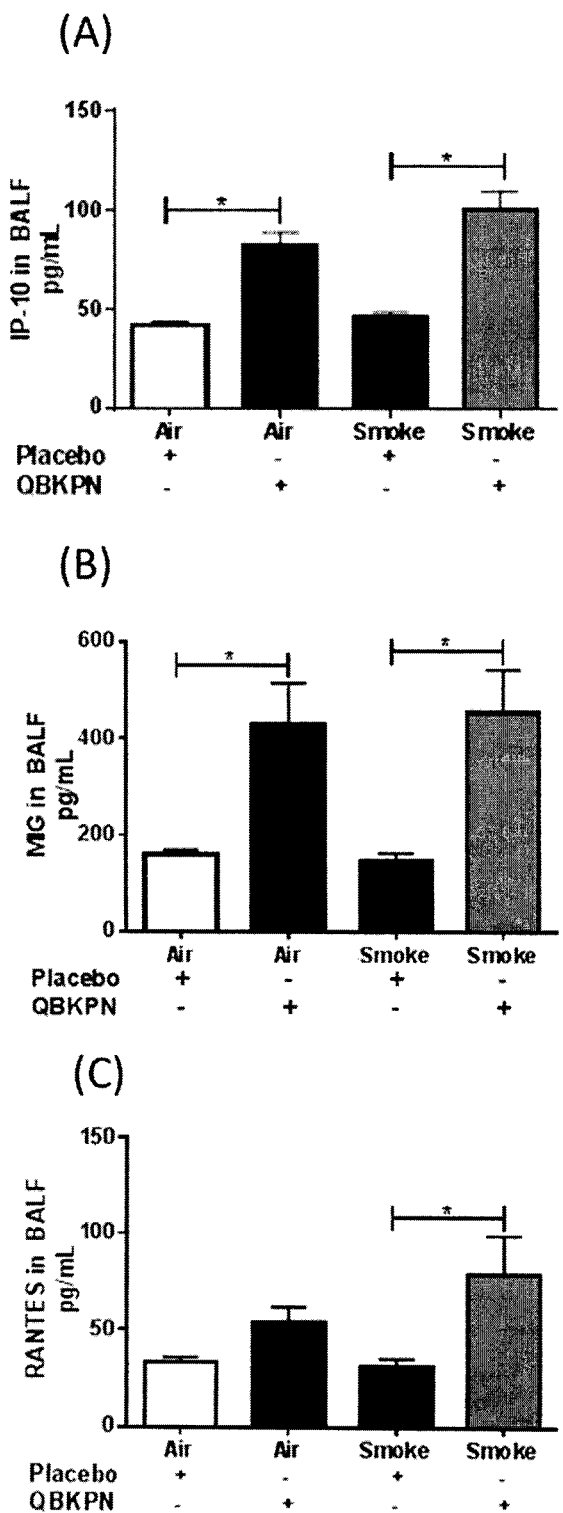
FIG. 30 is a series of bar graphs (A-C) illustrating aspects of an anti-inflammatory SSI treatment for COPD from an animal model, particularly serum cytokine expression profiles.

FIG. 30 illustrates serum cytokine expression profiles, identifying a number of markers for SSI efficacy, particularly elevated serum levels of IP-10, MIG and RANTES. These serum markers may accordingly be used as a biomarker for SSI efficacy, for example to identify responders or non-responders to a particular SSI, or as a marker of efficacious dosing in a dose adjustment protocol.

This Example illustrates that a QBKPN SSI decreased a number of markers of an inflammatory environment in a COPD model, in particular: decreased BAL total cells, lymphocytes and macrophages; decreased gene expression of cytokines that are usually elevated in COPD including IL-6, IL-1beta and IL-17A, and decreased levels of cytokines of importance in the BAL in COPD including IL-6, IP-10 and G-CSF. More particularly, these results demonstrate that KPN treatment attenuated cigarette smoke-induced TH1-skewed lung inflammation and BAL cellularity. In control air-exposed and experimental cigarette smoke-exposed animals, KPN SSI induced a systemic immune response that included immune mediator production, and mobilization of monocytes and neutrophils, which was mirrored in the local lung environment with an increase in Ly6C$^{HI}$ monocytes/macrophages and neutrophils. This Example therefore indicates that interventions with microbial components that enhance certain aspects of an immune response, rather than generally suppressing the immune responses, may be used to alter the course of cigarette smoke exposure related COPD pathogenesis.

COPD has many underlying pathways with other inflammatory diseases, including asthma and inflammatory bowel disease (IBD). IBD and COPD share common observations including an altered microbiome, immune dysfunction, altered epithelial cell function, and chronic inflammation. There is also significant overlap between asthma and IBD including altered respiratory microbiome and immune dysfunction. Over all, the similarities between COPD and other inflammatory disease that benefit from SSIs, as evidenced herein, indicates that enhancing aspects of the immune response with a repertoire of PRR agonists, such as microbial products or synthetic formulations, may be employed as a therapeutic approach to COPD.

In this Example of acute cigarette smoke exposure-induced inflammation, we observe an elevation in IFN-γ, CXCL9, CXCL10, CCL-5, IL-6, G-CSF and IL-17 in the BAL that is attenuated with KPN treatment. This reduction in TH1-skewed inflammatory mediators was associated with a concomitant reduction in lung macrophage and lymphocyte recruitment, with KPN treatment attenuating the quantity of BAL lymphocytes and macrophages. Interestingly, systemically, KPN induced a $T_H1$-skewed chemokine signature (CXCL9, CXCL10, CCL-5) in both the air-exposed and cigarette smoke exposed animals, similar to what is seen in infection. In effect, in parallel to the attenuation of $T_H1$ lung inflammation, KPN treatment induced a systemic immune activation with increases in $Ly6C^{HI}$ monocytes/macrophages and neutrophils. This Example accordingly indicates that KPN SSI actively stimulates aspects of an immune response that may be adapted to lead to mobilization and recruitment of TH1-skewed immune cells systemically, but a reduction locally in the BAL.

Systemically, this Example indicates that KPN SSI administration increased pro-inflammatory cytokines (e.g. IL-1β) and blood inflammatory monocytes (defined as $Ly6C^{HI}$) and neutrophils, similar to the response seen with an acute infection. We further identified an increase in the inflammatory monocytes and neutrophils in the lung tissue by flow cytometry. In the lung inflammation examples, Examples 15 and 16, in control mice (air exposed in the COPD study and saline exposed in asthma study) QBKPN SSI increases cytokine levels in the serum. These are accordingly available as biomarkers for efficacy, particularly IP-10 (CXCL10) which was increased in both the asthma and COPD examples in the QBKPN SSI treated control mice.

Example 17: *Klebsiella varicola* SSI

Figure 31:
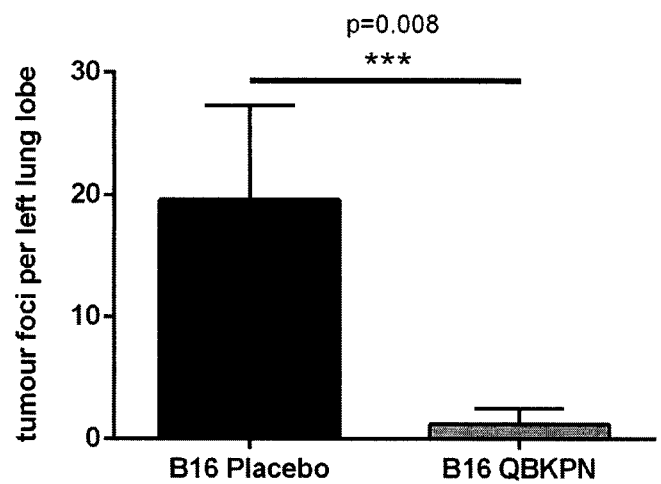
FIG. 31 is a bar graph illustrating reduced tumour burden in a B16 melanoma model of metastases to the lung using a *Klebsiella variicola* SSI.

In a murine B16 melanoma model of metastases to the lung, an SSI formulated with whole killed cells of *Klebsiella* phylogroup III (*K. varicolla*) was effective in reducing tumour burden, as illustrated in FIG. 31 (in which the *K. varicola* is identified as "QBKPN").

Example 18: CD25 Depletion

Figure 32:
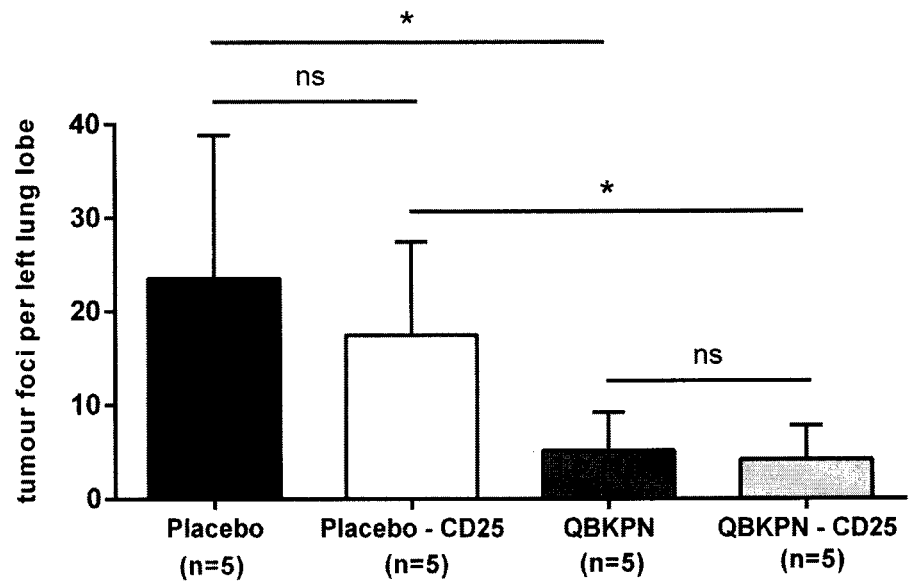
FIG. 32 is a bar graph illustrating QBKPN SSI efficacy in reducing lung nodules in the absence of CD25 positive cells.

CD25 is expressed on activated T cells, activated B cells, $T_{regs}$ and resting memory T cells (cells involved in adaptive immunity). Utilizing an anti-CD25 antibody, this example illustrates QBKPN SSI efficacy in reducing lung nodules in the absence of CD25 positive cells, as shown in FIG. 32. This illustrates that aspects of SSI efficacy are independent of CD25 positive adaptive immune cells in the B16 melanoma model (SSI was administered prophylactically, with mice challenged with B16 melanoma cells injected IV and tumour foci counted 18 days post B16 injection). Accordingly, aspects of the invention relate to modulating an immune response that is not dependent upon CD25+ cells, for example an innate immune response.

Example 19: Dose Dependency and Rae-1 Expression

Figure 33A:
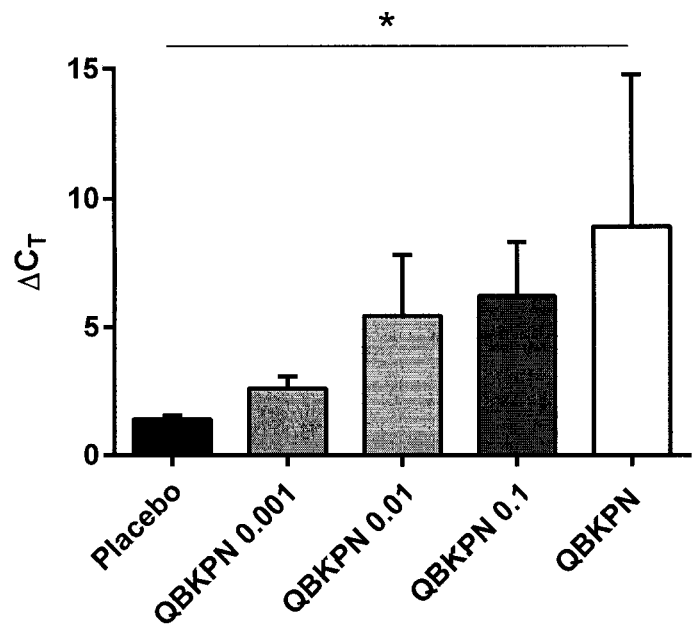
FIG. 33A is a bar graph illustrating delta $C_t$ (cycle threshold) values associated with a KPN SSI formulation (QBKPN) administered in a B16 melanoma model of metastases to the lung, with progressive dilutions of the KPN SSI (10×, 100× and 1000×). Delta $C_t$ values are inversely proportional to the amount of target nucleic acid in the sample. As illustrated, tumour burden increased with increasing dilution of the SSI.
Figure 33B:
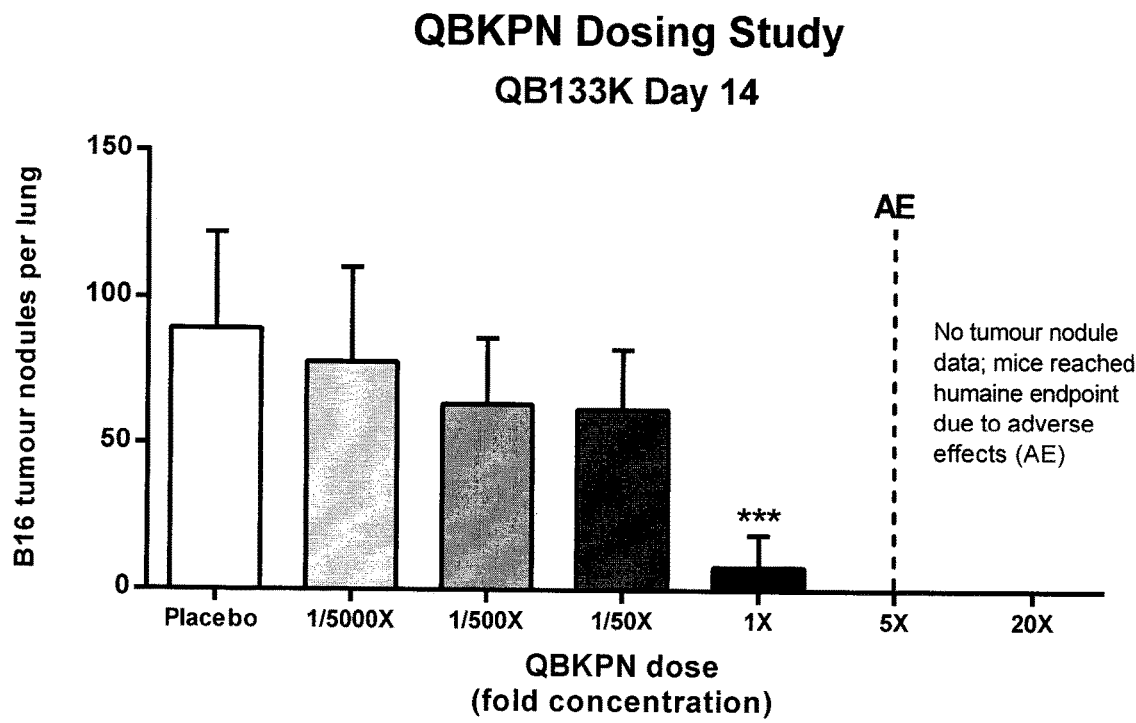
FIG. 33B is a bar graph illustrating a similar dose-dependent effect of the KPN SSI as measured by the number of B16 tumour nodules in the lung.
Figure 33C:
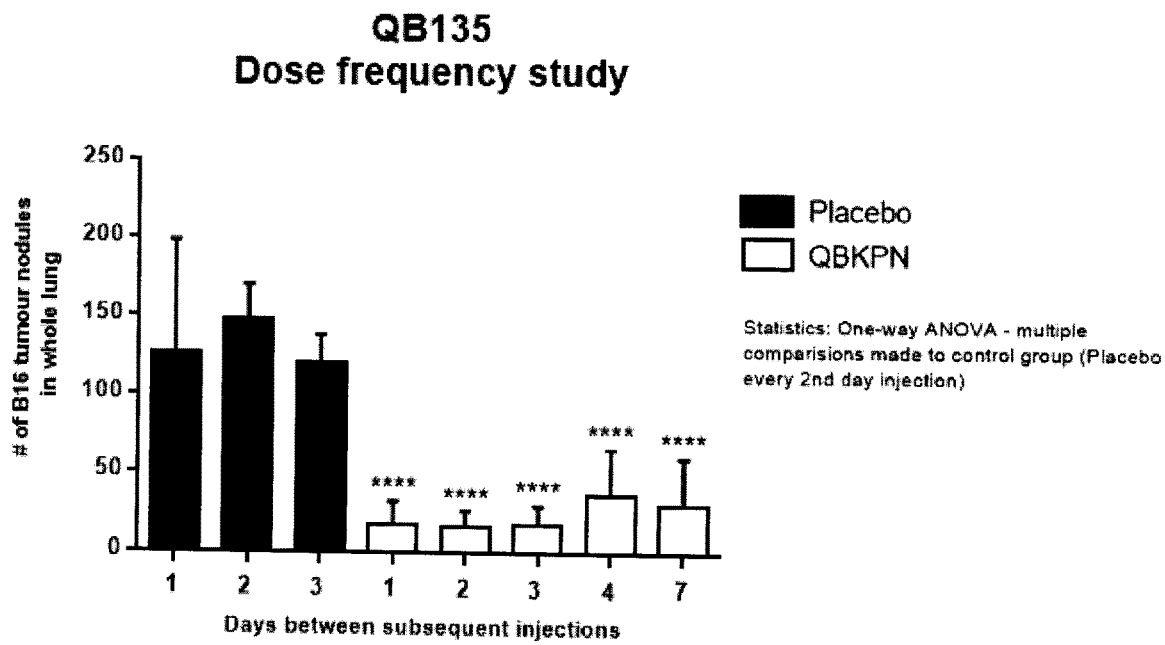
FIG. 33C is a bar graph illustrating that a variety of dosing regimes provide a therapeutic effect, with intervals between injections varying from 1 to 7 days all providing a therapeutic effect.

In a murine B16 melanoma model of metastases to the lung, the dilution of a KPN SSI progressively reduced efficacy (with tumour burden measured by QPCR quantification of Trp-1 expression). FIG. 33A shows the $C_t$ (cycle threshold) values associated with a KPN SSI formulation (QBKPN), and progressive dilutions of the KPN SSI (10×, 100× and 1000×), on day 5 following B16 challenge. $C_t$ values accordingly indicate the number of PCR cycles required for the fluorescent signal to cross the threshold (i.e. to exceed background level). Delta $C_t$ values took into account of $C_t$ values of a housekeeping gene, and the levels are accordingly inversely proportional to the amount of target nucleic acid in the sample. As illustrated, tumour burden increased with increasing dilution of the SSI. As shown in FIG. 33B, this dose dependency is also reflected in an assay of the number of B16 tumour nodules in the lung. FIG. 33C is a bar graph illustrating that a variety of dosing regimes provide a therapeutic effect, with intervals between injections varying from 1 to 7 days all providing a therapeutic effect.

Figure 34:
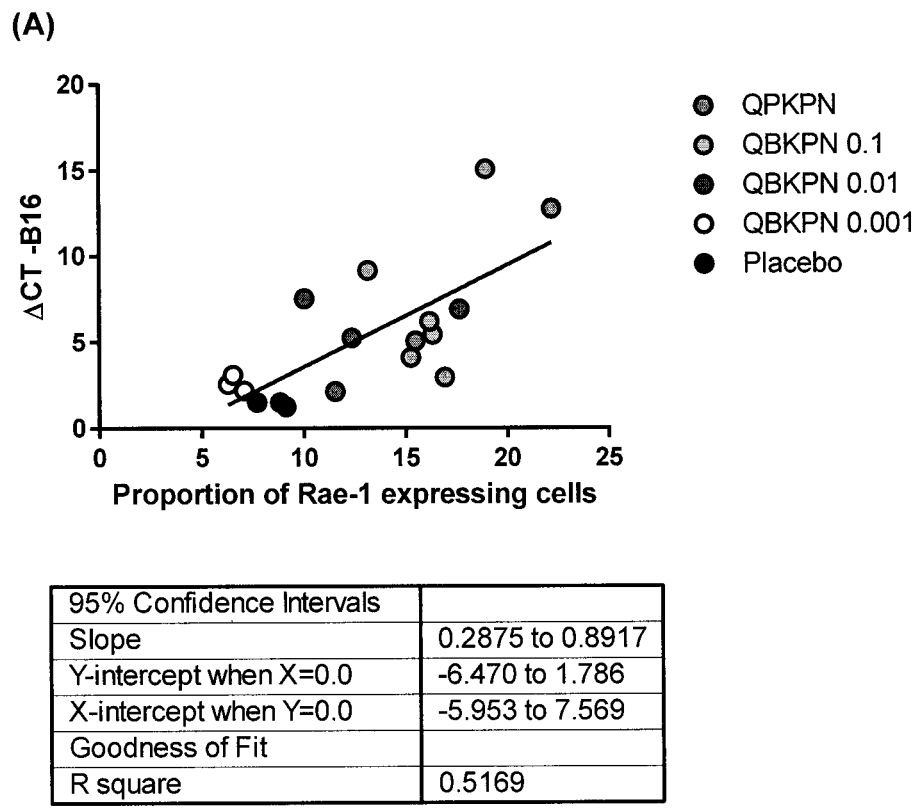
FIG. 34 includes two bar graphs illustrating that the proportion of cells that express Rae-1 was inversely correlated with tumour burden in a B16 melanoma model of metastases to the lung (A) and this is dependent on NKG2D expression (B).
Figure 34:
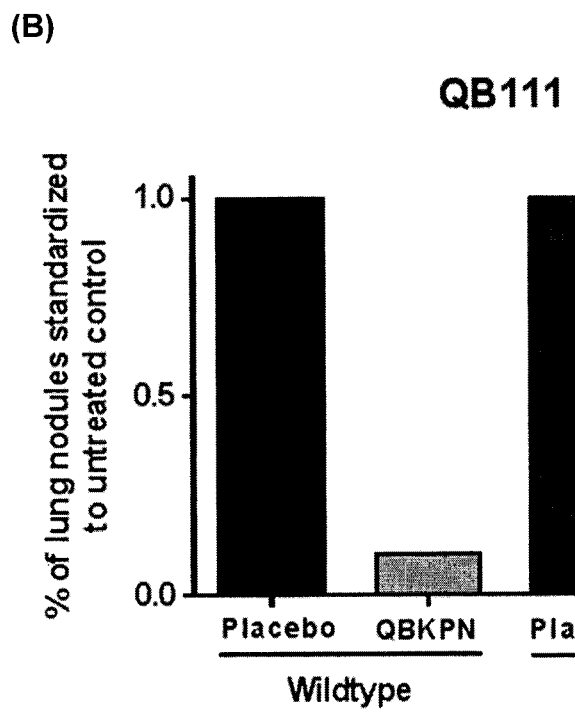

Further analysis, as shown in FIG. 34, illustrated that the proportion of cells that express Rae-1 was inversely correlated with tumour burden, evidencing the fact that SSIs increase target tissue Rae-1 expression in a dose-dependent manner. The increased Rae-1 signal would facilitate immune stimulation through NKG2D (see below) receptors on innate lymphoid cells, such as NK cells, leading to increased cancer cell killing and the reduced tumour burden evidenced in this example. In effect, high SSI induced Rae-1 expression leads to decreased cancer burden.

As shown in FIG. 34(B), in NKG2D (natural-killer group 2, member D) knockout mice, the therapeutic efficacy of QBKPN in the B16 lung metastasis model is abrogated. This illustrates the significant role of NKG2D signalling in various aspects of a therapeutic SSI response, reinforcing the significance of the evidence of increased Rae-1 expression in target tissues.

Example 20: Site Specificity

Lung

Figure 35:
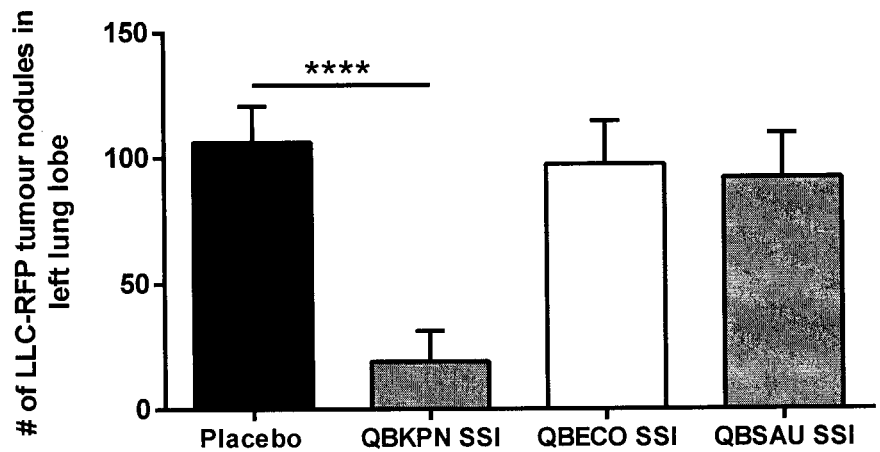
FIG. 35 is a bar graph illustrating that a QBKPN SSI provided a markedly stronger effect in reducing tumour nodules in the lung in a Lewis lung carcinoma (LLC)-RFP model.
Figure 36:
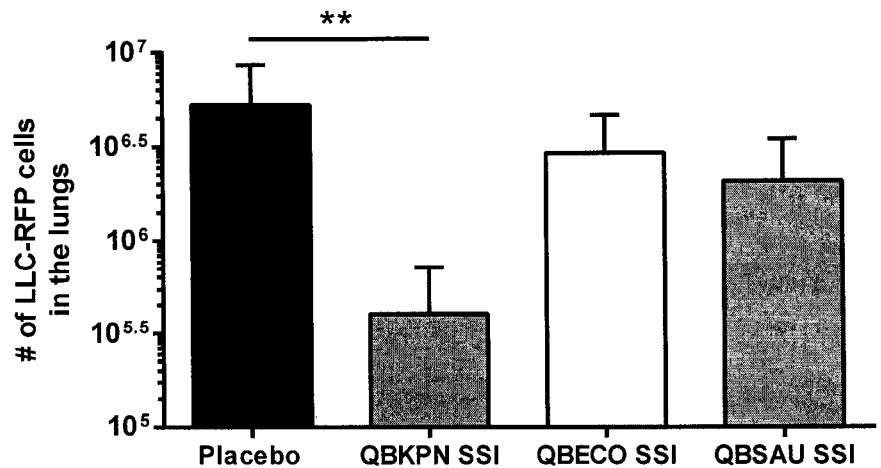
FIG. 36 is a bar graph illustrating a concomitant reduction in the number of LLC-RFP cells in the lungs at day 15 after inoculation with LLC.

In a murine Lewis lung carcinoma expressing red fluorescent protein (LLC-RFP), the efficacy of a KPN SSI (QBKPN) was compared to *E. coli* (QBECO) and *Staphylococcus aureus* (QBSAU) SSIs (KPN being a lung pathogen in mice while ECO and SAU are not). As illustrated in FIG. 35, QBKPN provided a markedly stronger effect in reducing tumour nodules in the lung. As illustrated in FIG. 36, there was a concomitant reduction in the number of LLC-RFP cells in the lungs at day 15 after inoculation with LLC.

Alternative data illustrates that while immune infiltrates with QBKPN and QBECO may be comparable at early time points in some systems, neutrophil levels are enhanced at day 7 (flow data) with QBKPN compared to QBECO. Also, gene array analyses evidences prolonged persistence of innate infiltrates in QBKPN vs QBECO (~72 hrs). These data further indicate that the ongoing immune response in lungs is different in response to QBKPN vs QBECO.

Colon

Figure 37:
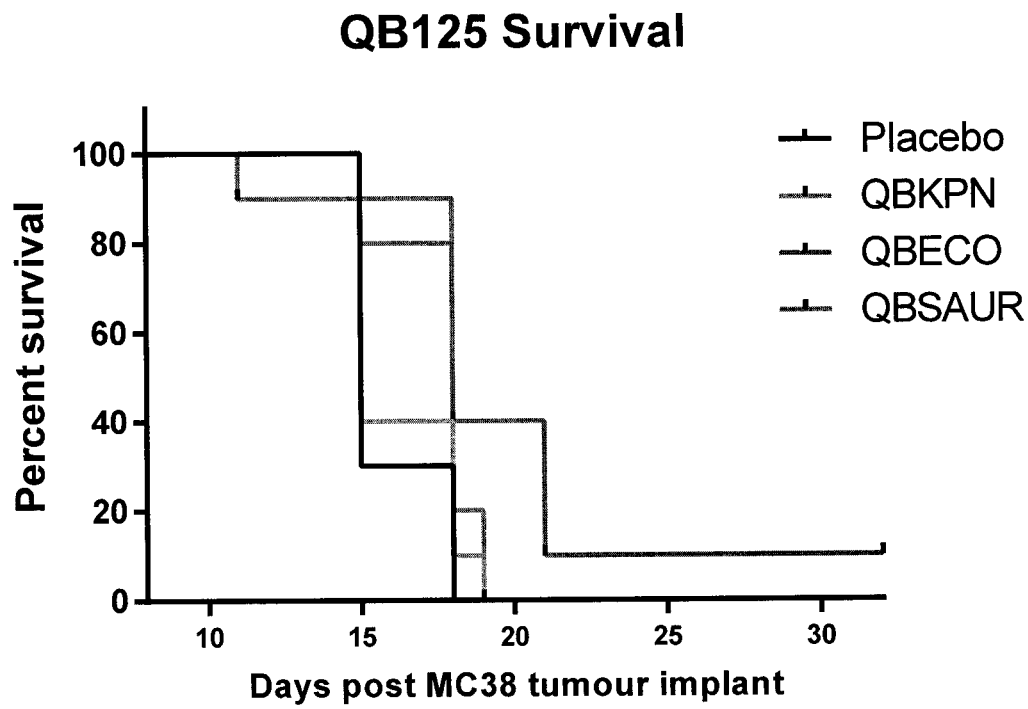
FIG. 37 is a line graph showing that a QBECO SSI conferred a greater survival advantage than did either QBKPN or QBSAU in an MC38 colon cancer model.

In an MC38 colon cancer model, QBECO conferred a greater survival advantage than did either QBKPN or 10× concentrated QBSAU (QBSAUR), as illustrated in FIG. 37.

Skin

Figure 5:
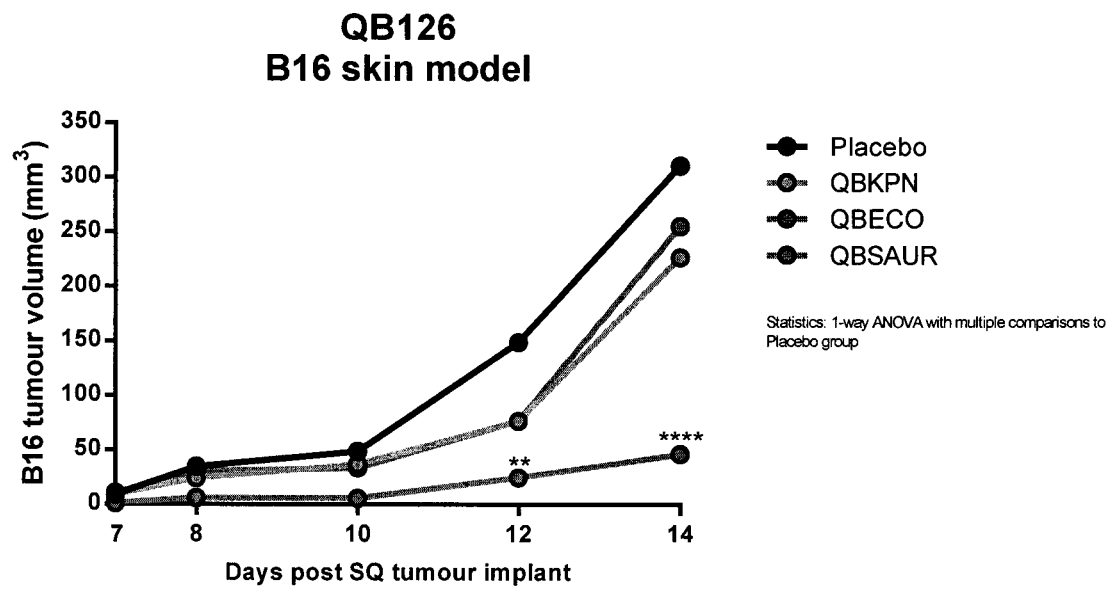
FIG. 5 is a line graph illustrating tumour volume over time for alternative SSI therapies in a murine B16 skin cancer model. 10×QBSAU and 1× QBSAU are denoted as QBSAUR and QBSAU, respectively, herein.
Figure 6:
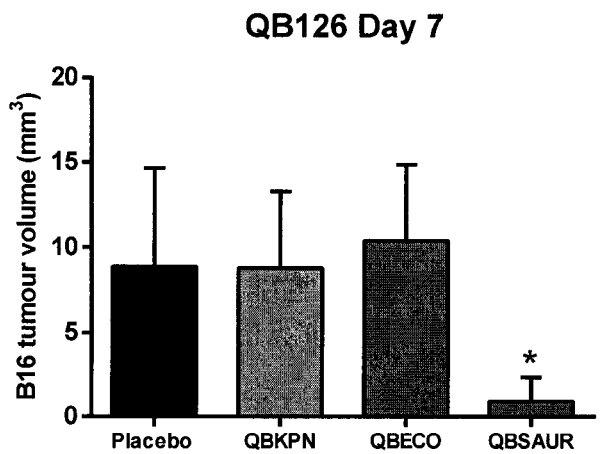
FIG. 6 is a bar graph illustrating tumour volume at day 7 for alternative SSI therapies in a murine B16 skin cancer model.
Figure 7:
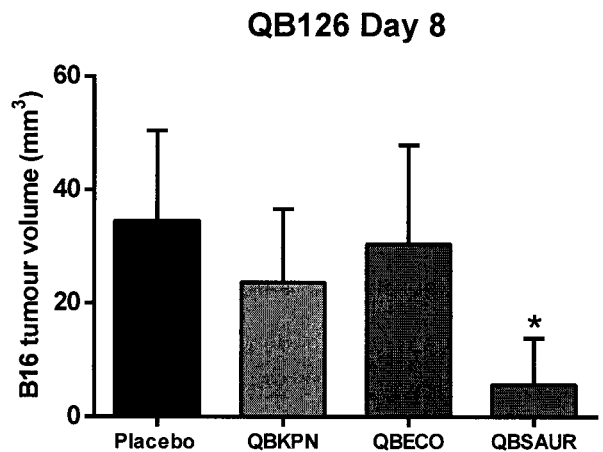
FIG. 7 is a bar graph illustrating tumour volume at day 8 for alternative SSI therapies in a murine B16 skin cancer model.
Figure 8:
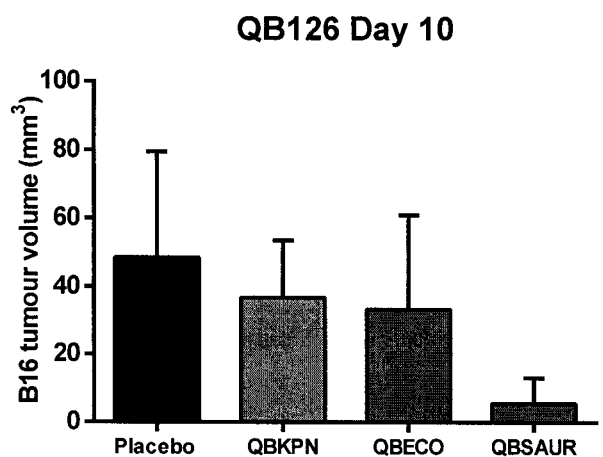
FIG. 8 is a bar graph illustrating tumour volume at day 10 for alternative SSI therapies in a murine B16 skin cancer model.
Figure 9:
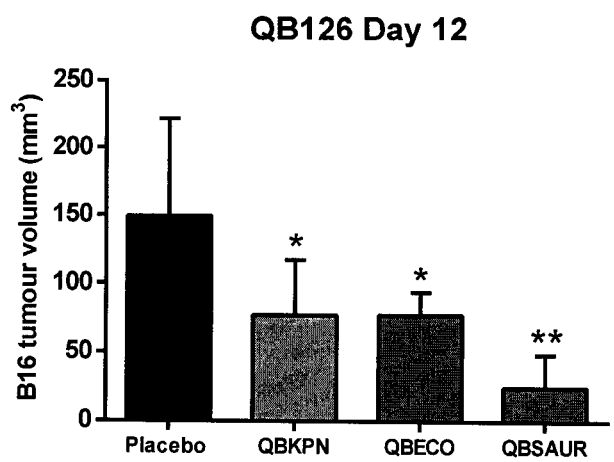
FIG. 9 is a bar graph illustrating tumour volume at day 12 for alternative SSI therapies in a murine B16 skin cancer model.
Figure 10:
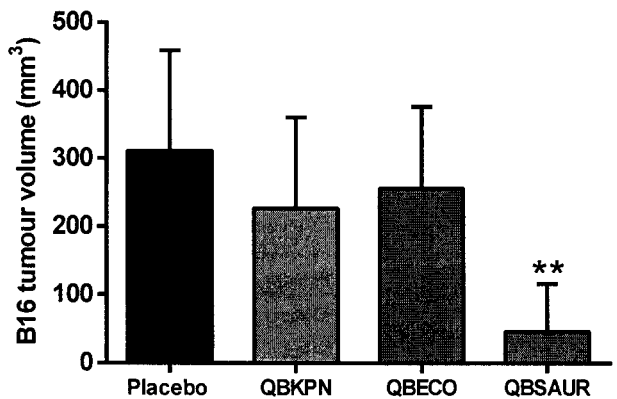
FIG. 10 is a bar graph illustrating tumour volume at day 14 for alternative SSI therapies in a murine B16 skin cancer model.

In a B16 melanoma model, 100,000 B16 melanoma cells were injected into the right flank of C57BL6 mice in a volume of 100 µl on Day 0, SSI treatment started on Day −10 and continued till Day +12. Tumour volume was monitored starting on Day 7, with the endpoint reached at Day 14. As shown in FIG. 5, 10× concentrated QBSAU or QBSAUR was much more effective than either QBKPN or QBECO at reducing B16 tumour volume in the skin.

Skin and Lung

The B16 melanoma model was used to seed lung tumours by IV administration, and to seed a skin tumour by subcutaneous dorsal injection, so that each animal has both cancer situated in the skin and cancer situated in the lung. In this study, mice (N=5/group) in the experimental group were injected SQ with the placebo (30 µl), QBKPN (30 µl of 4.91 $OD_{600}$), or 10×QBSAU (30 µl of 8.6 $OD_{600}$) every other day on day −8, −6, −4 and −2 prior to being implanted with the B16 melanoma cells ($1\times10^5$ cells/100 µl/mouse) both IV and SQ. Mice (N=5/group) in the 4 control groups were injected SQ with either QBKPN or 10×QBSAU on day −8, −6, −4, and −2:2 groups of these control mice were inoculated with the B16 tumour either IV (QBKPN single positive control) or SQ (10×QUSAU single positive control) on day 0, serving as single positive controls, whereas 2 groups of these control mice did not receive any tumour inoculation, serving as negative controls. SQ administration of either the SSI treatment or the placebo control was given to mice continuously every other day until the experiment was terminated on day 5 post tumour implant. Tumour burden in the lung and the skin were enumerated on day 5.

Figure 38:
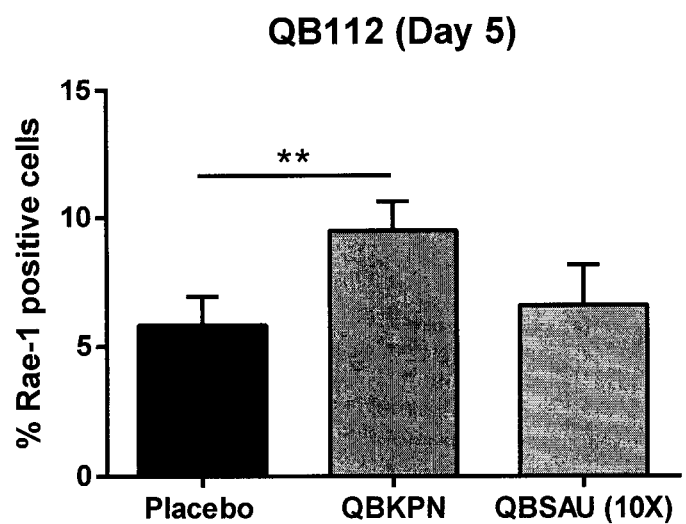
FIG. 38 is a bar graph illustrating that mice treated with a QBKPN SSI, but not 10×QBSAU, exhibited elevated lung-specific Rae-1 expression in a skin and lung tumour model.
Figure 39:
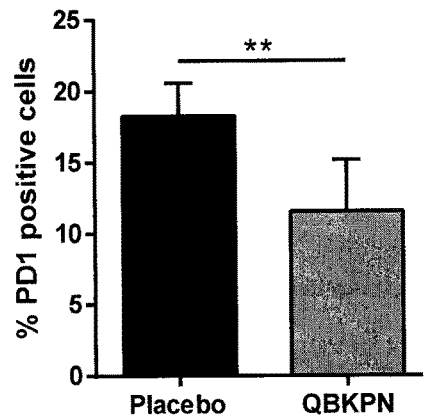
FIG. 39 is a bar graph illustrating decreased PD-1 expression in the lung of QBKPN-treated mice as compared to placebo-treated mice in the skin and lung tumour model.
Figure 40:
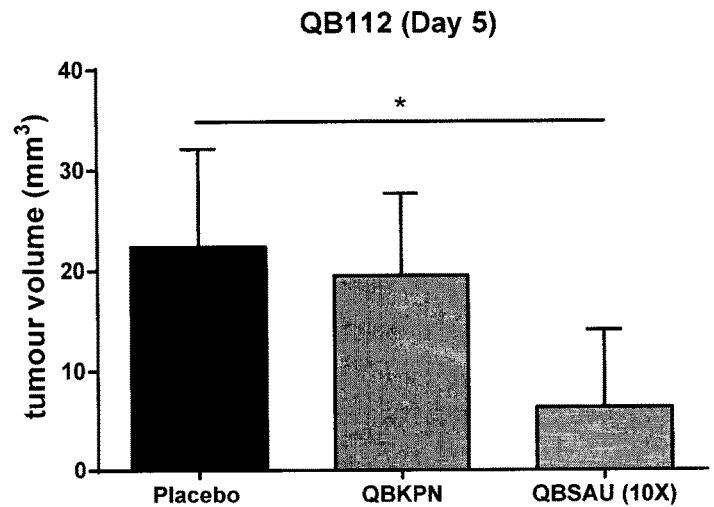
FIG. 40 is a bar graph illustrating that treating mice with 10×QBSAU, but not QBKPN, led to a decrease in the skin tumour burden as compared to placebo control in the B16 skin and lung tumour model.

Mice treated with QBKPN, but not 10×QBSAU, exhibited elevated lung-specific Rae-1 expression (FIG. 38) and recruitment of monocytes and neutrophils to the lung. There was also decreased PD-1 expression in the lung of QBKPN-treated mice as compared to placebo-treated mice in the same model (FIG. 39). In contrast, PD-L1 expression was not different among the groups in the lung. Treating mice with 10×QBSAU, but not QBKPN, led to a decrease in the skin tumour burden as compared to placebo control in the B16 skin and lung tumour model (FIG. 40).

Accordingly, QBKPN demonstrated site specificity in the lung by elevating Rae-1 expression and the recruitment of monocytes and neutrophils in animals having both skin and lung tumours. Similarly, 10×QBSAU demonstrated site-specific efficacy by reducing skin tumour in these animals.

Example 21: Dosing Routes and Schedules

Intravenous SSI vs. Subcutaneous SSI

Figure 41:
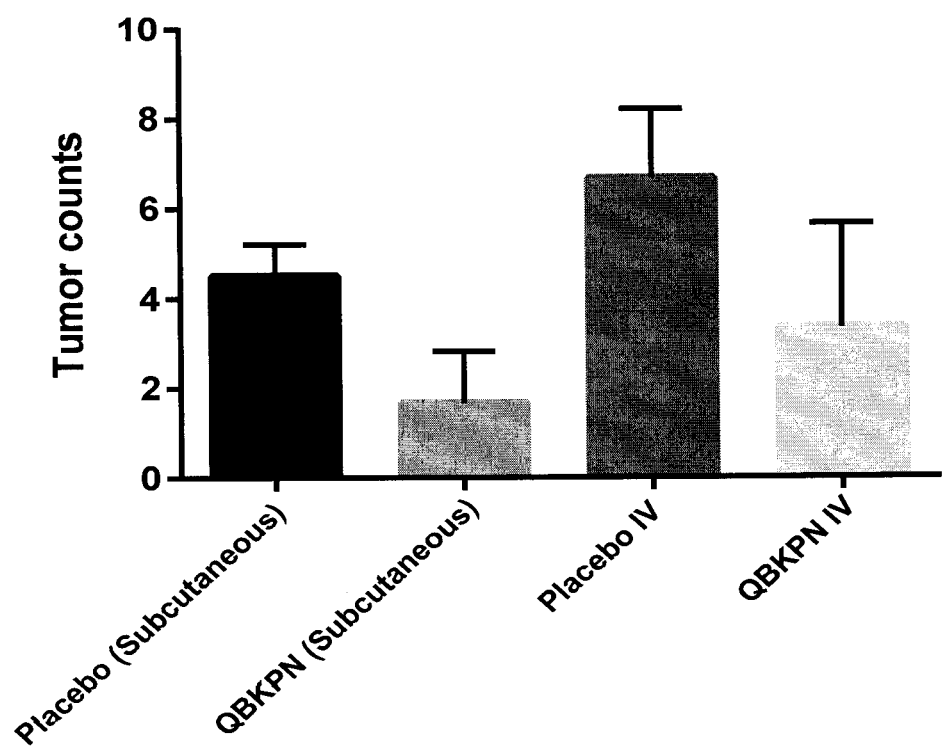
FIG. 41 is a bar graph illustrating that both intravenous (IV) SSI and subcutaneous (SQ) SSI treatments provide therapeutic benefit in a B16 lung metastasis model.

In this example, a KPN SSI (QBKPN) was administered either IV or SQ in a B16 lung metastasis model. On day 0, B16 cells were administered IV to seed tumours. On days 1, 3, 5, and 7, KPN SSI was administered (IV or SQ). On day 9, the endpoint was reached and tumour counts measured. As illustrated in FIG. 41, both routes of administration provide therapeutic benefit.

Prophylaxis vs Treatment Schedules

Figure 42:
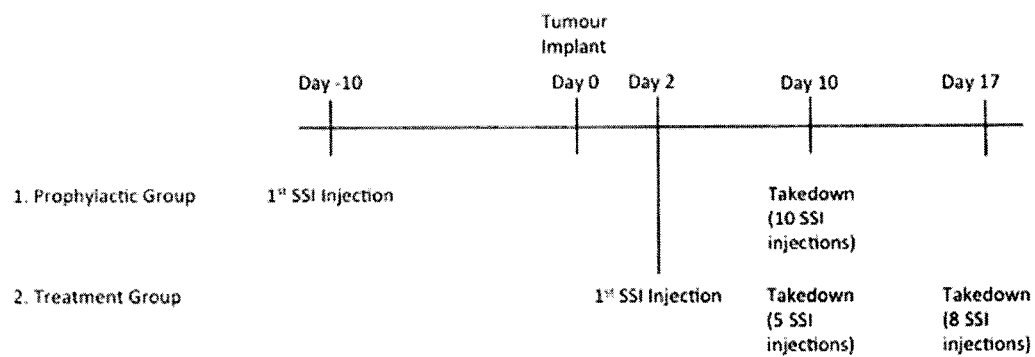
FIG. 42 is a schematic time line illustrating the study design for an example based on efficacy of QBKPN in a treatment and prophylaxis of cancer in a B16 lung cancer model.
Figure 43:
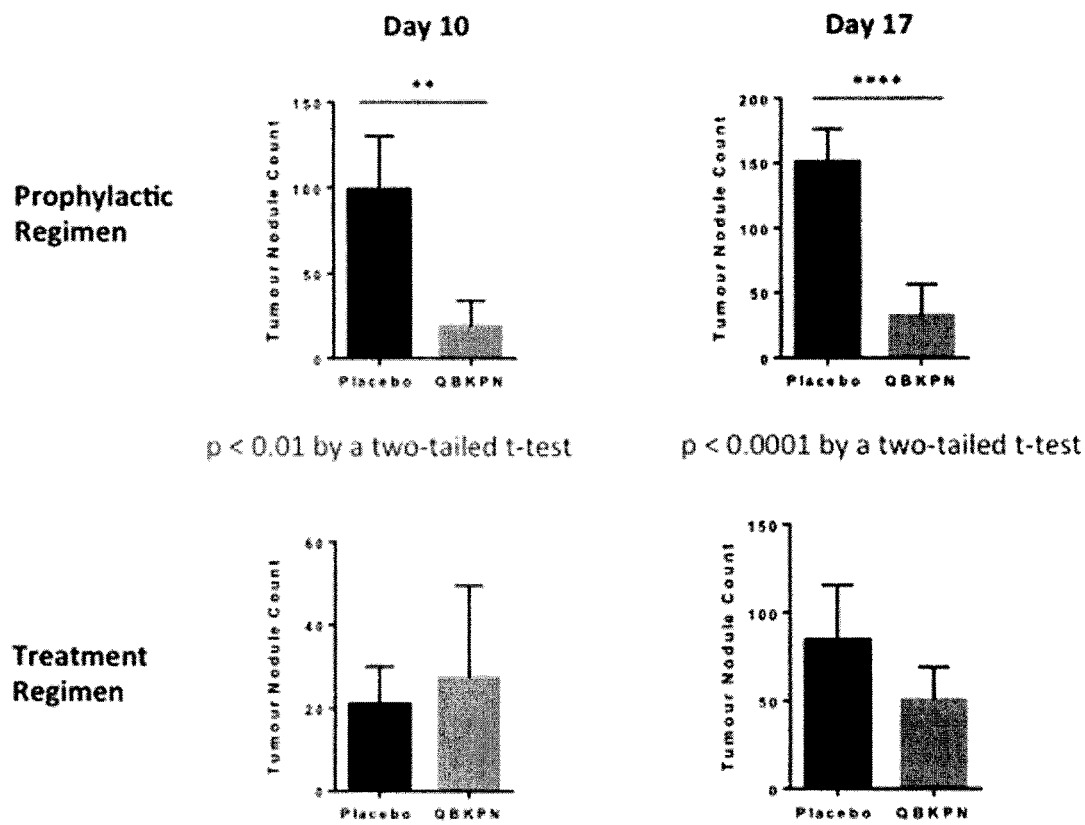
FIG. 43 includes 4 bar graphs illustrating efficacy of QBKPN in a treatment and prophylaxis of cancer in a B16 lung cancer model.
Figure 44:
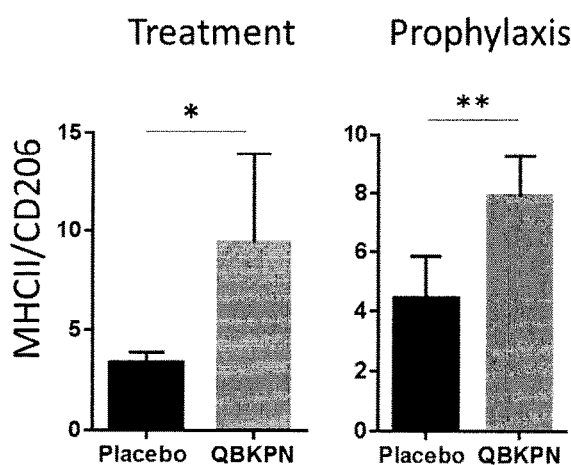
FIG. 44 is a bar graph illustrating aspects of the efficacy of QBKPN in a treatment and prophylaxis of cancer in a B16 lung cancer model.

In this example, the scheduling of SSI treatment, either before challenge with cancer cells (prophylaxis) or after challenge (treatment) was compared. This example also demonstrates immune correlates linked with efficacy, particularly the M1/M2 ratio of macrophages. FIG. 42 is a schematic illustration of the study design, based on efficacy of QBKPN in a treatment versus prophylactic regimen in the B16 lung cancer model. As illustrated in FIG. 43, while the prophylactic regimen provided earlier therapeutic benefit, by day 17 the treatment regimen shows a very strong trend of efficacy. The efficacy of both prophylactic and treatment regimens was reflected in common correlates of efficacy in the M1/M2 macrophage ratios in the lung with alternative M2 marker CD206, as illustrated for the treatment group at day 10 and the prophylactic group at day 17 in FIG. 44.

Early Time Point Blood Analysis

Figure 45:
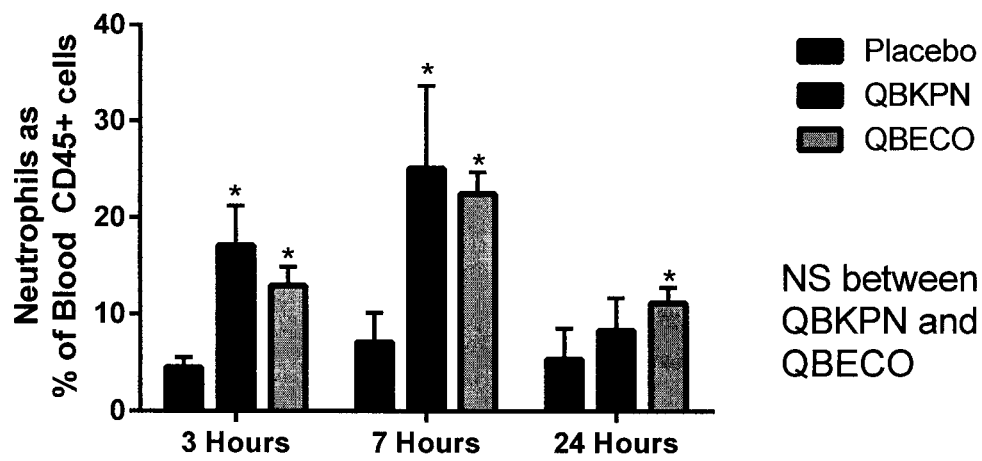
FIG. 45 is a bar graph illustrating aspects of how quickly SSI therapies have detectable therapeutic effects involving myeloid cell populations, particularly neutrophils.
Figure 46:
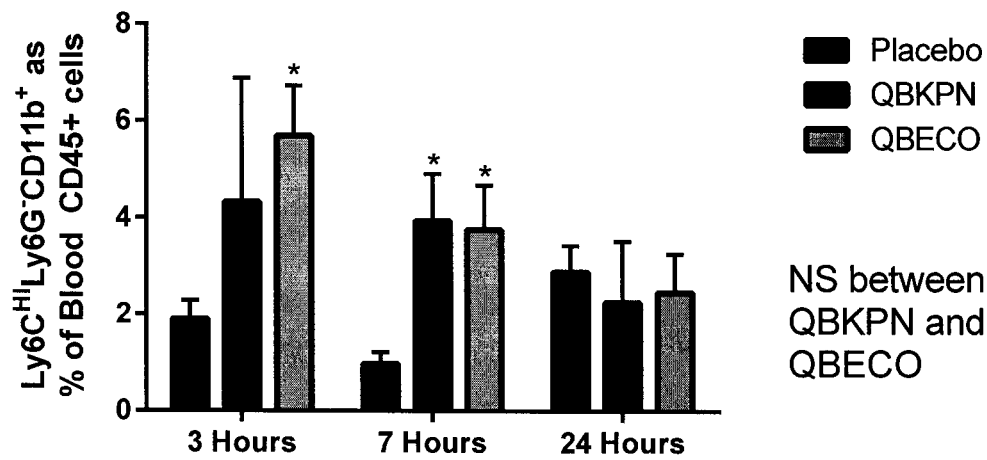
FIG. 46 is a bar graph illustrating aspects of how quickly SSI therapies have detectable therapeutic effects involving myeloid cell populations, particularly Ly6C monocytes.

This example illustrates aspects of how quickly SSI therapies have detectable therapeutic effects involving myeloid cell populations, providing examples of therapeutic biomarkers. As illustrated in FIG. 45, neutrophils increase at all time points for QBKPN and QBECO SSIs, with significant increases seen even within 3 hours post injection. As illustrated in FIG. 46, $Ly6C^{HI}Ly6G+CD11b+$ cells (Ly6C monocytes) were significantly increased at both 3 and 7 hours, with a decreasing trend that falls back to placebo levels by around 24 hours. The cellular immune response provoked by an SSI therapy may accordingly be characterized by a rapid onset, within hours, followed by a resolution within days. This pattern of cellular response supports a dosing schedule with repeated administrations at an interval that is measured in days, for example one administration every 1, 2, 3, 4, 5, 6, or 7 days.

Example 22: SSI Cytotoxicity

Figure 48:
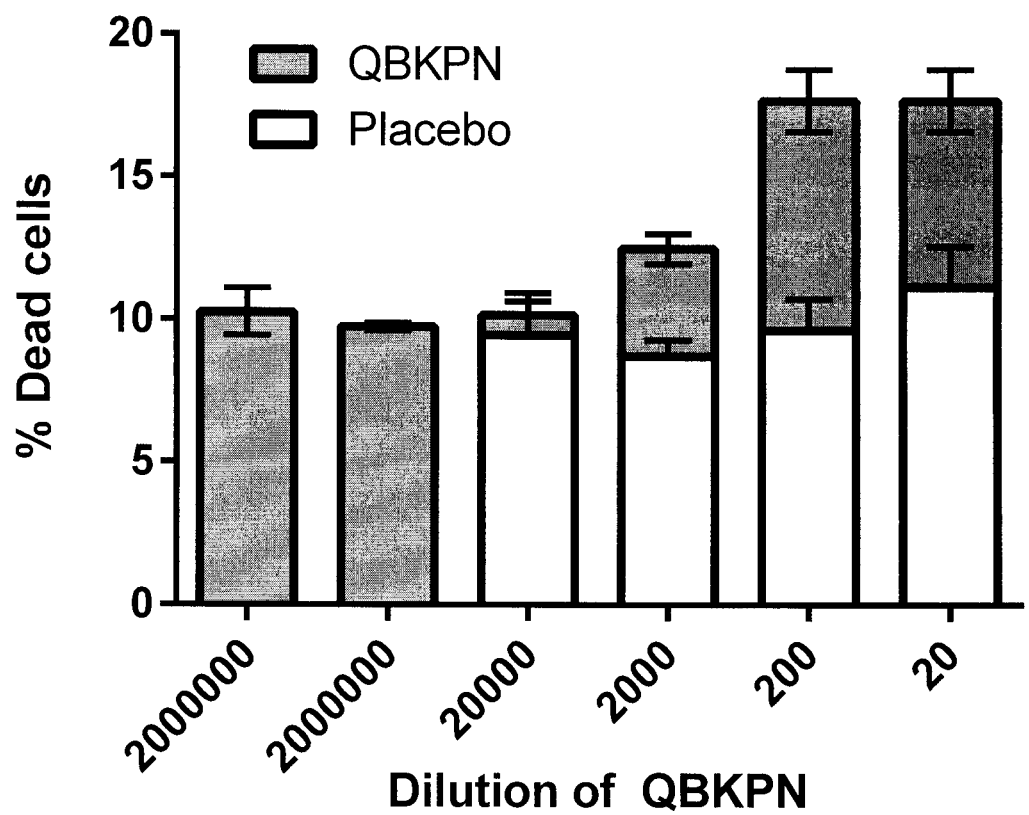
FIG. 48 is a bar graph illustrating that a QBKPN SSI increases NCI-H358 cancer cell death at high doses (1/20, 1/200 dilution) in a 24-hour killing assay.
Figure 49:
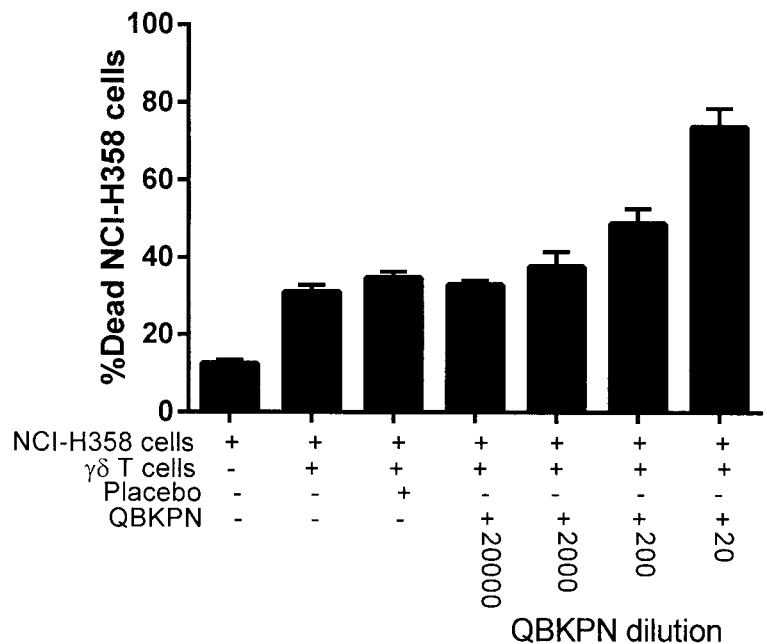
FIG. 49 is a bar graph illustrating that a KPN SSI increases γδT cell mediated killing of NCI-H358 cancer cells at alternative doses (1/20 dilution, 1/200 dilution) in a 24 hour cell killing assay.
Figure 50:
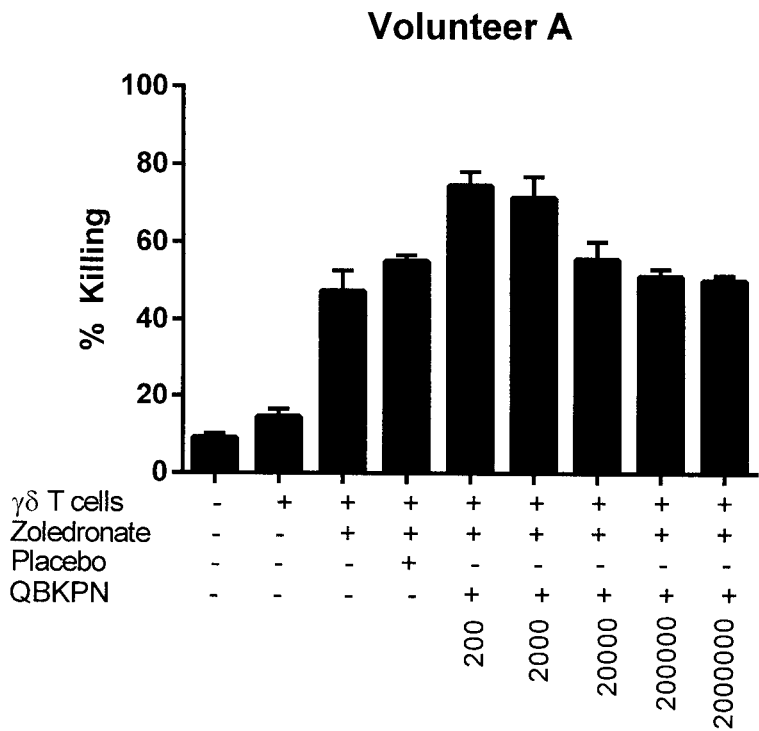
FIG. 50 is a bar graph illustrating that a KPN SSI (QBKPN) potentiated the effect of zoledronate in inducing γδ T cell mediated cancer cell lysis, at 1/200 and 1/2000 dilutions in a 24 hour cell killing assay.

This example illustrates that an SSI (QBKPN) can directly cause an increase in cancer cell death at high doses. NCI-H358 cells (a human lung cell line) were incubated in vitro with successive dilutions of QBKPN for 24 hours. Efficacy was assessed using a carboxyfluorescein succinimidyl ester (CFSE) labelling assay (a green fluorescent cell staining dye to label target cells) with the red live/dead viability dye 7-AAD (7-aminoactinomycin D) used to identify the killed/dead cells present in the cytotoxicity assay sample. As illustrated in FIG. 48, QBKPN increases NCI-H358 cancer cell death at high doses (1/20, 1/200 dilution) in this 24 hour killing assay. Using the same assay, it was also shown that the KPN SSI increases γδ T cell mediated killing of the NCI-H358 cancer cells at similar doses (1/20 dilution, 1/200 dilution) in the 24 hour killing assay, as illustrated in FIG. 49. In addition, the KPN SSI (QBKPN) potentiated the effect of zoledronate in inducing γδ T cell mediated cancer cell lysis, at 1/200 and 1/2000 dilutions, as shown in FIG. 50.

As this example illustrates, in select embodiments, SSIs can be administered directly to cancerous tissues, for example at the site of surgical resection of a cancer. For example, an SSI, such as QBSAU, may be applied topically to a melanoma in the skin or to the site of a surgical excision of a skin melanoma.

Example 23: NKG2D Knockout Mice in the MC-38 IP Injection Model

This example illustrates the involvement of the NKG2D receptor in mediating a therapeutic response to an SSI. This was shown in a murine survival study after IP injection of MC-38 cells (a murine adenocarcinoma cell line derived from a primary mouse colon carcinoma). The tumour cells were injected intraperitoneally in order to allow the tumour cells to seed the gut, creating a MC-38 cell colon cancer model. QBECO treatment was compared to placebo in wildtype mice (C57BL/6 mice) and NKG2D knockout mice (on a C57BL/6 background). Wildtype and NKG2D mice were treated with either QBECO or placebo (10 per group) for 10 days every second day before MC-38 injection. Treatment was continued throughout the survival study every second day.

Figure 51:
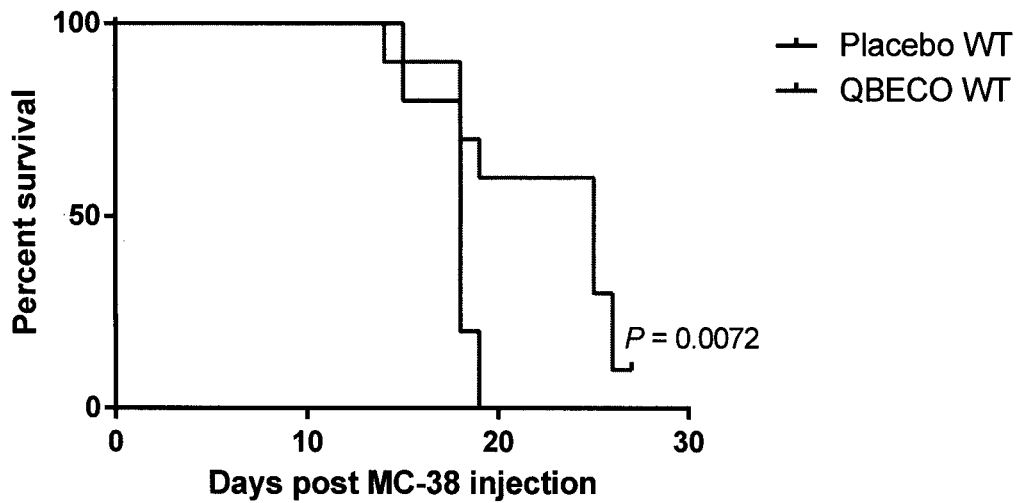
FIG. 51 is a line graph illustrating the therapeutic efficacy of a QBECO SSI in a MC-38 colon cancer model.
Figure 52:
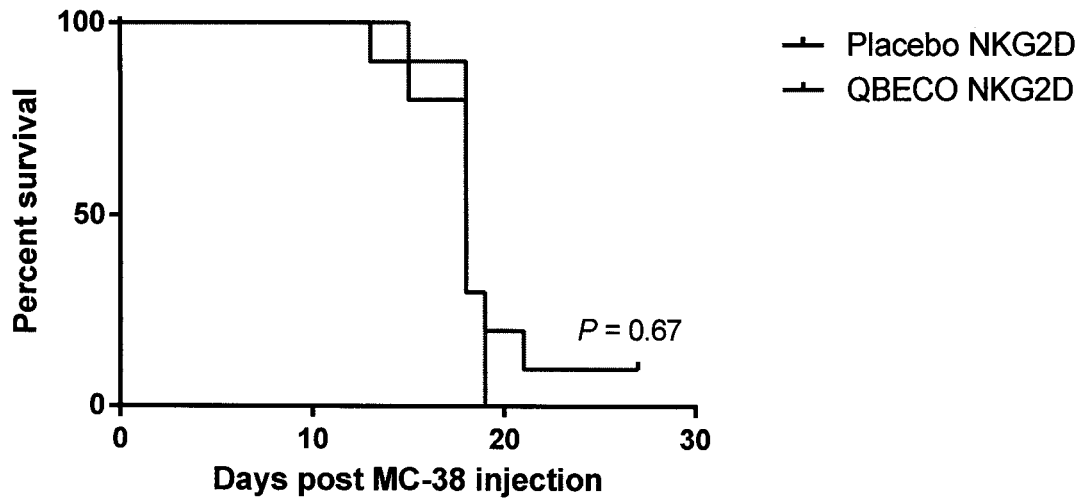
FIG. 52 is a line graph illustrating that NKG2D expression is correlated with QBECO efficacy in a MC-38 colon cancer model using NKG2D knockout mice.

As illustrated in FIG. 51, this study confirmed the therapeutic efficacy of QBECO in the MC-38 colon cancer model, showing in the wildtype mice a statistically significant increase in survival with QBECO treatment compared to placebo treatment. As illustrated in FIG. 52, NKG2D expression is correlated with QBECO efficacy, as there was no statistical difference in survival between NKG2D knockout mice treated with either QBECO or placebo. Immunophenotyping confirmed that the NKG2D knockout mice had reduced levels of NKG2D positive cells. Interestingly, QBECO caused a decrease in NKG2D at each time point within the wildtype mice (illustrating the use of NKG2D expression as a biomarker for SSI efficacy). Immunophenotyping also showed a characteristic increase in neutrophils by day −9 and monocytes by day −1 in both wildtype and NKG2D KO mice treated with QBECO compared to placebo. There was also an increase in PDL1+ after QBECO treatment, with QBECO causing an increase in PDL1+ cells in the blood throughout the experiment, with significance in wildtype mice at day −9 and −1, and a similar by attenuated pattern in NKG2D knockout mice. In wildtype mice, QBECO caused an increase in PD1+ cells in the blood in non-tumour bearing mice (Day −9, Day −1), while in tumour bearing mice QBECO induced an initial increase in PD1+ cells which was attenuated by Day 11 in a trend that continued so that at survival QBECO caused a decrease in PD1+ cells in the blood. NKG2D knockout mice follow this trend with less magnitude and no significance. Together, this data illustrates that PD1 and PDL1 may be used as biomarkers indicative of SSI efficacy.

Example 24: Treating Neutropenia

Figure 53:
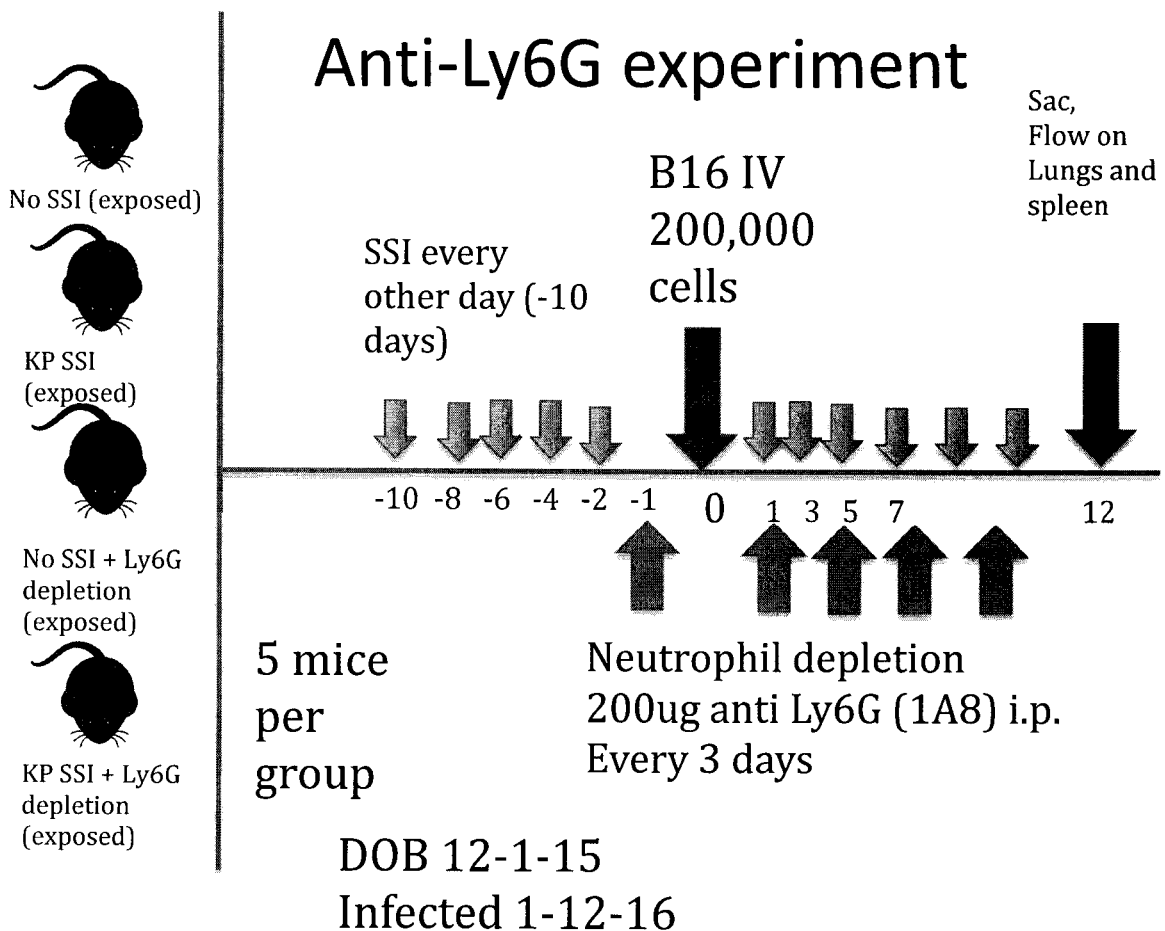
FIG. 53 is a schematic representation of a treatment schema in a model neutropenia system.
Figure 54:
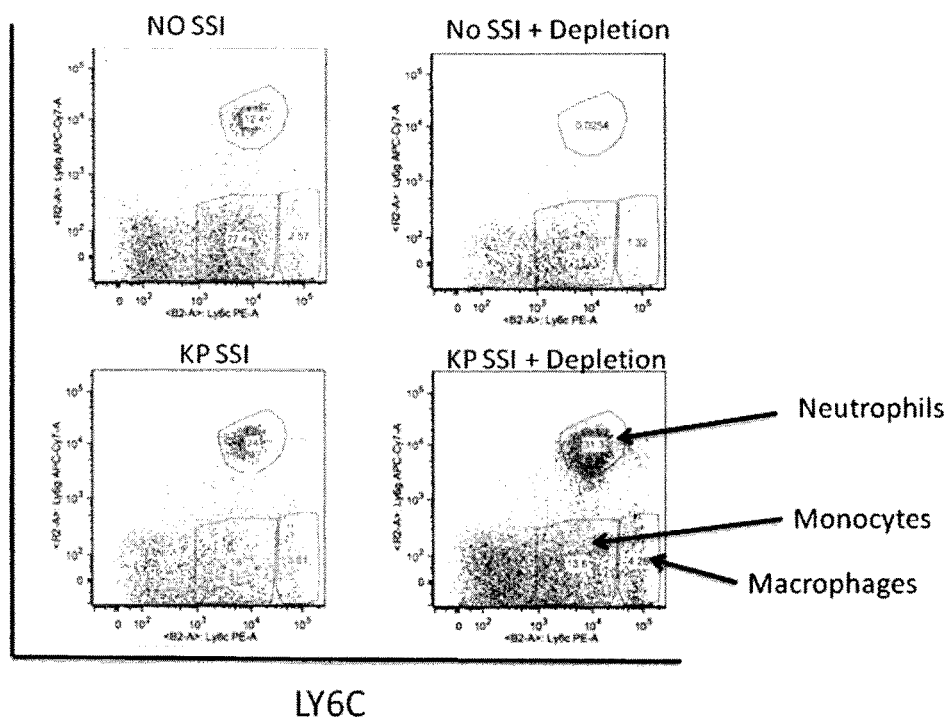
FIG. 54 is a series of 4 graphs that depict the results of flow cytometry in the neutropenia model, illustrating counts of particular cell populations from lung samples, gated on live, CD45+CD11 b+ cells.

This example illustrates the use of an SSI to treat neutropenia in a mouse model. Neutrophil populations were assessed in spleen (in mouse, representative of circulation) and lungs in response to SSI treatment (QBKPN) and neutrophil-depleting (anti-Ly6G) monoclonal antibody, as illustrated in the treatment schema in FIG. 53. In indicated mice, SSI treatment was performed every two days from Day −10 to Day +10. SSI (QBKPN) was injected SC in alternating sites at a dose of 0.03 ml of an $OD_{5.0}$ solution. In indicated mice, anti-Ly6G treatment was performed every three days from Day −1 to Day +11. Antibody (Bio-X-Cel clone 1A8) was injected IP at a dose of 200 pg/mouse. All mice were IV injected with B16 melanoma (200,000 cells/mouse) at Day 0. On Day +12, mice were sacrificed. Single cell suspensions were generated from spleen and lungs. Neutrophil populations (CD45+ CD11b+ Ly6G-hi Ly6C-intermediate) were assessed by flow cytometry, using monoclonal antibodies (BioLegend) and a Miltenyi MacsQuant cytometer, and analyzed using FlowJo software. Representative staining data from lungs is illustrated in FIG. 54, from lung samples, gated on live, CD45+ CD11b+ cells. The proportions of neutrophils in lungs (FIG. 55A, showing % of live CD45+ CD11b+ cells) and spleen (FIG. 56A) were calculated from primary cytometry data. Numbers of neutrophils (CD45+ CD11b+ Ly6G+ Ly6C+ cells) in the lungs (FIG. 55B) and spleen (FIG. 56B) were calculated by multiplying the proportion of cells by the total cellularity.

In both lungs and spleen, QBKPN treatment significantly increased the proportion (FIG. 55A and FIG. 56A) of neutrophils. QBKPN treatment significantly increased the number of neutrophils in spleen (FIG. 56B). These data illustrate that QBKPN SSI induces an expansion in the proportion and number of circulating neutrophils.

Figure 55:
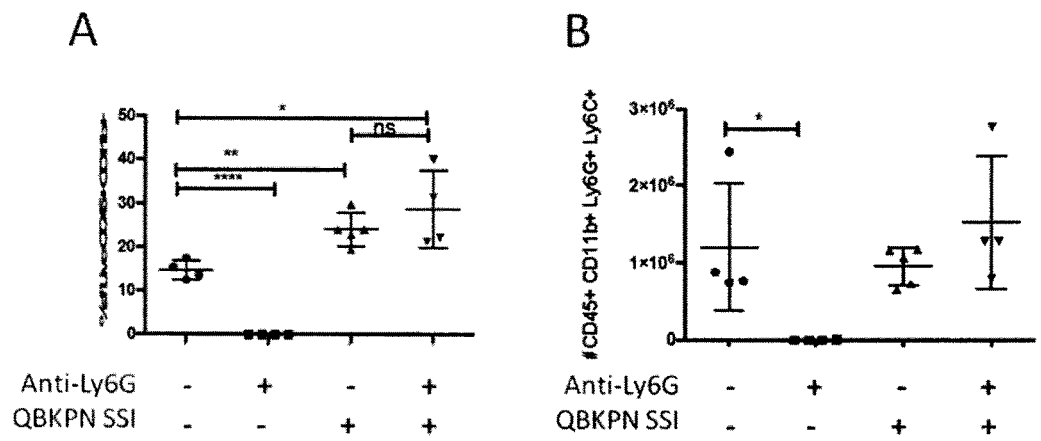
FIG. 55 includes two column scatter graph plots illustrating the proportion (A) and number (B) of neutrophils in lung samples in the neutropenia model.
Figure 56:
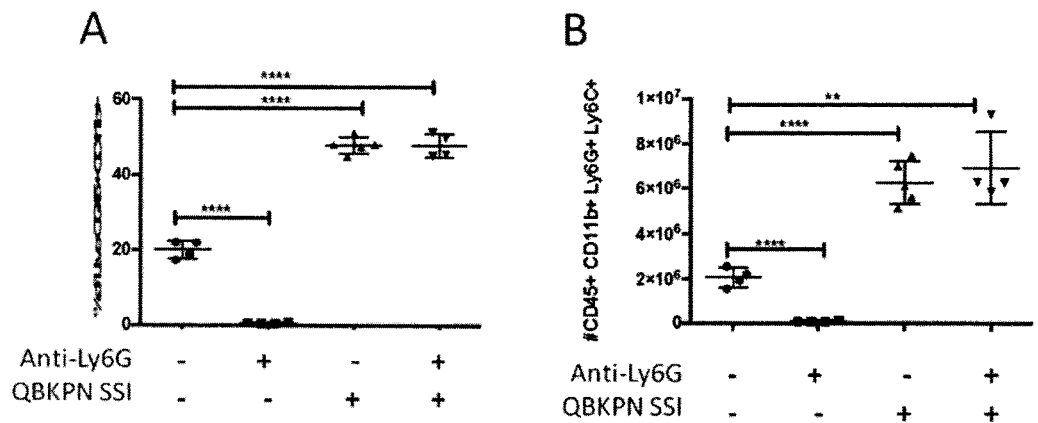
FIG. 56 includes two plots illustrating the proportion (A) and number (B) of neutrophils in spleen samples in the neutropenia model.

Parallel cohorts of mice were treated with anti-Ly6G monoclonal antibody. Absent QBKPN treatment, anti-Ly6G completely depleted the neutrophils in lungs and spleen, both in terms of proportions and numbers (FIGS. 55 and 56). However, neutrophil populations in lung (FIG. 55) and spleen (FIG. 56) remained at high levels in QBKPN-treated mice, despite anti-Ly6G monoclonal antibody treatment. As neutrophils were detected using a fluorescently-labeled anti-Ly6G antibody (indicating expression of the antigen), the data indicate that the QBKPN treatment did not render neutrophils resistant to anti-Ly6G-mediated depletion. Thus, these data illustrate QBKPN SSI-induced expansion of the neutrophil compartment in a model of neutropenia.

A number of common therapies, including chemotherapy drugs used to treat cancers, suppress bone marrow function and reduce neutrophil counts, causing neutropenia. As illustrated herein, an SSI may accordingly be given so as to restore neutrophil counts. There are additional therapeutic benefits available in SSI therapies of this kind. In addition to treating neutropenia, in the context of treating an underlying disease, the selection of a targeted SSI, with a PRR agonist signature that recapitulates a distinct portion of a PRR agonist signature of a microbial pathogen that is pathogenic in the target tissue, results in site specific restoration of innate immune function in the target tissue. This may for example involve an anti-cancer immune response, or an anti-inflammatory immune response mediated by the SSI (in addition to the effect of treating the neutropenia).

Chemotherapy commonly produces myelosuppression, of which the most clinically relevant component is neutropenia occurring between 2-10 days post-chemotherapy. The clinical implications of this are serious, interfering with the ability to maintain a chemotherapeutic dose and schedule, and giving rise to the risk of neutropenic sepsis. Accordingly, an SSI may be given to patients undergoing a myelosuppressive chemotherapy as a prophylaxis or treatment for neutropenia, for example being administered every other day between cycles of chemotherapy.

Example 25: PD1 and PDL1 Markers in Patients

This Example provides clinical data illustrating the efficacy of an SSI acting to down-regulate PD1 and PDL1 expression in neoplastic disease. This also illustrates the use of PD1 and PDL1 as markers of SSI efficacy, augmenting the NKG2D mouse model data in Example 23. This is significant, given the understanding that PD1 (expressed on T-cells) and it's ligand PD-L1 play a role in preventing T-cell activation and mediating pathological immunosuppression.

In a lung cancer clinical trial of a KPN SSI, 6 patients presented in two distinct disease groups: pre-neoplastic and neoplastic (2 of the 6 patients were neoplastic). This Example provides data obtained from blood samples, analyzed by flow cytometry.

Figure 57:
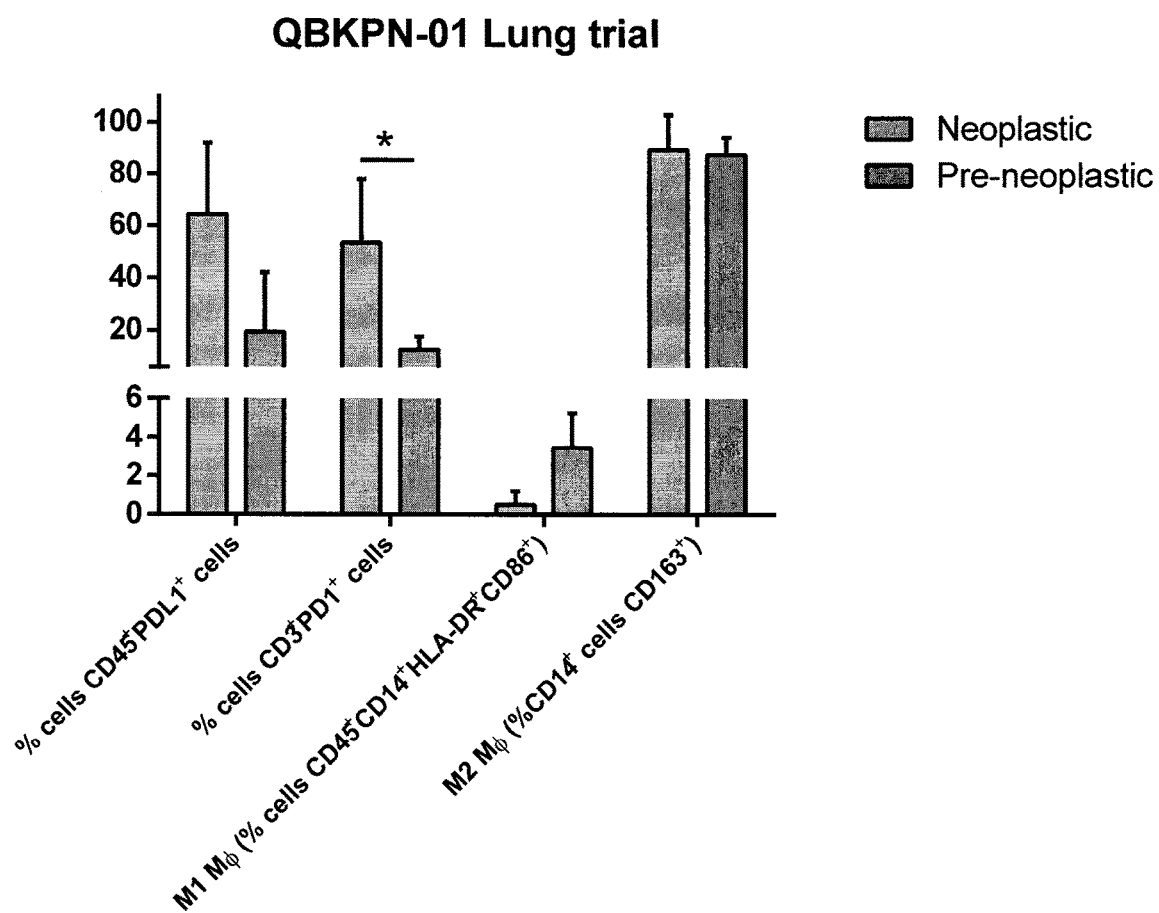
FIG. 57 is a bar graph illustrating the proportion of cells having the denoted characteristics in blood samples from lung cancer patients segregated into a neoplastic patient population and a pre-neoplastic patient population, showing elevated PDL1 and PD1 expression in the neoplastic patient population compared to the pre-neoplastic patients.
Figure 58:
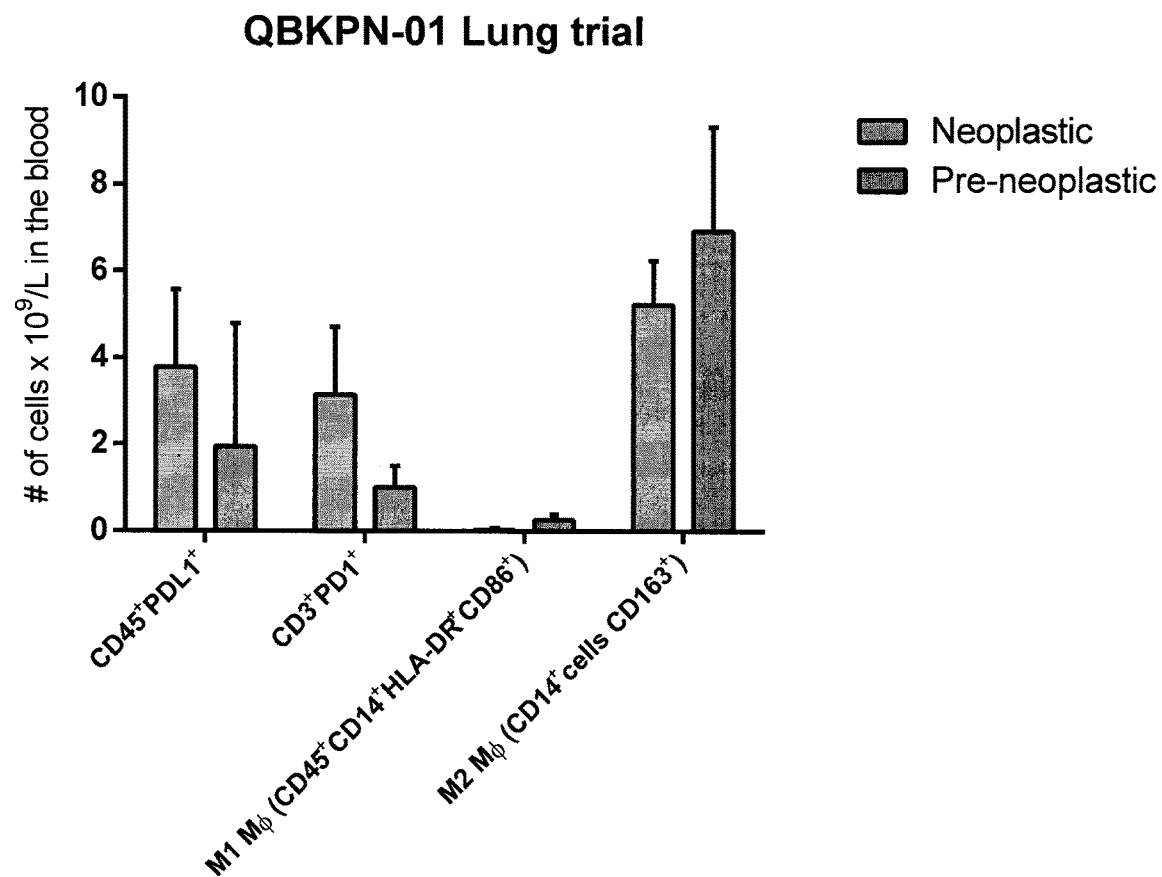
FIG. 58 is a bar graph illustrating the relative number of cells having the denoted characteristics in blood samples from lung cancer patients segregated into a neoplastic patient population and a pre-neoplastic patient population, showing elevated PDL1 and PD1 expression in the neoplastic patient population compared to the pre-neoplastic patients.

As shown in Table 21, the 2 neoplastic patients presented with elevated PDL1 and PD1 expression compared to the pre-neoplastic patients. This is shown in the bar graph of FIG. 57 as a percentage of the distinct cell populations, and in FIG. 58 as the relative number of cells having the denoted characteristics. The neoplastic patients (01-001 and 01-002) express higher levels of PD1 and PDL1, and have a lower level of M1 macrophages than the pre-neoplastic patients.

TABLE 21

PD1 and PDL1 Markers in Patients Prior to SSI Treatment

| | Subject # | | | | | |
|---|---|---|---|---|---|---|
| | Pre-neoplastic 01-007 | Pre-neoplastic 01-006 | Pre-neoplastic 01-005 | Pre-neoplastic 01-004 | Neoplastic 01-002 | Neoplastic 01-001 |
| % of CD45$^+$ PDL1$^+$ cells | 6.9 | 4.9 | 12.8 | 53.0 | 44.8 | 83.9 |
| % of CD3$^+$ PD1$^+$ cells | 7.6 | 10.7 | 19.0 | 14.2 | 36.3 | 70.8 |
| M1 macrophages % of cell CD45$^+$ CD14$^+$ HLA-DR$^+$ CD86$^+$ | 2.9 | 1.8 | 6.0 | 3.2 | 1.0 | 0.0 |
| M2 macrophages % of CD14$^+$ cells CD163$^+$ | 85.4 | 96.7 | 80.8 | 87.8 | 79.9 | 99.1 |

Figure 59A:
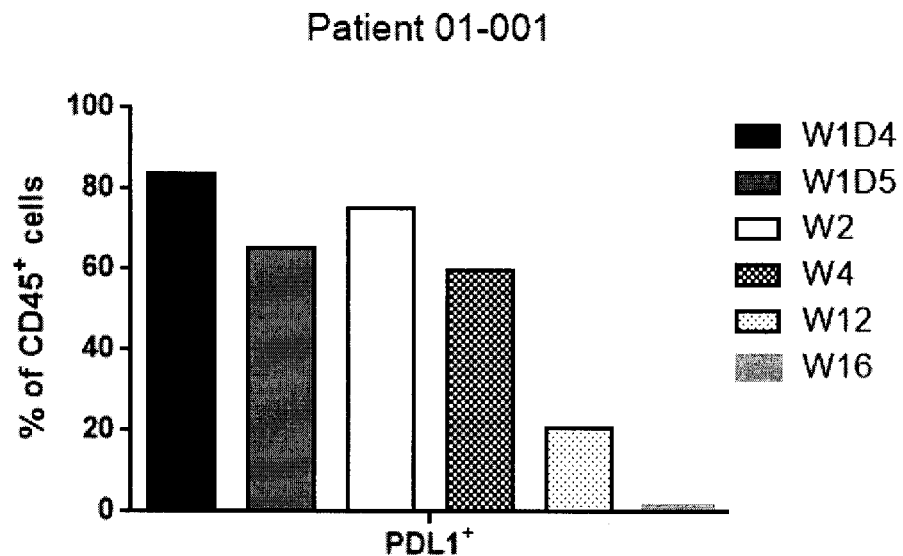
FIG. 59 includes two bar graphs illustrating the SSI mediated reduction of PD-L1 expression in neoplastic lung cancer in two patients, Patient 01-001 (panel A) and Patient 01-002 (panel B), at: week 1, day 4 (W1D4); week 1, day 5 (W1D5); week 2 (W2); week 4 (W4), week 12 (W12) and week 16 (W16)
Figure 59A:
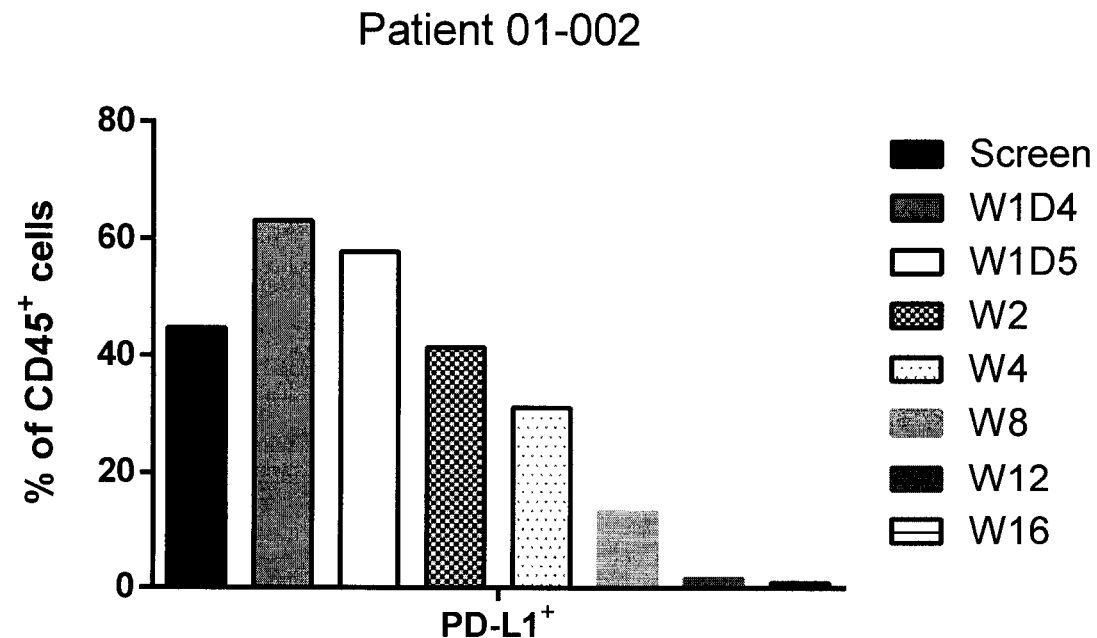
Figure 60A:
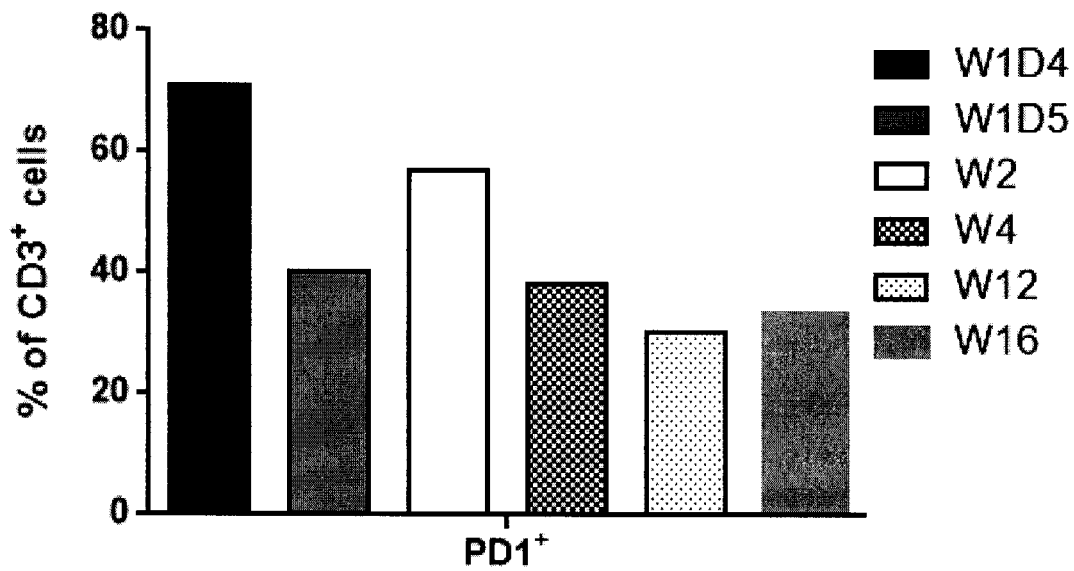
FIG. 60 includes two bar graphs illustrating the SSI mediated reduction in PD-1 expression in two neoplastic lung cancer patients, Patient 01-001 (panel A) and Patient 01-002 (panel B).
Figure 60B:
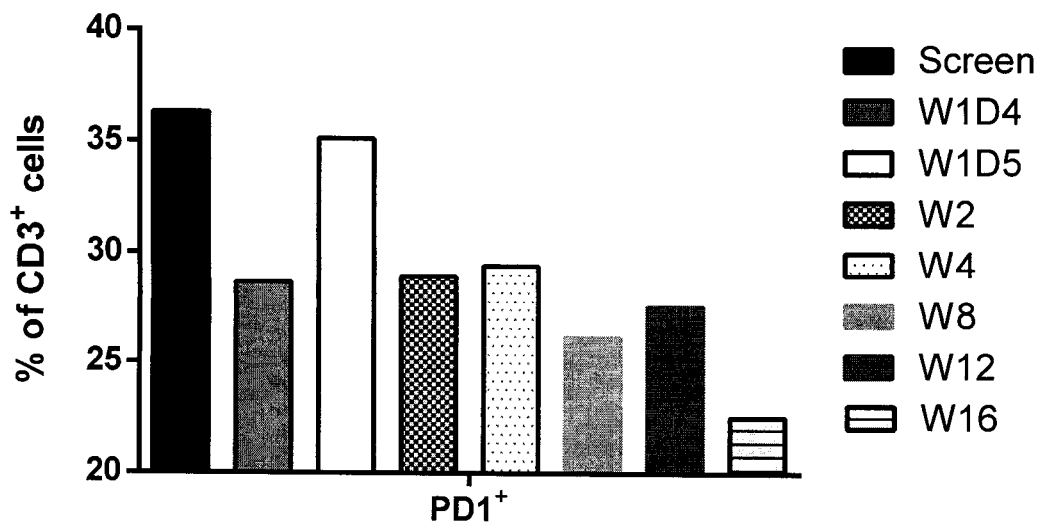
Figure 61A:
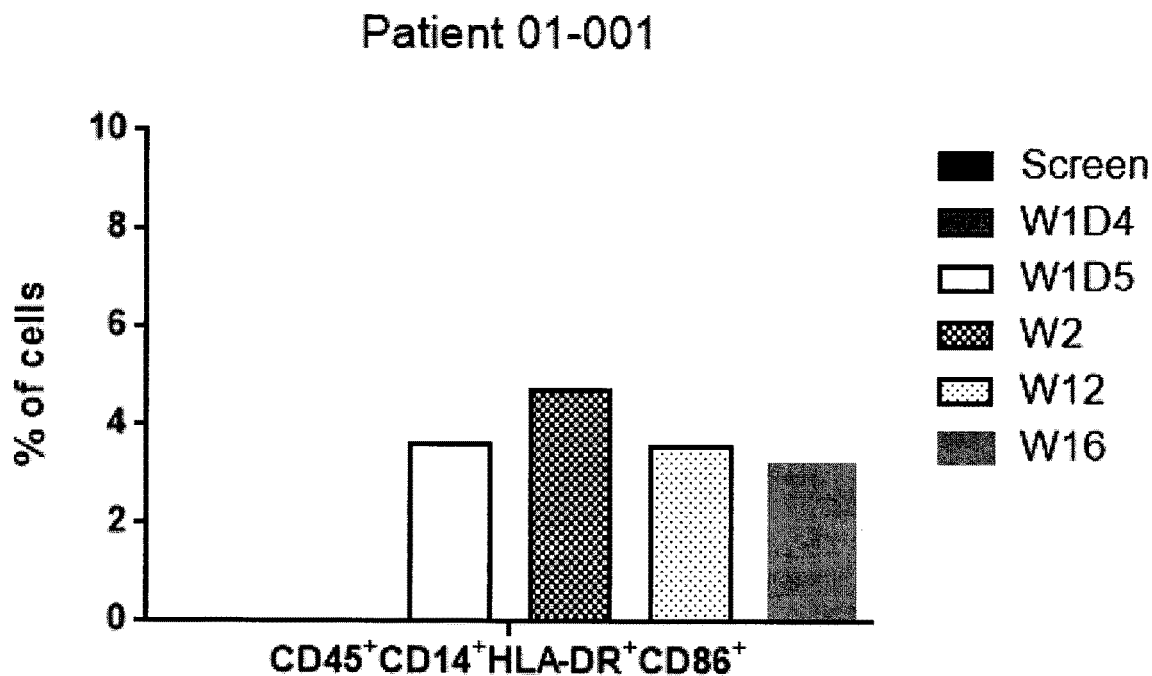
FIG. 61 includes two bar graphs illustrating the increase in the proportion of M1 macrophages in two neoplastic lung cancer patients, Patient 01-001 (panel A) and Patient 01-002 (panel B).
Figure 61B:
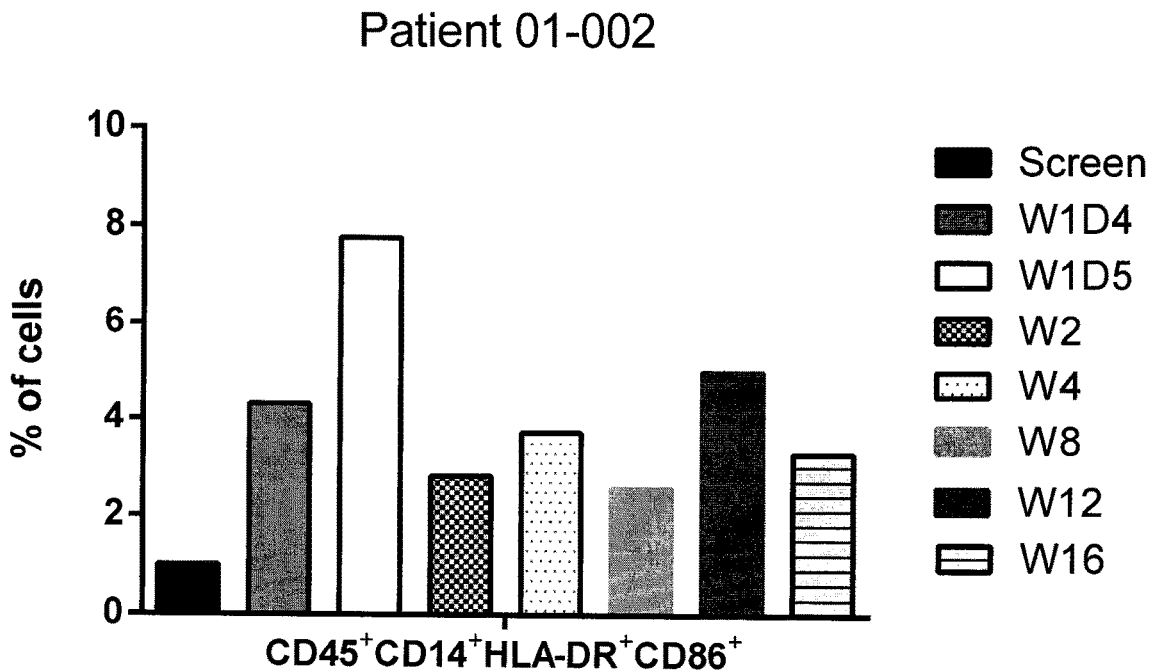

With SSI treatment, the neoplastic patients showed a significant decrease in PD1 and PDL1 expression, as well as a significant increase in the percentage of M1 (CD45$^+$ CD14$^+$ HLA-DR$^+$ CD86$^+$) macrophage cells. FIG. 59 illustrates the reduction of PD-L1 expression in Patient 01-001 (panel A) and Patient 01-002 (panel B), at: week 1, day 4 (W1D4), week 1, day 5 (W1D5), week 2 (W2); week 4 (W4), week 12 (W12) and week 16 (W16), during the course of SSI treatment every other day. FIG. 60 illustrates the reduction in PD-1 expression in these patients at these time points. FIG. 61 illustrates the increase in the proportion of M1 macrophages in these patients at these time points. As illustrated, with SSI treatment, over time, PDL1 expression decreases on CD45+ cells (all white blood cells), PD1 expression decreases in CD3+ cells (lymphocytes), and M1 macrophages increase in the blood (CD45$^+$ CD14$^+$ HLA-DR$^+$ CD86$^+$). In these patients, SSI treatment was discontinued at week 12 (W12), and the assays indicated that the relative M2 macrophage populations (CD14+CD163+) generally decreased until the cessation of treatment, and then rebounded.

Example 26: Granzyme and Perforin Expression

This Example illustrates the relationship between SSI dosage, tumour load, and expression of granzyme A, granzyme B, and perforin in B16 melanoma mouse lung models, providing evidence that efficacious SSI therapy elevates granzyme and perforin levels while reducing tumour load.

Mice were intravenously injected with B16 melanoma cells to provide a mouse lung cancer model. Five groups of mice (n=5) were subcutaneously injected as follows: placebo (saline), 1×QBKPN, 1/50×QBKPN, 1/500×QBKPN, or 1/5000×QBKPN (a series of dilutions of the 1×KPN SSI). SSIs were administered prophylactically ten days prior to tumour inoculation at every second day. Mice were continually injected with SSIs every two days until they were euthanized at fourteen days post-tumour injection. The right lung post-caval lobe was removed and stored in RNAlater®.

The entire mouse right lung post-caval lobe was homogenized in lysis buffer by a small bead mill (Qiagen, Cat No. 85600). All of the homogenate was extracted for RNA using the PureLink® RNA Mini Kit (ThermoFisher Scientific, Cat No. 12183018A). A Nanodrop™ spectrophotometer was used to quantify the RNA concentrations and purity. One microgram of RNA was reverse transcribed into cDNA using the iScript cDNA Synthesis Kit (Bio-Rad, Cat no. 170-8891). For quantitative PCR, fifty nanograms of cDNA were loaded into each well of the reaction plate. In addition to cDNA, the wells contained TaqMan® Fast Advanced Master Mix (ThermoFisher Scientific, Cat No. 4444554), and TaqMan® Gene Expression Assays probes. Samples were quantified for granzyme A (ThermoFisher Scientific, Mm01304452_m1), granzyme B (ThermoFisher Scientific, Mm00442837_m1), perforin (ThermoFisher Scientific, Mm00812512_m1), tyrosinase (ThermoFisher Scientific, Mm00495817_m1), and GAPDH (ThermoFisher Scientific, Mm99999915_g1) as the housekeeping gene. Two technical replicates were plated for the genes of interest (GOI), and in singlicate for the housekeeping gene.

The ddC$_t$ method was used to calculate gene expression fold changes. Technical replicates for the GOI were averaged, and biological replicates were tested for outliers using the ROUT method on GraphPad Prism 7.00 at 95% confidence. The technical outliers for GzmB: 1/500×-3 and Prf1: 1/500×-3 were removed from further analyses. The dCt value was calculated by subtracting C$_t$.GOI by C$_t$.GAPDH. The ddC$_t$ values were calculated by subtracting dCt of the sample by average dCt of the placebo group. Fold change was calculated by taking the negative exponent of ddC$_t$ with base two (2-ddC$_t$). The average fold change of each treatment group was analyzed for significance using a one-way Tukey's multiple comparison ANOVA test at 95% confidence.

Figure 62A:
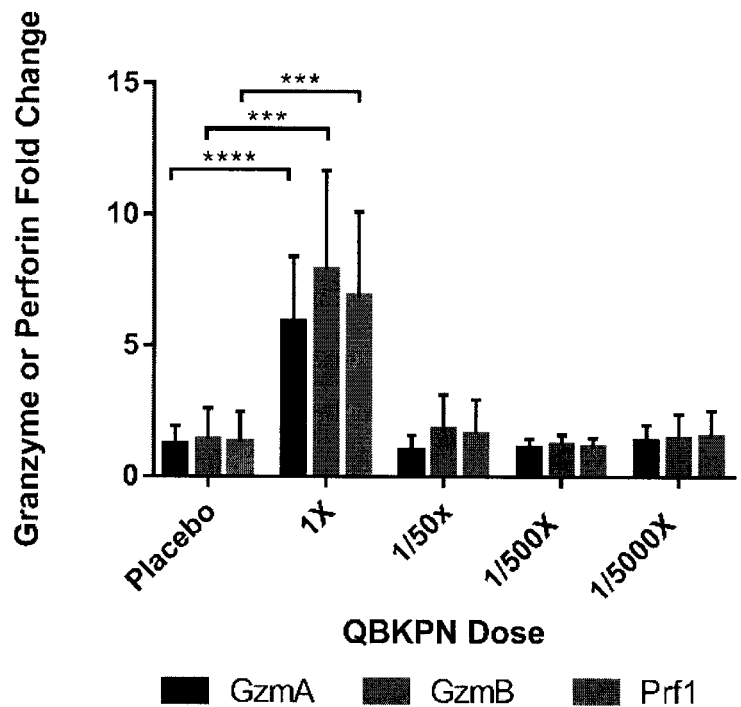
FIG. 62 includes two bar graphs, showing RT-qPCR fold changes in (A) GzmA, GzmB, Prf1, and (B) Tyr in lungs of B16 inoculated mice with differing QBKPN doses. Data points are mean+/−SD. Significance was calculated using a one-way Tukey's multiple comparison ANOVA test. $p<0.01$, * $p<0.001$ and ****$p<0.0001$.
Figure 62B:
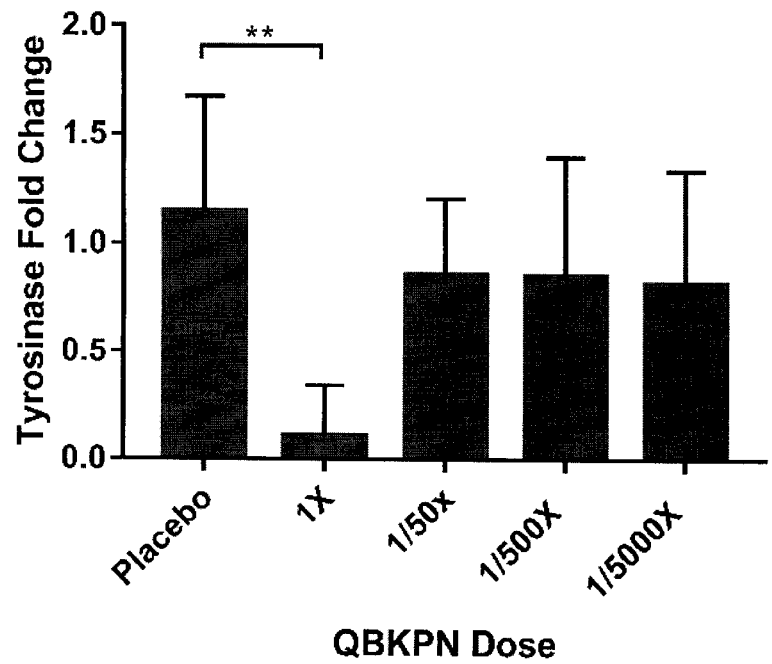

FIG. 62 illustrates the results of the foregoing assays, showing RT-qPCR fold changes in (A) GzmA, GzmB, Prf1, and (B) Tyr in lungs of B16 inoculated mice euthanized on day 14 with differing QBKPN doses. Taqman® Gene Expression Assays were performed on 50 ng of cDNA isolated from the right lung post-caval lobe of mice. Values are normalized to GAPDH, and relative to the gene expression of the placebo group, which were mice injected with saline. Data points are mean+/−SD. All data points have n=5 except GzmB-1/500× and Prf1-1/500×, which have n=4 after removal of dCt outliers. Significance was calculated using a one-way Tukey's multiple comparison ANOVA test. p<0.01, * p<0.001 and ****p<0.0001.

In accordance with one aspect of this Example, SSIs may be formulated and administered in a dosage regime that is effective in a target organ or tissue to mediate increased expression of one or more granzyme or perforin, such as of granzyme A, granzyme B, and perforin.

Example 27: Distinct SSIs Agonize Distinct PRRs

This Example illustrates that both QBECO and QBKPN SSIs activate multiple PRRs, and QBECO and QBKPN each activate different PRRs, with different PRR repertoire fingerprints being identified for each SSI.

This data in this Example was obtained from assays of QBKPN and QBECO PRR activation in cell lines that have a single PRR. The cell lines used were HEK293 cells lines that express a single human Toll-Like Receptor (TLR2, 3, 4, 5, 7, 8 and 9), NOD-Like Receptor (NOD1 and NOD2), C-Type Lectin (Dectin 1a, Dectin 1 b, and Mincle) or RIG-1-like receptor (RIG-1 and MDA5).

Figure 63:
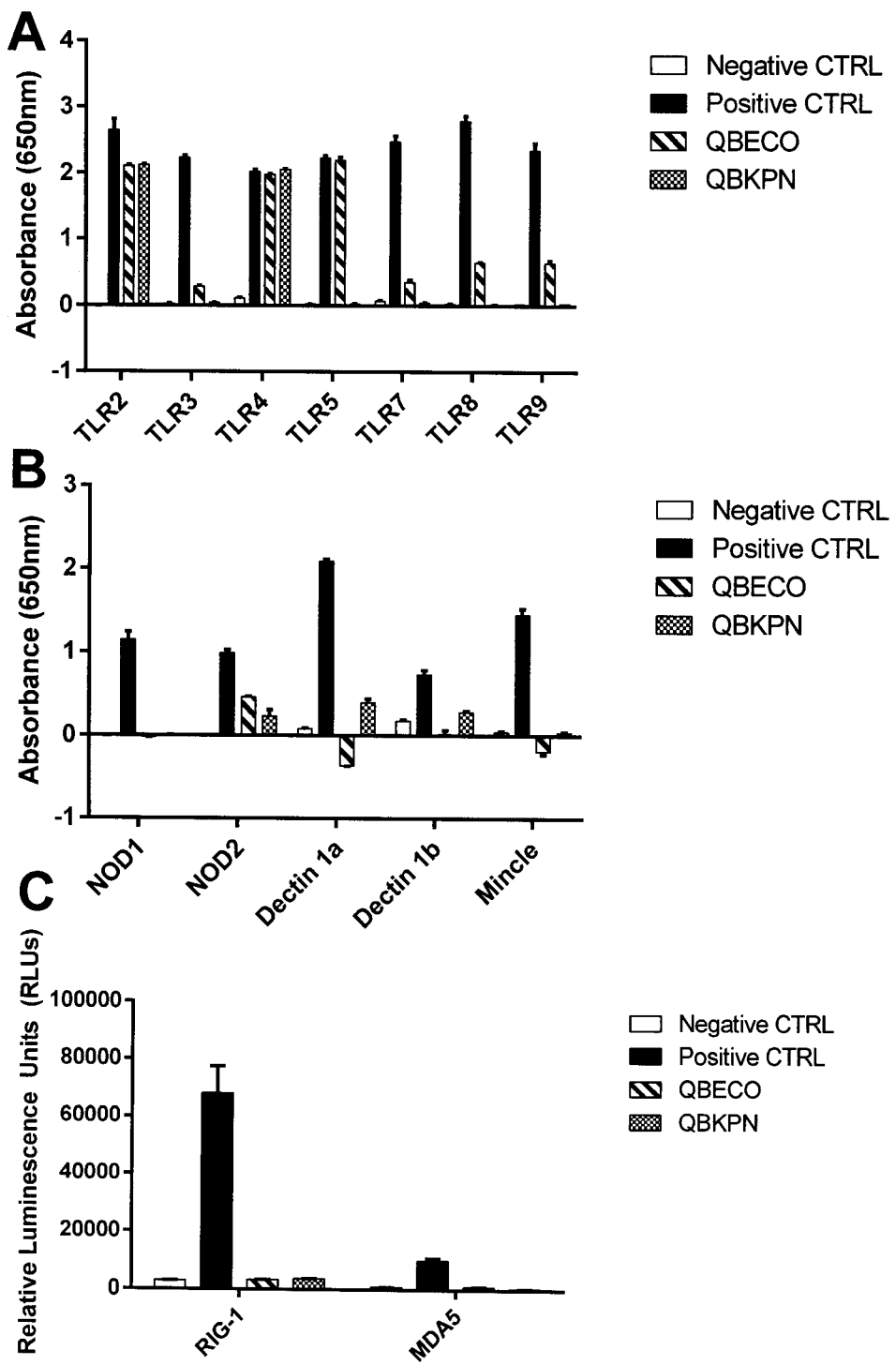
FIG. 63 includes three bar graphs illustrating the activation of pattern recognition receptors in HEK cells after QBECO or QBKPN stimulation, showing respectively: A) Toll-like receptor (TLR) activation as measured by NK-κB activation; B) NOD2 and C-type lectin receptors (CTL) as measured by NK-κB activation; and, C) RLR (Rig-1-like receptors) as measured by IRF3 activation.

As illustrated in FIG. 63, two TLRs were highly activated by both QBECO and QBKPN (TLR 2 and TLR4). One TLR was highly activated by just QBKPN (TLR5). 1 PRR was moderately activated by bother QBECO and QBKPN (NOD2). 4 were moderately activated by only QBECO (TLR3, TLR7, TLR8, TLR9) while 2 were moderately activated by only QBKPN (Dectin 1a, Dectin 1b). NOD1, Mincle, RIG-1 and MDA5 were not activated by either QBECO or QBKPN.

TLR2 and TLR4 are localized on the plasma membrane and primarily recognize lipoprotein and LPS respectively. TLR5 is a plasma membrane receptor that responds to Flagellin. Of the RNA/DNA recognition TLR's, TLR3 was only slightly activated by QBECO (and not by QBKPN). TLR3 is primarily a dsRNA receptor for viral RNA. TLR7 and 8, which are located in the endolysosome and also recognize RNA (bacterial and viral) were activated by only QBECO. Finally, TLR9 which recognized CpG-DNA and is located in the endolysosome was also activated by only QBECO. In this context, it is relevant that HEK cells are not known to highly uptake bacteria in endolysosomes. Therefore, the lack of QBKPN activation for TLR 7, 8 and 9 may be due to no interaction of the DNA/RNA with these receptors. Nod-Like Receptors (NLR) are cytoplasmic receptors. NOD1 was not activated by either QBECO or QBKPN, but NOD2, which recognizes muramyl dipeptide (MDP) was activated by both QBECO and QBKPN. The other cytoplasmic receptors, RIG-1 and MDA5 which recognize short dsRNA and long dsRNA respectively, were not activated. The C-type lectin receptors (CLR) are located in the plasma membrane and primarily recognize carbohydrates. Mincle was not increased by either QBKPN or QBECO. Dectin 1a and Dectin 1b are primarily fungi receptors for beta-Glucans but can also see bacteria carbohydrates.

Figure 64:
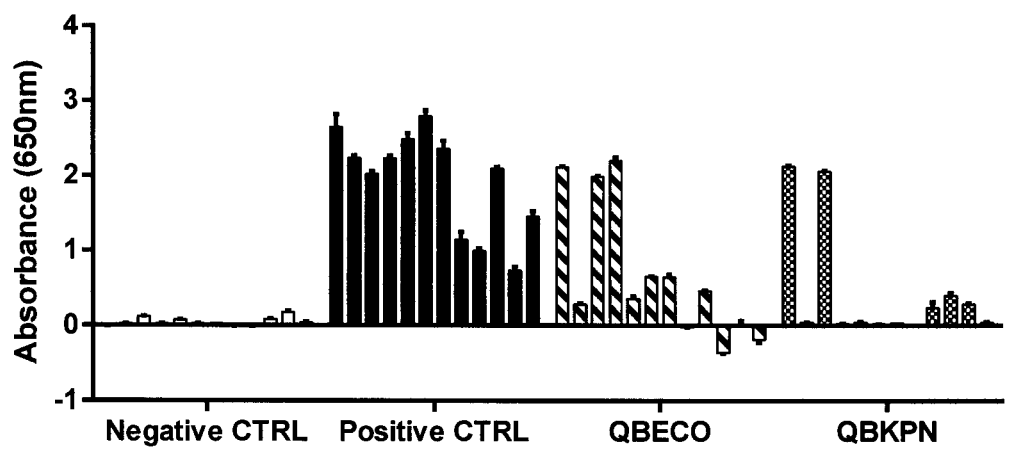
FIG. 64 is a PRR reoertoire fingerprint bar graph, in which a PRR fingerprint was constructed for QBECO and QBKPN SSIs from the 1/10 dilution data, after subtracted the negative control data. Bars, in order, represent TLR2, 3, 4, 5, 7, 8, 9, NOD1, NOD2, Dectin 1a, Dectin 1b and Mincle. RIG-1 and MDA5 are not shown. The positive control is specific for each PRR (ie LPS for TLR4).
Figure 65:
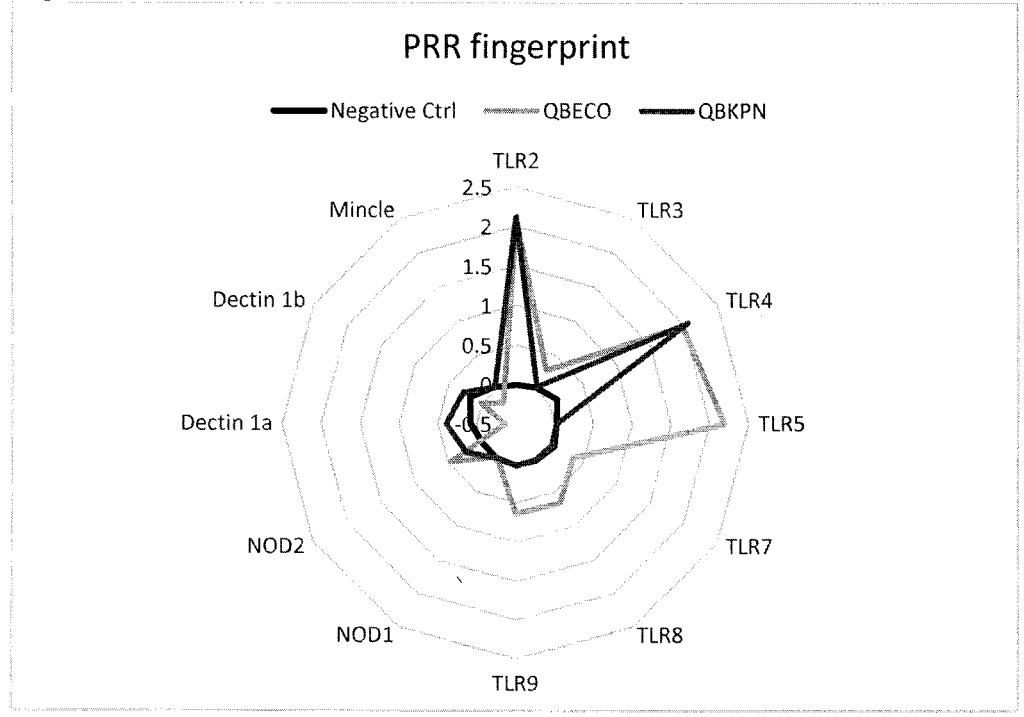
FIG. 65 is a PRR fingerprint radar graph, in which a PRR fingerprint was constructed for QBECO and QBKPN SSIs from the 1/10 dilution data, after subtracted the negative control data, and plotted on a radar graph.

When graphed as either bar graphs (FIG. 64) or radar graphs (FIG. 65), an overall PRR repertoire fingerprint appears. These results are all derived from the 1/10 dilution of the relevant SSI, with the negative control subtracted from the absorbance value.

Example 28: Viral SSIs

This Example illustrates that viral SSIs induce immune changes are similar to bacterial SSIs, as evidenced by immune correlates in the blood after 7 days of Viral SSI treatment compared to QBKPN SSI treatment. Mice were treated with Placebo, QBKPN, or three viral SSI models: Rabies Vaccine, Feline Rhinotracheitis-Calici-Panleukopenia Vaccine and Canine Influenza Vaccine. 30 µL of the treatments were injected subcutaneously every second day. The endpoint was 24 hours after the 4th SSI injection (day 7). At endpoint, blood was collected and stained for flow cytometry to determine the numbers of neutrophils and Ly6C$^{HI}$ monocytes in the blood as a percentage of CD45$^+$ cells.

Figure 66:
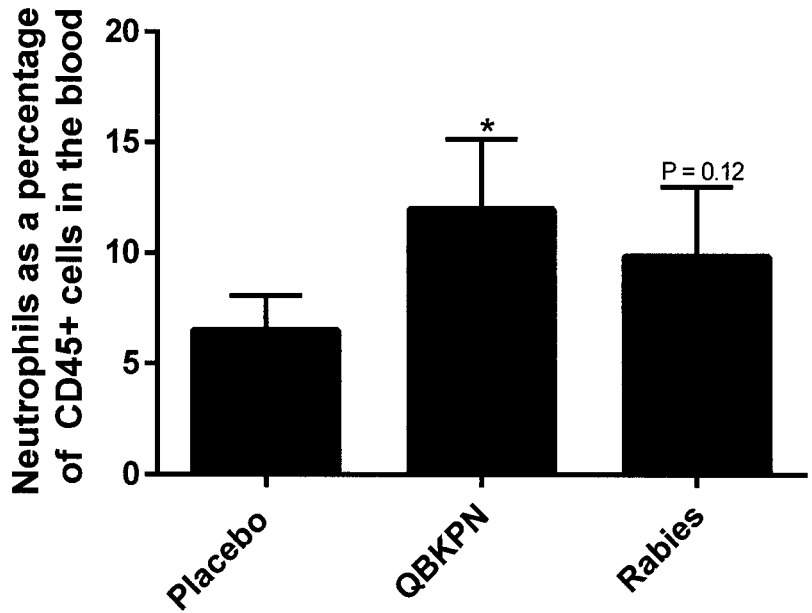
FIG. 66 is a bar graph illustrating neutrophil levels in the blood at day 7 after treatment with Placebo, QBKPN or Rabies Vaccine. Neutrophil levels were measured by flow cytometry and were assessed as the percentage of neutrophils (Ly6G+) of total CD45+ cells. N=4-5 mice per group. * is P<0.05 compared to placebo as assessed by Student's t-test. Average±standard deviation shown. QBKPN is a bacterial SSI derived from *Klebsiella*. Rabies is the Imrab 3TF Rabies Vaccine which contains killed rabies virus.
Figure 67:
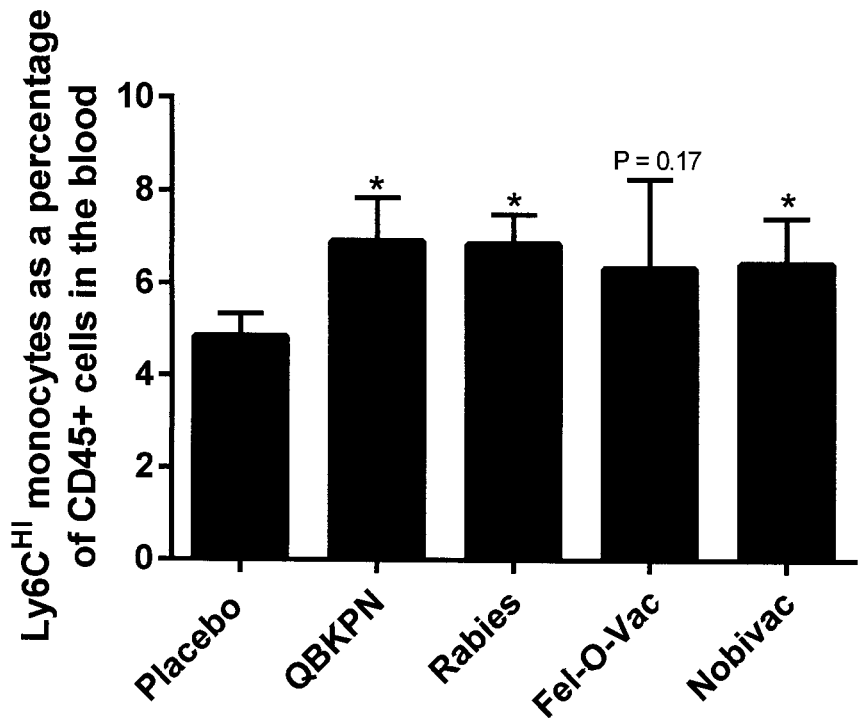
FIG. 67 is a bar graph illustrating Ly6C$^{HI}$ monocyte levels in the blood at day 7 after treatment with Placebo, QBKPN or Rabies Vaccine. Ly6C$^{HI}$ monocyte levels were measured by flow cytometry and were assessed as the percentage of Ly6C$^{HI}$ monocyte (Ly6C$^{HI}$Ly6G$^-$) of total CD45$^+$ cells. N=4-5 mice per group. * is P <0.05 compared to placebo as assessed by Student's t-test. Average±standard deviation shown. QBKPN is a bacterial SSI derived from *Klebsiella*. Rabies is the Imrab 3TF Rabies Vaccine which contains killed rabies virus. Fel-O-Vac is Feline Rhinotracheitis-Calici-Panleukopenia Vaccine which contains the three killed viruses. Nobivac is Canine Influenza H3H8 which contains killed influenza H3H8.

As illustrated in FIG. 66, Rabies vaccine (killed rabies virus) increased neutrophil levels when compared to placebo, to levels comparable to levels seen with QBKPN treatment. As illustrated in FIG. 67, treatment with Rabies vaccine, Fel-O-Vac (Feline Rhinotracheitis-Calici-Panleukopenia virus) and Nobivac (Canine Influence H3H8 virus) all had similar increases in Ly6C$^{HI}$ monocytes, comparable to QBKPN treatment.

This data illustrates that SSIs produced from viral compositions induce similar immune response to SSIs produced from bacterial compositions. Viral SSIs are demonstrated to provide an equivalent response in neutrophil and Ly6C$^{HI}$ monocyte levels in the blood as does QBKPN.

Example 29: Cancer Antigen Potentiation

This Example illustrates that SSIs potentiate an immune response when used in combination with cancer antigens. As set out below in more detail, the lung-targeted SSI QBKPN mediated a reduction in tumour burden, and when used in combination therapy with a melanoma-associated antigen (gp100) further reduced tumour burden. This effect was specific to the use of the cancer antigen, as evidenced by the fact that an irrelevant (immunogenic but non tumour-associated) antigen did not impact tumour burden. The SSI cancer antigen combination therapy was effective both as co-formulated compositions and as separate injections of SSI and antigen. This evidences the use of an SSI as a adjuvant to drive immune responses to immunogenic cancer antigens.

The anti-tumour efficacy of QBKPN SSI in combination with the melanoma-specific antigen gp100 was compared to the irrelevant control antigen OVA (also called SIINFEKL) in C57Bl/6 mice sourced from Jackson Laboratories. On ~day −31, mice were infected with K. pneumoniae ($2.5 \times 10^5$ cells/mouse, by oropharyngeal instillation after being anaesthetized with isofluorane), then rested. Within 5-7 days, all mice were fully recovered from K. pneumoniae challenge. Starting on day −10, some mice were S.C. injected with QBKPN SSI; mice were injected every other day from Day −10 to day +12. Injections were performed in rotating sites (in accordance with the typical protocol in the Examples herein) at a dose of 0.03 ml of a 5.0 OD suspension.

On days −10, −6, and −4, some mice were also treated with indicated antigens and/or adjuvants, either co-mixed with SSI or s.c. in a distal site (nape). Peptide vaccines consisted of the melanoma-specific antigen gp100$_{25-33}$ (KVPRNQDWL, 100 µg/mouse) or the immunogenic control antigen from OVA (OVA$_{257-264}$, SIINFEKL, 100 µg/mouse). Adjuvant consisted of commercial CpG (ODN 1585 VacciGrade, 30 µg/mouse s.c). On day 0, mice were challenged with B16 melanoma ($3 \times 10^5$ cells/mouse, i.v.). On day +14, mice were sacrificed, surface metastases enumerated, and spleens and blood collected. Splenocytes were pooled among each group. Splenocytes ($1 \times 10^6$ cells/well) were cultured with gp100$_{25-33}$, OVA$_{257-264}$, or control peptide (influenza NP366-374) (all peptides at 10 µg/ml) for 5 days, then supernatants assessed for IFN-γ (by specific ELISA) as a readout of immunogenicity. Blood was collected into heparin-containing tubes, then centrifuged to remove cells. ELISA (RND Systems DuoSet DY485, limit of detection 31.2 µg/ml) was performed per the manufacturer's protocol. ELISA was performed with technical replicates (n=3) on all samples to generate a cytokine value for each culture condition (restimulated splenocytes) or animal (serum analyses); cytokine data are reported as group mean+/−standard deviation. Statistical differences were evaluated by unpaired T test (GraphPad PRISM).

Figure 68:
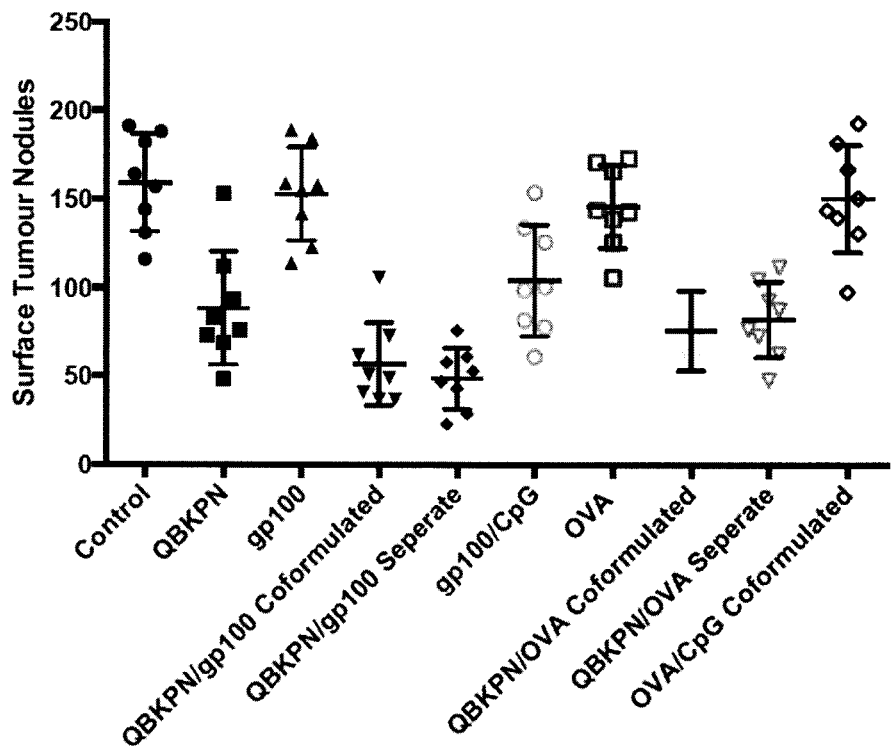
FIG. 68 is a column scatter plot illustrating cancer antigen potentiation using QBKPN to potentiate the effect of the melanoma-associated antigen gp100. The anti-tumour efficacy of QBKPN SSI in combination with gp100 is compared to the irrelevant control antigen OVA (SIINFEKL), including OVA adjuvanted with CpG.

As illustrated in FIG. 68, QBKPN treatment of *K. pneumoniae*-pre-exposed mice significantly ($p<0.0001$) reduced metastatic-like B16 melanoma in the lungs. Administration of cancer antigen (gp100) without adjuvant had no significant effect, in keeping with the relative paucity of response to non-adjuvanted vaccines in murine systems. Administration of cancer antigen with adjuvant (CpG) reduced tumour burden ($p=0.0023$), to a lesser extent that SSI alone. Combination of QBKPN SSI with gp100 (tumour-associated antigen) significantly ($p<0.05$) enhanced anti-tumour efficacy, compared with QBKPN alone. There was no statistical difference in anti-tumour efficacy between SSI/antigen combination used as a coformulation vs separate injection. Combining the SSI with a non-specific antigen (OVA) did not enhance anti-tumour efficacy, beyond the level of QBKPN SSI alone.

These data illustrate that QBKPN SSI can act as an adjuvant to induce/enhance the efficacy of cancer vaccines, and this adjuvant effect may be utilized either as a coformulation or separate administration. These results evidence an anti-cancer effect in which the SSI (alone or with antigen) was superior to adjuvanted antigen (gp100+CpG). Consistent with this, SSI treatment, without or with antigen, enhanced circulating levels of IFN-γ.

Example 30: STING Agonists and SSIs

This Example illustrates enhanced efficacy of a microbial SSI augmented with an additional PRR agonist, in this case a STING agonist. These formulations constitute a class of artificial PRR agonist repertoires in which a microbial PRR agonist repertoire is augmented with one or more additional heterologous PRR agonists.

The anti-tumour efficacy of QBKPN SSI in combination with the STING agonist 2'2'-cGMAP (inVivoGen) was evidenced in C57Bl/6 mice, as follows. On ~day −31, mice were infected with *K. pneumoniae* ($2.5\times10^5$ cells/mouse) by oropharyngeal instillation after being anaesthetized with isofluorane, then rested. Within 5-7 days, all mice were fully recovered from *K. pneumonia* challenge. Starting on day −10, some mice were S.C. injected with QBKPN SSI; mice were injected every other day from Day −10 to day +12. Injections were performed in rotating sites at a dose of 0.03 ml of a 5.0 OD suspension. On days −10, −6, and −4, some mice were also treated with STING agonist (SC injection of 10 µg/mouse in 20 µl of saline), either co-mixed with SSI or s.c. in a distal site (nape). On Day 0, mice were challenged with B16 melanoma by tail-vein (I.V.) injection of singlecell suspensions of tumour cells ($2.0\times10^5$ cells/mouse). On day +14, plasma was collected for ELISA, then mice were sacrificed and visual metastases counted and recorded. Serum was collected into heparin-containing tubes, then centrifuged to remove cells. ELISA (RND Systems DuoSet DY485, limit of detection 31.2 µg/ml) was performed per the manufacturer's protocol. ELISA was performed with technical replicates (n=3) on all plasma samples to generate a cytokine value for each animal; cytokine data are reported as group mean+/−standard deviation (n=7 mice/group). Statistical differences were evaluated by unpaired T test (GraphPad PRISM).

Figure 69:
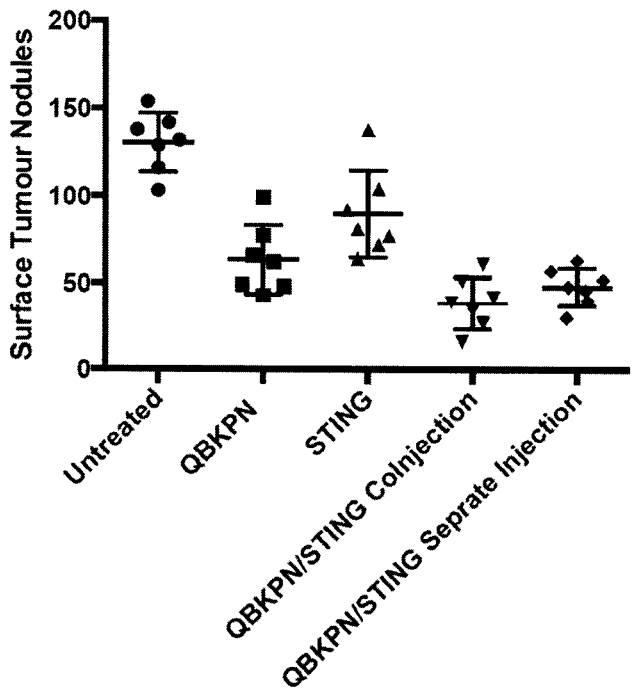
FIG. 69 is a column scatter plot illustrating surface metastatic-like tumour nodules in mice challenged with B16 melanoma, evidencing enhanced efficacy of the microbial SSI QBKPN augmented with an additional PRR agonist, the STING agonist 2'2'-cGMAP.

As illustrated in FIG. 69, QBKPN treatment of *K. pneumoniae*-pre-exposed mice significantly ($p<0.0001$) reduced metastatic-like B16 melanoma in the lungs. Administration of STING agonist alone also reduced tumour burden ($p=0.0038$). The combination of SSI and STING agonist further reduced tumour burden; the number of tumour nodules was significantly reduced following coinjection of SSI and agonist, compared with untreated ($p<0.0001$), SSI alone ($p=0.0206$), or STING agonist alone ($p=0.0006$) (FIG. 1). Likewise, simultaneous therapy (separate injection sites) with SSI and STING agonist reduced tumour burden, compared with untreated ($p<0.0001$) or agonist alone ($p=0016$).

Figure 70:
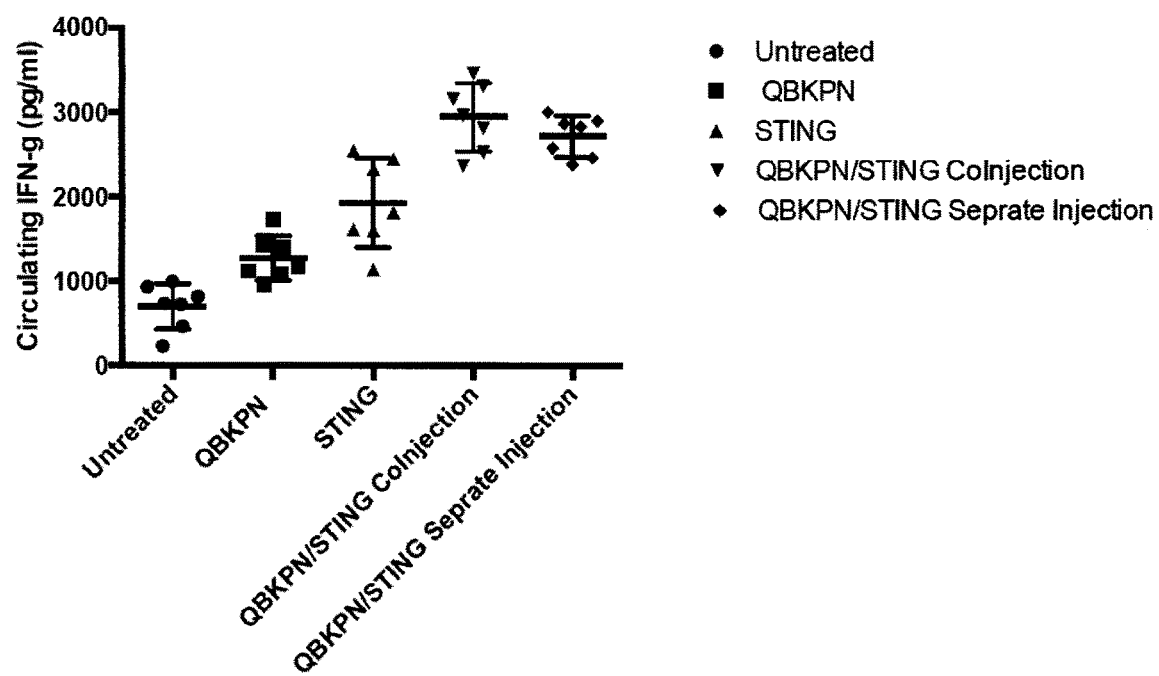
FIG. 70 is a column scatter plot illustrating treatment-induced IFN-γ levels in plasma in mice challenged with B16 melanoma, evidencing enhanced IFN-γ levels when the microbial SSI QBKPN is augmented with a STING agonist.

As shown in FIG. 70, both SSI treatment and STING agonist treatment enhanced circulating levels of IFN-γ ($p<0.0001$ and $p=0.0038$, respectively). The combination of SSI and STING agonist further increased cytokine levels, even though STING agonist treatment had not occurred for 18 days. Cytokine levels following combination treatment were statistically greater than single agent treatment. There was a significant inverse correlation between tumour burden and plasma IFN-γ levels. In sum, this data illustrate effective combination therapy using a STING agonist and an SSI.

Example 31: Genetic Markers for SSI Therapy Response

This Example provides a genetic analysis of subjects with IBD undergoing treated with an SSI therapy, illustrating the use of genetic markers associated with IBD to identify patient populations amenable to SSI treatments. In this Example there were 48 subjects with IBD and approximately 2.4 million single nucleotide polymorphisms (SNPs) which were the subject of analyses following genotyping on the Infinium Omni2.5-8 bead chip. The end-points used for these genetic analyses were varied and encompassed both clinical response and also the use of object markers of disease activity. Following standard quality control measures (including call frequency, minor allele frequency, and Hardy-Weinberg equilibrium test) a total of 1,271,655 SNPs were available for analyses. 113 known IBD loci were represented on the chip and passed quality control. Of the study subjects there were 31 Crohn's disease (CD) and 12 ulcerative colitis (UC) cases included.

A number of IBD-associated SNPs are associated with SSI treatment outcomes in IBD cases, using $p=0.05$ as a nominal significance, for example: CD phenotype and IBD-associated SNPs Last recorded response in CD (response vs no response)—a SNP tagging the FASLG, TNFSF18 genes was the top association ($p=0.0033$).
The same FASLG, TNFSF18 locus was also associated with drop in CDAI in CD cases ($p=0.018$).
CD drop in calprotectin was associated with a number of SNPs tagging 4 loci:
  NEXN, FUBP1, DNAJB4, GIPC2, MGC27382,
  ATF4, TAB1;
  IL23R,
  IL8, CXCL1, CXCL6, CXCL3, PF4, CXCL5, CXCL2 (all $p<0.05$).
8 week drop in CRP was associated with a SNP tagging NOTCH2 ($p=0.002$).
UC phenotype and IBD-associated SNPs
Mayo score drop at 16 weeks associated with SNPs tagging:
  HNF4A
  IRFI
  GPR12
  nd FOXO1 (all $p<0.05$)

HNF4A, and GPR12 are also associated with drop in CRP in UC after 16 weeks of treatment.

IBD Phenotype and IBD-Associated SNPs

Last response in all IBD cases combined showed associations with SNPs that tagged loci tagging FASLG, TNFSF18 (p=0.02) and also JAK2 (p=0.04).

An analyses of all the SNPs across the chip against the phenotypes listed above revealed a number of associations as summarized in the Table 22:

TABLE 22

Unbiased analyses of all SNPs across the genotyping platform

| SNP ID | P value | Genes |
| --- | --- | --- |
| kgp10600643 | 0.00037 | BMPR1B |
| rs1998639 | 0.00043 | CD1D, KIRREL |
| rs9578586 | 0.00046 | SGCG, SACS |
| rs1467073 | 0.00055 | DENND3, SLC45A4 |
| rs12364461 | 0.00062 | P2RY2, P2RY6, ARHGEF17, FCHSD2 |
| kgp8836175 | 0.00069 | ZFHX3 |

Figure 71A:
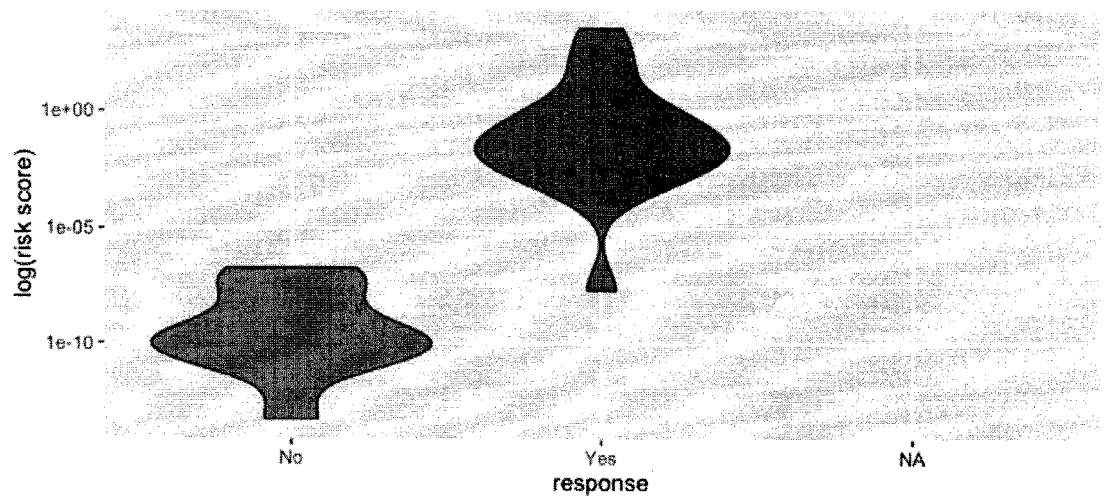
FIG. 71A is a violin plot representing the log distribution of risk scores, comparing last recorded response for all CD subjects using risk scores based on 112 IBD SNPs (P-value: 2.430E-05).
Figure 71B:
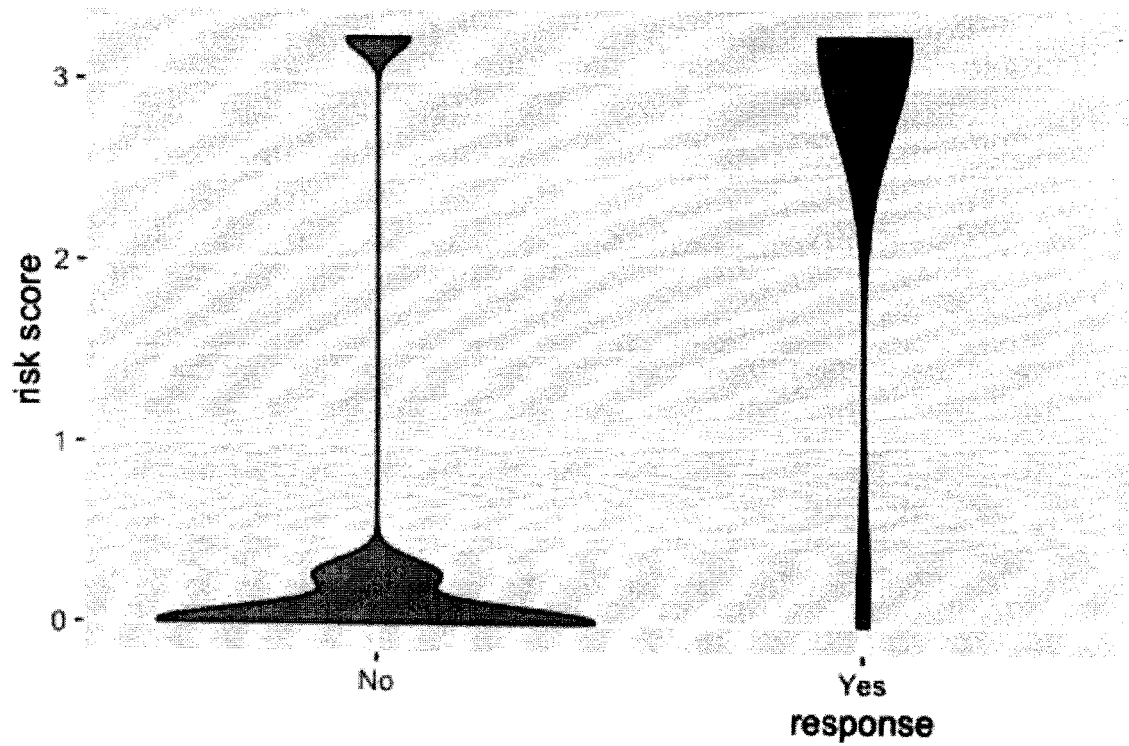
FIG. 71B is a violin plot representing the log distribution of risk scores, comparing last recorded response for all CD subjects using risk scores based on 3 IBD SNPs (P-value: 1.385E-04).
Figure 72:
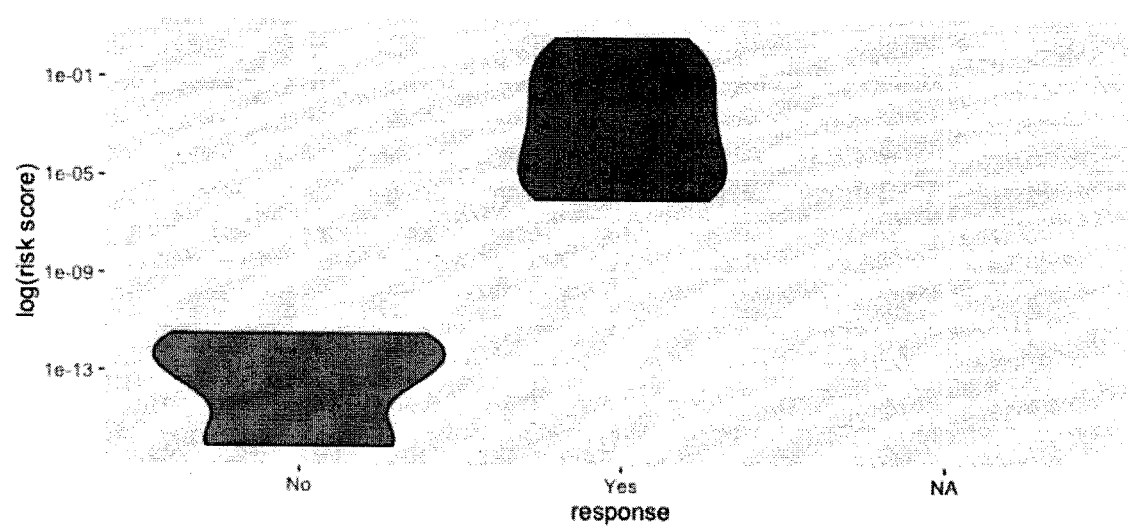
FIG. 72 is a violin plot representing the log distribution of risk scores, comparing last recorded response for all UC subjects using risk scores based on 84 IBD SNPs (P-value: 1.255E-02).
Figure 73:
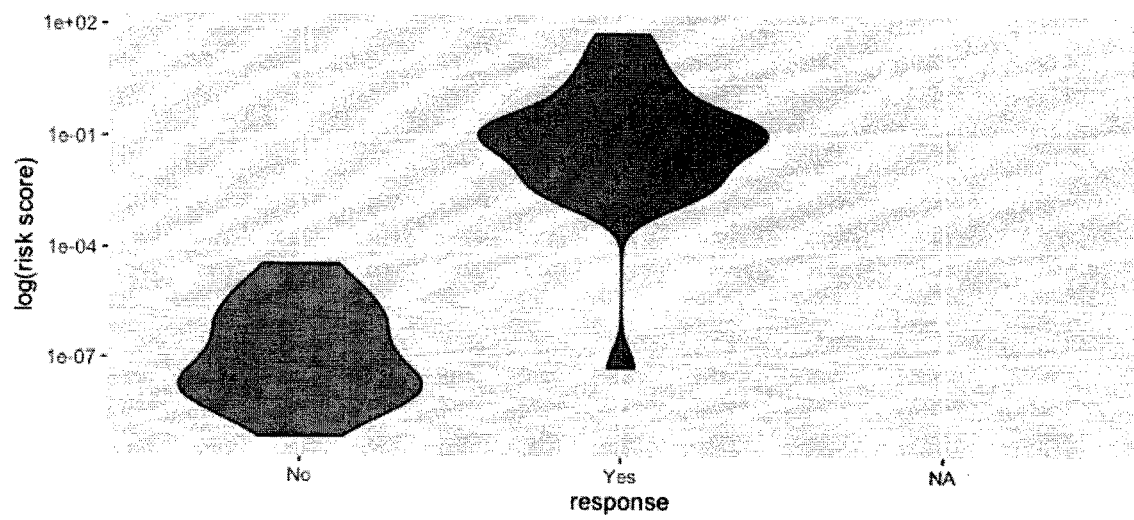
FIG. 73 is a violin plot representing the log distribution of risk scores, comparing last recorded response for all CD and UC subjects using risk scores based on 112 IBD SNPs (P-value: 8.184E-07).

Using a cumulative gene-risk score (GRS; see Jostins et al., (2013) PLoS ONE 8(10): e76328) based on all known IBD associated SNPs, a highly significant association was identified with CD responders to SSI treatment having higher GRS developed from 112 IBD-associated SNPs (listed below) than non-responders (p=2.43×10$^{-5}$), as illustrated in FIG. 71A. Using just 3 of these SNPs, with raw p-values <0.05 (rs9286879, rs7517810, rs17391694), also evidenced a significant association (P-value: 1.385E-04) with CD responders, as illustrated in FIG. 71B. Similarly there was an association with higher GRSs observed in UC responders than non-responders, as illustrated in FIG. 72 (p=0.012), providing an independent verification of the CD phenotype and GRS finding summarized above. Given that the overwhelming majority of IBD-associated loci are shared between CD and UC combining these data as cumulative GRS in all IBD cases is valid. Despite the small number of cases there is a very significant association between GRS and response at last follow up, as illustrated in FIG. 73 (p=8.18×10$^{-7}$).

The remarkable association of the cumulative GRS with last documented response in CD, UC, and combined IBD patient populations indicates that individuals with IBD that are genetically enriched for genetic markers associated with IBD are more likely to respond to SSI. Furthermore, since the majority of these genetic variants are associated with other immune-mediated diseases, this indicates that this approach may be extended to other patient cohorts beyond IBD when treated with an SSI. These findings indicate that it is possible to identify subjects, such as IBD subjects, more likely to respond to an SSI treatment. Accordingly, an aspect of the present invention involves the provision of companion diagnostic genetic testing assays in association with an SSI therapy. SNPs and genetic loci that may be used in such assays are set out below.

List of 243 IBD susceptibility SNPs: rs1748195, rs34856868, rs11583043, rs6025, rs10798069, rs7555082, rs11681525, rs4664304, rs3116494, rs7556897, rs111781203, rs35320439, rs113010081, rs616597, rs724016, rs2073505, rs4692386, rs6856616, rs2189234, rs395157, rs4703855, rs564349, rs7773324, rs13204048, rs7758080, rs1077773, rs2538470, rs17057051, rs7011507, rs3740415, rs7954567, rs653178, rs11064881, rs9525625, rs3853824, rs17736589, rs9319943, rs7236492, rs727563, rs17391694, rs6679677, rs3897478, rs9286879, rs1728918, rs10865331, rs6716753, rs12994997, rs6837335, rs13126505, rs10065637, rs7702331, rs17695092, rs12663356, rs9264942, rs9491697, rs13204742, rs212388, rs10486483, rs864745, rs7015630, rs6651252, rs3764147, rs16967103, rs2066847, rs2945412, rs2024092, rs4802307, rs516246, rs2284553, rs10797432, rs6426833, rs2816958, rs1016883, rs17229285, rs9847710, rs3774959, rs11739663, rs254560, rs6927022, rs798502, rs4722672, rs4380874, rs4728142, rs483905, rs561722, rs28374715, rs11150589, rs1728785, rs7210086, rs1126510, rs6088765, rs6017342, rs12103, rs35675666, rs12568930, rs11209026, rs2651244, rs4845604, rs670523, rs4656958, rs1801274, rs2488389, rs7554511, rs3024505, rs6545800, rs925255, rs10495903, rs7608910, rs6740462, rs917997, rs2111485, rs1517352, rs2382817, rs3749171, rs4256159, rs3197999, rs2472649, rs7657746, rs2930047, rs11742570, rs1363907, rs4836519, rs2188962, rs6863411, rs11741861, rs6871626, rs12654812, rs17119, rs9358372, rs1847472, rs6568421, rs3851228, rs6920220, rs12199775, rs1819333, rs1456896, rs9297145, rs1734907, rs38904, rs921720, rs1991866, rs10758669, rs4743820, rs4246905, rs10781499, rs12722515, rs1042058, rs11010067, rs2790216, rs10761659, rs2227564, rs1250546, rs6586030, rs7911264, rs4409764, rs907611, rs10896794, rs11230563, rs4246215, rs559928, rs2231884, rs2155219, rs6592362, rs630923, rs11612508, rs11564258, rs11168249, rs7134599, rs17085007, rs941823, rs9557195, rs194749, rs4899554, rs8005161, rs17293632, rs7495132, rs529866, rs7404095, rs26528, rs10521318, rs3091316, rs12946510, rs12942547, rs1292053, rs1893217, rs7240004, rs727088, rs11879191, rs17694108, rs11672983, rs6142618, rs4911259, rs1569723, rs913678, rs259964, rs6062504, rs2823286, rs2836878, rs7282490, rs2266959, rs2412970, rs2413583, rs2641348, rs7517810, rs1260326, rs7438704, rs10061469, rs2503322, rs5743289, rs6667605, rs1440088, rs3774937, rs477515, rs1182188, rs17780256, rs11083840, rs3766606, rs13407913, rs6708413, rs2457996, rs10051722, rs4976646, rs7746082, rs38911, rs13277237, rs2227551, rs7097656, rs12778642, rs11229555, rs174537, rs568617, rs2226628, rs566416, rs11054935, rs3742130, rs1569328, rs2361755, rs3091315, rs1654644, rs4243971, rs6087990, rs6074022, rs5763767.

Subset of 112 SNPs which together generated the GRS of FIG. 71A: rs10065637, rs1016883, rs1042058, rs10521318, rs10758669, rs1077773, rs10781499, rs10865331, rs10896794, rs11054935, rs11083840, rs11150589, rs11168249, rs11209026, rs11583043, rs11672983, rs11739663, rs11742570, rs1182188, rs1260326, rs12778642, rs13204048, rs13277237, rs1517352, rs1569723, rs1654644, rs17085007, rs17119, rs17229285, rs1728918, rs1734907, rs17391694, rs1748195, rs17780256, rs1801274, rs1847472, rs1893217, rs194749, rs2024092, rs2111485, rs212388, rs2155219, rs2188962, rs2189234, rs2227551, rs2231884, rs2413583, rs2472649, rs2641348, rs2651244, rs26528, rs2816958, rs2823286, rs2836878, rs2930047, rs3024505, rs35320439, rs3742130, rs3764147, rs3766606, rs38904, rs395157, rs4243971, rs4409764, rs4692386, rs4728142, rs477515, rs4802307, rs4836519, rs483905, rs4976646, rs516246, rs559928, rs564349, rs566416, rs568617, rs6017342, rs6088765, rs616597, rs6426833, rs6651252, rs6667605, rs6856616, rs6863411, rs6920220, rs7097656, rs7134599, rs7210086, rs7236492, rs7240004, rs724016, rs7282490, rs7495132, rs7517810, rs7702331, rs7758080, rs864745, rs917997, rs921720, rs925255, rs9264942, rs9286879, rs9297145, rs9319943, rs941823, rs9491697, rs9847710, rs12199775, rs12654812, rs1292053, rs2227564, rs3197999, rs6074022.

The foregoing subset of 112 SNPs exhibited varying degrees of association with response to SSI therapy, as set out in Tables 23A and 23B, which identifies the relevant allele for each SNP and the odds ratio reflecting the association of that allele with SSI response. In Table 23A, odds ratios greater than 1 indicate that the designated allele is positively associated with response to SSI therapy, odds ratios less 1 indicate that alternative allele is positively associated with response to SSI therapy and the allele set out in the Table is negatively associated with response to SSI therapy. In Table 23B, the odds ratios that are negative in Table 23A have been converted to positive odds ratios for the alternative allele, so that all odds ratios are greater than one and the Response Allele is the allele associated with response to SSI therapy.

TABLE 23A

SNP alleles associated (or nagatively associated) with Response to SSI Therapy

| rsID | Response Allele | Odds Ratio |
|---|---|---|
| rs7517810 | G | 19.83 |
| rs17391694 | G | 12.00 |
| rs2413583 | G | 5.67 |
| rs13204048 | G | 3.84 |
| rs11209026 | G | 3.64 |
| rs1734907 | G | 3.56 |
| rs212388 | G | 3.19 |
| rs11739663 | G | 3.19 |
| rs3742130 | G | 3.00 |
| rs11672983 | G | 2.99 |
| rs1801274 | G | 2.94 |
| rs559928 | G | 2.68 |
| rs1042058 | G | 2.68 |
| rs9847710 | G | 2.66 |
| rs4802307 | C | 2.49 |
| rs4836519 | G | 2.37 |
| rs194749 | G | 2.31 |
| rs4243971 | C | 2.28 |
| rs10781499 | G | 2.26 |
| rs26528 | G | 1.99 |
| rs864745 | G | 1.90 |
| rs516246 | G | 1.87 |
| rs2472649 | G | 1.87 |
| rs12654812 | G | 1.85 |
| rs3764147 | G | 1.85 |
| rs2155219 | C | 1.79 |
| rs12199775 | G | 1.69 |
| rs4728142 | G | 1.63 |
| rs1182188 | G | 1.63 |
| rs17119 | G | 1.60 |
| rs2189234 | C | 1.59 |
| rs483905 | G | 1.58 |
| rs925255 | G | 1.49 |
| rs7702331 | G | 1.48 |
| rs564349 | G | 1.44 |

TABLE 23A-continued

SNP alleles associated (or nagatively associated) with Response to SSI Therapy

| rsID | Response Allele | Odds Ratio |
|---|---|---|
| rs35320439 | G | 1.43 |
| rs10865331 | G | 1.37 |
| rs7495132 | G | 1.33 |
| rs1016883 | G | 1.33 |
| rs1292053 | G | 1.29 |
| rs1260326 | G | 1.27 |
| rs724016 | G | 1.25 |
| rs9264942 | G | 1.23 |
| rs11742570 | G | 1.21 |
| rs3024505 | G | 1.20 |
| rs11083840 | C | 1.20 |
| rs6863411 | T | 1.18 |
| rs11150589 | G | 1.16 |
| rs2188962 | G | 1.15 |
| rs38904 | G | 1.15 |
| rs2231884 | G | 1.14 |
| rs568617 | G | 1.14 |
| rs566416 | C | 1.09 |
| rs941823 | G | 1.09 |
| rs2930047 | G | 1.08 |
| rs1748195 | G | 1.06 |
| rs2227564 | G | 1.05 |
| rs9491697 | G | 1.00 |
| rs7240004 | G | 0.98 |
| rs3766606 | C | 0.96 |
| rs2227551 | C | 0.95 |
| rs11054935 | G | 0.95 |
| rs7758080 | G | 0.95 |
| rs477515 | G | 0.94 |
| rs1847472 | C | 0.93 |
| rs10896794 | G | 0.92 |
| rs6426833 | G | 0.91 |
| rs1893217 | G | 0.90 |
| rs4409764 | C | 0.89 |
| rs13277237 | G | 0.86 |
| rs6017342 | C | 0.82 |
| rs1517352 | C | 0.82 |
| rs11583043 | G | 0.81 |
| rs4692386 | G | 0.79 |
| rs2823286 | G | 0.79 |
| rs2111485 | G | 0.77 |
| rs395157 | G | 0.76 |
| rs17780256 | C | 0.76 |
| rs7210086 | C | 0.76 |
| rs921720 | G | 0.75 |
| rs616597 | C | 0.74 |
| rs10521318 | G | 0.71 |
| rs9319943 | G | 0.71 |
| rs7282490 | G | 0.70 |
| rs1569723 | C | 0.69 |
| rs4976646 | G | 0.68 |
| rs9297145 | C | 0.67 |
| rs6074022 | G | 0.67 |
| rs7097656 | G | 0.66 |
| rs1077773 | G | 0.66 |
| rs11168249 | G | 0.63 |
| rs10758669 | C | 0.62 |
| rs1728918 | G | 0.61 |
| rs2651244 | G | 0.59 |
| rs12778642 | C | 0.58 |
| rs17229285 | G | 0.56 |
| rs2836878 | G | 0.56 |
| rs6667605 | G | 0.50 |
| rs1654644 | C | 0.48 |
| rs10065637 | G | 0.48 |
| rs2641348 | G | 0.44 |
| rs2816958 | G | 0.43 |
| rs7134599 | G | 0.41 |
| rs6651252 | G | 0.40 |
| rs917997 | G | 0.38 |
| rs6088765 | C | 0.38 |
| rs2024092 | G | 0.38 |
| rs3197999 | G | 0.34 |
| rs7236492 | G | 0.32 |

TABLE 23A-continued

SNP alleles associated (or nagatively associated) with Response to SSI Therapy

| rsID | Response Allele | Odds Ratio |
|---|---|---|
| rs17085007 | G | 0.24 |
| rs6920220 | G | 0.21 |
| rs9286879 | G | 0.05 |

TABLE 23B

SNP alleles associated with Response to SSI Therapy

| rsID | Response Allele | Odds Ratio |
|---|---|---|
| rs9286879 | A | 19.83 |
| rs7517810 | G | 19.83 |
| rs17391694 | G | 12.00 |
| rs2413583 | G | 5.67 |
| rs6920220 | A | 4.87 |
| rs17085007 | A | 4.20 |
| rs13204048 | G | 3.84 |
| rs11209026 | G | 3.64 |
| rs1734907 | G | 3.56 |
| rs212388 | G | 3.19 |
| rs11739663 | G | 3.19 |
| rs7236492 | A | 3.08 |
| rs3742130 | G | 3.00 |
| rs11672983 | G | 2.99 |
| rs3197999 | A | 2.98 |
| rs1801274 | G | 2.94 |
| rs559928 | G | 2.68 |
| rs1042058 | G | 2.68 |
| rs2024092 | A | 2.67 |
| rs6088765 | T | 2.66 |
| rs9847710 | G | 2.66 |
| rs917997 | A | 2.64 |
| rs6651252 | A | 2.52 |
| rs4802307 | C | 2.49 |
| rs7134599 | A | 2.46 |
| rs4836519 | G | 2.37 |
| rs2816958 | A | 2.33 |
| rs194749 | G | 2.31 |
| rs2641348 | A | 2.29 |
| rs4243971 | C | 2.28 |
| rs10781499 | G | 2.26 |
| rs10065637 | A | 2.10 |
| rs1654644 | T | 2.06 |
| rs26528 | G | 1.99 |
| rs6667605 | A | 1.99 |
| rs864745 | G | 1.90 |
| rs516246 | G | 1.87 |
| rs2472649 | G | 1.87 |
| rs12654812 | G | 1.85 |
| rs3764147 | G | 1.85 |
| rs2836878 | A | 1.80 |
| rs17229285 | A | 1.79 |
| rs2155219 | C | 1.79 |
| rs12778642 | T | 1.73 |
| rs2651244 | A | 1.71 |
| rs12199775 | G | 1.69 |
| rs1728918 | A | 1.65 |
| rs4728142 | G | 1.63 |
| rs1182188 | G | 1.63 |
| rs10758669 | T | 1.60 |
| rs17119 | G | 1.60 |
| rs2189234 | C | 1.59 |
| rs483905 | G | 1.58 |
| rs11168249 | A | 1.58 |
| rs1077773 | A | 1.53 |
| rs7097656 | A | 1.51 |
| rs6074022 | A | 1.50 |
| rs925255 | G | 1.49 |
| rs9297145 | T | 1.48 |
| rs7702331 | G | 1.48 |
| rs4976646 | A | 1.46 |

TABLE 23B-continued

SNP alleles associated with Response to SSI Therapy

| rsID | Response Allele | Odds Ratio |
|---|---|---|
| rs1569723 | T | 1.45 |
| rs564349 | G | 1.44 |
| rs35320439 | G | 1.43 |
| rs7282490 | A | 1.42 |
| rs9319943 | A | 1.41 |
| rs10521318 | A | 1.40 |
| rs10865331 | G | 1.37 |
| rs616597 | T | 1.35 |
| rs7495132 | G | 1.33 |
| rs1016883 | G | 1.33 |
| rs921720 | A | 1.33 |
| rs17780256 | T | 1.32 |
| rs7210086 | T | 1.32 |
| rs395157 | A | 1.32 |
| rs2111485 | A | 1.30 |
| rs1292053 | G | 1.29 |
| rs1260326 | G | 1.27 |
| rs2823286 | A | 1.27 |
| rs4692386 | A | 1.26 |
| rs724016 | G | 1.25 |
| rs11583043 | A | 1.23 |
| rs9264942 | G | 1.23 |
| rs1517352 | T | 1.21 |
| rs6017342 | T | 1.21 |
| rs11742570 | G | 1.21 |
| rs3024505 | G | 1.20 |
| rs11083840 | C | 1.20 |
| rs6863411 | T | 1.18 |
| rs13277237 | A | 1.16 |
| rs11150589 | G | 1.16 |
| rs2188962 | G | 1.15 |
| rs38904 | G | 1.15 |
| rs2231884 | G | 1.14 |
| rs568617 | G | 1.14 |
| rs4409764 | T | 1.13 |
| rs1893217 | A | 1.11 |
| rs6426833 | A | 1.10 |
| rs566416 | C | 1.09 |
| rs941823 | G | 1.09 |
| rs10896794 | A | 1.09 |
| rs2930047 | G | 1.08 |
| rs1847472 | T | 1.07 |
| rs1748195 | G | 1.06 |
| rs477515 | A | 1.06 |
| rs7758080 | A | 1.06 |
| rs11054935 | A | 1.05 |
| rs2227564 | G | 1.05 |
| rs2227551 | T | 1.05 |
| rs3766606 | T | 1.05 |
| rs7240004 | A | 1.02 |
| rs9491697 | G | 1.00 |

Within the foregoing subset of 112 SNPs, a number were individually associated with particular markers of clinical efficacy, and these SNPs are in turn spacially associated with genes, so that alternative markers, such as SNPs, associated with these genes may also serve as markers of SSI efficacy, as set out in Table 24.

TABLE 24

Select SNPs and associated Genes

| Efficacy Metric | SNP | Raw p-value | Important genes in area |
|---|---|---|---|
| CD - Response score - Comparing last recorded response for all CD subjects | rs9286879 | 3.32E-03 | TNFSF18, TNFSF4, FASLG |
| | rs7517810 | 3.32E-03 | TNFSF18, TNFSF4, FASLG |
| | rs17391694 | 4.06E-02 | DNAJB4 (HSP-40 family member), GIPC2, NEXN, FUBP1, MGC27382 |
| CD - CDAI: Comparing drop in CADI after 8 weeks of treatment for all CD subjects | rs1734907 | 1.43E-02 | EPHB4, EPO, GNB2, TFR2, ZAN, POP7, ACTL6B, GIGYF |
| | rs9286879 | 1.84E-02 | See CD - response |
| | rs7517810 | 1.84E-02 | See CD - response |
| | rs4836519 | 4.37E-02 | |
| CD - Calprotectin: Comparing drop in fecal calprotectin after 8 weeks of treatment for all CD subjects | rs17391694 | 7.21E-03 | See CD - response |
| | rs2413583 | 1.09E-02 | MAP3K7IP1, PDGFB, RPL3, SYNGR1, SNORD43, SNORD83A, SNORD83B, FLJ23865, TAB1, ATF4 |
| | rs11209026 | 1.62E-02 | IL12RB2, IL23R |
| | rs2472649 | 2.85E-02 | CXCL3, PF4, PPBP, CXCL5, PPBPL2, IL8, CXCL1, CXCL6, CXCL2 |
| CD - CRP: Comparing drop in CRP after 8 weeks of treatment for all CD subjects | rs2641348 | 2.20E-03 | NOTCH2, ADAM30, REG4, NBPF7 |
| UC - Mayo: Comparing drop in Mayo score after 16 weeks of treatment for all UC subjects | rs17085007 | 1.81E-02 | GPR12 |
| | rs2024092 | 2.50E-02 | CNN2, GPX4, POLR2E, STK11, ABCA7, SBNO2, HMHA1 |
| | rs6017342 | 2.50E-02 | HNF4A, SERINC3, PKIG, TTPAL, R3HDM |
| | rs2188962 | 3.65E-02 | IRF1, SLC22A4, SLC22A5, C5orf56 |
| | rs941823 | 3.71E-02 | LOC646982, FOX01 |
| UC-CRP: Comparing drop in CRP after 16 weeks of treatment for all UC subjects | rs17085007 | 1.95E-02 | see UC-Mayo |
| | rs2024092 | 1.95E-02 | see UC-Mayo |
| | rs6017342 | 3.81E-02 | see UC-Mayo |
| | rs17229285 | 3.96E-02 | |

The foregoing IBD associated SNPs are specially associated with genes (Liu et al., Nature Genetics. 47.9 (September 2015): p 979), so that alternative markers, such as SNPs, associated with these genes may also serve as markers of SSI efficacy, as set out in Table 25:

TABLE 25

Additional SNPs and associated Genes

| SNP | Candidate Gene | GRAIL gene |
|---|---|---|
| rs1748195 | USP1 | |
| rs34856868 | BTBD8 | |
| rs11583043 | SLC30A, EDG1 | EDG1 |
| rs6025 | SELP, SELE, SELL | SELP, SELE, SELL |
| NA (rs10798069) | | PTGS2, PLA2G4A |
| NA (rs7555082) | | PTPRC |
| rs11681525 | — | |
| rs4664304 | MARCH7, LY75, PLA2R1 | LY75 |
| rs3116494 | ICOS, CD28, CTLA4 | ICOS, CD28, CTLA4 |
| rs7556897, rs111781203 | CCL20 | CCL20 |
| rs35320439 | PDCD1, ATG4B | PDCD1, ATG4B |
| rs113010081 | FLJ78302, LTF, CCR1/2/3/5 | FLJ78302, LTF, CCR1, CCR3, CCR5 |
| rs616597 | NFKBIZ | NFKBIZ |
| rs724016 | — | |
| rs2073505 | HGFAC | |
| rs4692386 | — | |
| rs6856616 | | |
| rs2189234 | | |
| rs395157 | OSMR, FYB, LIFR | OSMR, FYB |
| rs4703855 | — | |
| rs564349 | C5orf4, DUSP1 | DUSP1 |
| rs7773324 | IRF4, DUSP22 | IRF4, DUSP22 |
| rs13204048 | — | |
| rs7758080 | MAP3K7IP2 | MAP3K7IP2 |
| rs1077773 | AHR | AHR |
| rs2538470 | CNTNAP2 | |
| rs17057051 | PTK2B, TRIM35, EPHX2 | PTK2B |
| rs7011507 | — | |
| rs3740415 | NFKB2, TRIM8, TMEM180 | NFKB2 |
| rs7954567 | CD27, TNFRSF1A, LTBR | CD27, TNFRSF1A, LTBR |
| rs653178 | SH2B3, ALDH2, ATXN2 | SH2B3 |
| rs11064881 | PRKAB1 | |
| rs9525625 | AKAP1, TNFSF11 | TNFSF11 |
| rs3853824 | — | |
| rs17736589 | — | |
| rs9319943 | | |
| rs7236492 | NFATC1, TST | NFATC1 |
| rs727563 | TEF, NHP2L1, PMM1, L3MBTL2, CHADL | |

The foregoing IBD associated SNPs are spacially associated with genes (Jostins, et al., Nature. 2012; 491: 119-124), so that alternative markers, such as SNPs, associated with these genes may also serve as markers of SSI efficacy, as set out in Table 26:

TABLE 26

Further SNPs and associated Genes

| SNP | IC_SNP | Key Genes (N) |
|---|---|---|
| rs17391694 | rs17391694 | (5) |
| rs6679677 | rs6679677 | PTPN22, (8) |
| rs3897478 | rs2641348 | ADAM30, (6) |
| rs9286879 | rs7517810 | TNFSF18, FASLG |
| rs1728918 | rs1260326 | UCN, (22) |
| rs10865331 | rs10865331 | (3) |
| rs6716753 | rs6716753 | SP140, (5) |
| rs12994997 | rs12994997 | ATG16L1, (8) |
| rs6837335 | rs7438704 | TEC, TXK, SLC10A4, (3) |
| rs13126505 | rs13126505 | (1) |
| rs10065637 | rs10065637 | IL6ST, IL31RA, (2) |
| rs7702331 | rs10061469 | (4) |
| rs17695092 | rs17695092 | CPEB4, (2) |
| rs12663356 | rs12663356 | (2) |
| rs9264942 | rs9264942 | HLA-C, PSORS1C1, (1) |

TABLE 26-continued

Further SNPs and associated Genes

| SNP | IC_SNP | Key Genes (N) |
|---|---|---|
| rs9491697 | rs2503322 | (3) |
| rs13204742 | rs13204742 | (2) |
| rs212388 | rs212388 | (6) |
| rs10486483 | rs10486483 | (2) |
| rs864745 | rs864745 | CREB5, JAZF1 |
| rs7015630 | rs7015630 | RIPK2, (4) |
| rs6651252 | rs6651252 | (0) |
| rs3764147 | rs3764147 | LACC1, FLJ38725, (2) |
| rs16967103 | rs16967103 | RASGRP1, SPRED1, (2) |
| rs2066847** | rs5743289 | NOD2, (?) |
| rs2945412 | rs2945412 | LGALS9, NOS2, (4) |
| rs2024092 | rs2024092 | APC2, GPX4, (21) |
| rs4802307 | rs4802307 | (11) |
| rs516246 | rs516246 | DBP, IZUMO1, FUT2, SPHK2, (22) |
| rs2284553 | rs2284553 | IFNGR2, IFNAR1, IL10RB, TMEM50B, IFNAR2, GART, (7) |

The foregoing IBD associated SNPs are spacially associated with genes (Jostins, et al., Nature. 2012; 491: 119-124), so that alternative markers, such as SNPs, associated with these genes may also serve as markers of SSI efficacy, as set out in Table 27a:

TABLE 27a

Further Select SNPs and associated Genes

| SNP | IC_SNP | All Genes |
|---|---|---|
| rs17391694 | rs17391694 | NEXN, FUBP1, DNAJB4, GIPC2, MGC27382 |
| rs6679677 | rs6679677 | MAGI3, PHTF1, RSBN1, PTPN22, BCL2L15, AP4B1, DCLRE1B, HIPK1, OLFML3 |
| rs3897478 | rs2641348 | PHGDH, HMGCS2, REG4, NBPF7, ADAM30, NOTCH2 |
| rs9286879 | rs7517810 | FASLG, TNFSF18 |
| rs1728918 | rs1260326 | SLC5A6, C2orf28, CAD, SLC30A3, DNAJC5G, TRIM54, UCN, MPV17, GTF3C2, EIF2B4, SNX17, ZNF513, PPM1G, FTH1P3, NRBP1, KRTCAP3, IFT172, FNDC4, GCKR, C2orf16, ZNF512, CCDC121, GPN1, SUPT7L |
| rs10865331 | rs10865331 | COMMD1, B3GNT2, TMEM17 |
| rs6716753 | rs6716753 | FBXO36, SLC16A14, SP110, SP140, SP140L, SP100 |
| rs12994997 | rs12994997 | NGEF, NEU2, INPP5D, ATG16L1, SCARNA5, SCARNA6, SAG, DGKD, USP40 |
| rs6837335 | rs7438704 | TXK, TEC, SLAIN2, SLC10A4, ZAR1, FRYL |
| rs13126505 | rs13126505 | BANK1 |
| rs10065637 | rs10065637 | IL31RA, IL6ST, ANKRD55 |
| rs7702331 | rs10061469 | FCHO2, TMEM171, TMEM174, FOXD1 |
| rs17695092 | rs17695092 | CPEB4, C5orf47, HMP19 |
| rs12663356 | rs12663356 | CDKAL1, SOX4, FLJ22536 |
| rs9264942 | rs9264942 | HCG22, C6orf15, PSORS1C1, CDSN, PSORS1C2, CCHCR1, TCF19, POU5F1, PSORS1C3, HCG27, HLA-C, HLA-B, MICA, HCP5, HCG26, MICB, MCCD1, DDX39B, SNORD117, SNORD84, ATP6V1G2, NFKBIL1 |
| rs9491697 | rs2503322 | RSPO3, RNF146, ECHDC1 |
| rs13204742 | rs13204742 | THEMIS, PTPRK |
| rs212388 | rs212388 | EZR, OSTCP1, C6orf99, RSPH3, TAGAP, FNDC1 |
| rs10486483 | rs10486483 | C7orf71, SKAP2 |
| rs864745 | rs864745 | JAZF1, LOC100128081, CREB5 |
| rs7015630 | rs7015630 | RIPK2, OSGIN2, NBN, DECR1, CALB1 |
| rs6651252 | rs6651252 | |
| rs3764147 | rs3764147 | ENOX1, CCDC122, LACC1, LINC00284 |
| rs16967103 | rs16967103 | SPRED1, FAM98B, RASGRP1, C15orf53 |
| rs2066847** | rs5743289 | ADCY7, BRD7, NKD1, SNX20, NOD2, CYLD |
| rs2945412 | rs2945412 | WSB1, LOC440419, KSR1, LGALS9, NOS2 |
| rs2024092 | rs2024092 | MED16, R3HDM4, KISS1R, ARID3A, WDR18, GRIN3B, C19orf6, CNN2, ABCA7, HMHA1, POLR2E, GPX4, SBNO2, STK11, C19orf26, ATP5D, MIDN, CIRBP-AS1, CIRBP, C19orf24, EFNA2, MUM1 |
| rs4802307 | rs4802307 | IGFL3, IGFL2, DKFZp434J0226, IGFL1, HIF3A, PPP5C, CCDC8, PNMAL1, PNMAL2 |
| rs516246 | rs516246 | GRWD1, KCNJ14, CYTH2, LMTK3, SULT2B1, FAM83E, SPACA4, RPL18, SPHK2, DBP, CA11, SEC1, NTN5, FUT2, MAMSTR, RASIP1, |

TABLE 27a-continued

Further Select SNPs and associated Genes

| SNP | IC_SNP | All Genes |
|---|---|---|
| rs2284553 | rs2284553 | IZUMO1, FUT1, FGF21, BCAT2, HSD17B14, PLEKHA4, PPP1R15A, TULP2, NUCB1, DHDH C21orf54, IFNAR2, IL10RB, IFNAR1, IFNGR2, TMEM50B, DNAJC28, GART, SON, DONSON, CRYZL1, ITSN1 |

The correlation coefficient between pairs of loci may be reflected by the term r-squared ($r^2$), which may be used a measure of the degree to which alternative genetic markers provide similar diagnostic or prognostic information. The value of $r^2$ ranges between 0 and 1 (1 when two markers provide identical information, and 0 when they are in perfect equilibrium). Conventionally, markers with $r^2>0.8$ may be considered to be in high linkage disequilibrium, so that they may provide similar diagnostic or prognostic information. Accordingly, an aspect of the assays described herein involves the use of makers that are in linkage disequilibrium with the markers identified above, having for example $r^2>0.7$, $r^2>0.8$, $r^2>0.9$ or $r^2>0.95$. In addition, markers that provide related information may be characterized by physical proximity in the genome, for example being within 1Mbp of each other, for example within 50 Kb, 60 Kb, 70 Kb, 80 Kb, 90 Kb, 100 Kb, 200 Kb, 300 Kb, 400 Kb or 500 Kb of each other.

In accordance with the foregoing, a "genetic SSI response marker" means a genetic biomarker, the presence of which is correlated with the probability of response to a treatment with an SSI. Exemplary genetic SSI response markers are disclosed in this Example, evidencing a correlation with response to an SSI in IBD patients. Genetic SSI response markers may be detected by a wide range of genomic assays, and may also be detected by assays that interrogate the transcription or translation products of a genome, for example protein isoforms associated with a particular genomic allele. Similarly, "biochemical SSI response markers" are disclosed herein that provide a biochemical indication of response to an SSI therapy, these for example include temporal or special changes in cellular populations or in the abundance or concentration of biologically relevant molecules. Biochemical and genetic SSI response markers may be used as diagnostic or prognostic indicators in the context of an SSI treatment, for example for IBD in general, or for specific forms of IBD such as Crohn's Disease and ulcerative colitis. Exemplary genetic SSI response markers are set out in Table 27b, as well as Tables 23 to 26.

TABLE 27b

Genetic SSI Response Markers

| SNP | Response Allele | SNP related allele (or isoform) | IBD |
|---|---|---|---|
| rs9286879 | A | TNFSF18, TNFSF4, FASLG | Crohn's |
| rs7517810 | G | TNFSF18, TNFSF4, FASLG | Crohn's |
| rs17391694 | G | DNAJB4 (HSP-40 family member), GIPC2, NEXN, FUBP1, MGC27382 | Crohn's |
| rs17085007 | A | GPR12 | UC |
| rs2024092 | A | CNN2, GPX4, POLR2E, STK11, ABCA7, SBNO2, HMHA1 | UC |
| rs6017342 | T | HNF4A, SERINC3, PKIG, TTPAL, R3HDM | UC |

Example 32: PRR Receptor Targets

This Example provides an analysis of the PRR receptors that are the targets for alternative SSIs.

TABLE 28

List of PRRs stimulated by select SSIs, including QBKPN, QBECO and QBSAU. Where a PRR is "Optional", this indicates that some embodiments may be designed to include agonists for the specificed PRR.

| Pattern Recognition Receptor | Major Agonists | QBECO | QBKPN | QBSAU |
|---|---|---|---|---|
| TLRs (Toll-Like Receptors) | | | | |
| TLR1 | Triacyl lipoprotein/peptidoglycan | Yes | Yes | Yes |
| TLR2 | Glycolipds, Lipoprotein, lipopeptides, lipoteichoic acid, others | Yes | Yes | Yes |
| TLR3 | dsRNA (viral) | No | No | No |
| TLR4 | Lipopolysaccharide (LPS), heat shock proteins, others | Yes | Yes | No |
| TLR5 | Flagellin, Profilin | Yes | No | No |
| TLR6 | Diacyl lipoprotein | Yes | Yes | Yes |
| TLR7 | ssRNA | No | No | No |
| TLR9 | CpG-DNA | Yes | Yes | Yes |
| TLR10 | Unclear | Optional | Optional | Optional |
| CLR (C-Type Lectin Receptors) (PMID 21616435) | | | | |
| Mannose Receptor (MR) | Mannose, N-acetylglucosamine and fucose on glycans | Optional | Optional | Optional |
| DEC-205 | Promiscuous antigen receptor - Class B CpG-DNA (Lahoud et al. 2012. PNAS) | Optional | Optional | Optional |

TABLE 28-continued

List of PRRs stimulated by select SSIs, including QBKPN, QBECO and QBSAU. Where a PRR is "Optional", this indicates that some embodiments may be designed to include agonists for the specified PRR.

| Pattern Recognition Receptor | Major Agonists | QBECO | QBKPN | QBSAU |
|---|---|---|---|---|
| Macrophage galactose-type lectin (MGL) | α- or β-N-acetylgalactosamine (GalNAc, Tn) residues of N- and O-glycans carried by glycoproteins and/or glycosphingolipids (PMID 15802303) | Optional | Optional | Optional |
| DC-SIGN (CD-209) | High-mannose-containing glycoproteins | Optional | Optional | Optional |
| Langerin (CD207) | Similar to CD-209 | Optional | Optional | Optional |
| Mannose Binding Lectin (MBL) | Mannose and N-acetylucosamine | Optional | Optional | Optional |
| Myeloid DAP12-associating lectin (MDL-1/CLEC5A) | Unclear, dengue viral particles (PMC3204838) | Optional | Optional | Optional |
| Dectin1/CLEC7A | B glucans on fungi, mycobacteria | Optional | Optional | Optional |
| DNGR1/CLEC9A | Actin filaments (no microbial ligands identified) | Optional | Optional | Optional |
| SIGNR3 | Mycobacterium tuberculosis | Optional | Optional | Optional |
| CLEC4B1 | Not Determined | Optional | Optional | Optional |
| CLEC4B2 | Not Determined | Optional | Optional | Optional |
| CLEC2 | Endogenous (prodoplanin), snake venom, HIV | Optional | Optional | Optional |
| CLEC12B | Not Determined | Optional | Optional | Optional |
| CLEC12A | Not Determined | Optional | Optional | Optional |
| DCIR/CLEC4A | HIV-1 | Optional | Optional | Optional |
| Dectin 2/CLEC6A | Mannose-type carbohydrates | Optional | Optional | Optional |
| CLEC4C | Unclear | Optional | Optional | Optional |
| CLEC4E (Mincle) | Fungal a-mannose and others | Optional | Optional | Optional |
| NLR (Nod-Like Receptors) | | | | |
| NOD1 | diaminopimelatic acid (DAP)-containing muropeptide | Optional | Optional | Optional |
| NOD2 | muramyl dipeptide (MDP) moieties universal to all bacterial peptidoglycan | Yes | Yes | Optional |
| NLRC3 (NOD3) | Cytosolic DNA, cyclic di-GMP, DNA viruses (PMID 24560620) This is an inhibitory PRR. | Optional | Optional | Optional |
| NLRC4 (NOD4) | Flagellin, components of the type three secretion system, others | Optional | Optional | Optional |
| NLRC6 | Unclear | Optional | Optional | Optional |
| NLRX1 (NOD5) | Unclear | Optional | Optional | Optional |
| NALP1-14 | Pathway unclear (Anthrax and muramyldipeptide for NALP1) | Optional | Optional | Optional |
| NAIP | Unclear | Optional | Optional | Optional |
| CIITA (NLRA) | Unclear (does not directly bind DNA) | Optional | Optional | Optional |
| RLR (Rig-1 Like Receptors) | | | | |
| RIG-1 | dsRNA (viral), maybe bacterial | Optional | Optional | Optional |
| MDA5 | dsRNA (viral) | Optional | Optional | Optional |
| LGP2 | dsRNA (viral) | Optional | Optional | Optional |
| Others | | | | |
| DAI (DNA-dependent activator of IRFs) (PMID 20098460) | DNA | Optional | Optional | Optional |
| AIM2 (PMID 20098460) | dsDNA | Optional | Optional | Optional |
| Caspase 11 (PMID 25145754) | LPS | Optional | Optional | Optional |
| LBP (Lipopolysaccharide Binding Protein) | LPS | Optional | Optional | Optional |
| CD14 | LPS | Optional | Optional | Optional |
| Scavenger Receptors | LPS | Optional | Optional | Optional |
| Beta2 Integrins | LPS | Optional | Optional | Optional |

TABLE 28-continued

List of PRRs stimulated by select SSIs, including QBKPN, QBECO and QBSAU. Where a PRR is "Optional", this indicates that some embodiments may be designed to include agonists for the specified PRR.

| Pattern Recognition Receptor | Major Agonists | QBECO | QBKPN | QBSAU |
|---|---|---|---|---|
| Peptidoglycan receptor proteins (4 different receptors) | Peptidoglycan | Minor | Minor | Major |

TABLE 29

PRR agonists in select fractionated SSIs, particularly in the DNA fractions Examplified herein.
DNA Fractions

| Component | QBECO | QBKPN |
|---|---|---|
| DNA | TLR9<br>AIM2<br>DAI<br>RIG-1<br>DEC205<br>NLRC3 | TLR9<br>AIM2<br>DAI<br>RIG-1<br>DEC205<br>NLRC3 |

TABLE 30

PRR agonists in select fractionated SSIs, particularly in the outer membrane fractions as Examplified herein.
Outer Membrane Fractions

| Component | QBECO | QBKPN |
|---|---|---|
| LPS | TLR4<br>LBP<br>CD14<br>Caspase 11<br>Other Scavenger Receptors | TLR4<br>LBP<br>CD14<br>Caspase 11<br>Other Scavenger Receptors |
| Lipoprotein | TLR1<br>TLR2<br>TLR6 | TLR1<br>TLR2<br>TLR6 |
| Flagellin | TLR5<br>NOD4 | N/A<br>NOD4 |
| Peptidoglycan | NOD2 | NOD2 |
| Capsule | N/A | TLRs and CLRs |
| Other | Collection of CLRs | |

Accordingly, in select embodiments, SSI therapies are provided that target a select subset of PRRs, using microbial PRR agonists derived from microbial pathogens of a target tissue. For example, an immunogenic composition is provided that comprises microbial agonists for at least a select number of distinct PRRs, for use so as to illicit an innate response in a target tissue, wherein the PRR agonists are microbial components from a single species of microbe that is selectively pathogenic in the target tissue. The number of distinct PRRs targeted by the agonists may for example be a number from 5 to 25, or at least a number within that range of integers, for example at least 5, 6, etc. The distinct PRRs may for example be selected from the PRRs set out in Tables 28, 29 and/or 30.

Example 33: Cytokine Markers of SSI Therapy

This Example provides an indication of cytokine markers indicative of various facets of SSI therapies. This data reflects the analysis of 42 cytokines/chemokines from a cohort of Crohn's Disease patients undergoing SSI therapy with QBECO, at baseline, week 4, week 8, week 16, and week 24, of a randomized placebo-controlled trial involving 68 patients.

Cytokines Changes with QBECO Exposure

Figure 74:
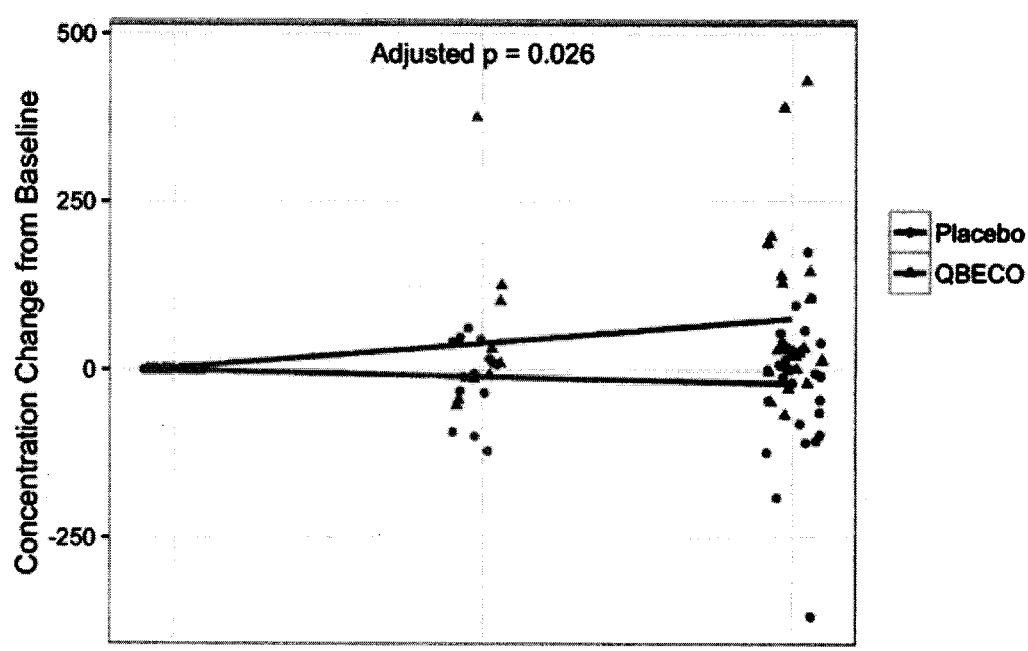
FIG. 74 is a graph illustrating the change in serum IL-18 levels in patients treated with QBECO vs. Placebo.

QBECO exposure increased IL-18 and IP-10 at both the 8 week and 16 week time points. Serum levels of IL-18 showed the most significant differences between patients treated with QBECO vs. Placebo at week 8 (median change 24 μg/mL, adjusted p=0.0256) (FIG. 74). This increase in IL-18 was evident at the week 16 time point as well. The second serum biomarker to show significant differences was IFNγ-inducible protein 10 (IP-10, also known as CXCL10) which showed greater increases in QBECO exposed patients at both week 8 (median change 7 μg/mL, adjusted p=0.036) and week 16 (median change 22 μg/mL, adjusted p=0.0151).

Vascular endothelial growth factor A (VEGF-A) showed some increase in the QBECO group at the week 8 mark (median change 14 μg/mL, adjusted p=0.0483), but this difference was lost at the end of the week 16 treatment point. A number of other immune factors showed strong trends in being increased from baseline to 8 weeks of QBECO exposure; these included: granulocyte colony stimulating factor (GCSF), IFNγ, IL-17A, IL-6, IL-7, and transforming growth factor-α (TGFα).

None of the serum immune factors remained elevated after patients were taken off all treatment after week 16 and evaluated again at week 24, illustrating that these biomarkers are most helpful to assess the immune responsiveness to QBECO while on treatment.

Figure 75:
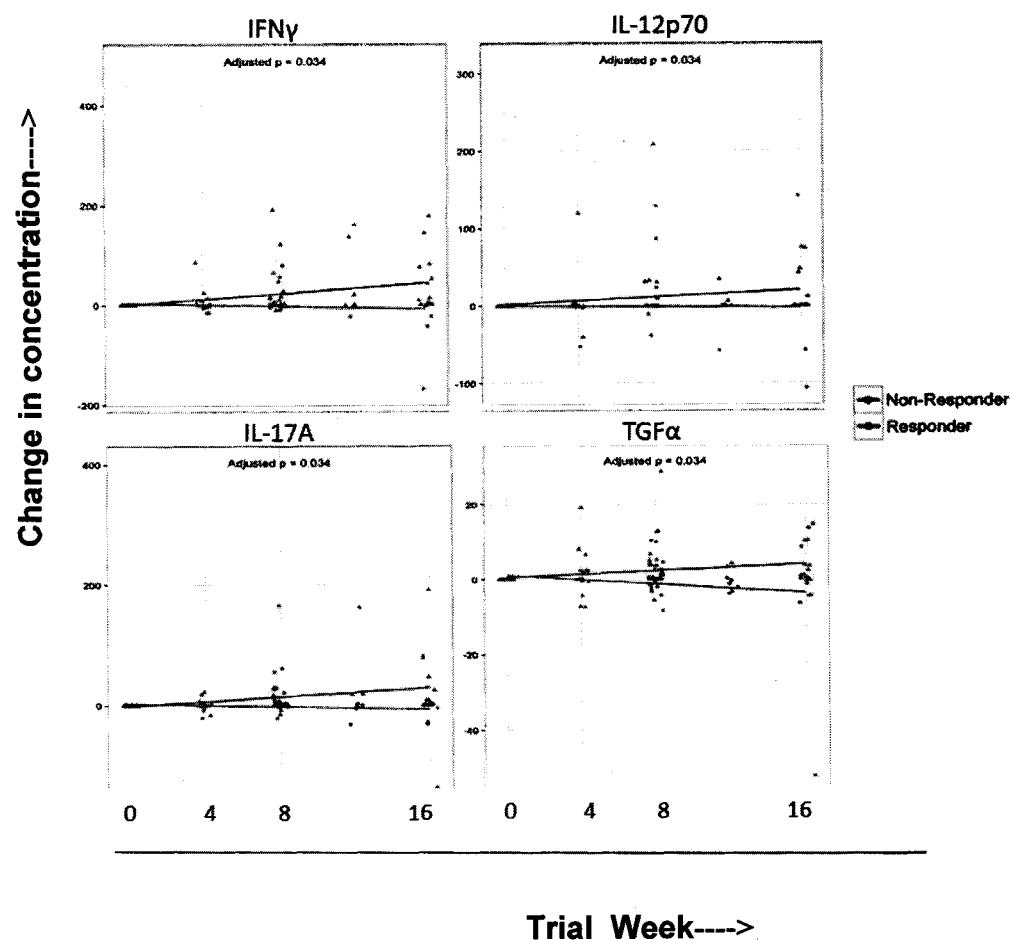
FIG. 75 is a set of 4 graphs illustrating serum immune cytokine changes with QBECO treatment that associated with clinical response.

Serum Biomarker Cytokine Concentration Changes that Associate with Clinical Response A sub-analysis was performed in patients exposed to QBECO (N=42, including those initially randomized to QBECO and those who were switched from placebo at week 8) to assess whether any of the immune changes over time associated with clinical outcome. 11-18 increased less among those with clinical response and remission, compared to non responders. IP-10 increased less among those with clinical response and remission, compared to non responders. IFNγ, IL-12p70, IL-17A and TGFα showed a significant difference in increase over time for responders compared to non responders. In particular, IFNγ, IL-12p70, IL-17A and TGFα, had greater increases over-time (adjusted p=0.0344) in patients who experienced a clinical response to QBECO in comparison to non-responders at week 8 (FIG. 75).

Baseline Serum Immune Factors that Associate with Clinical Response

Figure 76:
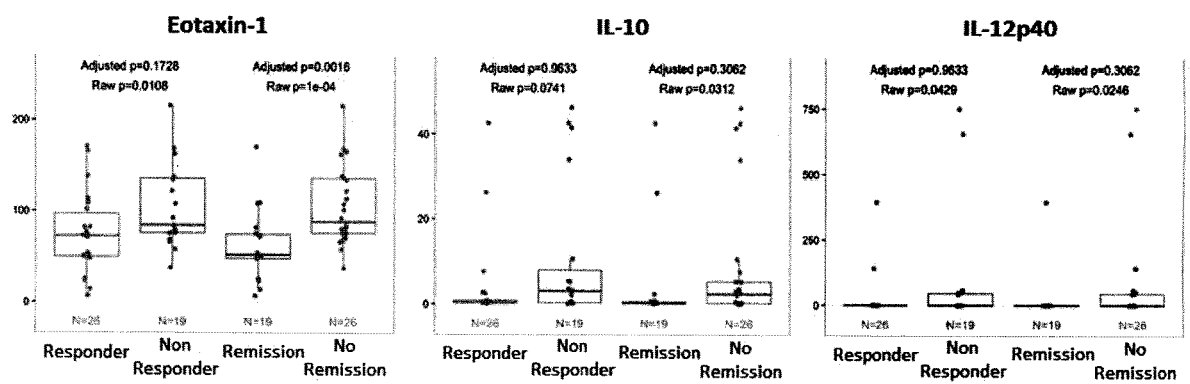
FIG. 76 is a set of 3 graphs illustrating baseline levels of Eotaxin-1, IL-10 and IL-12p40 by patient response to QBECO.

Lower Eotaxin 1 was a predictive biomarker for remission in response to QBECO treatment. In particular, baseline serum levels of Eotaxin-1 (C-C chemokine 11) had the strongest link to clinical remission (adjusted p=0.0016), with patients who had higher levels at baseline being less likely to go intoclinical into into clinical remission by week 8 with QBECO treatment (FIG. 76). Although not reaching statistical significance after correcting for multiple comparisons, patients with higher baseline IL-10 and IL-12p40 were also less likely to have a clinical response to QBECO treatment by week 8 (FIG. 76).

Trial results indicate that patients who had been previously exposed to TNFα inhibitors, such as Remicade™ or Humera™ were less likely to experience clinical remission or response after 8 weeks of QBECO treatment. This more difficult to treat group may have more severe immune dysfunction, due to their exposure to these immunosuppressive drugs and/or by virtue of the nature of their condition. Stratifying the mean baseline serum levels of the immune factors that associated with clinical outcome by previous TNFα inhibitor exposure provides evidence to support this. The baseline serum immune factors that inversely associated with patient response to QBECO, Eoxtaxin-1, IL-10 and IL-12p40, were higher in patients previously exposed to anti-TNFα therapy relative to unexposed patients (Table 31).

TABLE 31

Mean baseline serum levels of Eotaxin-1, IL-10 and IL-12p40 stratified by previous TNFα inhibitor exposure

| | Previous anti-TNFα therapy | N* | Mean ± SD | Mean Difference ± SD | 95% Confidence Interval of the Difference |
|---|---|---|---|---|---|
| Eotaxin-1 | No | 39 | 84 ± 43 | −17 ± 12 | (−41, 7) |
| | Yes | 26 | 100 ± 54 | | |
| IL-10 | No | 28 | 6 ± 14 | −5 ± 5 | (−14, 4) |
| | Yes | 17 | 11 ± 17 | | |
| IL-12p40 | No | 36 | 19 ± 67 | −52 ± 36 | (−123, 20) |
| | Yes | 24 | 70 ± 198 | | |

*20 reads from the IL-10 assay and 5 reads from the IL-12p40 were out of range of the assay or unraliable High Response and Remission Rates in Anti-TNFα Naïve Patients In anti-TNFα naïve patients, treatment with QBECO SSI for 8 weeks resulted in a statistically significant response rate of 64% compared to 27% in the placebo control (p=0.041). Clinical remission rates after 8 weeks of treatment were also impressive at 50%, more than double the placebo rate of 23% (p=0.16). Clinical response and remission rates were assessed using the standard Crohn's Disease Activity Index (CDAI), defined as a decrease in CDAI of 70 points (response) and CDAI score 150 points (remission). Anti-TNFα naïve patients include, for example, patients who have not been treated with the immunosuppressive drugs Remicade®, Humira®, Cimzia® and Simponi®. In patients previously been treated with TNFα inhibitors who completed 16 weeks of SSI treatment, 40% were in remission, indicating that this more challenging patient group may respond to QBECO SSI with longer treatment.

Building a composite prediction model to assess likelihood of patient response to QBECO by 8 weeks of therapy Using a Regularized Logistic Regression modelling approach, which simultaneously selects variables with the strongest association with response and optimally weights them to generate a prediction score, a composite prediction model was built including both the baseline biomarker measures (i.e. the 42 immune factors including cytokines, chemokines and growth factors) and baseline clinical and demographic characteristics. The variables available for the latter included enrollment year, age at randomization, age at diagnosis, time from diagnosis to randomization, sex, race (Caucasian or not), site (Vancouver or not), prior anti-TNFα therapy, baseline Crohn's Disease Activity Index (CDAI) score, baseline fecal calprotectin levels, and baseline C-reactive protein levels.

An "optimism-adjusted" area-under the receiver operating curve (AUROC) was made to correct for the potential over-estimation of the model fit. This "optimism-adjusted" AUROC can thus be more readily reliably applied to future independent data.

As shown in the analysis in this Example, high baseline serum Eotaxin-1 was the strongest negative biomarker predictor for clinical response after 8 weeks of QBECO treatment and was included in all models generated. Of the clinical/demographic variables—sex (females were more likely to respond to QBECO treatment) and previous anti-TNFα therapy (those previously exposed less likely to respond to QBECO) were the strongest predictors. Table 32 summarizes the different models generated. Typical commercial biomarker standards require an AUROC >7 for commercial viability of a prediction model. After optimism-adjustment, the composite model generated from this data achieved this level of predictive value with the inclusion of the following variables: sex, prior TNFα therapy, and baseline levels of Eotaxin-1, GROα (also called CXCL1—a neutrophil chemokine), IL-10, PDGF AA and RANTES (also called CCL5—a chemokine for activated T cells, eosinophils, basophils). Alternatively, a predictive model may also be developed using Eotaxin, GROα, IL10, PDGF AA, RANTES, Sex and prior aTNFα, predicting response with high confidence.

TABLE 32

Performance of four prediction models for clinical response and clinical remission following 8 weeks of QBECO treatment

| | | Clinical Response @ 8 Weeks | | | Clinical Remission @ 8 Weeks | | |
|---|---|---|---|---|---|---|---|
| Candidates | Variables Included | Raw AUROC | Optimism-Adjusted AUROC | Variables Included | Raw AUROC | Optimism-Adjusted AUROC |
| Reliable Cytokines Only | Eotaxin 1 PDGF AA | 0.737 (0.59, 0.88) | 0.591 (0.44, 0.73) | Eotaxin 1 GRO α PDGF AA | 0.846 (0.72, 0.97) | 0.644* (0.52, 0.77) |
| All Cytokines | Eotaxin 1 IL 10 PDGF AA | 0.753 (0.60, 0.90) | 0.588 (0.43, 0.73) | Eotaxin 1 GRO α PDGF AA | 0.842 (0.71, 0.97) | 0.612 (0.50, 0.74) |
| Clinical/ Demographic Variables | Sex Prior aTNFα | 0.760 (0.62, 0.90) | 0.642 (0.50, 0.78) | Sex | 0.674 (0.53, 0.81) | 0.627 (0.48, 0.76) |

TABLE 32-continued

Performance of four prediction models for clinical response
and clinical remission following 8 weeks of QBECO treatment

| Candidates | Clinical Response @ 8 Weeks | | | Clinical Remission @ 8 Weeks | | |
| --- | --- | --- | --- | --- | --- | --- |
| | Variables Included | Raw AUROC | Optimism-Adjusted AUROC | Variables Included | Raw AUROC | Optimism-Adjusted AUROC |
| All Cytokines and All Clinical/ Demographic Variables | Eotaxin 1 GRO α IL 10 PDGF AA RANTES Sex Prior aTNFα | 0.858 (0.75, 0.97) | 0.700* (0.59, 0.81) | Eotaxin 1 GRO α PDGF AA RANTES Sex | 0.881 (0.77, 0.99) | 0.707* (0.60, 0.82) |

*significant at 0.05 level.

Analysis

Cytokine Change with QBECO Exposure:

IL-18 (adjusted p=0.011 @ 8 weeks and 0.067 @ 16 weeks) and IP-10 (adjusted p=0.036 @ 8 weeks and 0.015 @ 16 Weeks) demonstrated a substantial and statistically significant increase with exposure to QBECO. These two cytokines also demonstrated significantly different trajectories for Clinical Responders vs Non-Responders (adjusted p=0.0328 for both) and those in and not in Clinical Remission (adjusted p=0.0368 for both) at week 8. Further, IL-18 demonstrated significantly different trajectory for those randomized to QBECO vs Placebo (adjusted p=0.0256).

Cytokine Association with Outcome:

Baseline Eotaxin-1 concentration was most strongly associated with clinical outcome among QBECO exposed subjects; those with higher Eotaxin-1 concentration at baseline were more likely to achieve Clinical Remission (adjusted p=0.0016) following 8 weeks of QBECO exposure.

Composite Biomarker:

Baseline concentration of Eotaxin-1, GRO-α, IL-10, PDGF AA and RANTES, combined with clinical variables Sex, and Prior anti-TNFAα exposure provided predictions of 8-week clinical outcomes that were significantly better than chance (optimism-adjusted AUROC=0.70, 95% CI [0.59, 0.81] for Response and 0.71, 95% CI [0.60, 0.82] for Remission). This model had some observable predictive ability for subjects in the Placebo group (AUROC=0.67 95% CI [0.45, 0.89] for Response and 0.70 [0.47, 0.93] for Remission.

Summary

QBECO SSI therapy provokes a biological response by increasing certain cytokines (IL-18 and IP-10) over time. Surprisingly, although both cytokines are increased after QBECO treatment, patients who were responders increased less. Treatment protocols, such as dosing, may accordingly be adjusted to achieve this result.

IFNg, IL-12P70, IL-17A and TGFα increased more in responders than non responders. Treatment protocols, such as dosing, may accordingly be adjusted to achieve this result. TGFα may for example be used as a marker of mucosal healing.

Lower Eotaxin 1 levels may be used as an indicator of patients more amenable to SSI treatment.

In conclusion:

an increase in serum IL-18 from baseline to week 8 and 16 of treatment was the best biomarker (of the 42 assessed) for QBECO exposure/activity;

a subsequent rise in serum levels of IFNγ, IL-12p70, IL-17A and TGFα after 8 weeks of QBECO treatment associated with clinical response;

Crohn's patients with higher baseline levels of Eotaxin-1 (and to a lesser extent, IL-10 and IL-12p40) were less likely to experience a clinical response or remission to QBECO after 8 weeks of treatment; previous anti-TNFα therapy may predispose to having higher levels of these factors, and anti-TNFα naïve patients represent a distinct Crohn's patient population amenable to QBECO SSI therapy;

a composite model that includes baseline serum biomarkers and clinical/demographic data would be able to predict, after optimism-adjustment (AUROC ≥7), a patient's likelihood to respond to 8 weeks of QBECO treatment; the variables in the final model includes sex, previous anti-TNFα therapy and baseline serum levels of Eotaxin-1, GROα, IL-10, PDGF AA and RANTES.

This biomarker analysis illustrates the formulation of a viable predictive composite model that can provide personalized treatment for Crohn's disease. This biomarker analysis maybe useful alone, or in combination with the genetic analysis exemplified herein, which showed significant stratification between responders and non-responders based on a derivation of a gene score.

Example 34: DSS Colitis Model

Figure 77:
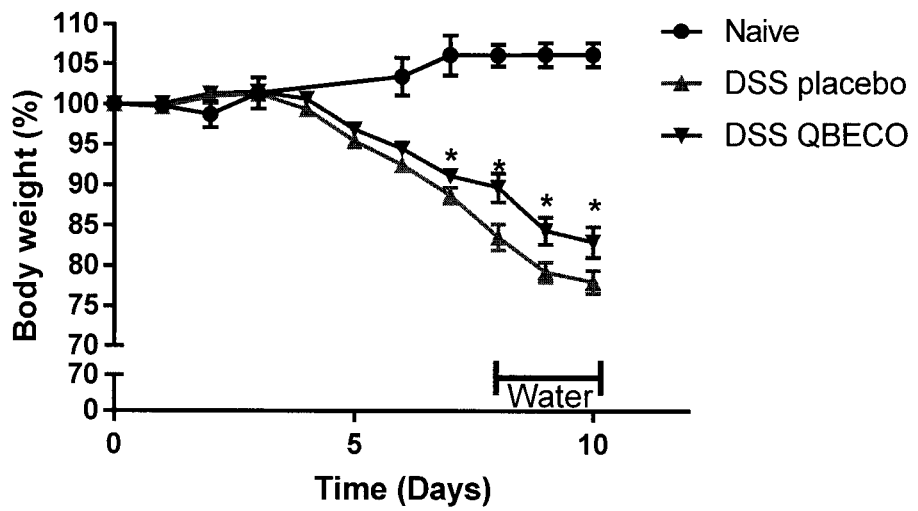
FIG. 77 is a graph illustrating the change in body weight over time in a murine DSS colitis model.
Figure 78:
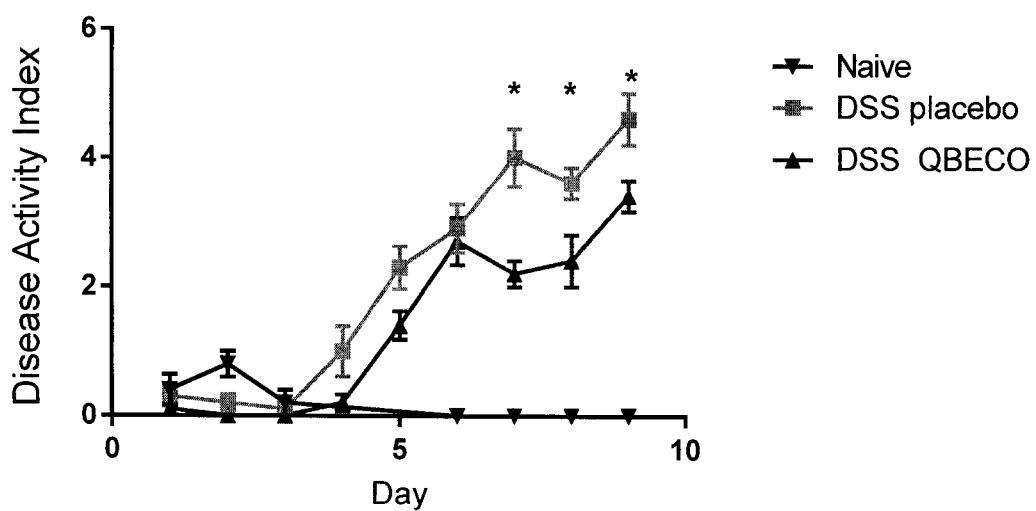
FIG. 78 is a graph illustrating change in disease activity index over time in a murine DSS colitis model.
Figure 79:
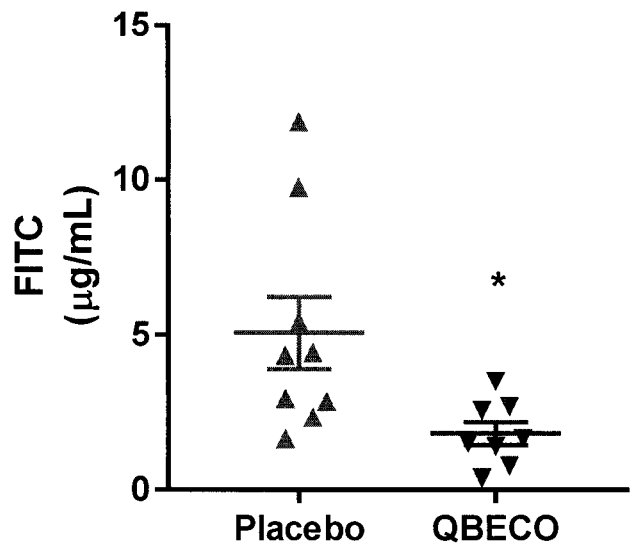
FIG. 79 is a graph illustrating change in the FITC-dextran assay over time in a murine DSS colitis model.
Figure 80:
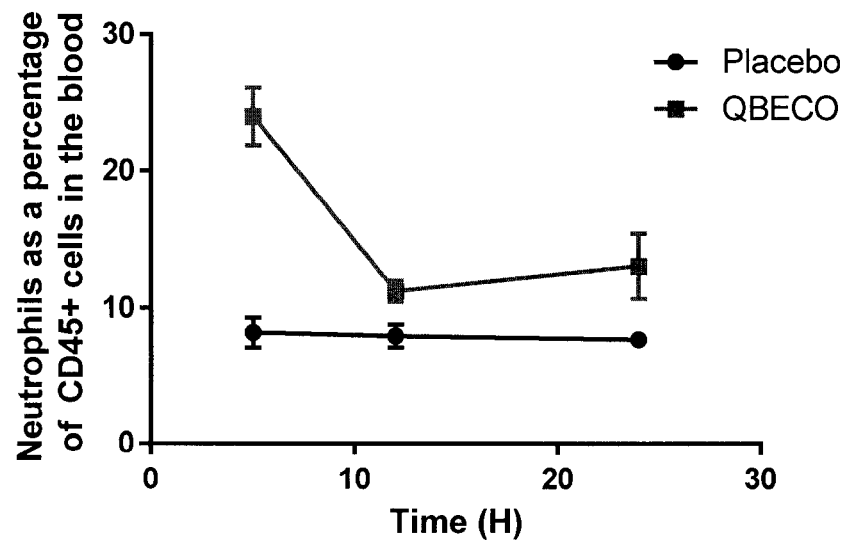
FIG. 80 is a graph illustrating blood neutrophil levels in disease free mice, over time, with or without an initial QBECO SSI treatment (mean+/−SEM, n=10 mice per group).
Figure 81:
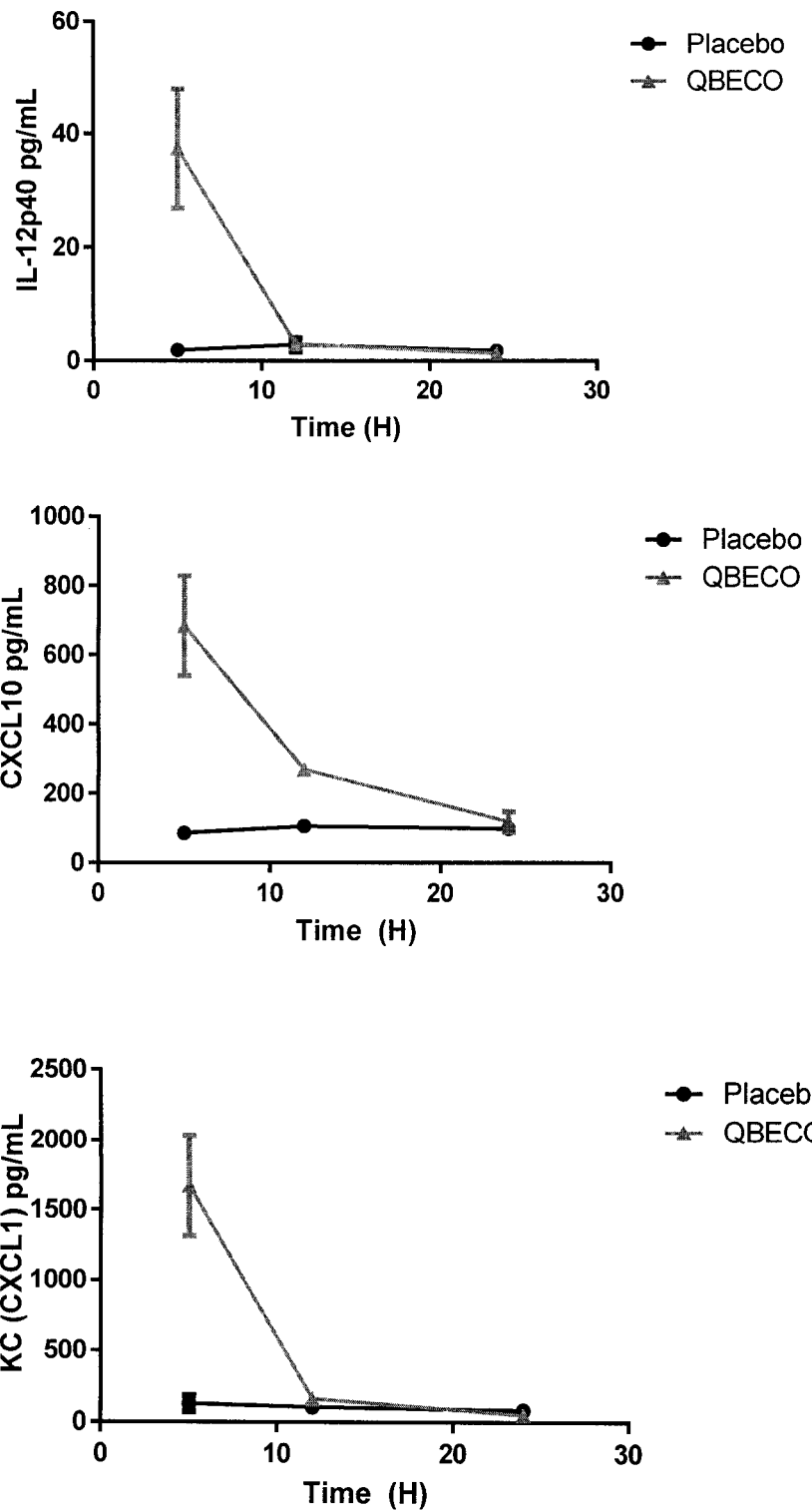
FIG. 81 is a collection of three graphs illustrating blood cytokine levels in disease free mice, over time, with or without an initial QBECO SSI treatment (mean+/−SEM, n=10 mice per group).
Figure 82:
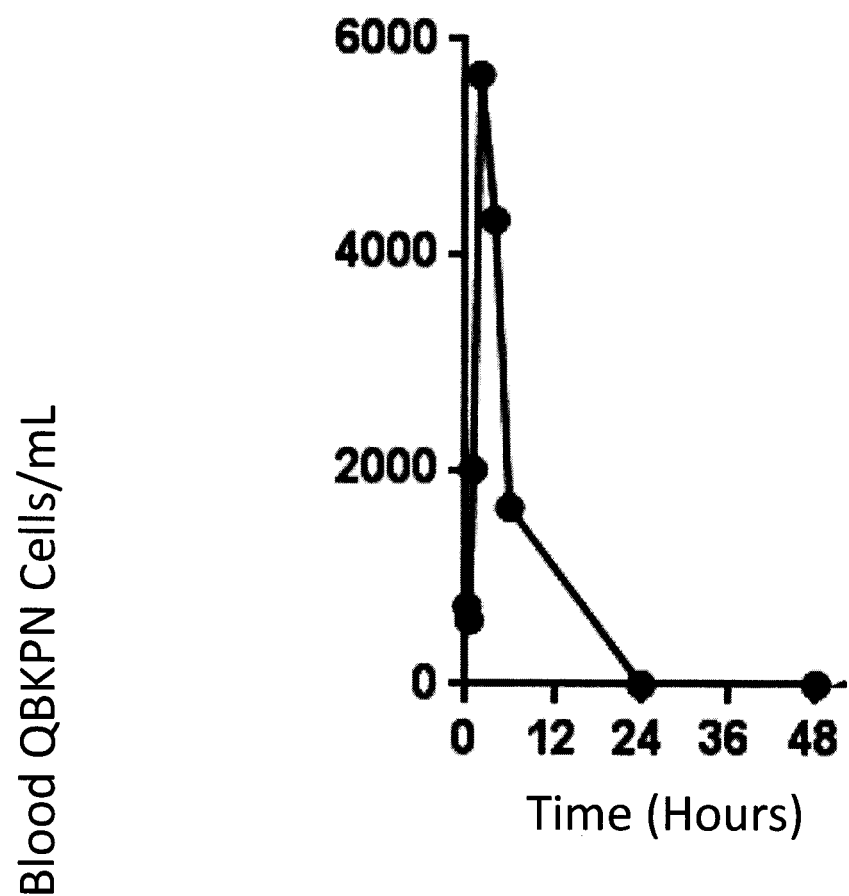
FIG. 82 is a graph illustrating the pharmacokinetics of QBKPN, in which QBKPN SSI was fluorescently labelled and subcutaneously injected into disease-free mice. Mice were bled at different timepoints over 48 hours and the blood cell count was quantified.

This Example illustrates results from a mouse model of chemically induced colitis, used to assess the efficacy of QBECO SSI therapy. Mice were given dextran sodium sulfate (DSS) in drinking water to induce colitis that mimics human ulcerative colitis. In the disease model, one cohort of mice was exposed to DSS for 7 days, a second cohort was exposed to DSS for 7 days followed by 3 days of water. Mice were given SSI injections every other day during a 10 day period prior to DSS exposure. The SSI injections continued every other day during DSS exposure. The results, as illustrated, indicate that SSI treatment with QBECO ameliorates disease severity by limiting weight loss (FIG. 77), lowering disease severity (FIG. 78) and maintaining mucosal barrier function (FIG. 79). The pharmacodynamics of QBECO SSI treatment in this model are illustrated by the blood neutrophil (FIG. 80) and blood cytokine (FIG. 81) levels in disease-free mice treated with QBECO or placebo, with the pharmacokinetics of QBKPN (FIG. 82) used to model the pharmacokinetics of SSIs in general, including QBECO (QBKPN SSI was fluorescently labelled and subcutaneously injected into disease-free mice, mice were bled at different timepoints over 48 hours).

Example 35: Tissue Biomarkers

Figure 83:
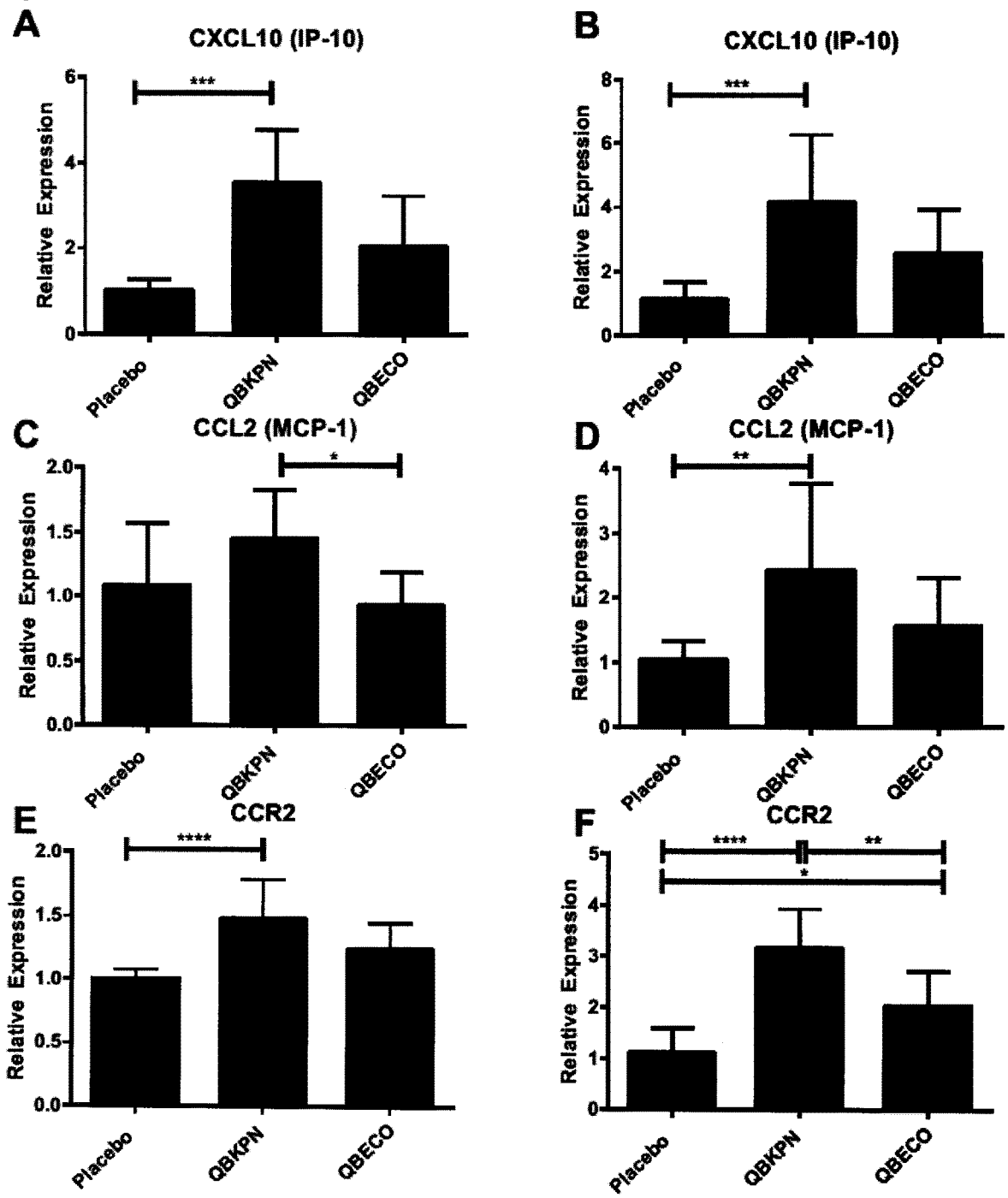
FIG. 83: includes 6 bar graphs, illustrating gene expression in the lung tissues for CXCL10 (IP-10), CCL2 (MCP-1) and CCR2. Mice were treated every second day for 10 days with Placebo, QBKPN or QBECO before B16F10 tumour implantation into the lungs via tail vein injection. Treatment continued every second day after tumour inoculation. Mice were euthanized on day 5 (A, C, E) or day 17 (B, D, F).

This Example illustrates results from a mouse cancer model, showing a tissue-specific biomarker response to SSI therapy. As illustrated in FIG. 83, gene expression in the lung tissues evidences tissue-specific SSI responses for CXCL10 (IP-10), CCL2 (MCP-1) and CCR2. In this Example, mice were treated every second day for 10 days with Placebo, QBKPN or QBECO before B16F10 tumour implantation into the lungs via tail vein injection. Treatment continued every second day after tumour inoculation. Mice were euthanized on day 5 (A, C, E) or day 17 (B, D, F). Accordingly, in alternative embodiments, CXCL10 (IP-10), CCL2 (MCP-1) and/or CCR2 may be used as biochemical SSI response markers, for example in biopsy tissue sample assays.

The invention claimed is:

1. A method for improving efficacy of a site specific immunotherapy (SSI) treatment of a human patient having Crohn's disease, wherein the SSI treatment comprises treatment with a formulation comprising a whole, killed or attenuated *E. coli* that is pathogenic in the gastrointestinal tract, the method comprising:
measuring or having measured in vitro a level of two or more of IFNgamma, IL-12P70 and IL-17A protein in a serum sample from the patient undergoing the SSI treatment; and
treating the patient with an adjusted dosage and/or dosage regimen of the SSI treatment based on the measured level of IFNgamma, IL-12P70 and/or IL-17A to thereby increase the level of IFNgamma, IL-12P70 and/or IL-17A in a subsequent serum sample from the patient undergoing the SSI treatment with the adjusted dosage and/or dosage regimen.

2. The method of claim 1, further comprising prior to the SSI treatment, measuring in a serum sample from the patient, a level of Eotaxin 1, GROα, IL-10, PDGF AA and/or RANTES.

3. The method of claim 2, wherein the measuring comprises measuring the level of Eotaxin 1 in the serum sample and wherein the level of Eotaxin 1 is below a predetermined threshold level.

4. The method of claim 1, wherein the patient is an anti-TNFα naïve patient.

5. The method of claim 1, wherein the patient comprises an A allele at SNP rs9286879.

6. The method of claim 5, wherein the patient is homozygous for the A allele at SNP rs9286879.

7. The method of claim 1, wherein the patient comprises a G allele at SNP rs751810.

8. The method of claim 7, wherein the patient is homozygous for the G allele at SNP rs751810.

9. The method of claim 1, wherein the patient comprises an A allele at SNP rs9286879 and a G allele at SNP rs751810.

10. The method of claim 1, comprising detecting the presence or absence of an A allele at SNP rs9286879 and/or a G allele at SNP rs751810 in the genome of the patient.

11. The method of claim 1, wherein the treating comprises administering a higher dosage of the formulation.

12. The method of claim 1, wherein the formulation comprises whole, killed *E. coli*.

13. The method of claim 1, wherein the formulation comprises whole, attenuated *E. coli*.

14. The method of claim 1, wherein the measuring comprises measuring in vitro levels of IFNgamma, IL-12P70 and IL-17A protein.

* * * * *